US012643904B2

(12) United States Patent
Chen et al.

(10) Patent No.: US 12,643,904 B2
(45) Date of Patent: Jun. 2, 2026

(54) RIPK1 INHIBITORS AND METHODS OF USE

(71) Applicant: Merck Sharp & Dohme LLC, Rahway, NJ (US)

(72) Inventors: Joanna L. Chen, Newton, MA (US); Yi-Heng Chen, Whippany, NJ (US); Erin F. DiMauro, Cambridge, MA (US); Min Lu, Brookline, MA (US); Joey L. Methot, Westwood, MA (US); Andrew J. Musacchio, Westborough, MA (US); Anandan Palani, Needham, MA (US); Barbara Pio, West Orange, NJ (US); Lorena Rico Duque, Canton, MA (US); Phieng Siliphaivanh, Newton, MA (US); Brandon A. Vara, Boston, MA (US); Xavier Fradera, Boston, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 364 days.

(21) Appl. No.: 18/318,760

(22) Filed: May 17, 2023

(65) Prior Publication Data

US 2024/0025912 A1 Jan. 25, 2024

Related U.S. Application Data

(60) Provisional application No. 63/491,422, filed on Mar. 21, 2023, provisional application No. 63/343,591, filed on May 19, 2022.

(51) Int. Cl.

| | |
|---|---|
| ***C07D 487/04*** | (2006.01) |
| ***A61K 31/4196*** | (2006.01) |
| ***A61K 31/429*** | (2006.01) |
| ***A61K 31/437*** | (2006.01) |
| ***A61K 31/4439*** | (2006.01) |
| ***A61K 31/497*** | (2006.01) |
| ***A61K 31/5383*** | (2006.01) |
| ***C07D 471/04*** | (2006.01) |
| ***C07D 498/04*** | (2006.01) |
| ***C07D 513/04*** | (2006.01) |

(52) U.S. Cl.
CPC ........ *C07D 487/04* (2013.01); *A61K 31/4196* (2013.01); *A61K 31/429* (2013.01); *A61K 31/437* (2013.01); *A61K 31/4439* (2013.01); *A61K 31/497* (2013.01); *A61K 31/5383* (2013.01); *C07D 471/04* (2013.01); *C07D 498/04* (2013.01); *C07D 513/04* (2013.01)

(58) Field of Classification Search
CPC .. C07D 487/04; C07D 498/04; C07D 513/04; C07D 471/04; A61P 25/00; A61P 25/28; A61K 31/4196; A61K 31/429; A61K 31/437; A61K 31/5383
See application file for complete search history.

(56) References Cited

FOREIGN PATENT DOCUMENTS

| | | | | |
|---|---|---|---|---|
| WO | WO 2005/085226 A1 * | 9/2005 | ........... | C07D 401/04 |
| WO | 2018107060 A1 | 6/2018 | | |
| WO | 2019012063 A1 | 1/2019 | | |
| WO | 2020146615 A1 | 7/2020 | | |

OTHER PUBLICATIONS

Gong, Yitao et al., The role of necroptosis in cancer biology and therapy, Molecular Cancer, 18:100, 1-17, 2019.
Caccamo, Antonella et al., Necroptosis activation in Alzheimer's disease, Nat Neurosci, 2017, 1236-1246, vol. 20 | No. 9.
Degterev, Alexei et al., Chemical inhibitor of nonapoptotic cell death with therapeutic potential for ischemic brain injury, Nat Chem Biol, 2005, 112-119, vol. 1 | No. 2.
Degterev, Alexei et al., Targeting RIPK1 for the treatment of human diseases, PNAS, 2019, 9714-9722, vol. 116 | No. 20.
Ito, Yasushi et al., RIPK1 mediates axonal degeneration by promoting inflammation and necroptosis in ALS, Science, 2016, 603-608, 353.
Ofengeim, Dimitry et al., Activation of necroptosis in multiple sclerosis, Cell Rep., 2015, 1836-1849, 10(11).
Philip A. Harris, Inhibitors of RIP1 kinase: a patent review (2016-present), Expert Opinion on Therapeutic Patents, 2021, 137-151, 31:2.
Wang, Jia-Nan et al., RIPK1 inhibitor Cpd-71 attenuates renal dysfunction in cisplatin-treated mice via attenuating necroptosis, inflammation and oxidative stress, Clin Sci, 2019, 1609-1627, 133(14).

* cited by examiner

*Primary Examiner* — Rebecca L Anderson
*Assistant Examiner* — David M Shim
(74) *Attorney, Agent, or Firm* — Daniel Woods; John C. Todaro

(57) ABSTRACT

Described herein are compounds of Formula I

I

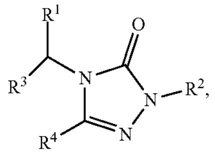

or a pharmaceutically acceptable salt thereof. The compounds of Formula I act as RIPK1 inhibitors and can be useful in preventing, treating or acting as a remedial agent for RIPK1-related diseases.

58 Claims, No Drawings

RIPK1 INHIBITORS AND METHODS OF USE

CROSS-REFERENCE TO RELATED APPLICATIONS

This application claims the benefit of priority to U.S. Provisional Patent Application Nos. 63/491,422 filed Mar. 21, 2023, and 63/343,591 filed May 19, 2022.

FIELD OF THE INVENTION

Disclosed herein are novel RIPK1 inhibitors. The RIPK1 inhibitors described herein can be useful in preventing, treating or acting as a remedial agent for RIPK1-related diseases.

BACKGROUND OF THE INVENTION

Receptor-interacting protein-1 kinase (RIPK1) belongs to the family serine/threonine protein kinase involved in innate immune signaling. RIPK1 has emerged as a promising therapeutic target for the treatment of a wide range of human neurodegenerative, autoimmune, and inflammatory diseases. This is supported by extensive studies which have demonstrated that RIPK1 is a key mediator of apoptotic and necrotic cell death as well as inflammatory pathways.

For example, RIPK1 inhibition has been found to be useful as a treatment of acute kidney injury (AKI), a destructive clinical condition induced by multiple insults including ischemic reperfusion, nephrotoxic drugs and sepsis. It has been found that RIPK1-mediated necroptosis plays an important role in AKI and a RIPK1 inhibitor may serve as a promising clinical candidate for AKI treatment. Wang J N, Liu M M, Wang F, Wei B, Yang Q, Cai Y T, Chen X, Liu X Q, Jiang L, Li C, Hu X W, Yu J T, Ma T T, Jin J, Wu Y G, Li J, Meng X M, RIPK1 Inhibitor Cpd-71 Attenuates Renal Dysfunction in Cisplatin-Treated Mice via Attenuating Necroptosis, Inflammation and Oxidative Stress. Clin Sci (Lond). 2019 Jul. 25; 133(14):1609-1627.

Additionally, human genetic evidence has linked the dysregulation of RIPK1 to the pathogenesis of amyotrophic lateral sclerosis (ALS), Alzheimer's disease and multiple sclerosis as well as other inflammatory and neurodegenerative diseases. Alexei Degterev, Dimitry Ofengeim, and Junying Yuan, *Targeting RIPK1 for the treatment of human diseases*, PNAS, May 14, 2019, 116 (20), 9714-9722; Ito Y, Ofengeim D, Najafov A, Das S, Saberi S, Li Y, et al., *RIPK1 mediates axonal degeneration by promoting inflammation and necroptosis in ALS*, Science, 2016, 353:603-8; Caccamo A, Branca C, Piras I S, Ferreira E, Huentelman M J, Liang W S, et al., *Necroptosis activation in Alzheimer's disease*, Nat Neurosci, 2017, 20:1236-46; Ofengeim D, Ito Y, Najafov A, Zhang Y, Shan B, DeWitt J P, et al., *Activation of necroptosis in multiple sclerosis*, Cell Rep., 2015, 10:1836-49.

It also has been demonstrated that necroptosis is a delayed component of ischemic neuronal injury, thus RIPK1 inhibition may also play a promising role as a treatment for stroke. Degterev A, et al., *Chemical inhibitor of nonapoptotic cell death with therapeutic potential for ischemic brain injury*, Nat Chem Biol 2005, 1(2):112-119.

Therefore, there is a need for inhibitors of RIPK1 that offer high selectivity which can penetrate the blood-brain barrier, thus offering the possibility to target neuroinflammation and cell death which drive various neurologic conditions including Alzheimer's disease, ALS, and multiple sclerosis as well as acute neurological diseases such as stroke and traumatic brain injuries.

SUMMARY OF THE INVENTION

Described herein are compounds of Formula I:

I

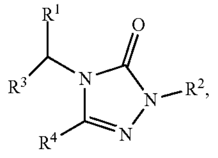

and pharmaceutically acceptable salts thereof, wherein $R^1$, $R^2$, $R^3$ and $R^4$ are described below.

The compounds described herein are RIPK1 inhibitors, which can be useful in the prevention, treatment or amelioration of neurodegenerative, autoimmune, inflammatory diseases and other RIPK1-related diseases.

Also described herein are methods of treating neurodegenerative, autoimmune, and inflammatory diseases comprising administering to a patient in need thereof a compound described herein, or a pharmaceutically acceptable salt thereof.

Also described herein are uses of a compound described herein, or a pharmaceutically acceptable salt thereof, to treat neurodegenerative, autoimmune, and inflammatory diseases in a patient in need thereof.

Also described herein are pharmaceutical compositions comprising a compound described herein, or a pharmaceutically acceptable salt thereof, and a pharmaceutically acceptable carrier.

Also described herein are pharmaceutical compositions comprising a compound described herein and a pharmaceutically acceptable carrier.

Also described herein are methods of treating neurodegenerative, autoimmune, and inflammatory diseases comprising administering to a patient in need thereof a compound described herein, or a pharmaceutically acceptable salt thereof, and at least one additional therapeutic agent.

Also described herein are uses of a compound described herein, or a pharmaceutically acceptable salt thereof, in combination with at least one additional agent, to treat neurodegenerative, autoimmune, and inflammatory diseases in a patient in need thereof.

Also described herein are pharmaceutical compositions comprising a compound described herein, or a pharmaceutically acceptable salt thereof, at least one additional therapeutic agent and a pharmaceutically acceptable carrier.

Also described herein are pharmaceutical compositions comprising a compound described herein, at least one additional therapeutic agent and a pharmaceutically acceptable carrier.

DETAILED DESCRIPTION OF THE INVENTION

Described herein are compounds of Formula I:

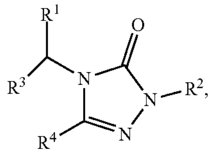

(I)

$R^1$ is selected from $C_3$-$C_6$cycloalkyl, aryl and heteroaryl, wherein each of the $C_3$-$C_6$cycloalkyl, aryl and heteroaryl is optionally substituted with one to four substituents independently selected from:

(1) halogen;

(2) —CN;

(3) —$C_1$-$C_6$alkyl, optionally substituted with one to four substituents independently selected from halogen and —CN;

(4) —$C_2$-$C_6$alkynyl;

(5) —$C_3$-$C_6$cycloalkyl;

(6) —O—$C_1$-$C_6$alkyl; and (7) —OH $R^2$ is selected from $C_3$-$C_{10}$cycloalkyl, heterocycloalkyl, aryl and heteroaryl, wherein each of the $C_3$-$C_{10}$cycloalkyl, heterocycloalkyl, aryl and heteroaryl is optionally substituted with one to four substituents independently selected from:

(1) halogen;

(2) —CN;

(3) —$C_1$-$C_6$alkyl, optionally substituted with one to four substituents independently selected from halogen, —CN, —OH, —O—$C_1$-$C_6$alkyl, and a heteroaryl;

(4) —O—$C_1$-$C_6$alkyl, optionally substituted with one to four substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NR^bR^c$, each of $R^b$ and $R^c$ is independently selected from hydrogen and —$C_1$-$C_6$alkyl optionally substituted with an heteroaryl; and (6) aryl, optionally substituted with one to three halogens; and $R^3$ and $R^4$ together with the atoms to which they are attached, form a 5- or 6-membered ring fused to the triazole ring, wherein the 5- or 6-membered ring optionally comprises heteroatoms selected from N, O, or S and is optionally substituted with one to four substituents independently selected from halogen, —OH, and —$C_1$-$C_6$alkyl.

In one embodiment of a compound of Formula I, or a pharmaceutically acceptable salt thereof:

$R^1$ is selected from —$C_4$-$C_6$cycloalkyl, phenyl and heteroaryl, wherein the heteroaryl is selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl;

wherein the —$C_4$-$C_6$cycloalkyl, phenyl and heteroaryl is optionally substituted with one to three substituents selected from:

(1) halogen;

(2) —CN;

(3) —$CH_3$, optionally substituted with one to three substituents independently selected from halogen and —CN;

(4) —$CH_2CH_3$, optionally substituted with one to three substituents independently selected from halogen and —CN;

(5) ethynyl;

(6) cyclopropyl;

(7) —O—$CH_3$; and (8) —O—$CH_2CH_3$.

In one embodiment of a compound of Formula I, or a pharmaceutically acceptable salt thereof:

$R^1$ is selected from cyclobutyl, cyclopentyl, cyclohexyl, phenyl, pyridyl, and pyrazinyl, wherein the cyclobutyl, cyclopentyl, phenyl, pyridyl, and pyrazinyl is optionally substituted with one to three substituents selected from:

(1) halogen;

(2) —CN;

(3) —$CH_3$, optionally substituted with one to three substituents independently selected from halogen and —CN;

(4) ethynyl;

(5) cyclopropyl; and (6) —O—$CH_3$.

In one embodiment of a compound of Formula I, or a pharmaceutically acceptable salt thereof:

$R^1$ is phenyl, optionally substituted with one to three substituents selected from:

(1) halogen;

(2) —CN; and (3) —$CH_3$, optionally substituted with one to three substituents independently selected from halogen and —CN.

In one embodiment of a compound of Formula I, or a pharmaceutically acceptable salt thereof:

$R^2$ is selected from bridged $C_5$-$C_{10}$cycloalkyl, and bridged heterocycloalkyl, phenyl and heteroaryl, wherein:

the bridged $C_5$-$C_{10}$cycloalkyl, or bridged heterocycloalkyl, is unsubstituted or substituted with one to three substituents independently selected from:

(1) halogen;

(2) —CN;

(3) —$C_1$-$C_4$alkyl, optionally substituted with one to three substituents independently selected from halogen, —CN, —OH, and —O—$C_1$-$C_4$alkyl;

(4) —O—$C_1$-$C_4$alkyl, optionally substituted with one to three substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NHR^c$, and $R^c$ is selected from hydrogen and —$C_1$-$C_4$alkyl optionally substituted with an heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl; and (6) phenyl, optionally substituted with one to three halogens.

In one embodiment of a compound of Formula I, or a pharmaceutically acceptable salt thereof:

$R^2$ is selected from $C_3$-$C_{10}$cycloalkyl, heterocycloalkyl, phenyl and heteroaryl, wherein:

the $C_3$-$C_{10}$cycloalkyl is selected from

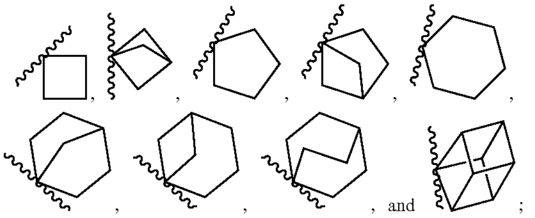

, , , , , , , and ;

the heterocycloalkyl is selected from

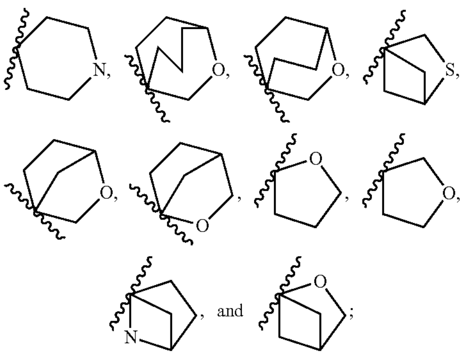

, , , , , , , , and ;

and the heteroaryl is selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl;

wherein each of the $C_3$-$C_{10}$cycloalkyl, heterocycloalkyl, phenyl and heteroaryl is optionally substituted with one to three substituents independently selected from:

(1) halogen;

(2) —CN;

(3) —$C_1$-$C_4$alkyl, optionally substituted with one to three substituents independently selected from halogen, —CN, —OH, and —O—$C_1$-$C_4$alkyl;

(4) —O—$C_1$-$C_4$alkyl, optionally substituted with one to three substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NHR^c$, and $R^c$ is selected from hydrogen and —$C_1$-$C_4$alkyl optionally substituted with an heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl; and (6) phenyl, optionally substituted with one to three halogens.

In one embodiment of a compound of Formula I, or a pharmaceutically acceptable salt thereof:

$R^2$ is selected from

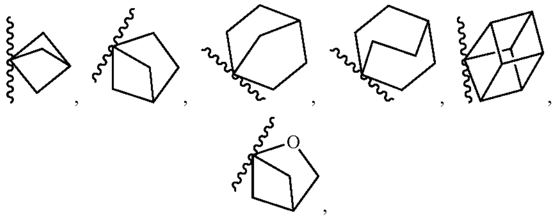

, , , , , , and phenyl, wherein each of the

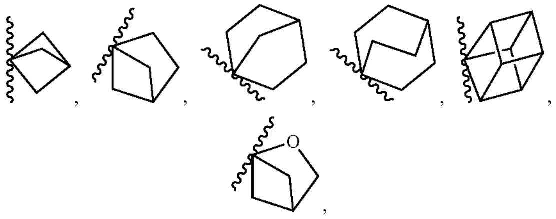

, , , , , , and phenyl is optionally substituted with one to three substituents independently selected from:

(1) halogen;

(2) —CN;

(3) —$CH_3$, optionally substituted with one to three substituents independently selected from halogen, —CN, —OH and —O—$CH_3$;

(4) —O—$CH_3$, optionally substituted with one to three substituents independently selected from halogen and —CN;

(5) —C(O)—$R^a$, wherein is $R^a$ is selected from —OH, —$CH_3$, —O—$CH_3$, and —$NHR^c$; and $R^c$ is selected from hydrogen and —$CH_3$ optionally substituted with a thienyl; and (6) phenyl, optionally substituted with one to three halogens.

In one embodiment of a compound of Formula I, or a pharmaceutically acceptable salt thereof:

$R^2$ is

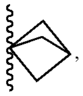

, optionally substituted with one to three substituents independently selected from:

(1) halogen;

(2) —CN;

(3) —$CH_3$, optionally substituted with one to three substituents independently selected from halogen, —CN, —OH and —O—$CH_3$;

(4) —C(O)—$OCH_3$;

(5) —C(O)$CH_2$-thienyl; and (6) phenyl.

In one embodiment of a compound of Formula I, or a pharmaceutically acceptable salt thereof:

$R^3$ and $R^4$ together with the atoms to which they are attached, form a 5-membered aliphatic ring fused to the triazole ring, wherein the 5-membered aliphatic ring is optionally substituted with one to four substituents independently selected from halogen, —OH, —$CH_3$, —$CH_2CH_3$, and —$CH_2CH_2CH_3$.

In one embodiment of a compound of Formula I, or a pharmaceutically acceptable salt thereof, the compound is of Formula Ia:

(Ia)

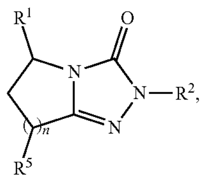

wherein:

n is 1 or 2;

$R^1$ is selected from $C_3$-$C_6$cycloalkyl, aryl and heteroaryl, wherein each of the $C_3$-$C_6$cycloalkyl, aryl and heteroaryl is optionally substituted with one to three substituents independently selected from:

(1) halogen;

(2) —CN;

(3) —$C_1$-$C_6$alkyl, optionally substituted with one to four substituents independently selected from halogen and —CN;

(4) —$C_2$-$C_6$alkynyl;

(5) —$C_3$-$C_6$cycloalkyl; and (6) —O—$C_1$-$C_6$alkyl;

$R^2$ is selected from $C_3$-$C_{10}$cycloalkyl, heterocycloalkyl, aryl and heteroaryl, wherein each of the $C_3$-$C_{10}$cycloalkyl, heterocycloalkyl, aryl and heteroaryl is optionally substituted with one to four substituents independently selected from:

(1) halogen;

(2) —CN;

(3) —$C_1$-$C_6$alkyl, optionally substituted with one to four substituents independently selected from halogen, —CN, —OH, —O—$C_1$-$C_6$alkyl, and a heteroaryl;

(4) —O—$C_1$-$C_6$alkyl, optionally substituted with one to four substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NR^bR^c$, each of $R^b$ and $R^c$ is independently selected from hydrogen and —$C_1$-$C_6$alkyl optionally substituted with an heteroaryl; and (6) aryl, optionally substituted with one to three halogens; and each occurrence of $R^5$ is independently selected from hydrogen, halogen, —$C_1$-$C_6$alkyl and —OH.

In one embodiment of a compound of Formula Ia, or a pharmaceutically acceptable salt thereof: n is 1.

In one embodiment of a compound of Formula Ia, or a pharmaceutically acceptable salt thereof:

$R^1$ is selected from —$C_4$-$C_6$cycloalkyl, phenyl and heteroaryl, wherein the heteroaryl is selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl;

wherein the —$C_4$-$C_6$cycloalkyl, phenyl and heteroaryl is optionally substituted with one to three substituents selected from:

(1) halogen;

(2) —CN;

(3) —$CH_3$, optionally substituted with one to three substituents independently selected from halogen and —CN;

(4) —$CH_2CH_3$, optionally substituted with one to three substituents independently selected from halogen and —CN;

(5) ethynyl;

(6) cyclopropyl;

(7) —O—$CH_3$; and (8) —O—$CH_2CH_3$.

In one embodiment of a compound of Formula Ia, or a pharmaceutically acceptable salt thereof:

$R^1$ is selected from cyclobutyl, cyclopentyl, cyclohexyl, phenyl, pyridyl, and pyrazinyl, wherein the cyclobutyl, cyclopentyl, cyclohexyl, phenyl, pyridyl and pyrazinyl is optionally substituted with one to three substituents selected from:

(1) halogen;

(2) —CN;

(3) —$CH_3$, optionally substituted with one to three substituents independently selected from halogen and —CN;

(4) ethynyl;

(5) cyclopropyl; and (6) —O—$CH_3$.

In one embodiment of a compound of Formula Ia, or a pharmaceutically acceptable salt thereof:

$R^2$ is selected from $C_3$-$C_{10}$cycloalkyl, heterocycloalkyl, phenyl and heteroaryl, wherein:

the $C_3$-$C_{10}$cycloalkyl is selected from

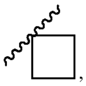, 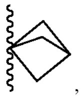, 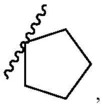, 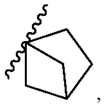, 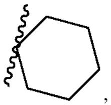, 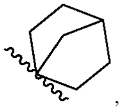, 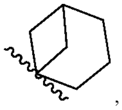, 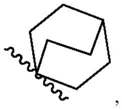, and 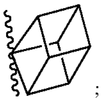;

the heterocycloalkyl is selected from

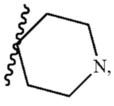, 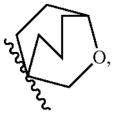, 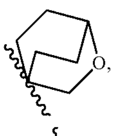, 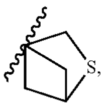, 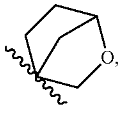, 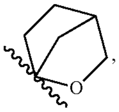, 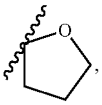, 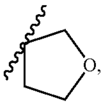, 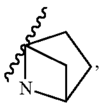, and 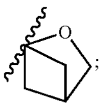;

and the heteroaryl is selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl;

wherein each of the $C_3$-$C_{10}$cycloalkyl, heterocycloalkyl, phenyl and heteroaryl is optionally substituted with one to three substituents independently selected from:

(1) halogen;

(2) —CN;

(3) —$C_1$-$C_4$alkyl, optionally substituted with one to three substituents independently selected from halogen, —CN, —OH, and —O—$C_1$-$C_4$alkyl;

(4) —O—$C_1$-$C_4$alkyl, optionally substituted with one to four substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NHR^c$, and $R^c$ is selected from hydrogen and —$C_1$-$C_4$alkyl optionally substituted with an heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl; and (6) phenyl, optionally substituted with one to three halogens.

In one embodiment of a compound of Formula Ia, or a pharmaceutically acceptable salt thereof:

$R^2$ is selected from

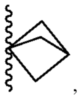, 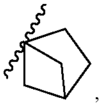, 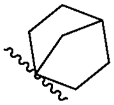, 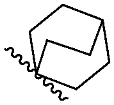, 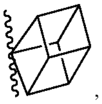, 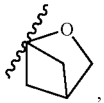, and phenyl, wherein each of the

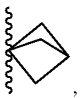, 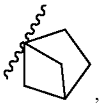, 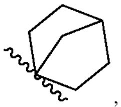, 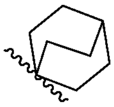, 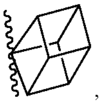, 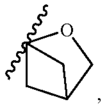, and phenyl is optionally substituted with one to three substituents independently selected from:

(1) halogen;

(2) —CN;

(3) —$CH_3$, optionally substituted with one to three substituents independently selected from halogen, —CN, —OH and —O—$CH_3$;

(4) —O—$CH_3$, optionally substituted with one to three substituents independently selected from halogen and —CN;

(5) —C(O)—$R^a$, wherein is $R^a$ is selected from —OH, —$CH_3$, —O—$CH_3$, and —$NHR^c$; and $R^c$ is selected from hydrogen and —$CH_3$ optionally substituted with a thienyl; and (6) phenyl, optionally substituted with one to three halogens.

In one embodiment of a compound of Formula Ia, or a pharmaceutically acceptable salt thereof:

$R^1$ is selected from —$C_4$-$C_6$cycloalkyl, phenyl and heteroaryl, wherein the heteroaryl is selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl;

wherein the —$C_4$-$C_6$cycloalkyl, phenyl and heteroaryl is optionally substituted with one to three substituents selected from:

(1) halogen;

(2) —CN;

(3) —$CH_3$, optionally substituted with one to three substituents independently selected from halogen and —CN;

(4) —$CH_2CH_3$, optionally substituted with one to three substituents independently selected from halogen and —CN;

(5) ethynyl;

(6) cyclopropyl;

(7) —O—$CH_3$; and (8) —O—$CH_2CH_3$;

$R^2$ is selected from

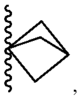, 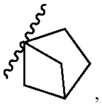, 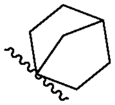, 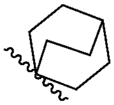, 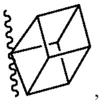, 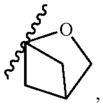, and phenyl, wherein each of the

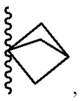, 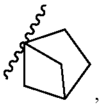, 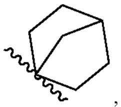, 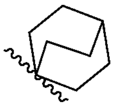, 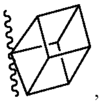, 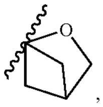, and phenyl is optionally substituted with one to three substituents independently selected from:

(1) halogen;

(2) —CN;

(3) —$CH_3$, optionally substituted with one to three substituents independently selected from halogen, —CN, —OH and —O—$CH_3$;

(4) —O—$CH_3$, optionally substituted with one to three substituents independently selected from halogen and —CN;

(5) —C(O)—$R^a$, wherein is $R^a$ is selected from —OH, —$CH_3$, —O—$CH_3$, and —$NHR^c$; and $R^c$ is selected from hydrogen and —$CH_3$ optionally substituted with a thienyl; and (6) phenyl, optionally substituted with one to three halogens; and $R^5$ is selected from hydrogen, halogen, —$C_1$-$C_4$alkyl and —OH.

In one embodiment of a compound of Formula I, or a pharmaceutically acceptable salt thereof:

$R^1$ is phenyl, optionally substituted with one to three substituents selected from:

(1) halogen;

(2) —CN;

(3) —$CH_3$, optionally substituted with one to three substituents independently selected from halogen and —CN;

(4) cyclopropyl; and (5) —O—$CH_3$;

$R^2$ is

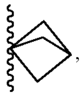

optionally substituted with one to three substituents independently selected from:

(1) halogen;

(2) —CN;

(3) —$CH_3$, optionally substituted with one to three substituents independently selected from halogen, —CN, —OH and —O—$CH_3$;

(4) —C(O)O—$CH_3$;

(5) —C(O)$CH_2$-thienyl; and (6) phenyl; and $R^5$ is selected from hydrogen, halogen, —$CH_3$, and —OH.

In one embodiment of a compound of Formula I, or a pharmaceutically acceptable salt thereof, the compound is of Formula Ib:

(Ib)

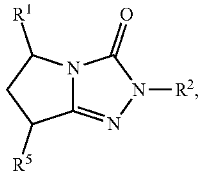

wherein:

$R^1$ is selected from $C_3$-$C_6$cycloalkyl, phenyl and heteroaryl, wherein each of the $C_3$-$C_6$cycloalkyl, phenyl and heteroaryl is optionally substituted with one to three substituents independently selected from:

(1) halogen;

(2) —CN;

(3) —$C_1$-$C_6$alkyl, optionally substituted with one to three substituents independently selected from halogen and —CN;

(4) —$C_2$-$C_6$alkynyl;

(5) —$C_3$-$C_6$cycloalkyl; and (6) —O—$C_1$-$C_6$alkyl;

$R^2$ is selected from $C_3$-$C_{10}$cycloalkyl and heterocycloalkyl, wherein each of the $C_3$-$C_{10}$cycloalkyl and heterocycloalkyl is optionally substituted with one to three substituents independently selected from:

(1) halogen;

(2) —CN;

(3) —$C_1$-$C_6$alkyl, optionally substituted with one to three substituents independently selected from halogen, —CN, —OH, and —O—$C_1$-$C_6$alkyl;

(4) —O—$C_1$-$C_6$alkyl, optionally substituted with one to three substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NR^bR^c$, each of $R^b$ and $R^c$ is independently selected from hydrogen and —$C_1$-$C_6$alkyl optionally substituted with an heteroaryl; and (6) aryl, optionally substituted with one to three halogens; and $R^5$ is selected from hydrogen, halogen, —$C_1$-$C_6$alkyl and —OH.

In one embodiment of a compound of Formula Ib, or a pharmaceutically acceptable salt thereof:

$R^1$ is phenyl, substituted with one to three substituents selected from:

(1) halogen;

(2) —CN;

(3) —$CH_3$, optionally substituted with one to three substituents independently selected from halogen and —CN;

(4) cyclopropyl; and (5) —O—$CH_3$;

$R^2$ is

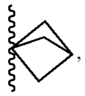

substituted with one to three substituents independently selected from:

(1) halogen;

(2) —CN;

(3) —$CH_3$, optionally substituted with one to three substituents independently selected from halogen, —CN, —OH and —O—$CH_3$;

(4) —C(O)O—$CH_3$;

(5) —C(O)$CH_2$-thienyl; and (6) phenyl; and $R^5$ is hydrogen.

In one embodiment of a compound of Formula I, or a pharmaceutically acceptable salt thereof, the compound is selected from:

(5S)-2-(bicyclo[2.2.1]heptan-1-yl)-5-phenyl-2,5,6,7-tetrahydro-3H-pyrrolo[2,1-c][1,2,4]triazol-3-one, (5S)-5-(3,5-difluorophenyl)-2-(3-fluorobicyclo[1.1.1]pentan-1-yl)-2,5,6,7-tetrahydro-3H-pyrrolo[2,1-c][1,2,4]triazol-3-one, (5S)-5-(3,5-difluorophenyl)-2-(4-fluorobicyclo[2.2.1]heptan-1-yl)-2,5,6,7-tetrahydro-3H-pyrrolo[2,1-c][1,2,4]triazol-3-one, (5S)-2-(bicyclo[2.1.1]hexan-1-yl)-5-(3,5-difluorophenyl)-2,5,6,7-tetrahydro-3H-pyrrolo[2,1-c][1,2,4]triazol-3-one, 3-[(5S)-5-(3,5-difluorophenyl)-3-oxo-6,7-dihydro-3H-pyrrolo[2,1-c][1,2,4]triazol-2(5H)-yl]bicyclo[1.1.1]pentane-1-carbonitrile, (5S)-2-(3-fluorobicyclo[1.1.1]pentan-1-yl)-5-phenyl-2,5,6,7-tetrahydro-3H-pyrrolo[2,1-c][1,2,4]triazol-3-one, (5S)-2-(bicyclo[1.1.1]pentan-1-yl)-5-(3,5-difluorophenyl)-2,5,6,7-tetrahydro-3H-pyrrolo[2,1-c][1,2,4]triazol-3-one, (5S)-2-(3-chlorobicyclo[1.1.1]pentan-1-yl)-5-(3,5-difluorophenyl)-2,5,6,7-tetrahydro-3H-pyrrolo[2,1-c][1,2,4]triazol-3-one, (5S)-2-(3-fluorobicyclo[1.1.1]pentan-1-yl)-5-(2-fluorophenyl)-2,5,6,7-tetrahydro-3H-pyrrolo[2,1-c][1,2,4]triazol-3-one, (5S)-2-(3-fluorobicyclo[1.1.1]pentan-1-yl)-5-(5-fluoropyridin-3-yl)-2,5,6,7-tetrahydro-3H-pyrrolo[2,1-c][1,2,4]triazol-3-one, 3-[(5S)-5-(5-fluoropyridin-3-yl)-3-oxo-6,7-dihydro-3H-pyrrolo[2,1-c][1,2,4]triazol-2(5H)-yl]bicyclo[1.1.1]pentane-1-carbonitrile, (5S)-5-(3,5-difluorophenyl)-2-(3-phenylbicyclo[1.1.1]pentan-1-yl)-2,5,6,7-tetrahydro-3H-pyrrolo[2,1-c][1,2,4]triazol-3-one, (5S)-5-(5-fluoropyridin-3-yl)-2-(3-phenylbicyclo[1.1.1]pentan-1-yl)-2,5,6,7-tetrahydro-3H-pyrrolo[2,1-c][1,2,4]triazol-3-one, (5S)-5-(3,5-difluorophenyl)-2-(1-methyl-2-oxabicyclo[2.1.1]hexan-4-yl)-2,5,6,7-tetrahydro-3H-pyrrolo[2,1-c][1,2,4]triazol-3-one, (5S)-2-(3-chlorobicyclo[1.1.1]pentan-1-yl)-5-(5-fluoropyridin-3-yl)-2,5,6,7-tetrahydro-3H-pyrrolo[2,1-c][1,2,4]triazol-3-one, (S)-2-(3-fluorobicyclo[1.1.1]pentan-1-yl)-5-(3-fluorophenyl)-2,5,6,7-tetrahydro-3H-pyrrolo[2,1-c][1,2,4]triazol-3-one, 3-[(5S)-3-oxo-5-phenyl-6,7-dihydro-3H-pyrrolo[2,1-c][1,2,4]triazol-2(5H)-yl]bicyclo[1.1.1]pentane-1-carbonitrile, methyl 3-[(5S)-5-(3,5-difluorophenyl)-3-oxo-6,7-dihydro-3H-pyrrolo[2,1-c][1,2,4]triazol-2(5H)-yl]bicyclo[1.1.1]pentane-1-carboxylate, methyl 3-[(5S)-3-oxo-5-phenyl-6,7-dihydro-3H-pyrrolo[2,1-c][1,2,4]triazol-2(5H)-yl]bicyclo[1.1.1]pentane-1-carboxylate, (5S)-5-(3,5-difluorophenyl)-2-(4-fluoropentacyclo[4.2.0.0~2,5~.0~3,8~.0~4,7~]octan-1-yl)-2,5,6,7-tetrahydro-3H-pyrrolo[2,1-c][1,2,4]triazol-3-one, 4-[(5S)-5-(3,5-difluorophenyl)-3-oxo-6,7-dihydro-3H-pyrrolo[2,1-c][1,2,4]triazol-2(5H)-yl]pentacyclo[4.2.0.0~2,5~.0~3,8~.0~4,7~]octane-1-carbonitrile, (S)-3-(5-(5-chloropyridin-3-yl)-3-oxo-6,7-dihydro-3H-pyrrolo[2,1-c][1,2,4]triazol-2(5H)-yl)bicyclo[1.1.1]pentane-1-carbonitrile, 3-[(5S)-5-(2-fluorophenyl)-3-oxo-6,7-dihydro-3H-pyrrolo[2,1-c][1,2,4]triazol-2(5H)-yl]bicyclo[1.1.1]pentane-1-carbonitrile, (S)-3-(5-(3-fluorophenyl)-3-oxo-6,7-dihydro-3H-pyrrolo[2,1-c][1,2,4]triazol-2(5H)-yl)bicyclo[1.1.1]pentane-1-carbonitrile, (5S)-2-(bicyclo[2.2.2]octan-1-yl)-5-(3,5-difluorophenyl)-2,5,6,7-tetrahydro-3H-pyrrolo[2,1-c][1,2,4]triazol-3-one, (5S)-5-(3,5-difluorophenyl)-2-(4-methoxybicyclo[2.2.1]heptan-1-yl)-2,5,6,7-tetrahydro-3H-pyrrolo[2,1-c][1,2,4]triazol-3-one, (5S)-2-[4-(difluoromethyl)bicyclo[2.2.1]heptan-1-yl]-5-(3,5-difluorophenyl)-2,5,6,7-tetrahydro-3H-pyrrolo[2,1-c][1,2,4]triazol-3-one, (5S)-2-[3-(difluoromethyl)bicyclo[1.1.1]pentan-1-yl]-5-(3,5-difluorophenyl)-2,5,6,7-tetrahydro-3H-pyrrolo[2,1-c][1,2,4]triazol-3-one, 4-[(5S)-5-(3,5-difluorophenyl)-3-oxo-6,7-dihydro-3H-pyrrolo[2,1-c][1,2,4]triazol-2(5H)-yl]bicyclo[2.2.1]heptane-1-carbonitrile, 4-[(5S)-3-oxo-5-phenyl-6,7-dihydro-3H-pyrrolo[2,1-c][1,2,4]triazol-2(5H)-yl]bicyclo[2.2.1]heptane-1-carbonitrile, (5S)-2-[3-(difluoromethyl)bicyclo[1.1.1]pentan-1-yl]-5-phenyl-2,5,6,7-tetrahydro-3H-pyrrolo[2,1-c][1,2,4]triazol-3-one, (5S)-2-[3-(1,1-difluoroethyl)bicyclo[1.1.1]pentan-1-yl]-5-phenyl-2,5,6,7-tetrahydro-3H-pyrrolo[2,1-c][1,2,4]triazol-3-one, (5S)-2-[3-(difluoromethyl)bicyclo[1.1.1]pentan-1-yl]-5-(3-fluorophenyl)-2,5,6,7-tetrahydro-3H-pyrrolo[2,1-c][1,2,4]triazol-3-one, (5S)-2-[3-(1,1-difluoroethyl)bicyclo[1.1.1]pentan-1-yl]-5-(3-fluorophenyl)-2,5,6,7-tetrahydro-3H-pyrrolo[2,1-c][1,2,4]triazol-3-one, 4-[(5S)-5-(3,5-difluorophenyl)-3-oxo-6,7-dihydro-3H-pyrrolo[2,1-c][1,2,4]triazol-2(5H)-yl]bicyclo[2.1.1]hexane-1-carbonitrile, methyl 3-[(5S)-5-(3,5-difluorophenyl)-3-oxo-6,7-dihydro-3H-pyrrolo[2,1-c][1,2,4]triazol-2(5H)-yl]-2,2-difluorobicyclo[1.1.1]pentane-1-carboxylate, (5S)-2-(3-fluorobicyclo[1.1.1]pentan-1-yl)-5-(4-fluorophenyl)-2,5,6,7-tetrahydro-3H-pyrrolo[2,1-c][1,2,4]triazol-3-one, 3-[(5S)-5-(4-fluorophenyl)-3-oxo-6,7-dihydro-3H-pyrrolo[2,1-c][1,2,4]triazol-2(5H)-yl]bicyclo[1.1.1]pentane-1-carbonitrile, 4-[(5S)-3-oxo-5-phenyl-6,7-dihydro-3H-pyrrolo[2,1-c][1,2,4]triazol-2(5H)-yl]bicyclo[2.1.1]hexane-1-carbonitrile, (S)-5-(2,6-difluorophenyl)-2-(3-fluorobicyclo[1.1.1]pentan-1-yl)-2,5,6,7-tetrahydro-3H-pyrrolo[2,1-c][1,2,4]triazol-3-one, (5S)-2-(3-chlorobicyclo[1.1.1]pentan-1-yl)-5-phenyl-2,5,6,7-tetrahydro-3H-pyrrolo[2,1-c][1,2,4]triazol-3-one, (S)-2-(3-chlorobicyclo[1.1.1]pentan-1-yl)-5-(3-fluorophenyl)-2,5,6,7-tetrahydro-3H-pyrrolo[2,1-c][1,2,4]triazol-3-one, (S)-3-(5-(2,6-difluorophenyl)-3-oxo-6,7-dihydro-3H-pyrrolo[2,1-c][1,2,4]triazol-2(5H)-yl)bicyclo[1.1.1]pentane-1-carbonitrile, (S)-3-(5-(3,4-difluorophenyl)-3-oxo-6,7-dihydro-3H-pyrrolo[2,1-c][1,2,4]triazol-2(5H)-yl)bicyclo[1.1.1]pentane-1-carbonitrile, (S)-5-(4-chlorophenyl)-2-(3-fluorobicyclo[1.1.1]pentan-1-yl)-2,5,6,7-tetrahydro-3H-pyrrolo[2,1-c][1,2,4]triazol-3-one, (S)-3-(5-(4-chlorophenyl)-3-oxo-6,7-dihydro-3H-pyrrolo[2,1-c][1,2,4]triazol-2(5H)-yl)bicyclo[1.1.1]pentane-1-carbonitrile, (S)-3-(5-(2,4-difluorophenyl)-3-oxo-6,7-dihydro-3H-pyrrolo[2,1-c][1,2,4]triazol-2(5H)-yl)bicyclo[1.1.1]pentane-1-carbonitrile, (S)-5-(2,4-difluorophenyl)-2-(3-fluorobicyclo[1.1.1]pentan-1-yl)-2,5,6,7-tetrahydro-3H-pyrrolo[2,1-c][1,2,4]triazol-3-one, (S)-3-(3-oxo-5-(3-(trifluoromethyl)phenyl)-6,7-dihydro-3H-pyrrolo[2,1-c][1,2,4]triazol-2(5H)-yl)bicyclo[1.1.1]pentane-1-carbonitrile, (S)-3-(3-oxo-5-(4-(trifluoromethyl)phenyl)-6,7-dihydro-3H-pyrrolo[2,1-c][1,2,4]triazol-2(5H)-yl)bicyclo[1.1.1]pentane-1-carbonitrile, (S)-3-(5-(3,5-difluoro-4-methylphenyl)-3-oxo-6,7-dihydro-3H-pyrrolo[2,1-c][1,2,4]triazol-2(5H)-yl)bicyclo[1.1.1]pentane-1-carbonitrile, 3-[5-(S or R)-(3,5-difluorophenyl)-6-(S or R)-methyl-3-oxo-6,7-dihydro-3H-pyrrolo[2,1-c][1,2,4]triazol-2(5H)-yl]bicyclo[1.1.1]pentane-1-carbonitrile, (S)-3-(5-(3,5-difluorophenyl)-3-oxo-5,6,7,8-tetrahydro-[1,2,4]triazolo[4,3-a]pyridin-2(3H)-yl)bicyclo[1.1.1]pentane-1-carbonitrile, 3-(5-(S or R)-cyclopentyl-3-oxo-6,7-dihydro-3H-pyrrolo[2,1-c][1,2,4]triazol-2(5H)-yl)bicyclo[1.1.1]pentane-1-carbonitrile,
3-(5-(S or R)-cyclohexyl-3-oxo-6,7-dihydro-3H-pyrrolo[2,1-c][1,2,4]triazol-2(5H)-yl)bicyclo[1.1.1]pentane-1-carbonitrile,
(5S)-5-(3,5-difluorophenyl)-2-[3-(methoxymethyl)bicyclo[1.1.1]pentan-1-yl]-2,5,6,7-tetrahydro-3H-pyrrolo[2,1-c][1,2,4]triazol-3-one,
3-[(5S)-5-(3,5-difluorophenyl)-3-oxo-6,7-dihydro-3H-pyrrolo[2,1-c][1,2,4]triazol-2(5H)-yl]-N-[(thiophen-2-yl)methyl]bicyclo[1.1.1]pentane-1-carboxamide,
3-[(5S)-5-(3,5-difluorophenyl)-3-oxo-6,7-dihydro-3H-pyrrolo[2,1-c][1,2,4]triazol-2(5H)-yl]-N-[(thiophen-3-yl)methyl]bicyclo[1.1.1]pentane-1-carboxamide,
(S)-2-(3-(5-(3,5-difluorophenyl)-3-oxo-6,7-dihydro-3H-pyrrolo[2,1-c][1,2,4]triazol-2(5H)-yl)bicyclo[1.1.1]pentan-1-yl)acetonitrile,
(5S)-2-(3-acetylbicyclo[1.1.1]pentan-1-yl)-5-(3,5-difluorophenyl)-2,5,6,7-tetrahydro-3H-pyrrolo[2,1-c][1,2,4]triazol-3-one,
3-[(5S)-5-(3,5-difluorophenyl)-3-oxo-6,7-dihydro-3H-pyrrolo[2,1-c][1,2,4]triazol-2(5H)-yl]-2,2-difluorobicyclo[1.1.1]pentane-1-carbonitrile,
2,2-difluoro-3-[(5S)-3-oxo-5-phenyl-6,7-dihydro-3H-pyrrolo[2,1-c][1,2,4]triazol-2(5H)-yl]bicyclo[1.1.1]pentane-1-carbonitrile,
(±)-3-(3-oxo-5-(pyrazin-2-yl)-6,7-dihydro-3H-pyrrolo[2,1-c][1,2,4]triazol-2(5H)-yl)bicyclo[1.1.1]pentane-1-carbonitrile,
(±)-2-(3-fluorobicyclo[1.1.1]pentan-1-yl)-5-(3-fluoro-5-methoxyphenyl)-2,5,6,7-tetrahydro-3H-pyrrolo[2,1-c][1,2,4]triazol-3-one,
(±)-3-[2-(3-fluorobicyclo[1.1.1]pentan-1-yl)-3-oxo-2,5,6,7-tetrahydro-3H-pyrrolo[2,1-c][1,2,4]triazol-5-yl]benzonitrile,
(±)-5-(3-ethynylphenyl)-2-(3-fluorobicyclo[1.1.1]pentan-1-yl)-2,5,6,7-tetrahydro-3H-pyrrolo[2,1-c][1,2,4]triazol-3-one,
(±)-5-(2,3-difluorophenyl)-2-(3-fluorobicyclo[1.1.1]pentan-1-yl)-2,5,6,7-tetrahydro-3H-pyrrolo[2,1-c][1,2,4]triazol-3-one,
(±)-2-(3-fluorobicyclo[1.1.1]pentan-1-yl)-5-(3-fluoro-5-methylphenyl)-2,5,6,7-tetrahydro-3H-pyrrolo[2,1-c][1,2,4]triazol-3-one,
(S)-3-(3-oxo-5-(p-tolyl)-6,7-dihydro-3H-pyrrolo[2,1-c][1,2,4]triazol-2(5H)-yl)bicyclo[1.1.1]pentane-1-carbonitrile,
(S)-3-(3-oxo-5-(pyrazin-2-yl)-6,7-dihydro-3H-pyrrolo[2,1-c][1,2,4]triazol-2(5H)-yl)bicyclo[1.1.1]pentane-1-carbonitrile,
(S)-5-(3-fluoro-5-methylphenyl)-2-(3-fluorobicyclo[1.1.1]pentan-1-yl)-2,5,6,7-tetrahydro-3H-pyrrolo[2,1-c][1,2,4]triazol-3-one,
(S)-5-(4-(difluoromethyl)phenyl)-2-(3-fluorobicyclo[1.1.1]pentan-1-yl)-2,5,6,7-tetrahydro-3H-pyrrolo[2,1-c][1,2,4]triazol-3-one,
(S)-5-(4-cyclopropylphenyl)-2-(3-fluorobicyclo[1.1.1]pentan-1-yl)-2,5,6,7-tetrahydro-3H-pyrrolo[2,1-c][1,2,4]triazol-3-one,
(S)-2-(3-fluorobicyclo[1.1.1]pentan-1-yl)-5-(pyrazin-2-yl)-2,5,6,7-tetrahydro-3H-pyrrolo[2,1-c][1,2,4]triazol-3-one,
(S)-2-(3-fluorobicyclo[1.1.1]pentan-1-yl)-5-(6-methylpyrazin-2-yl)-2,5,6,7-tetrahydro-3H-pyrrolo[2,1-c][1,2,4]triazol-3-one,
(S)-2-(3-fluorobicyclo[1.1.1]pentan-1-yl)-5-(5-methylpyrazin-2-yl)-2,5,6,7-tetrahydro-3H-pyrrolo[2,1-c][1,2,4]triazol-3-one,
(5S,7R)-5-(3,5-difluorophenyl)-2-(3-fluorobicyclo[1.1.1]pentan-1-yl)-7-hydroxy-2,5,6,7-tetrahydro-3H-pyrrolo[2,1-c][1,2,4]triazol-3-one,
(5S,7S)-5-(3,5-difluorophenyl)-2-(3-fluorobicyclo[1.1.1]pentan-1-yl)-7-hydroxy-2,5,6,7-tetrahydro-3H-pyrrolo[2,1-c][1,2,4]triazol-3-one,
(5S)-5-(3,5-difluorophenyl)-7-(S or R)-fluoro-2-(3-fluorobicyclo[1.1.1]pentan-1-yl)-2,5,6,7-tetrahydro-3H-pyrrolo[2,1-c][1,2,4]triazol-3-one,
(5S)-5-(3,5-difluorophenyl)-7-(S or R)-fluoro-2-(3-fluorobicyclo[1.1.1]pentan-1-yl)-2,5,6,7-tetrahydro-3H-pyrrolo[2,1-c][1,2,4]triazol-3-one,
(5S)-7-(S or R)-fluoro-2-(3-fluorobicyclo[1.1.1]pentan-1-yl)-5-phenyl-2,5,6,7-tetrahydro-3H-pyrrolo[2,1-c][1,2,4]triazol-3-one,
(5S)-7-(S or R)-fluoro-2-(3-fluorobicyclo[1.1.1]pentan-1-yl)-5-phenyl-2,5,6,7-tetrahydro-3H-pyrrolo[2,1-c][1,2,4]triazol-3-one,
3-[(5S)-5-(3,5-difluorophenyl)-7-(S or R)-fluoro-3-oxo-6,7-dihydro-3H-pyrrolo[2,1-c][1,2,4]triazol-2(5H)-yl]bicyclo[1.1.1]pentane-1-carbonitrile,
3-[(5S)-5-(3,5-difluorophenyl)-7-(S or R)-fluoro-3-oxo-6,7-dihydro-3H-pyrrolo[2,1-c][1,2,4]triazol-2(5H)-yl]bicyclo[1.1.1]pentane-1-carbonitrile,
3-[(5S)-7-(S or R)-fluoro-3-oxo-5-phenyl-6,7-dihydro-3H-pyrrolo[2,1-c][1,2,4]triazol-2(5H)-yl]bicyclo[1.1.1]pentane-1-carbonitrile,
3-[(5S)-7-(S or R)-fluoro-3-oxo-5-phenyl-6,7-dihydro-3H-pyrrolo[2,1-c][1,2,4]triazol-2(5H)-yl]bicyclo[1.1.1]pentane-1-carbonitrile,
3-[(5S)-7-(S or R)-fluoro-5-(2-fluorophenyl)-3-oxo-6,7-dihydro-3H-pyrrolo[2,1-c][1,2,4]triazol-2(5H)-yl]bicyclo[1.1.1]pentane-1-carbonitrile,
3-[(5S)-7-(S or R)-fluoro-5-(2-fluorophenyl)-3-oxo-6,7-dihydro-3H-pyrrolo[2,1-c][1,2,4]triazol-2(5H)-yl]bicyclo[1.1.1]pentane-1-carbonitrile
(S)-5-(3,5-difluoro-4-methylphenyl)-2-(3-fluorobicyclo[1.1.1]pentan-1-yl)-2,5,6,7-tetrahydro-3H-pyrrolo[2,1-c][1,2,4]triazol-3-one,
(S)-2-(3-(difluoromethyl)bicyclo[1.1.1]pentan-1-yl)-5-(5-fluoropyridin-3-yl)-2,5,6,7-tetrahydro-3H-pyrrolo[2,1-c][1,2,4]triazol-3-one,
(S)-5-(3,5-difluorophenyl)-2-(3-fluorobicyclo[1.1.1]pentan-1-yl)-5,6,7,8-tetrahydro-[1,2,4]triazolo[4,3-a]pyridin-3(2H)-one,
(S)-2-(3-chlorobicyclo[1.1.1]pentan-1-yl)-5-(pyrazin-2-yl)-2,5,6,7-tetrahydro-3H-pyrrolo[2,1-c][1,2,4]triazol-3-one,
(S)-4-(3-oxo-5-(pyrazin-2-yl)-6,7-dihydro-3H-pyrrolo[2,1-c][1,2,4]triazol-2(5H)-yl)bicyclo[2.1.1]hexane-1-carbonitrile,
(S)-2-(bicyclo[2.1.1]hexan-1-yl)-5-(pyrazin-2-yl)-2,5,6,7-tetrahydro-3H-pyrrolo[2,1-c][1,2,4]triazol-3-one,
(S)-3-(5-(3-chlorophenyl)-3-oxo-6,7-dihydro-3H-pyrrolo[2,1-c][1,2,4]triazol-2(5H)-yl)bicyclo[1.1.1]pentane-1-carbonitrile,
(S)-5-(3-chlorophenyl)-2-(3-fluorobicyclo[1.1.1]pentan-1-yl)-2,5,6,7-tetrahydro-3H-pyrrolo[2,1-c][1,2,4]triazol-3-one,
(S)-3-(5-(3,5-difluorophenyl)-3-oxo-5,6-dihydrothiazolo[2,3-c][1,2,4]triazol-2(3H)-yl)bicyclo[1.1.1]pentane-1-carbonitrile,
(R)-3-(5-(3,5-difluorophenyl)-3-oxo-5,6-dihydrothiazolo[2,3-c][1,2,4]triazol-2(3H)-yl)bicyclo[1.1.1]pentane-1-carbonitrile,
(S)-2-(3-fluorobicyclo[1.1.1]pentan-1-yl)-5-(4-methoxyphenyl)-2,5,6,7-tetrahydro-3H-pyrrolo[2,1-c][1,2,4]triazol-3-one, (S)-4-(2-(3-fluorobicyclo[1.1.1]pentan-1-yl)-3-oxo-2,5,6,7-tetrahydro-3H-pyrrolo[2,1-c][1,2,4]triazol-5-yl)benzonitrile,
(S)-2-(3-fluorobicyclo[1.1.1]pentan-1-yl)-5-(6-methylpyrazin-2-yl)-2,5,6,7-tetrahydro-3H-pyrrolo[2,1-c][1,2,4]triazol-3-one,
3-((5S,7R)-5-(3,5-difluorophenyl)-7-methyl-3-oxo-6,7-dihydro-3H-pyrrolo[2,1-c][1,2,4]triazol-2(5H)-yl)bicyclo[1.1.1]pentane-1-carbonitrile,
3-((5S,7S)-5-(3,5-difluorophenyl)-7-methyl-3-oxo-6,7-dihydro-3H-pyrrolo[2,1-c][1,2,4]triazol-2(5H)-yl)bicyclo[1.1.1]pentane-1-carbonitrile,
(S)-2-(3-chlorobicyclo[1.1.1]pentan-1-yl)-5-(5-fluoropyridin-2-yl)-2,5,6,7-tetrahydro-3H-pyrrolo[2,1-c][1,2,4]triazol-3-one,
(S)-5-(3-chloro-5-fluoro-4-methylphenyl)-2-(3-fluorobicyclo[1.1.1]pentan-1-yl)-2,5,6,7-tetrahydro-3H-pyrrolo[2,1-c][1,2,4]triazol-3-one,
(S)-5-(3,5-difluoro-4-hydroxyphenyl)-2-(3-fluorobicyclo[1.1.1]pentan-1-yl)-2,5,6,7-tetrahydro-3H-pyrrolo[2,1-c][1,2,4]triazol-3-one,
(S)-5-(2,6-difluoro-4-methylphenyl)-2-(3-fluorobicyclo[1.1.1]pentan-1-yl)-2,5,6,7-tetrahydro-3H-pyrrolo[2,1-c][1,2,4]triazol-3-one,
(S)-5-(4-chloro-3-fluorophenyl)-2-(3-fluorobicyclo[1.1.1]pentan-1-yl)-2,5,6,7-tetrahydro-3H-pyrrolo[2,1-c][1,2,4]triazol-3-one,
(S)-2-(3-fluorobicyclo[1.1.1]pentan-1-yl)-5-(3,4,5-trifluorophenyl)-2,5,6,7-tetrahydro-3H-pyrrolo[2,1-c][1,2,4]triazol-3-one,
(S)-5-(4-chloro-3,5-difluorophenyl)-2-(3-fluorobicyclo[1.1.1]pentan-1-yl)-2,5,6,7-tetrahydro-3H-pyrrolo[2,1-c][1,2,4]triazol-3-one,
(R)-2-(3-fluorobicyclo[1.1.1]pentan-1-yl)-5-phenyl-2,5,6,8-tetrahydro-3H-[1,2,4]triazolo[3,4-c][1,4]oxazin-3-one,
(R)-3-(5-(3,5-difluorophenyl)-3-oxo-5,6-dihydro-3H-[1,2,4]triazolo[3,4-c][1,4]oxazin-2(8H)-yl)bicyclo[1.1.1]pentane-1-carbonitrile,
(S)-2-(3-fluorobicyclo[1.1.1]pentan-1-yl)-5-phenyl-5,6,7,8-tetrahydro-[1,2,4]triazolo[4,3-a]pyridin-3(2H)-one,
3-[(5S)-5-(3,5-difluorophenyl)-3-oxo-6,7-dihydro-3H-pyrrolo[2,1-c][1,2,4]triazol-2(5H)-yl]-2,2-difluorobicyclo[1.1.1]pentane-1-carbonitrile,
methyl (S)-2,2-difluoro-3-(3-oxo-5-phenyl-6,7-dihydro-3H-pyrrolo[2,1-c][1,2,4]triazol-2(5H)-yl)bicyclo[1.1.1]pentane-1-carboxylate,
2,2-difluoro-3-[(5S)-3-oxo-5-phenyl-6,7-dihydro-3H-pyrrolo[2,1-c][1,2,4]triazol-2(5H)-yl]bicyclo[1.1.1]pentane-1-carbonitrile,
(S)-2-(3-fluorobicyclo[1.1.1]pentan-1-yl)-5-(o-tolyl)-2,5,6,7-tetrahydro-3H-pyrrolo[2,1-c][1,2,4]triazol-3-one,
(S)-2-(3-fluorobicyclo[1.1.1]pentan-1-yl)-5-(5-(trifluoromethyl)pyrazin-2-yl)-2,5,6,7-tetrahydro-3H-pyrrolo[2,1-c][1,2,4]triazol-3-one,
(5S,7S)-7-fluoro-2-(3-fluorobicyclo[1.1.1]pentan-1-yl)-5-(pyrazin-2-yl)-2,5,6,7-tetrahydro-3H-pyrrolo[2,1-c][1,2,4]triazol-3-one, and
(S)-3-(5-(4-(difluoromethyl)phenyl)-3-oxo-6,7-dihydro-3H-pyrrolo[2,1-c][1,2,4]triazol-2(5H)-yl)bicyclo[1.1.1]pentane-1-carbonitrile.

In one embodiment, disclosed herein is a method for treating RIPK1 dependent inflammation and cell death that occurs in inherited and sporadic diseases including Alzheimer's disease, amyotrophic lateral sclerosis, multiple sclerosis, Parkinson's disease, chronic traumatic encephalopathy, rheumatoid arthritis, ulcerative colitis, inflammatory bowel disease, psoriasis as well as acute tissue injury caused by stroke, traumatic brain injury, encephalitis comprising administering to a patient in need thereof a compound disclosed herein, or pharmaceutically acceptable salt thereof.

In one embodiment, disclosed herein is a method of treating amyotrophic lateral sclerosis comprising administering to a patient in need thereof a compound disclosed herein, or pharmaceutically acceptable salt thereof.

In one embodiment, disclosed herein is a pharmaceutical composition comprising a compound disclosed herein, or a pharmaceutically acceptable salt thereof and a pharmaceutically acceptable carrier.

In one embodiment, disclosed herein is a pharmaceutical composition comprising a compound disclosed herein and a pharmaceutically acceptable carrier.

In one embodiment of Formula Ia, n is 1.

In one embodiment of Formula Ia, n is 2.

In one embodiment of Formula I, Ia, or Ib:

$R^1$ is a $C_3$-$C_6$cycloalkyl, wherein the $C_3$-$C_6$cycloalkyl is optionally substituted with one to four substituents selected from (1) halogen; (2) —CN; (3) —$C_1$-$C_6$alkyl, optionally substituted with one to three substituents independently selected from halogen and —CN; (4) —$C_2$-$C_6$alkynyl; (5) —$C_3$-$C_6$cycloalkyl; and (6) —O—$C_1$-$C_6$alkyl.

In one embodiment, $R^1$ is a $C_3$-$C_6$cycloalkyl selected from:

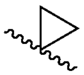, 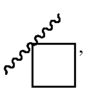, 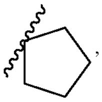, and 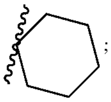;

each of which is unsubstituted.

In one embodiment, $R^1$ is a $C_3$-$C_6$cycloalkyl selected from:

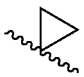, 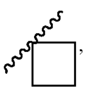, 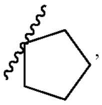, and 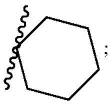;

wherein the $C_3$-$C_6$cycloalkyl is substituted with one to four substituents selected from (1) halogen; (2) —CN; (3) —$C_1$-$C_6$alkyl, optionally substituted with one to three substituents independently selected from halogen and —CN; (4) —$C_2$-$C_6$alkynyl; (5) —$C_3$-$C_6$cycloalkyl; and (6) —O—$C_1$-$C_6$alkyl.

In one embodiment, $R^1$ is a $C_3$-$C_6$cycloalkyl selected from:

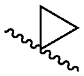, 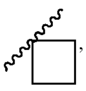, 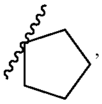, and 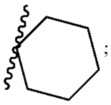;

wherein the $C_3$-$C_6$cycloalkyl is substituted with one to three halogens.

In one embodiment, $R^1$ is a $C_3$-$C_6$cycloalkyl selected from:

, , 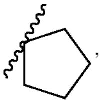, and 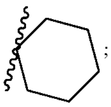;

wherein the $C_3$-$C_6$cycloalkyl is substituted with —CN.

In one embodiment, $R^1$ is a $C_3$-$C_6$cycloalkyl selected from:

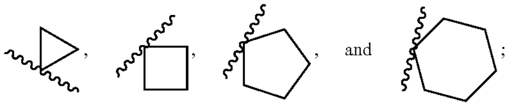

and wherein the $C_3$-$C_6$cycloalkyl is substituted with —$C_1$-$C_6$alkyl, optionally substituted with one to three substituents independently selected from halogen and —CN. In one embodiment, the $C_3$-$C_6$cycloalkyl is substituted with one to three substituents independently selected from methyl, ethyl, propyl, butyl, —$CH_2F$, —$CHF_2$, —$CF_3$, —$CH_2CHF_2$, —$CH_2CF_3$, and —$CH_2CN$.

In one embodiment, $R^1$ is a $C_3$-$C_6$cycloalkyl selected from:

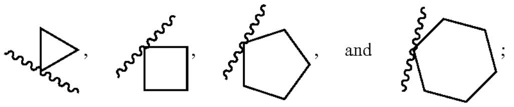

and wherein the $C_3$-$C_6$cycloalkyl is substituted with —$C_2$-$C_6$alkynyl. In one embodiment, the $C_3$-$C_6$cycloalkyl is substituted with ethynyl or propynyl. In one embodiments, the $C_3$-$C_6$cycloalkyl is substituted with ethynyl.

In one embodiment, $R^1$ is a $C_3$-$C_6$cycloalkyl selected from:

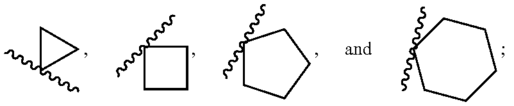

and wherein the $C_3$-$C_6$cycloalkyl is substituted with —$C_3$-$C_6$cycloalkyl. In one embodiment, the $C_3$-$C_6$cycloalkyl is substituted with cyclopropyl. In one embodiment, the $C_3$-$C_6$cycloalkyl is substituted with cyclobutyl.

In one embodiment, $R^1$ is a $C_3$-$C_6$cycloalkyl selected from:

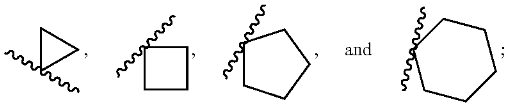

and wherein the $C_3$-$C_6$cycloalkyl is substituted with —O—$C_1$-$C_6$alkyl. In one embodiment, the $C_3$-$C_6$cycloalkyl is substituted with —$OCH_3$. In one embodiment, the $C_3$-$C_6$cycloalkyl is substituted with —$OCH_2CH_3$. In one embodiment, the $C_3$-$C_6$cycloalkyl is substituted with —$OCH_2CH_2CH_3$. In one embodiment, the $C_3$-$C_6$cycloalkyl is substituted with —$OCH_2CH_2CH_2CH_3$.

In one embodiment, $R^1$ is an aryl, optionally substituted with one to three substituents independently selected from (1) halogen; (2) —CN; (3) —$C_1$-$C_6$alkyl, optionally substituted with one to three substituents independently selected from halogen and —CN; (4) —$C_2$-$C_6$alkynyl; (5) —$C_3$-$C_6$cycloalkyl; and (6) —O—$C_1$-$C_6$alkyl.

In one embodiment, $R^1$ is an unsubstituted phenyl.

In one embodiment, $R^1$ is a phenyl, wherein the phenyl is substituted with one to three substituents independently selected from (1) halogen; (2) —CN; (3) —$C_1$-$C_6$alkyl, optionally substituted with one to three substituents independently selected from halogen and —CN; (4) —$C_2$-$C_6$alkynyl; (5) —$C_3$-$C_6$cycloalkyl; and (6) —O—$C_1$-$C_6$alkyl.

In one embodiment, $R^1$ is a phenyl, wherein the phenyl is substituted with one to three halogens. In one embodiment, $R^1$ is a phenyl, wherein the phenyl is substituted with one to three fluoros. In one embodiment, $R^1$ is a phenyl, wherein the phenyl is substituted with one to three chloros.

In one embodiment, $R^1$ is a phenyl, wherein the phenyl is substituted with one to three substituents independently selected from halogen and —CN.

In one embodiment, $R^1$ is a phenyl, wherein the phenyl is substituted with —$C_1$-$C_6$alkyl, optionally substituted with one to three substituents independently selected from halogen and —CN.

In one embodiment, $R^1$ is a phenyl, wherein the phenyl is substituted with one to three substituents independently selected from methyl, ethyl, propyl, butyl, pentyl, —$CH_2F$, —$CHF_2$, —$CF_3$, —$CH_2CHF_2$, —$CH_2CF_3$, and —$CH_2CN$. In one embodiment, $R^1$ is a phenyl, wherein the phenyl is substituted with one to three substituents independently selected from methyl, ethyl, propyl, butyl, and pentyl. In one embodiment, $R^1$ is a phenyl, wherein the phenyl is substituted with one to three substituents independently selected from —$CH_2F$, —$CHF_2$, —$CF_3$, —$CH_2CHF_2$, —$CH_2CF_3$, and —$CH_2CN$. In one embodiment, $R^1$ is a phenyl, wherein the phenyl is substituted with one to three substituents independently selected from methyl and —$CF_3$.

In one embodiment, $R^1$ is a phenyl, wherein the phenyl is substituted with one to three substituents independently selected from halogen, methyl, ethyl, —$CH_2F$, —$CHF_2$, and —$CF_3$.

In one embodiment, $R^1$ is a phenyl, wherein the phenyl is substituted with one to three substituents independently selected from halogen, —O-methyl, —O-ethyl, and —O-propyl.

In one embodiment, $R^1$ is a phenyl, wherein the phenyl is substituted with one to three substituents independently selected from halogen and —$C_3$-$C_6$cycloalkyl. In one embodiment, $R^1$ is a phenyl, wherein the phenyl is substituted with cyclopropyl. In one embodiment, $R^1$ is a phenyl, wherein the phenyl is substituted with cyclobutyl. In one embodiment, $R^1$ is a phenyl, wherein the phenyl is substituted with cyclopentyl. In one embodiment, $R^1$ is a phenyl, wherein the phenyl is substituted with cyclohexyl.

In one embodiment, $R^1$ is a heteroaryl, wherein the heteroaryl is optionally substituted with one to three substituents independently selected from (1) halogen; (2) —CN; (3) —$C_1$-$C_6$alkyl, optionally substituted with one to four substituents independently selected from halogen and —CN; (4) —$C_2$-$C_6$alkynyl; (5) —$C_3$-$C_6$cycloalkyl; and (6) —O—$C_1$-$C_6$alkyl.

In one embodiment, $R^1$ is an unsubstituted heteroaryl selected from pyridyl (pyridinyl), oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl.

In one embodiment, $R^1$ is an unsubstituted heteroaryl selected from pyridyl and pyrazinyl.

In one embodiment, $R^1$ is an unsubstituted pyridyl. In one embodiment, $R^1$ is an unsubstituted pyrazinyl.

In one embodiment, $R^1$ is a heteroaryl selected from pyridyl (pyridinyl), oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl, wherein the heteroaryl is substituted with one to three substituents independently selected from (1) halogen; (2) —CN; (3) —$C_1$-$C_6$alkyl, optionally substituted with one to four substituents independently selected from halogen and —CN; (4) —$C_2$-$C_6$alkynyl; (5) —$C_3$-$C_6$cycloalkyl; and (6) —O—$C_1$-$C_6$alkyl.

In one embodiment, $R^1$ is a heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl, wherein the heteroaryl is substituted with one to three halogens.

In one embodiment, $R^1$ is a heteroaryl selected from pyridyl and pyrazinyl, wherein the heteroaryl is substituted with one to three halogens.

In one embodiment, $R^1$ is a pyridyl substituted with a fluoro. $R^1$ is a pyridyl substituted with two fluoros. In one embodiment, $R^1$ is a pyridyl substituted with a chloro. In one embodiment, $R^1$ is a pyridyl substituted with two chloros.

In one embodiment, $R^1$ is a pyrazinyl substituted with a fluoro. $R^1$ is a pyrazinyl substituted with two fluoros. In one embodiment, $R^1$ is a pyrazinyl substituted with a chloro. In one embodiment, $R^1$ is a pyrazinyl substituted with two chloros.

In one embodiment, $R^1$ is a heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl, wherein the heteroaryl is substituted with —CN. In one embodiment, $R^1$ is a heteroaryl selected from pyridyl and pyrazinyl, wherein the heteroaryl is substituted with —CN.

In one embodiment, $R^1$ is a heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl, wherein the heteroaryl is substituted with one to two substituents independently selected from $C_1$-$C_6$alkyl. In one embodiment, $R^1$ is a heteroaryl selected from pyridyl and pyrazinyl, wherein the heteroaryl is substituted with one to two substituents independently selected from methyl, ethyl, propyl, butyl, pentyl and hexyl.

In one embodiment, $R^1$ is a pyridyl substituted with a methyl, ethyl, propyl, butyl, pentyl or hexyl. In one embodiment, $R^1$ is a pyridyl substituted with a methyl.

In one embodiment, $R^1$ is a pyrazinyl substituted with a methyl, ethyl, propyl, butyl, pentyl or hexyl. In one embodiment, $R^1$ is a pyrazinyl substituted with a methyl.

In one embodiment, $R^1$ is a heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl, wherein the heteroaryl is substituted with —$C_2$-$C_6$alkynyl. In one embodiment, $R^1$ is a heteroaryl selected from pyridyl and pyrazinyl, wherein the heteroaryl is substituted with an —C═$CH_3$.

In one embodiment, $R^1$ is a heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl, wherein the heteroaryl is substituted with —$C_3$-$C_6$cycloalkyl. In one embodiment, $R^1$ is a heteroaryl selected from pyridyl and pyrazinyl, wherein the heteroaryl is substituted with a cyclopropyl, cyclobutyl, cyclopentyl or cyclohexyl. In one embodiment, $R^1$ is a pyridyl substituted with a cyclopropyl or cyclobutyl. In one embodiment, $R^1$ is a pyrazinyl substituted with a cyclopropyl or cyclobutyl.

In one embodiment, $R^1$ is a heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl, wherein the heteroaryl is substituted with —O—$C_1$-$C_6$alkyl. In one embodiment, $R^1$ is a heteroaryl selected from pyridyl and pyrazinyl, wherein the heteroaryl is substituted with —O— methyl, —O-ethyl, —O-propyl, —O-butyl, —O-pentyl or —O-hexyl. In one embodiment, $R^1$ is a pyridyl substituted with —O-methyl, —O-ethyl, or —O-propyl. In one embodiment, $R^1$ is a pyridyl substituted with —O-methyl. In one embodiment, $R^1$ is a pyrazinyl substituted with —O-methyl, —O— ethyl, or —O-propyl. In one embodiment, $R^1$ is a pyrazinyl substituted with —O-methyl.

In one embodiment, $R^2$ is a $C_3$-$C_{10}$cycloalkyl, optionally substituted with one to three substituents independently selected from:

(1) halogen;

(2) —CN;

(3) —$C_1$-$C_6$alkyl, optionally substituted with one to three substituents independently selected from halogen, —CN, —OH, —O—$C_1$-$C_6$alkyl, and a heteroaryl;

(4) —O—$C_1$-$C_6$alkyl, optionally substituted with one to three substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NR^bR^c$, each of $R^b$ and $R^c$ is independently selected from hydrogen and —$C_1$-$C_6$alkyl optionally substituted with an heteroaryl; and (6) aryl, optionally substituted with one to three halogens.

In one embodiment, $R^2$ is an unsubstituted $C_3$-$C_{10}$cycloalkyl selected from

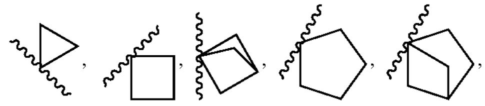

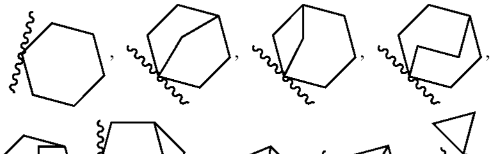

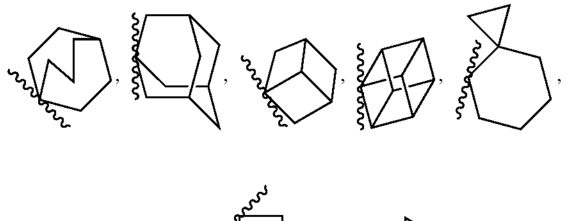

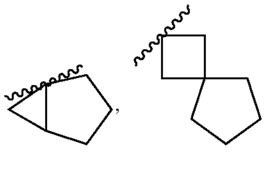

and

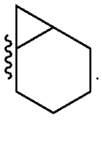

.

In one embodiment, $R^2$ is an unsubstituted $C_3$-$C_{10}$cycloalkyl selected from

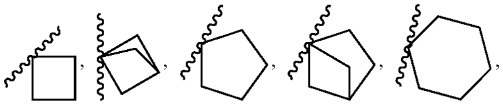

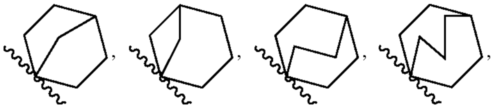

and

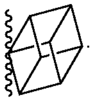

In one embodiment, $R^2$ is unsubstituted

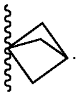

In one embodiment, $R^2$ is unsubstituted

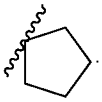

In one embodiment, $R^2$ is unsubstituted

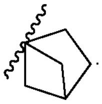

In one embodiment, $R^2$ is unsubstituted

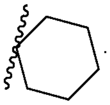

In one embodiment, $R^2$ is unsubstituted

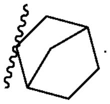

In one embodiment, $R^2$ is unsubstituted

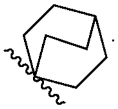

In one embodiment, $R^2$ is unsubstituted

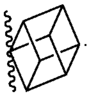

In one embodiment, $R^2$ is a $C_3$-$C_{10}$cycloalkyl selected from

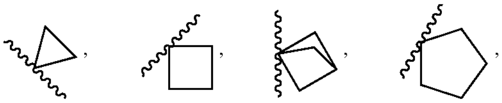

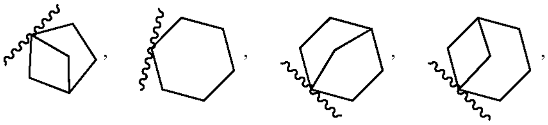

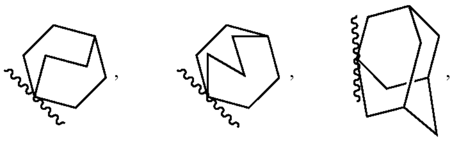

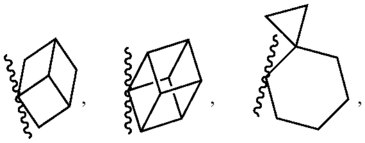

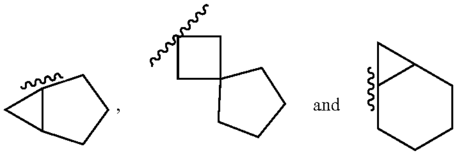

wherein the $C_3$-$C_{10}$cycloalkyl is substituted with one to three substituents independently selected from:

(1) halogen;

(2) —CN;

(3) —$C_1$-$C_6$alkyl, optionally substituted with one to three substituents independently selected from halogen, —CN, —OH, —O—$C_1$-$C_6$alkyl, and a heteroaryl;

(4) —O—$C_1$-$C_6$alkyl, optionally substituted with one to three substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NR^bR^c$, each of $R^b$ and $R^c$ is independently selected from hydrogen and —$C_1$-$C_6$alkyl optionally substituted with an heteroaryl; and (6) aryl, optionally substituted with one to three halogens.

In one embodiment, $R^2$ is a $C_3$-$C_{10}$cycloalkyl selected from

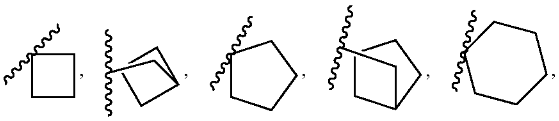

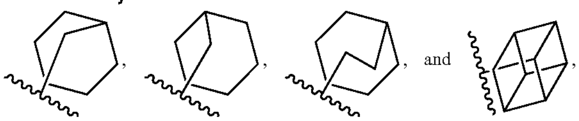

wherein the $C_3$-$C_{10}$cycloalkyl is substituted with one to three substituents independently selected from:

(1) halogen;

(2) —CN;

(3) —$C_1$-$C_6$alkyl, optionally substituted with one to three substituents independently selected from halogen, —CN, —OH, —O—$C_1$-$C_6$alkyl, and a heteroaryl;

(4) —O—$C_1$-$C_6$alkyl, optionally substituted with one to three substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NR^bR^c$, each of $R^b$ and $R^c$ is independently selected from hydrogen and —$C_1$-$C_6$alkyl optionally substituted with an heteroaryl; and (6) aryl, optionally substituted with one to three halogens.

In one embodiment, $R^2$ is a $C_3$-$C_{10}$cycloalkyl selected from

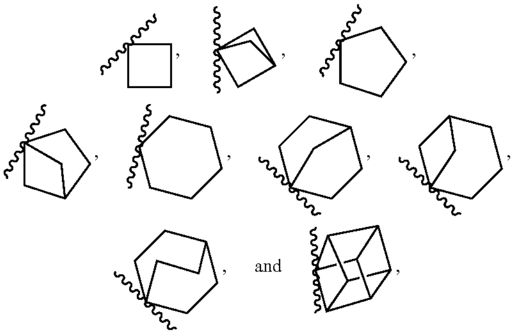

and wherein the $C_3$-$C_{10}$cycloalkyl is substituted with one to three substituents independently selected from:

(1) halogen;

(2) —CN;

(3) —$C_1$-$C_4$alkyl, optionally substituted with one to three substituents independently selected from halogen, —CN, —OH, —O—$C_1$-$C_4$alkyl, and a heteroaryl, wherein the heteroaryl is selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl;

(4) —O—$C_1$-$C_4$alkyl, optionally substituted with one to three substituents independently selected from halogen and —CN;

(5) —C(O)—$R^a$, wherein is $R^a$ is selected from —OH, —$C_1$-$C_4$alkyl, —O—$C_1$-$C_4$alkyl, and —$NR^bR^c$, each of $R^b$ and $R^c$ is independently selected from hydrogen and —$C_1$-$C_4$alkyl optionally substituted with an heteroaryl, wherein the heteroaryl is selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl; and (6) phenyl, optionally substituted with one to three halogens.

In one embodiment, $R^2$ is a $C_3$-$C_{10}$cycloalkyl selected from

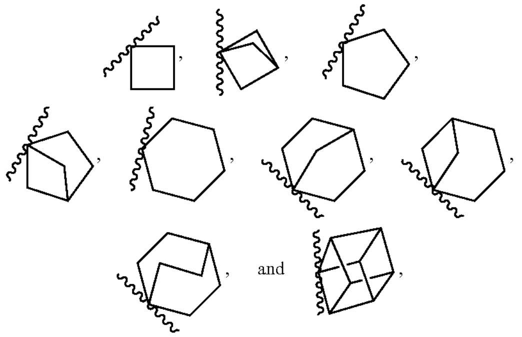

and wherein the $C_3$-$C_{10}$cycloalkyl is substituted with one to three substituents independently selected from:

(1) halogen;

(2) —CN;

(3) —$C_1$-$C_4$alkyl, optionally substituted with one to three substituents independently selected from halogen, —CN, —OH, —O—$CH_3$, —$OCH_2CH_3$, and a heteroaryl, wherein the heteroaryl is selected from pyridyl, oxazolyl, imidazolyl, triazolyl, furyl, triazinyl, thienyl, pyrimidyl, pyridazinyl, and indolizinyl;

(4) —O—$C_1$-$C_4$alkyl;

(5) —C(O)—$R^a$, wherein is $R^a$ is selected from —OH, —$CH_3$, —$CH_2CH_3$, —O—$CH_3$, —$CH_2CH_3$, and —NH—$CH_2$-heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl; and (6) phenyl.

In one embodiment, $R^2$ is a $C_3$-$C_{10}$cycloalkyl selected

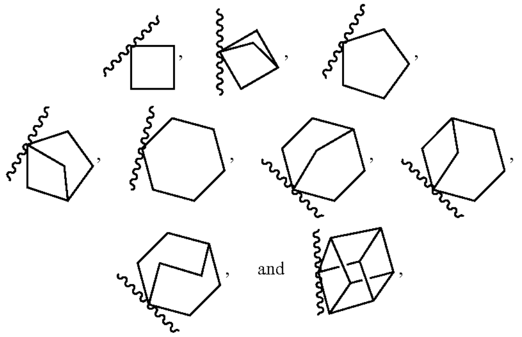

and wherein the $C_3$-$C_{10}$cycloalkyl is substituted with one to three substituents independently selected from:

(1) halogen;

(2) —CN;

(3) —$CH_3$;

(4) —$CH_2CH_3$;

(5) —$CH_2OH$;

(6) —$CH_2$—O—$CH_3$;

(7) —$CH_2CN$;

(8) —$CHF_2$;

(9) —$CF_3$;

(10) —$CH_2$-heteroaryl, wherein the heteroaryl is selected from pyridyl, oxazolyl, imidazolyl, triazolyl, furyl, triazinyl, thienyl, pyrazinyl, and pyrimidyl;

(11) —O—$CH_3$;

(12) —C(O)—$CH_3$;

(13) —C(O)—O—$CH_3$;

(14) —C(O)—NH—$CH_2$-heteroaryl, wherein the heteroaryl is selected from pyridyl, oxazolyl, imidazolyl, triazolyl, furyl, triazinyl, thienyl, pyrazinyl, and pyrimidyl; and

(15) phenyl.

In one embodiment, $R^2$ is

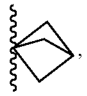

substituted with one to three substituents independently selected from:

(1) halogen;

(2) —CN;

(3) —$C_1$-$C_4$alkyl, optionally substituted with one to three substituents independently selected from halogen, —CN, —OH, —O—$CH_3$, —$OCH_2CH_3$, and a heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl;

(4) —O—$C_1$-$C_4$alkyl;

(5) —C(O)—$R^a$, wherein is $R^a$ is selected from —OH, —$CH_3$, —$CH_2CH_3$, —O—$CH_3$, —$CH_2CH_3$, and —NH—$CH_2$-heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl; and (6) phenyl.

In one embodiment, $R^2$ is

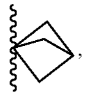

substituted with one to three substituents independently selected from:

(1) halogen;

(2) —CN;

(3) —$CH_3$;

(4) —$CH_2CH_3$;

(5) —$CH_2OH$;

(6) —$CH_2$—O—$CH_3$;

(7) —$CH_2CN$;

(8) —$CHF_2$;

(9) —$CF_3$;

(10) —$CH_2$-heteroaryl, wherein the heteroaryl is selected from furyl, triazinyl, and thienyl;

(11) —O—$CH_3$;

(12) —C(O)—$CH_3$;

(13) —C(O)—O—$CH_3$;

(14) —C(O)—NH—$CH_2$-heteroaryl, wherein the heteroaryl is selected from furyl, triazinyl, and thienyl; and

(15) phenyl.

In one embodiment, $R^2$ is

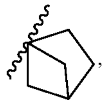

substituted with one to three substituents independently selected from:

(1) halogen;

(2) —CN;

(3) —$C_1$-$C_4$alkyl, optionally substituted with one to three substituents independently selected from halogen, —CN, —OH, —O—$CH_3$, —$OCH_2CH_3$, and a heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl;

(4) —O—$C_1$-$C_4$alkyl;

(5) —C(O)—$R^a$, wherein is $R^a$ is selected from —OH, —$CH_3$, —$CH_2CH_3$, —O—$CH_3$, —$CH_2CH_3$, and —NH—$CH_2$-heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl; and (6) phenyl.

In one embodiment, $R^2$ is

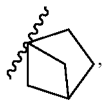

substituted with one to three substituents independently selected from:

(1) halogen;

(2) —CN;

(3) —$CH_3$;

(4) —$CH_2CH_3$;

(5) —$CH_2OH$;

(6) —$CH_2$—O—$CH_3$;

(7) —$CH_2CN$;

(8) —$CHF_2$;

(9) —$CF_3$;

(10) —$CH_2$-heteroaryl, wherein the heteroaryl is selected from furyl, triazinyl, and thienyl;

(11) —O—$CH_3$;

(12) —C(O)—$CH_3$;

(13) —C(O)—O—$CH_3$;

(14) —C(O)—NH—$CH_2$-heteroaryl, wherein the heteroaryl is selected from furyl, triazinyl, and thienyl; and

(15) phenyl.

In one embodiment, $R^2$ is

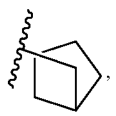 [SMILES: *CC1CCCC1]

substituted with one to three substituents independently selected from:

(1) halogen;

(2) —CN;

(3) —$CH_3$; and (4) —$CHF_2$.

In one embodiment, $R^2$ is

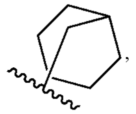 [SMILES: *CC1CCCCC1]

substituted with one to three substituents independently selected from:

(1) halogen;
(2) —CN;
(3) —$C_1$-$C_4$alkyl, optionally substituted with one to three substituents independently selected from halogen, —CN, —OH, —O—$CH_3$, —$OCH_2CH_3$, and a heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl;
(4) —O—$C_1$-$C_4$alkyl;
(5) —C(O)—$R^a$, wherein is $R^a$ is selected from —OH, —$CH_3$, —$CH_2CH_3$, —O—$CH_3$, —$CH_2CH_3$, and —NH—$CH_2$-heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl; and
(6) phenyl.

In one embodiment, $R^2$ is

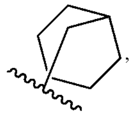 [SMILES: *CC1CCCCC1]

substituted with one to three substituents independently selected from:

(1) halogen;
(2) —CN;
(3) —$CH_3$;
(4) —$CH_2CH_3$;
(5) —$CH_2OH$;
(6) —$CH_2$—O—$CH_3$;
(7) —$CH_2CN$;
(8) —$CHF_2$;
(9) —$CF_3$;
(10) —$CH_2$-heteroaryl, wherein the heteroaryl is selected from furyl, triazinyl, and thienyl;
(11) —O—$CH_3$;
(12) —C(O)—$CH_3$;
(13) —C(O)—O—$CH_3$;
(14) —C(O)—NH—$CH_2$-heteroaryl, wherein the heteroaryl is selected from furyl, triazinyl, and thienyl; and
(15) phenyl.

In one embodiment, $R^2$ is

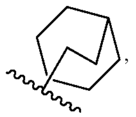

substituted with one to three substituents independently selected from:

(1) halogen;
(2) —CN;
(3) —$CH_3$;
(4) —$CHF_2$; and
(5) —O—$CH_3$.

In one embodiment, $R^2$ is

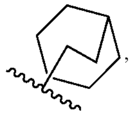

substituted with one to three substituents independently selected from:

(1) halogen;
(2) —CN;
(3) —$C_1$-$C_4$alkyl, optionally substituted with one to three substituents independently selected from halogen, —CN, —OH, —O—$CH_3$, —$OCH_2CH_3$, and a heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl;
(4) —O—$C_1$-$C_4$alkyl;
(5) —C(O)—$R^a$, wherein is $R^a$ is selected from —OH, —$CH_3$, —$CH_2CH_3$, —O—$CH_3$, —$CH_2CH_3$, and —NH—$CH_2$-heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl; and
(6) phenyl.

In one embodiment, $R^2$ is

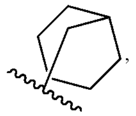 [SMILES: *CC1CCCCC1]

substituted with one to three substituents independently selected from:

(1) halogen;
(2) —CN;
(3) —$CH_3$;
(4) —$CH_2CH_3$;
(5) —$CH_2OH$;
(6) —$CH_2$—O—$CH_3$;
(7) —$CH_2CN$;
(8) —$CHF_2$;
(9) —$CF_3$;
(10) —$CH_2$-heteroaryl, wherein the heteroaryl is selected from furyl, triazinyl, and thienyl;
(11) —O—$CH_3$;
(12) —C(O)—$CH_3$;
(13) —C(O)—O—$CH_3$;
(14) —C(O)—NH—$CH_2$-heteroaryl, wherein the heteroaryl is selected from furyl, triazinyl, and thienyl; and
(15) phenyl.

In one embodiment, $R^2$ is

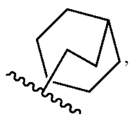 [SMILES: *CCC1CCCCC1]

substituted with one to three substituents independently selected from:

(1) halogen;
(2) —CN;
(3) —$CH_3$;
(4) —$CHF_2$;
(5) —O—$CH_3$.

In one embodiment, $R^2$ is

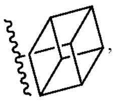, substituted with one to three substituents independently selected from:

(1) halogen;
(2) —CN;
(3) —$C_1$-$C_4$alkyl, optionally substituted with one to three substituents independently selected from halogen, —CN, —OH, —O—$CH_3$, —$OCH_2CH_3$, and a heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl;
(4) —O—$C_1$-$C_4$alkyl;
(5) —C(O)—$R^a$, wherein is $R^a$ is selected from —OH, —$CH_3$, —$CH_2CH_3$, —O—$CH_3$, —$CH_2CH_3$, and —NH—$CH_2$-heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl; and
(6) phenyl.

In one embodiment, $R^2$ is

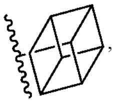, substituted with one to three substituents independently selected from:

(1) halogen;
(2) —CN;
(3) —$CH_3$;
(4) —$CH_2CH_3$;
(5) —$CH_2OH$;
(6) —$CH_2$—O—$CH_3$;
(7) —$CH_2CN$;
(8) —$CHF_2$;
(9) —$CF_3$;
(10) —$CH_2$-heteroaryl, wherein the heteroaryl is selected from furyl, triazinyl, and thienyl;
(11) —O—$CH_3$;
(12) —C(O)—$CH_3$;
(13) —C(O)—O—$CH_3$;
(14) —C(O)—NH—$CH_2$-heteroaryl, wherein the heteroaryl is selected from furyl, triazinyl, and thienyl; and
(15) phenyl.

In one embodiment, $R^2$ is

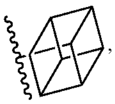, substituted with one to three substituents independently selected from:

(1) halogen;
(2) —CN; and
(3) —$CH_3$.

In one embodiment, $R^2$ is a heterocycloalkyl selected from:

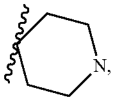 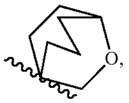 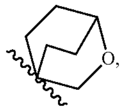

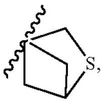 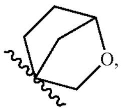 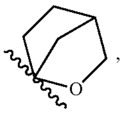,

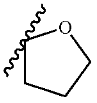, 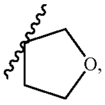 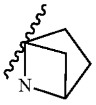, and 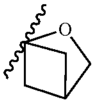, wherein the heterocycloalkyl is optionally substituted with one to three substituents selected from:

(1) halogen;
(2) —CN;
(3) —$C_1$-$C_4$alkyl, optionally substituted with one to three substituents independently selected from halogen, —CN, —OH, —O—$CH_3$, —$OCH_2CH_3$, and a heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl;
(4) —O—$C_1$-$C_4$alkyl;
(5) —C(O)—$R^a$, wherein is $R^a$ is selected from —OH, —$CH_3$, —$CH_2CH_3$, —O—$CH_3$, —$CH_2CH_3$, and —NH—$CH_2$-heteroaryl, wherein the heteroaryl is selected from pyridyl, oxazolyl, imidazolyl, triazolyl, furyl, triazinyl, thienyl, pyrimidyl, pyrazinyl, pyridazinyl, and indolizinyl; and
(6) phenyl.

In one embodiment, $R^2$ is an unsubstituted heterocycloalkyl selected from:

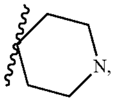 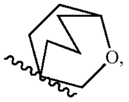 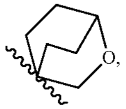

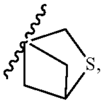 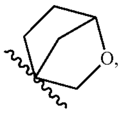 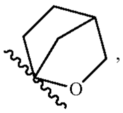,

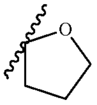, 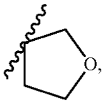 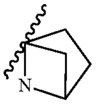, and 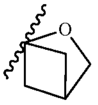.

In one embodiment, $R^2$ is an unsubstituted

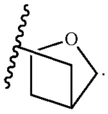 [SMILES: *CC1CCOC1].

In one embodiment, $R^2$ is

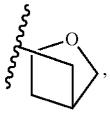, substituted with one to three substituents selected from:

(1) halogen;

(2) —CN;

(3) —$C_1$-$C_4$alkyl, optionally substituted with one to three substituents independently selected from halogen, —CN, —OH, —O—$CH_3$, and —$OCH_2CH_3$.

In one embodiment, $R^2$ is

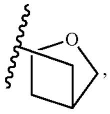 [SMILES: *CC1CCOC1], substituted with one to three substituents selected from:

(1) halogen;

(2) —CN;

(3) —$CH_3$;

(4) —$CH_2CH_3$.

In one embodiment, $R^2$ is

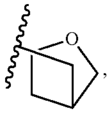 [SMILES: *CC1CCOC1], substituted with —$CH_3$.

In one embodiment, $R^2$ is an unsubstituted phenyl.

In one embodiment, $R^2$ is a phenyl, substituted with one to three substituents selected from:

(1) halogen;

(2) —CN;

(3) —$C_1$-$C_4$alkyl, optionally substituted with one to three substituents independently selected from halogen, —CN, —OH, —O—$CH_3$, and —$OCH_2CH_3$.

In one embodiment, $R^2$ is a phenyl, substituted with one to three substituents selected from:

(1) halogen;

(2) —CN;

(3) —$CH_3$;

(4) —$CH_2CH_3$.

In one embodiment, $R^2$ is an unsubstituted heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl.

In one embodiment, $R^2$ is a heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl, substituted with one to three substituents selected from:

(1) halogen;

(2) —CN;

(3) —$C_1$-$C_4$alkyl, optionally substituted with one to three substituents independently selected from halogen, —CN, —OH, —O—$CH_3$, and —$OCH_2CH_3$.

In one embodiment, $R^2$ is a heteroaryl selected from pyridyl, oxazolyl, imidazolyl, triazolyl, furyl, triazinyl, thienyl, pyrimidyl, pyrazinyl, and pyridazinyl, substituted with one to three substituents selected from:

(1) halogen;

(2) —CN;

(3) —$C_1$-$C_4$alkyl, optionally substituted with one to three substituents independently selected from halogen, —CN, —OH, —O—$CH_3$, and —$OCH_2CH_3$.

In one embodiment of Formula Ia, each occurrence of $R^5$ is independently selected from hydrogen, halogen, —$C_1$-$C_6$alkyl and —OH. In one embodiment, n is 1.

In one embodiment of Formula Ia, each occurrence of $R^5$ is independently selected from hydrogen, halogen, —$CH_3$, —$CH_2CH_3$ and —OH. In one embodiment, n is 1.

In one embodiment of Formula Ia, n is 1 and $R^5$ is hydrogen.

In one embodiment of Formula Ia, each occurrence of $R^5$ is halogen. In one embodiment, n is 1 and $R^5$ is —F. In one embodiment, n is 1 and $R^5$ is —Cl.

In one embodiment of Formula Ia, each occurrence of $R^5$ is —OH.

Definitions

The term "halogen" includes fluorine, chlorine, bromine or iodine.

The term "$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "$C_3$-$C_6$cycloalkyl" encompasses bridged, saturated or unsaturated cycloalkyl groups having 3 to 6 carbons. Examples of cycloalkyl include cyclopropyl, cyclobutyl, cyclopentyl and cyclohexyl.

The term "$C_3$-$C_{10}$cycloalkyl" encompasses bridged, saturated or unsaturated cycloalkyl groups having 3 to 10 carbons. "Cycloalkyl" also includes non-aromatic rings as well as monocyclic, non-aromatic rings fused to a saturated cycloalkyl group. Examples of cycloalkyl include cyclopropyl, cyclobutyl, cyclopentyl, cyclohexyl, cycloheptyl, tetrahydronaphthyl, decahydronaphthyl, indanyl and the like. Examples described by structure include,

, 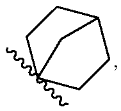, 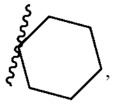, 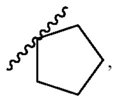,

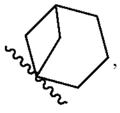, , 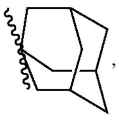, 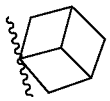,

-continued

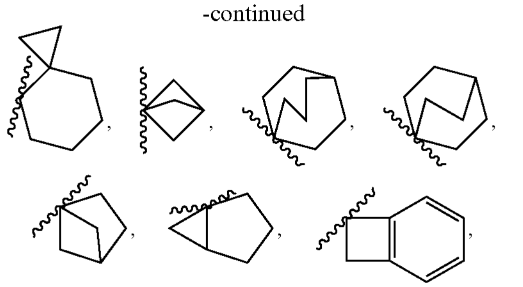

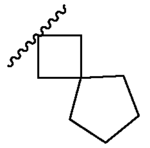

or

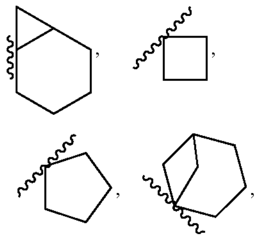

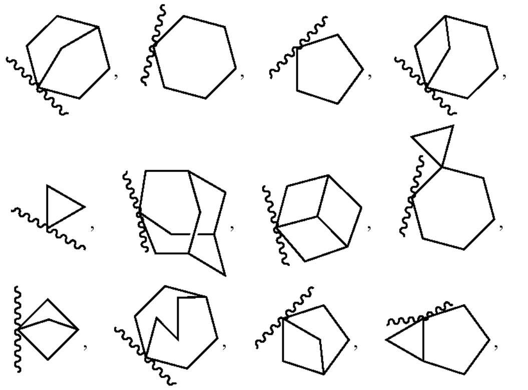

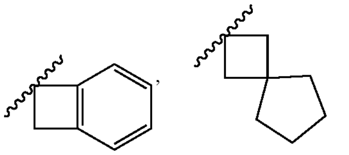

or

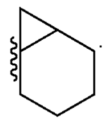

The term “heteroaryl” means a monocyclic or multicyclic, including bicyclic, aromatic heterocycloalkyl that contains at least one ring heteroatom selected from O, S and N. Examples of heteroaryl groups include pyridyl (pyridinyl), oxazolyl, azabenzothiazole, benzothiazole, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl, isoquinolyl, and the like.

The term “heterocycloalkyl” means mono- or bicyclic or bridged partially unsaturated and saturated rings containing at least one heteroatom selected from N, S and O, each of said rings having from 3 to 10 atoms in which the point of attachment may be carbon or nitrogen. Examples include azetidine, tetrahydropyranyl, tetrahydrofuranyl, pyrrolidinyl, piperidinyl, piperazinyl, dioxanyl, imidazolidinyl, 2,3-dihydrofuro(2,3-b)pyridyl, benzoxazinyl, benzoxazolinyl, 2-H-phthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl, and the like. The term also includes partially unsaturated monocyclic rings that are not aromatic, such as 2- or 4-pyridones attached through the nitrogen or n-substituted-(1H, 3H)-pyrimidine-2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, and azabicyclo[2.2.1]heptanyl. Examples described by structure include,

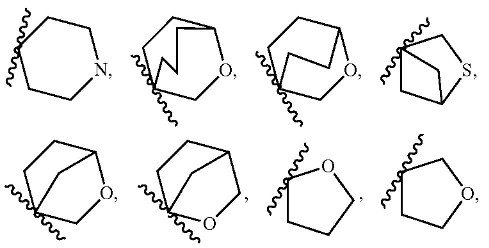

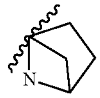

or

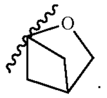

The term “pharmaceutically acceptable salt” refers to salts prepared from pharmaceutically acceptable non-toxic bases or acids including inorganic or organic bases and inorganic or organic acids. Salts of basic compounds encompassed within the term “pharmaceutically acceptable salt” refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, n-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, n-ethylmorpholine, n-ethylpiperidinyl, glucamine, glucosamine, histidine, hydrabamine, isopropylamine, lysine, methylglucamine, morpholine, piperazine, piperidinyl, polyamine resins, procaine, purines, theobromine, triethylamine, trimethylamine, tripropylamine, tromethamine, and the like.

The term “patient” refers to a mammalian patient, preferably a human patient, receiving or about to receive medical treatment.

The compounds of the present invention may contain one or more asymmetric centers and can thus occur as racemates, racemic mixtures, single enantiomers, diastereomeric mixtures, and individual diastereomers. The present invention is meant to comprehend all such isomeric forms of these compounds.

Some of the compounds described herein contain olefinic double bonds, and unless specified otherwise, are meant to include both E and Z geometric isomers.

Some of the compounds described herein contain substituted cycloalkanes having cis- and trans-isomers, and unless specified otherwise, are meant to include both cis- and trans-geometric isomers.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that the present invention is meant to include the pharmaceutically acceptable salts, and also salts that are not pharmaceutically acceptable, of the compounds described herein, when they are used as precursors to the free compounds or their pharmaceutically acceptable salts or in other synthetic manipulations.

Solvates, and in particular, the hydrates of the compounds of the structural formulas described herein are included in the present invention as well.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

In the compounds described herein, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the formulas described herein. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. A $^{3}H$, $^{11}C$, $^{18}F$ labeled compound may be used for PET or SPECT or other imaging studies.

Isotopically-enriched compounds can be prepared without undue experimentation by conventional techniques well known to those skilled in the art or by processes analogous to those described in the Schemes and Examples herein using appropriate isotopically-enriched reagents or Intermediates.

It should be noted that chemically unstable compounds are excluded from the embodiments contained herein.

Methods of Treatment

The compounds described herein may be particularly useful for the prevention, treatment or amelioration of RIPK1-mediated diseases or disorders. Such RIPK1-mediated diseases or disorders are likely to be regulated at least in part by programmed necrosis, apoptosis or the production of inflammatory cytokines, particularly inflammatory bowel disease (including Crohn's disease and ulcerative colitis), psoriasis, retinal detachment, retinal degeneration, retinitis pigmentosa, macular degeneration, age-related macular degeneration, pancreatitis, atopic dermatitis, arthritis (including rheumatoid arthritis, spondyloarthritis, gout, juvenile idiopathic arthritis (systemic onset juvenile idiopathic arthritis (SoJIA)), psoriatic arthritis), lupus, systemic lupus erythematosus (SLE), Sjogren's syndrome, systemic scleroderma, anti-phospholipid syndrome (APS), vasculitis, osteoarthritis, liver damage/diseases (non-alcohol steatohepatitis (NASH), alcohol steatohepatitis (ASH), autoimmune hepatitis, autoimmune hepatobiliary diseases, primary sclerosing cholangitis (PSC), acetaminophen toxicity, hepatotoxicity), non-alcohol steatohepatitis (NASH), alcohol steatohepatitis (ASH), autoimmune hepatitis, non-alcoholic fatty liver disease (NAFL D), kidney damage/injury (nephritis, renal transplant, surgery, administration of nephrotoxic drugs e.g., cisplatin, acute kidney injury (AKI)), Celiac disease, autoimmune idiopathic thrombocytopenic purpura (autoimmune ITP), transplant rejection (rejection of transplant organs, tissues and cells), ischemia reperfusion injury of solid organs, sepsis, systemic inflammatory response syndrome (SIRS), cerebrovascular accident (CV A, stroke), myocardial infarction (Ml), atherosclerosis, Huntington's disease, Alzheimer's disease, Parkinson's disease, amyotrophic lateral sclerosis (ALS), progressive supranuclear palsy (PSP), neonatal brain injury, neonatal hypoxic brain injury, ischemic brain injury, traumatic brain injury allergic diseases (including asthma and atopic dermatitis), peripheral nerve injury, burns, multiple sclerosis, type I diabetes, type II diabetes, obesity, Wegener's granulomatosis, pulmonary sarcoidosis, Behcet's disease, interleukin-I converting enzyme (ICE, also known as caspase-1) associated fever syndrome, chronic obstructive pulmonary disease (COPD), cigarette smoke-induced damage, cystic fibrosis, tumor necrosis factor receptor-associated periodic syndrome (TRAPS), a neoplastic tumor, peridontitis, NEMO-mutations (mutations of NF-kappa-B essential modulator gene (also known as IKK gamma or IKKG)), particularly, NEMO-deficiency syndrome, HOIL-1 deficiency (also known as RBCKI) heme-oxidized IRP 2 ubiquitin ligase-1 deficiency), linear ubiquitin chain assembly complex (LUBAC) deficiency syndrome, hematological and solid organ malignancies, bacterial infections and viral infections (such as influenza, *Staphylococcus*, and *Mycobacterium* (tuberculosis)), and Lysosomal storage diseases (particularly, Gaucher disease, and including GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs, and Wolman disease), Stevens-Johnson syndrome, toxic epidermal necrolysis, glaucoma, spinal cord injury, fibrosis, complement-mediated cytotoxicity, pancreatic ductal adenocarcinoma, hepatocellular carcinoma, mesothelioma, melanoma, metastasis, breast cancer, non-small cell lung carcinoma (NSCLC), radiation induced necrosis, ischemic kidney damage, ophthalmologic ischemia, intracerebral hemorrhage, subarachnoid hemorrhage, acute liver failure and radiation protection/mitigation, auditory disorders such as noise-induced hearing loss and drugs associated with ototoxicity such as cisplatin, or for the treatment of cells ex vivo to preserve vitality and function.

The compounds of the Formulae described herein, or a pharmaceutically acceptable salt thereof, may be particularly useful for the treatment of the following RIPK1-mediated diseases or disorders: inflammatory bowel disease (including Crohn's disease and ulcerative colitis), psoriasis, retinal detachment, retinal degeneration, retinitis pigmentosa, macular degeneration, age-related macular degeneration, pancreatitis, atopic dermatitis, arthritis (including rheumatoid arthritis, spondyloarthritis, gout, systemic onset juvenile idiopathic arthritis (SoJIA), psoriatic arthritis), lupus, systemic lupus erythematosus (SLE), Sjogren's syndrome, systemic scleroderma, anti-phospholipid syndrome (APS), vasculitis, osteoarthritis, liver damage/diseases (non-alcohol steatohepatitis (NASH), alcohol steatohepatitis (ASH) autoimmune hepatitis, autoimmune hepatobiliary diseases, primary sclerosing cholangitis (PSC), acetaminophen toxicity, hepatotoxicity), non-alcoholic steatohepatitis (NASH), alcoholic steatohepatitis (ASH), autoimmune hepatitis, non-alcoholic fatty liver disease (NAFLD), kidney damage/injury (nephritis, renal transplant, surgery, administration of nephrotoxic drugs e.g., cisplatin, acute kidney injury (AKI)), Celiac disease, autoimmune idiopathic thrombocytopenic purpura (autoimmune ITP), transplant rejection (rejection of transplant organs, tissues and cells), ischemia reperfusion injury of solid organs, sepsis, systemic inflammatory response syndrome (SIRS), cerebrovascular accident (CVA, stroke), myocardial infarction (MI), atherosclerosis, Huntington's disease, Alzheimer's disease, Parkinson's disease, amyotrophic lateral sclerosis (ALS), progressive supranuclear palsy (PSP), neonatal brain injury, neonatal hypoxic brain injury, traumatic brain injury, allergic diseases (including asthma and atopic dermatitis), peripheral nerve injury, burns, multiple sclerosis, type I diabetes, type II diabetes, obesity, Wegener's granulomatosis, pulmonary sarcoidosis, Behcet's disease, interleukin-I converting enzyme (ICE, also known as caspase-1) associated fever syndrome, chronic obstructive pulmonary disease (COPD), cigarette smoke-induced damage, cystic fibrosis, tumor necrosis factor receptor-associated periodic syndrome (TRAPS), a neoplastic tumor, melanoma, metastasis, breast cancer, non-small cell lung carcinoma (NSCLC), radiation induced necrosis, ischemic kidney damage, ophthalmologic ischemia, intracerebral hemorrhage, subarachnoid hemorrhage, peridontitis, NEMO-mutations (mutations of NF-kappa-B essential modulator gene (also known as IKK gamma or IKKG)), particularly, NEMO-deficiency syndrome, HOIL-1 deficiency ((also known as RBCKI) heme-oxidized IRP 2 ubiquitin ligase-1 deficiency), linear ubiquitin chain assembly complex (LUBAC) deficiency syndrome, hematological and solid organ malignancies, bacterial infections and viral infections (such as influenza, *Staphylococcus*, and *Mycobacterium* (tuberculosis)), and Lysosomal storage diseases (particularly, Gaucher disease, and including GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, GM1 gangliosidosis, mucolipidosis, infantile free sialic acid storage disease, juvenile hexosaminidase A deficiency, Krabbe disease, lysosomal acid lipase deficiency, metachromatic leukodystrophy, mucopolysaccharidoses disorders, multiple sulfatase deficiency, Niemann-Pick disease, neuronal ceroid lipofuscinoses, Pompe disease, pycnodysostosis, Sandhoff disease, Schindler disease, sialic acid storage disease, Tay-Sachs, and Wolman disease), spinal cord injury, Stevens-Johnson syndrome, fibrosis, complement-mediated cytotoxicity, toxic epidermal necrolysis, and/or for the treatment of cells ex vivo to preserve vitality and function.

The compounds of the Formulae described herein, or a pharmaceutically acceptable salt thereof, may be useful for the treatment of glaucoma.

The compounds of the Formulae described herein, or a pharmaceutically acceptable salt thereof, may be particularly useful for treatment of pancreatic ductal adenocarcinoma, hepatocellular carcinoma, mesothelioma, or melanoma.

The compounds of the Formulae described herein, or a pharmaceutically acceptable salt thereof, may be particularly useful for the treatment of the following RIPK1-mediated disease or disorder: rheumatoid arthritis, inflammatory bowel disease (including Crohn's disease and ulcerative colitis), and psoriasis.

The treatment of the above-noted diseases/disorders may concern, more specifically, the amelioration of organ injury or damage sustained as a result of the noted diseases/disorders. For example, the compounds of this invention may be particularly useful for amelioration of brain tissue injury or damage following ischemic brain injury or traumatic brain injury, or for amelioration of heart tissue injury or damage following myocardial infarction, or for amelioration of brain tissue injury or damage associated with Huntington's disease, Alzheimer's disease or Parkinson's disease, or for amelioration of liver tissue injury or damage associated with non-alcohol steatohepatitis, alcohol steatohepatitis, autoimmune hepatitis autoimmune hepatobiliary diseases, or primary sclerosing cholangitis, or overdose of acetaminophen.

The compounds of this invention may be particularly useful for the amelioration of organ injury or damage sustained as a result of radiation therapy, or amelioration of spinal tissue injury or damage following spinal cord injury or amelioration of liver tissue injury or damage associated acute liver failure. The compounds of this invention may be particularly useful for amelioration of auditory disorders, such as noise-induced hearing loss or auditory disorders following the administration of ototoxic drugs or substances e.g., cisplatin.

The compounds of this invention may be particularly useful for amelioration of solid organ tissue (particularly kidney, liver, and heart and/or lung) injury or damage following transplant or the administration of nephrotoxic drugs or substances e.g., cisplatin. It will be understood that amelioration of such tissue damage may be achieved where possible, by pre-treatment with a compound of the Formulae described herein, or a pharmaceutically acceptable salt thereof; for example, by pre-treatment of a patient prior to administration of cisplatin or pre-treatment of an organ or the organ recipient prior to transplant surgery. Amelioration of such tissue damage may be achieved by treatment with a compound of the Formulae described herein, or a pharmaceutically acceptable salt thereof, during transplant surgery.

Amelioration of such tissue damage may also be achieved by short-term treatment of a patient with a compound of the Formulae described herein, or a pharmaceutically acceptable salt thereof, after transplant surgery.

In one embodiment, the compounds of the Formulae described herein, or a pharmaceutically acceptable salt thereof, may be useful for the treatment of retinal detachment, macular degeneration, and retinitis pigmentosa.

In another embodiment, the compounds of the Formulae described herein, or a pharmaceutically acceptable salt thereof, may be useful for the treatment of multiple sclerosis.

In one embodiment, the compounds of the Formulae described herein, or a pharmaceutically acceptable salt thereof, may be useful for the treatment of traumatic brain injury.

In another embodiment, the compounds of the Formulae described herein, or a pharmaceutically acceptable salt thereof, may be useful for the treatment of Huntington's Disease or Niemann-Pick disease.

In another embodiment, the compounds of the Formulae described herein, or a pharmaceutically acceptable salt thereof, may be useful for the treatment of amyotrophic lateral sclerosis (ALS), progressive supranuclear palsy (PSP), and Alzheimer's disease.

In another embodiment, the compounds of the Formulae described herein, or a pharmaceutically acceptable salt thereof, may be useful for the treatment of age-related macular degeneration.

The treatment of retinal detachment, macular degeneration, retinitis pigmentosa, multiple sclerosis, traumatic brain injury, Huntington's Disease, Alzheimer's Disease, amyotrophic lateral sclerosis, and Niemann-Pick disease may concern, more specifically, the amelioration of organ injury or damage sustained as a result of these diseases/disorders. For example, the compounds described herein may be particularly useful for amelioration of brain tissue injury or damage following traumatic brain injury, or for amelioration of brain tissue injury or damage associated of Huntington's Disease, Alzheimer's Disease, amyotrophic lateral sclerosis, and Niemann-Pick disease.

In another embodiment, the compounds of the Formulae described herein, or a pharmaceutically acceptable salt thereof, may be useful for the treatment of retinal detachment, macular degeneration, and retinitis pigmentosa, and the amelioration of brain tissue injury or damage as a result of multiple sclerosis, traumatic brain injury, Huntington's Disease, Alzheimer's Disease, amyotrophic lateral sclerosis, and Niemann-Pick disease.

In another embodiment, the compounds of the Formulae described herein, or a pharmaceutically acceptable salt thereof, may be useful for the treatment of Crohn's disease, ulcerative colitis, psoriasis, rheumatoid arthritis, spondyloarthritis, systemic onset juvenile idiopathic arthritis (SoJIA), and osteoarthritis.

In yet another embodiment, the compounds of the Formulae described herein, or a pharmaceutically acceptable salt thereof, may be useful for the treatment of psoriasis, rheumatoid arthritis, and ulcerative and colitis.

In another embodiment, the compounds of the Formulae described herein, or a pharmaceutically acceptable salt thereof, may be useful for the treatment of lupus, inflammatory bowel disease (IBD), Crohn's disease, and ulcerative colitis.

In another embodiment, the compounds of the Formulae described herein, or a pharmaceutically acceptable salt thereof, may be useful for the treatment of cerebrovascular accident (CVA, stroke), Huntington's disease, Alzheimer's disease, amyotrophic lateral sclerosis (ALS), traumatic brain injury, multiple sclerosis, Gaucher disease, Niemann-Pick disease, and spinal cord injury.

In another embodiment, the compounds of the Formulae described herein, or a pharmaceutically acceptable salt thereof, may be useful for the treatment of amyotrophic lateral sclerosis (ALS).

In another embodiment, the compounds of the Formulae described herein, or a pharmaceutically acceptable salt thereof, may be useful for the treatment of multiple sclerosis.

In another embodiment, the compounds of the Formulae described herein, or a pharmaceutically acceptable salt thereof, may be useful for the treatment of pancreatic ductal adenocarcinoma (PDAC), metastasis, melanoma, breast cancer, non-small cell lung carcinoma (NSCLC), and radiation induced necrosis.

In another embodiment, the compounds of the Formulae described herein, or a pharmaceutically acceptable salt thereof, may be useful for the treatment of pancreatic ductal adenocarcinoma (PDAC), metastasis, melanoma, breast cancer, and non-small cell lung carcinoma (NSCLC).

In another embodiment, the compounds of the Formulae described herein, or a pharmaceutically acceptable salt thereof, may be useful for the treatment of pancreatic ductal adenocarcinoma (PDAC).

In another embodiment, the compounds of the Formulae described herein, or a pharmaceutically acceptable salt thereof, may be useful for the treatment of intracerebral hemorrhage and subarachnoid hemorrhage.

In another embodiment, the compounds of the Formulae described herein, or a pharmaceutically acceptable salt thereof, may be useful for the treatment of type II diabetes and obesity.

In another embodiment, the compounds of the Formulae described herein, or a pharmaceutically acceptable salt thereof, may be useful for the treatment of atherosclerosis.

In another embodiment, the compounds of the Formulae described herein, or a pharmaceutically acceptable salt thereof, may be useful for the treatment of vasculitis.

In another embodiment, the compounds of the Formulae described herein, or a pharmaceutically acceptable salt thereof, may be useful for the treatment of dependent inflammation and cell death that occurs in inherited and sporadic diseases including Alzheimer's disease, amyotrophic lateral sclerosis, multiple sclerosis, Parkinson's disease, chronic traumatic encephalopathy, rheumatoid arthritis, ulcerative colitis, inflammatory bowel disease, psoriasis as well as acute tissue injury caused by stroke, traumatic brain injury, encephalitis.

In another embodiment, the compounds of the Formulae described herein, or pharmaceutically acceptable salt thereof, may be useful for the treatment of ischemic kidney damage, ophthalmologic ischemia, intracerebral hemorrhage, and subarachnoid hemorrhage.

In another embodiment, the compounds of the Formulae described herein, or pharmaceutically acceptable salt thereof, may be useful for the treatment of non-alcoholic steatohepatitis (NASH), alcoholic steatohepatitis (ASH), autoimmune hepatitis, and non-alcoholic fatty liver disease (NAFLD).

The compounds of the invention, particularly the compounds of the Formulae described herein, or a pharmaceutically acceptable salt thereof, may be particularly useful for the treatment of the RIPK1-mediated, cancer-related diseases or disorders. Gong et al., The role of necroptosis in cancer biology and therapy, Molecular Cancer (2019) 18:100. In one aspect the human has a solid tumor. In one aspect the tumor is selected from head and neck cancer, gastric cancer, melanoma, renal cell carcinoma (RCC), esophageal cancer, non-small cell lung carcinoma (NSCLC), prostate cancer, colorectal cancer, ovarian cancer, pancreatic cancer, and pancreatic ductal adenocarcinoma. In one aspect the human has one or more of the following: colorectal cancer (CRC), esophageal cancer, cervical, bladder, breast cancer, head and neck cancer, ovarian cancer, melanoma, renal cell carcinoma (RCC), EC squamous cell carcinoma, non-small cell lung carcinoma, mesothelioma, prostate cancer, and pancreatic ductal adenocarcinoma. In another aspect, the human has a liquid tumor such as diffuse large B cell lymphoma (DLBCL), multiple myeloma, chronic lyphomblastic leukemia (CLL), follicular lymphoma, acute myeloid leukemia and chronic myelogenous leukemia.

The present disclosure also relates to a method for treating or lessening the severity of a cancer selected from: brain (gliomas), glioblastomas, astrocytomas, Bannayan-Zonana syndrome, Cowden disease, Lhermitte-Duclos disease, breast cancer, triple negative breast cancer, inflammatory breast cancer, Wilm's tumor, Ewing's sarcoma, Rhabdomyosarcoma, ependymoma, medulloblastoma, colon cancer, head and neck cancer (including squamous cell carcinoma of head and neck), kidney cancer, lung cancer (including lung squamous cell carcinoma, lung adenocarcinoma, lung small cell carcinoma, and non-small cell lung carcinoma), liver cancer (including hepatocellular carcinoma), melanoma, ovarian cancer, pancreatic cancer (including squamous pancreatic cancer), prostate cancer, sarcoma, osteosarcoma, giant cell tumor of bone, thyroid cancer, lymphoblastic T-cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T-cell leukemia, plasmacytoma, immunoblastic large cell leukemia, mantle cell leukemia, multiple myeloma megakaryoblastic leukemia, multiple myeloma, acute megakaryocytic leukemia, promyelocytic leukemia, erythroleukemia, malignant lymphoma, Hodgkin's lymphoma, Non-Hodgkin's lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, cancer of the uterus, renal cancer (including kidney clear cell cancer, kidney papillary cancer, renal cell carcinoma), mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyeloid (or promyelocytic or promyelogenous or promyeloblastic) leukemia, acute myelomonocytic (or myelomonoblastic) leukemia, acute monocytic (or monoblastic) leukemia, erythroleukemia and megakaryocytic (or megakaryoblastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polcythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Specific examples of clinical conditions based on hematologic tumors include leukemias such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like. Hematopoietic cancers also include lymphoid malignancies, which may affect the lymph nodes, spleens, bone marrow, peripheral blood, and/or extranodal sites. Lymphoid cancers include B-cell malignancies, which include, but are not limited to, B-cell non-Hodgkin's lymphomas (B-NHLs). B-NHLs may be indolent (or low-grade), intermediate grade (or aggressive) or high-grade (very aggressive). Indolent B cell lymphomas include follicular lymphoma (FL); small lymphocytic lymphoma (SLL); marginal zone lymphoma (MZL) including nodal MZL, extranodal MZL, splenic MZL and splenic MZL with villous lymphocytes; lymphoplasmacytic lymphoma (LPL); and mucosa-associated-lymphoid tissue (MALT or extranodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkitt's lymphoma (BL), Burkitt-like lymphoma, small non-cleaved cell lymphoma (SNCCL) and lymphoblastic lymphoma. Other B-NHLs include immunoblastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (PTCL), anaplastic large cell lymphoma (ALCL), angioimmunoblastic lymphoid disorder (AILD), nasal natural killer (NK) cell/T-cell lymphoma, gamma/delta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

Pharmaceutical Compositions

Compounds described herein may be administered orally or parenterally. As formulated into a dosage form suitable for administration, the compounds described herein can be used as a pharmaceutical composition for the prevention, treatment, or remedy of the above diseases.

In clinical use of the compounds described herein, usually, the compound is formulated into various preparations together with pharmaceutically acceptable additives according to the dosage form and may then be administered. By "pharmaceutically acceptable" it is meant the additive, carrier, diluent or excipient must be compatible with the other ingredients of the formulation and not deleterious to the recipient thereof. As such, various additives ordinarily used in the field of pharmaceutical preparations are usable. Specific examples thereof include gelatin, lactose, sucrose, titanium oxide, starch, crystalline cellulose, hydroxypropyl methylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, hydroxypropyl cyclodextrin, and the like.

Preparations to be formed with those additives include, for example, solid preparations such as tablets, capsules, granules, powders and suppositories; and liquid preparations such as syrups, elixirs and injections. These may be formulated according to conventional methods known in the field of pharmaceutical preparations. The liquid preparations may also be in such a form that may be dissolved or suspended in water or in any other suitable medium in their use. Especially for injections, if desired, the preparations may be dissolved or suspended in physiological saline or glucose liquid, and a buffer or a preservative may be optionally added thereto.

The pharmaceutical compositions may contain the compound of the invention in an amount of from 1 to 99.9 by weight, preferably from 1 to 60% by weight of the composition. The compositions may further contain any other therapeutically-effective compounds.

In case where the compounds of the invention are used for prevention or treatment for the above-mentioned diseases, the dose and the dosing frequency may be varied, depending on the sex, the age, the body weight and the disease condition of the patient and on the type and the range of the intended remedial effect. In general, when orally administered, the dose may be from 0.001 to 50 mg/kg of body weight/day, and it may be administered at a time or in several times. In specific embodiments, the dose is from about 0.01 to about 25 mg/kg/day, in particular embodiments, from about 0.05 to about 10 mg/kg/day. For oral administration, the compositions are preferably provided in the form of tablets or capsules containing from 0.01 mg to 1,000 mg. In specific embodiments, the dose is 0.01, 0.05, 0.1, 0.2, 0.5, 1.0, 2.5, 5, 10, 15, 20, 25, 30, 40, 50, 75, 100, 125, 150, 175, 200, 225, 250, 500, 750, 850 or 1,000 milligrams of a compound described herein. This dosage regimen may be adjusted to provide the optimal therapeutic response.

Combination Therapy

The compounds of the present invention are further useful in methods for the prevention or treatment of the aforementioned diseases, disorders and conditions in combination with other therapeutic agents.

The compounds of the present invention may be used in combination with one or more other drugs in the treatment, prevention, suppression or amelioration of diseases or conditions for which compounds described herein or the other drugs may have utility, where the combination of the drugs together are safer or more effective than either drug alone. Such other drug(s) may be administered in an amount commonly used therefore, contemporaneously or sequentially with a compound described herein or a pharmaceutically acceptable salt thereof. When a compound described herein is used contemporaneously with one or more other drugs, the pharmaceutical composition may in specific embodiments contain such other drugs and the compound described herein or its pharmaceutically acceptable salt in unit dosage form. However, the combination therapy may also include therapies in which the compound described herein or its pharmaceutically acceptable salt and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound described herein or a pharmaceutically acceptable salt thereof.

EXAMPLES

Abbreviations

The abbreviations used herein have the following tabulated meanings. Abbreviations not tabulated below have their meanings as commonly used unless specifically stated otherwise.

| | |
|---|---|
| ACN | acetonitrile |
| AcOH | acetic acid |
| Aq. | aqueous |
| $CH_2Cl_2$ | dichloromethane |
| $ClCH_2CH_2Cl$ | 1,2-dichloroethane |
| $Cu(OAc)_2$ | copper(II) acetate |
| DCM | dichloromethane |

-continued

| | |
|---|---|
| DIEA | diisopropylethylamine |
| DMA | dimethylacetamide |
| DMF | dimethylformamide |
| DMPU | N,N'-dimethylpropyleneurea |
| DMSO | dimethylsulfoxide |
| EI | electron ionization |
| EtOAc or EA | ethyl acetate |
| EtOH | ethanol |
| $H_2O$ | water |
| h | hour |
| HCl | hydrochloric acid |
| $^1H$ NMR | proton nuclear magnetic resonance |
| HPLC | high performance liquid chromatography |
| $Ir(ppy)_3$ | tris(2-phenylpyridine)iridium(III) |
| IPA | isopropyl alcohol |
| i-PrMgCl•LiCl | isopropylmagnesium chloride lithium chloride complex |
| $K_2CO_3$ | potassium carbonate |
| LC/MS | liquid chromatography coupled to mass spectrometer |
| LDA | lithium diisopropylamide |
| LIHMDS/LHMDS | lithium bis(trimethylsilyl)amide |
| LiOH | lithium hydroxide |
| $MgSO_4$ | magnesium sulfate |
| MeCN | acetonitrile |
| MeOH | methanol |
| MHz | megahertz |
| Min | minute/minutes |
| MS | mass spectrum |
| Ms—Cl | methanesulfonyl chloride (mesyl chloride) |
| MTBE | methyl tert-butyl ether |
| $NaHCO_3$ | sodium bicarbonate |
| $Na_2SO_4$ | sodium sulfate |
| NaOH | sodium hydroxide |
| $NaBH_4$ | sodium borohydride |
| $NaBH_3CN$ | sodium cyanoborohydride |
| $NH_4Cl$ | ammonium chloride |
| $NH_4HCO_3$ | ammonium bicabonate |
| $NH_4OH$ | ammonium hydroxide |
| NMR | nuclear magnetic resonance |
| o/n | overnight |
| PE | petroleum ether |
| PhMgBr | phenylmagnesium bromide |
| RT or rt | room temperature |
| Sat. | saturated |
| Selectfluor | 1-chloromethyl-4-fluoro-1,4-diazoniabicyclo[2.2.2] octane bis(tetrafluoroborate) |
| SFC | supercritical fluid chromatography |
| SnAr | nucleophilic aromatic substitution |
| TEA | triethylamine |
| TFA | trifluoroacetic acid |
| THF | tetrahydrofuran |
| TLC | thin layer chromatography |
| TsOH | toluenesulfonic acid |

Synthesis of Common Intermediates (Table A)

Preparation of Intermediate I-1A ((S)-5-phenyl-2,5,6,7-tetrahydro-3H-pyrrolo[2,1-c][1,2,4]triazol-3-one)

Intermediate I-1A was prepared from pyrrolidine-2,5-dione as outlined below.

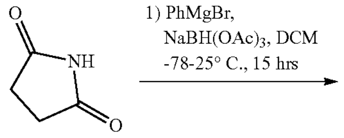

-continued

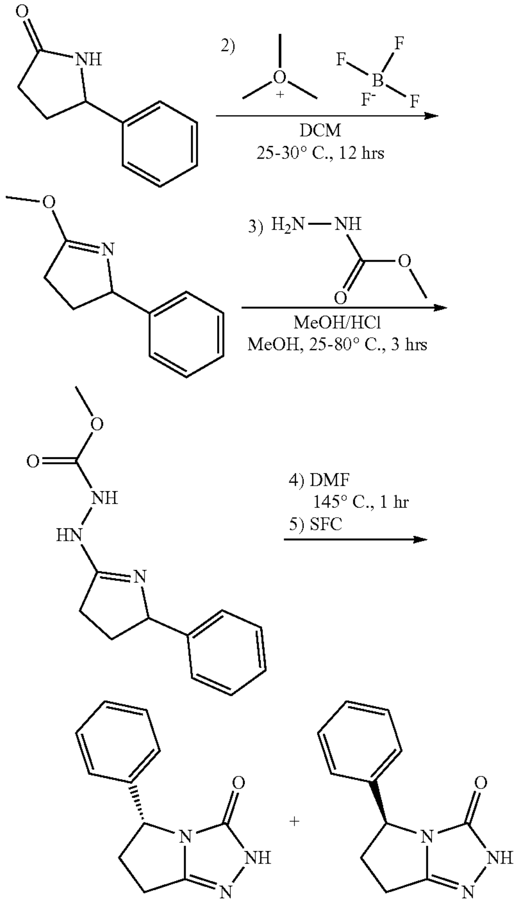

I-1A

Step 1. Synthesis of 5-phenylpyrrolidin-2-one

Two reactions of identical scales were carried out in parallel: to a solution of pyrrolidine-2,5-dione (500 g, 5.05 mol) in DCM (12.5 L) was added PhMgBr (3 M, 4.21 L) at −70-−65° C. under $N_2$ and the reaction was stirred at 25-30° C. for 12 h. To the mixture was added $NaBH_3CN$ (1.28 kg, 6.06 mol) at 5-10° C. and stirred for 1 h. The reaction was acidified with TFA (2.31 kg, 20.3 mol) to pH=3-4. It was stirred at 25-30° C. for 2 h.

The two reactions were combined to work up together. The mixture was added to ice-$H_2O$ (25 L) and extracted by DCM (5.0 L×2) to get the organic layer. The organic layer was washed with sat. $NaHCO_3$ (15 L) and separated. The organic layer and then purified by flash silica gel chromatography (petroleum ether/ethyl acetate) to give 5-phenylpyrrolidin-2-one. $^1H$ NMR (400 MHz, $CDCl_3$) δ 7.28-7.41 (m, 5H), 6.11 (br, s, 1H), 4.78 (t, J=7.2 Hz, 1H), 2.44-2.61 (m, 3H), 1.99-2.03 (m, 1H).

Step 2. Synthesis of 5-methoxy-2-phenyl-3,4-dihydro-2H-pyrrole

Five reactions of identical scales were carried out in parallel: trimethyloxonium tetrafluoroborate (109 g, 736 mmol) was added to a solution of 5-phenylpyrrolidin-2-one (99.0 g, 614 mmol) and $K_2CO_3$ (169 g, 1.23 mol) in DCM (990 mL) at 25-30° C. The mixture was stirred at 25-30° C.

for 12 h. The mixture was added to sat. $NaHCO_3$ (5.0 L) and extracted by DCM (1.0 L×2) to get the organic layer. The organic layer was concentrated to afford the crude product. The crude product was purified by column chromatography (petroleum ether/ethyl) to obtain 5-methoxy-2-phenyl-3,4-dihydro-2H-pyrrole. $^1H$ NMR (400 MHz, $CDCl_3$) δ 7.20-7.34 (m, 5H), 4.97 (t, J=7.2 Hz, 1H), 3.91 (s, 3H), 2.55-2.61 (m, 3H), 1.85-1.90 (m, 1H).

Step 3. Synthesis of methyl 2-(2-phenyl-3,4-dihydro-2H-pyrrol-5-yl)hydrazine-1-carboxylate A solution of HCl/MeOH (4 M, 180 mL) was added to a mixture of 5-methoxy-2-phenyl-3,4-dihydro-2H-pyrrole (180 g, 1.03 mol) and compound methyl hydrazinecarboxylate (97.1 g, 1.08 mol) in MeOH (1.8 L) at 25-30° C. The reaction was stirred at 80° C. for 3 h. Upon completion, the mixture was concentrated. The crude product was washed with MTBE (300 mL) to afford methyl 2-(2-phenyl-3,4-dihydro-2H-pyrrol-5-yl)hydrazine-1-carboxylate. $^1H$ NMR (400 MHz, $CD_3OD$) δ 7.33-7.40 (m, 5H), 5.07 (t, J=7.2 Hz, 1H), 3.76 (s, 3H), 2.96-3.00 (m, 2H), 2.69-2.72 (m, 1H), 2.06-2.09 (m, 1H).

Steps 4-5. Synthesis of 5-phenyl-2,5,6,7-tetrahydro-3H-pyrrolo[2,1-c][1,2,4]triazol-3-one followed by SFC to afford I-1A Two reactions of identical scales were carried out in parallel: a solution of methyl 2-(2-phenyl-3,4-dihydro-2H-pyrrol-5-yl)hydrazine-1-carboxylate (50.0 g, 214 mmol) in DMF (500 mL) was stirred at 145° C. for 1 h. Upon completion, the two reactions were combined and worked up together. The mixture was concentrated to remove DMF to get the crude product. The crude product was purified by column chromatography (petroleum ether/ethyl acetate) and washed with MTBE (100 mL) to obtain 5-phenyl-2,5,6,7-tetrahydro-3H-pyrrolo[2,1-c][1,2,4]triazol-3-one (30.0 g).

The compound of 5-phenyl-2,5,6,7-tetrahydro-3H-pyrrolo[2,1-c][1,2,4]triazol-3-one (30.0 g, 149 mmol) was separated by preparative SFC (Method Column DAICEL AD; Condition MeOH/IPA) to afford (R)-5-phenyl-2,5,6,7-tetrahydro-3H-pyrrolo[2,1-c][1,2,4]triazol-3-one, the first eluting isomer and I-1A ((S)-5-phenyl-2,5,6,7-tetrahydro-3H-pyrrolo[2,1-c][1,2,4]triazol-3-one), the second eluting isomer.

(R)-5-phenyl-2,5,6,7-tetrahydro-3H-pyrrolo[2,1-c][1,2,4]triazol-3-one $^1HNMR$ (400 MHz, $CD_3OD$) δ 7.21-7.39 (m, 5H), 5.23 (dd, J=8.0, 4.4 Hz, 1H), 2.92-3.06 (m, 1H), 2.82-2.90 (m, 2H), 2.40-2.43 (m, 1H).

(S)-5-phenyl-2,5,6,7-tetrahydro-3H-pyrrolo[2,1-c][1,2,4]triazol-3-one (I-1A)

$^1H$ NMR (400 MHz, $CD_3OD$) δ 7.22-7.39 (m, 5H), 5.23 (dd, J=8.0, 4.4 Hz, 1H), 2.92-3.06 (m, 1H), 2.82-2.90 (m, 2H), 2.40-2.42 (m, 1H).

Preparation of Intermediate I-2A ((5S)-5-(3,5-difluorophenyl)-2H,5H,6H,7H-pyrrolo[2,1-c][1,2,4]triazol-3-one)

Intermediate I-2A was prepared from 1-bromo-3,5-difluorobenzene as outlined below.

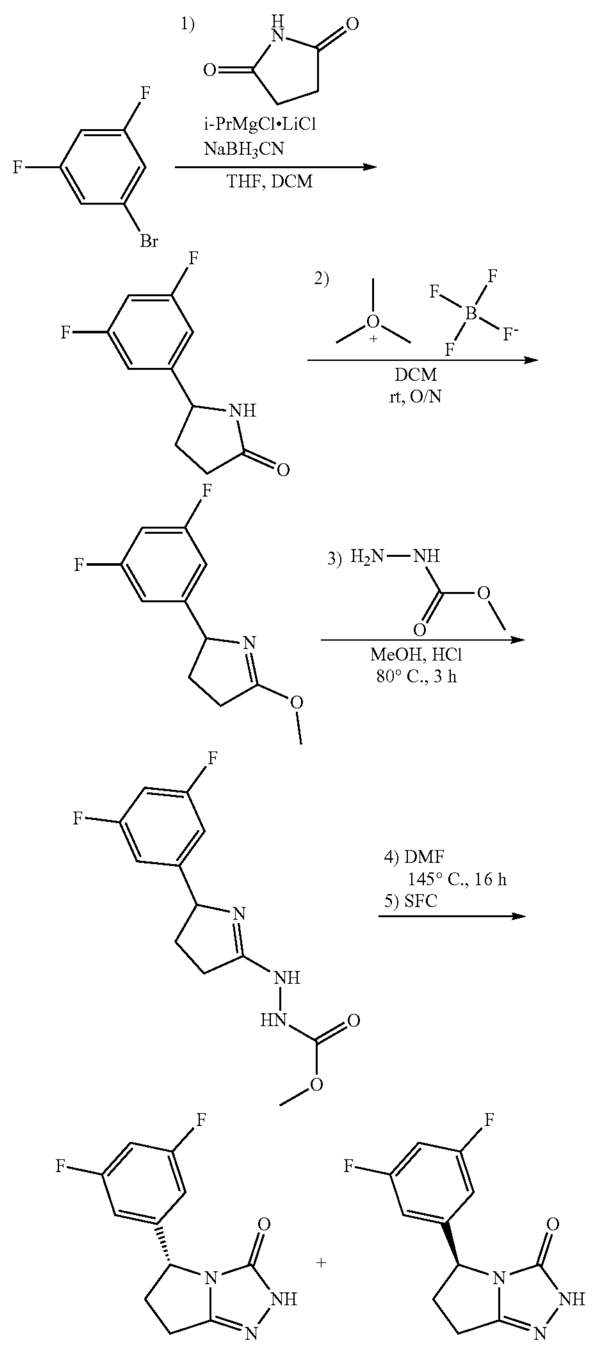

I-2A

Step 1. Synthesis of 5-(3,5-difluorophenyl)pyrrolidin-2-one

To a solution of 1-bromo-3,5-difluorobenzene (906 g, 469 mmol) in THF (6.75 L) was added i-PrMgCl·LiCl (6 L) at 0° C., the reaction was stirred at 50° C. for 1 h. Then to the mixture was added succinimide (310 g, 313 mmol) and DCM (300 mL) at −78° C. The mixture was stirred at 25° C. for 16 h. To the mixture was added $NaBH_3CN$ (236 g, 3750 mmol) at 25° C., then the mixture was stirred at 25° C. for 1 h. The reaction was acidified to pH=3-4 with HCl (6 M), stirred for 30 min, and neutralized with aq. NaOH (3 M).

The mixture was quenched with water (5000 mL) and extracted with DCM (5000 mL×3). The combined organic layers were dried over $Na_2SO_4$, filtered and concentrated in vacuum to give crude product which was purified by flash silica gel chromatography (hexanes/ethyl acetate) to give 5-(3,5-difluorophenyl)pyrrolidin-2-one. Calculated $C_{10}H_{10}F_2NO$ $[M+H]^+$, 198; Found 198.

Step 2. Synthesis of 2-(3,5-difluorophenyl)-5-methoxy-3,4-dihydro-2H-pyrrole

To a solution of 5-(3,5-difluorophenyl)pyrrolidin-2-one (180 g, 913 mmol) in DCM (2000 mL) was added trimethyloxonium tetrafluoroborate (250 g, 1.69 mol) at 25° C. The mixture was stirred at 25° C. for 16 h. The mixture was quenched with sat. aq. $NaHCO_3$ (3000 mL), extracted with DCM (2000 mL×3). The combined organic layers were dried over $Na_2SO_4$, filtered and concentrated in vacuum to give crude 2-(3,5-difluorocyclohexyl)-5-methoxy-3,4-dihydro-2H-pyrrole, which was used for next step directly. Calculated $C_{11}H_{12}F_2NO$ $[M+H]^+$, 212; Found 212.

Step 3. Synthesis of N'-[5-(3,5-difluorophenyl)-4,5-dihydro-3H-pyrrol-2-yl]methoxycarbohydrazide To a solution of 2-(3,5-difluorophenyl)-5-methoxy-3,4-dihydro-2H-pyrrole (185 g, 876 mmol) in MeOH (2000 mL) was added hydrazine carboxylic acid, methyl ester (103 g, 1140 mmol) and HCl/MeOH (240 mL, 4.0 M). The mixture was stirred at 80° C. for 3 h. The mixture was purified by flash silica gel chromatography (EtOAc/MeOH) to give N'-[5-(3,5-difluorophenyl)-4,5-dihydro-3H-pyrrol-2-yl] methoxycarbohydrazide. Calculated $C_{12}H_{14}F_2N_3O_2$ $[M+H]^+$, 270; Found 270.

Steps 4-5. Synthesis of 5-(3,5-difluorophenyl)-2H,5H,6H,7H-pyrrolo[2,1-c][1,2,4]triazol-3-one Followed by SFC to afford I-2A A solution of N'-[5-(3,5-difluorophenyl)-4,5-dihydro-3H-pyrrol-2-yl]methoxycarbohydrazide (161 g) in DMF (1600 mL) was stirred at 145° C. for 16 h. The mixture was concentrated in vacuum to give crude product, it was slurried with $CH_3CN$/PE (3:5) to give 5-(3,5-difluorophenyl)-2H,5H,6H,7H-pyrrolo[2,1-c][1,2,4]triazol-3-one (75 g). The compound of 5-(3,5-difluorophenyl)-2H,5H,6H,7H-pyrrolo [2,1-c][1,2,4]triazol-3-one (75 g, 316 mmol, 1.00 equiv) was separated by preparative SFC (Method Column CHIRALPAK IC-3; Condition 10% EtOH) to afford (5R)-5-(3,5-difluorophenyl)-2H,5H,6H,7H-pyrrolo[2,1-c][1,2,4]triazol-3-one, the first eluting isomer, and I-2A, ((5S)-5-(3,5-difluorophenyl)-2H,5H,6H,7H-pyrrolo[2,1-c][1,2,4]triazol-3-one) (25.7 g), the second eluting isomer.

(5R)-5-(3,5-difluorophenyl)-2H,5H,6H,7H-pyrrolo [2,1-c][1,2,4]triazol-3-one $^1H$ NMR (300 MHz, DMSO-$d_6$) δ 11.32 (s, 1H), 7.20 (tt, J=9.4, 2.4 Hz, 1H), 7.10-6.96 (m, 2H), 5.20 (dd, J=8.0, 4.8 Hz, 1H), 3.06-2.72 (m, 3H), 2.39-2.21 (m, 1H). $^{19}F$ NMR (282 MHz, DMSO-$d_6$) δ −109.22. Calculated $C_{11}H_{10}F_2N_3O$ $[M+H]^+$, 238; Found 238.

(5S)-5-(3,5-difluorophenyl)-2H,5H,6H,7H-pyrrolo [2,1-c][1,2,4]triazol-3-one (I-2A)

$^1H$ NMR (300 MHz, DMSO-$d_6$) δ 11.32 (s, 1H), 7.20 (tt, J=9.3, 2.4 Hz, 1H), 7.10-6.96 (m, 2H), 5.20 (dd, J=8.0, 4.8 Hz, 1H), 3.06-2.72 (m, 3H), 2.39-2.23 (m, 1H). $^{19}F$ NMR (282 MHz, DMSO-$d_6$) δ −109.22. Calculated $C_{11}H_{10}F_2N_3O$ $[M+H]^+$, 238; Found 238.

Preparation of Intermediate I-3A ((S)-5-(2-fluorophenyl)-2,5,6,7-tetrahydro-3H-pyrrolo[2,1-c][1,2,4] triazol-3-one)

Intermediate I-3A was prepared from 1-(2-fluorophenyl) ethan-1-one as outlined below.

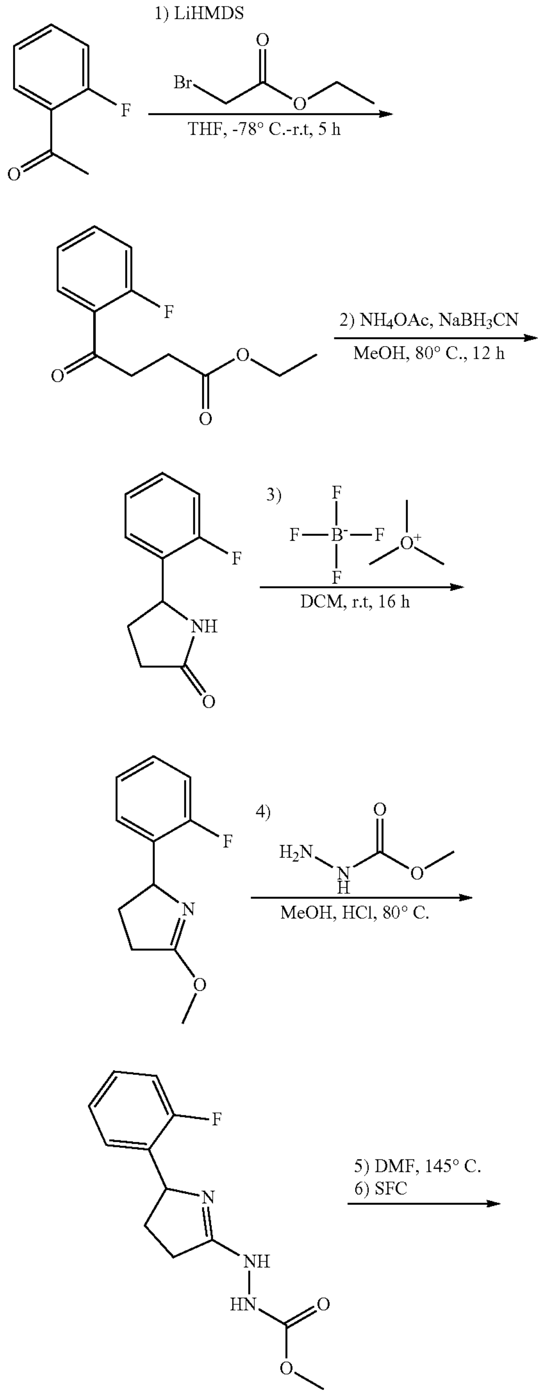

-continued

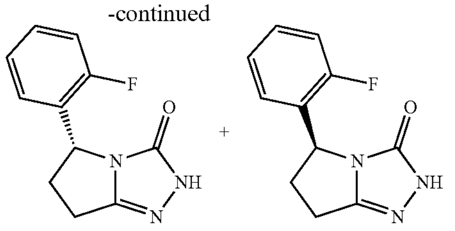

I-3A

Step 1. Synthesis of ethyl 4-(2-fluorophenyl)-4-oxobutanoate

To a stirred solution of 1-(2-fluorophenyl)ethan-1-one (10.0 g, 72.4 mmol) in THF (150 mL) and DMPU (50 mL, 72.4 mmol) was added LiHMDS (72.4 mL, 72.4 mmol) (1 M in THF) at ~−60° C. (dry ice-acetone bath). After the addition was finished, the reaction was stirred at −60° C. for 30 min. Then ethyl 2-bromoacetate (12.7 g, 76 mmol) was added to the mixture in one portion at −60° C. The resulting mixture was continuously stirred for another 30 min at −60° C. The reaction was then warmed to RT and stirred at RT for 2 h. The mixture was diluted with tert-butyl methyl ether (300 mL) and quenched with sat. aq. $NH_4Cl$ (250 mL). The mixture was extracted with tert-butyl methyl ether (300 mL×2). The combined organic fractions were washed with brine (200 mL), dried with $Na_2SO_4$, filtered and the solvent was evaporated under reduced pressure. The residue was purified by flash silica gel chromatography (ethyl acetate/petroleum ether) to give ethyl 4-(2-fluorophenyl)-4-oxobutanoate. Calculated $C_{12}H_{14}FO_3$ $[M+H]^+$, 225; Found 225.

Step 2. Synthesis of 5-(2-fluorophenyl)pyrrolidin-2-one

To a solution of methyl 4-(2-fluorophenyl)-4-oxobutanoate (5 g, 23.8 mmol) in MeOH (100 mL) was added ammonium acetate (5.50 g, 71.4 mmol) and sodium cyanotrihydroborate (3.74 g, 59.5 mmol) at RT. Then the mixture was stirred at 80° C. for 12 h. The reaction mixture was quenched with HCl (2M, ~5 mL) and concentrated. The residue was purified by flash silica gel chromatography (DCM/MeOH) to give 5-(2-fluorophenyl)pyrrolidin-2-one. Calculated $C_{10}H_{11}FNO$ $[M+H]^+$, 180; Found 180.

Step 3. Synthesis of 2-(4-fluorophenyl)-5-methoxy-3,4-dihydro-2H-pyrrole

A mixture of 5-(2-fluorophenyl)pyrrolidin-2-one (2.0 g, 11.2 mmol) and trimethyloxonium tetrafluoroborate (2.15 g, 14.5 mmol) in DCM (50 ml) was stirred at 25° C. for 16 h. The reaction mixture was quenched with sat. $NaHCO_3$ (30 mL) and extracted with DCM (30 mL×3). The combined organic phases were washed with brine (20 mL), dried over anhydrous $Na_2SO_4$, filtered and concentrated under reduced pressure to give crude 2-(4-fluorophenyl)-5-methoxy-3,4-dihydro-2H-pyrrole. The crude was used in the next step without further purification. Calculated $C_{11}H_{13}FNO$ $[M+H]^+$, 194; Found 194.

Step 4. Synthesis of methyl 2-(2-(2-fluorophenyl)-3,4-dihydro-2H-pyrrol-5-yl)hydrazine-1-carboxylate To a stirred solution of 2-(2-fluorophenyl)-5-methoxy-3,4-dihydro-2H-pyrrole (2.0 g, 10.4 mmol) in MeOH (20 mL) was added methyl hydrazinecarboxylate (1.21 g, 13.5 mmol) at 20° C. after the addition was finished. The reaction was stirred at 80° C. for 2 h and then concentrated in vacuo. The residue was purified by p-HPLC (Boston Green ODS 150×30 mm×5 um; Condition water (0.1% TFA)-MeCN) to give methyl 2-(2-(2-fluorophenyl)-3,4-dihydro-2H-pyrrol-5-yl)hydrazine-1-carboxylate. Calculated $C_{12}H_{15}FN_3O_2[M+H]^+$, 252; Found 252.

Steps 5-6. Synthesis of 5-(2-fluorophenyl)-2,5,6,7-tetrahydro-3H-pyrrolo[2,1-c][1,2,4]triazol-3-one and chiral separation to isolate I-3A A stirred solution of methyl 2-(2-(2-fluorophenyl)-3,4-dihydro-2H-pyrrol-5-yl)hydrazine-1-carboxylate (450 mg, 1.80 mmol) in DMF (30 mL) was heated to 145° C. under $N_2$ atmosphere and stirred at 145° C. for 2 h. The mixture was concentrated in vacuo. The residue was purified by preparative HPLC (Method Column Boston Green ODS 150×30 mm×5 um; Condition water (0.1% TFA)-MeCN) to give 5-(2-fluorophenyl)-2,5,6,7-tetrahydro-3H-pyrrolo[2,1-c][1,2,4]triazol-3-one. The racemic mixture of 5-(2-fluorophenyl)-2,5,6,7-tetrahydro-3H-pyrrolo[2,1-c][1,2,4]triazol-3-one (320 mg, 1.46 mmol) was separated by SFC (Method Column (S,S)WHELK-O1 (250 mm×30 mm, 5 um); Condition 0.1% $NH_3H_2O$/EtOH) to give (R)-5-(2-fluorophenyl)-2,5,6,7-tetrahydro-3H-pyrrolo[2,1-c][1,2,4]triazol-3-one (SFC-P1, ee=100%) and I-3A ((S)-5-(2-fluorophenyl)-2,5,6,7-tetrahydro-3H-pyrrolo[2,1-c][1,2,4]triazol-3-one) (SFC-P2, ee=100%).

(R)-5-(2-fluorophenyl)-2,5,6,7-tetrahydro-3H-pyrrolo[2,1-c][1,2,4]triazol-3-one $^1H$ NMR (400 MHz, $CD_3OD$) δ 7.40-7.33 (m, 1H), 7.22-7.11 (m, 3H), 5.45-5.42 (m, 1H), 3.13-3.09 (m, 1H), 2.97-2.80 (m, 2H), 2.50-2.40 (m, 1H).

(S)-5-(2-fluorophenyl)-2,5,6,7-tetrahydro-3H-pyrrolo[2,1-c][1,2,4]triazol-3-one (I-3A)

$^1H$ NMR (400 MHz, $CD_3OD$) δ 7.37-7.36 (m, 1H), 7.22-7.11 (m, 3H), 5.45-5.42 (m, 1H), 3.13-3.09 (m, 1H), 2.98-2.85 (m, 2H), 2.46-2.44 (m, 1H).

Preparation of Intermediate I-4A ((S)-5-(5-fluoropyridin-3-yl)-2,5,6,7-tetrahydro-3H-pyrrolo[2,1-c][1,2,4]triazol-3-one)

Intermediate I-4A was prepared from 3-bromo-5-fluoropyridine as outlined below.

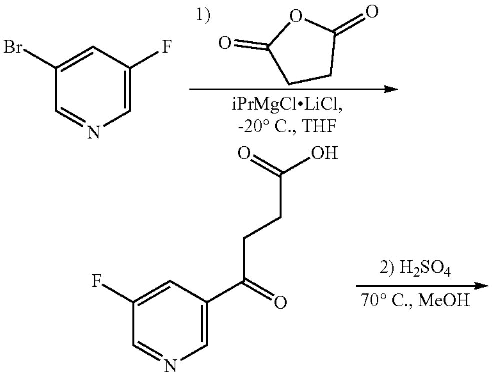

-continued

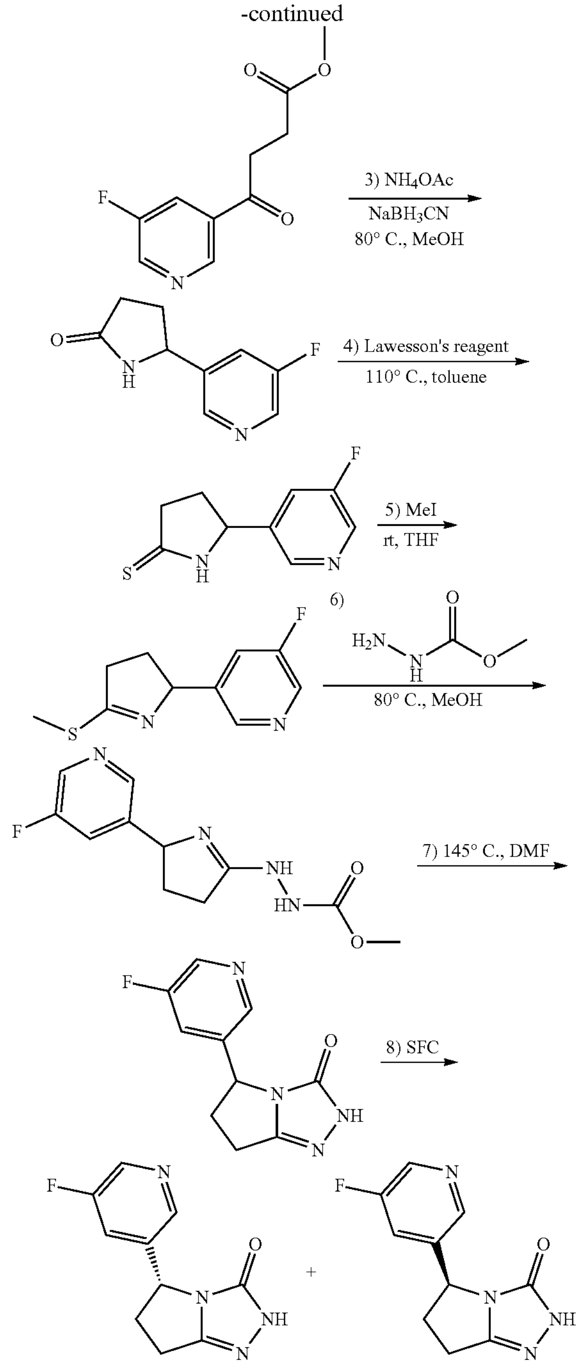

I-4A

Step 1. Preparation of 4-(5-fluoropyridin-3-yl)-4-oxobutanoic acid

To a solution of 3-bromo-5-fluoropyridine (40 g, 227 mmol) in THF (250 mL) was added iPrMgCl·LiCl (1.3 M in THF) (192 mL, 250 mmol) at 0° C. for 2 h. Then the mixture was added to a solution of dihydrofuran-2,5-dione (27.3 g, 273 mmol) in THF (450 mL) at −20° C. and the resulting mixture was stirred at −20° C. for 3 h. To the reaction was added sat. $NH_4Cl$ (200 mL) and aq. NaOH (2 M) until pH-11. After stirring for 30 min, the reaction was extracted with EtOAc (100 mL) and the aqueous phase was added HCl (2 M) until PH-5, then extracted with EtOAc (100 mL×3). The combined organic layers were dried over $Na_2SO_4$, filtered and concentrated to give 4-(5-fluoropyridin-3-yl)-4-oxobutanoic acid, which was used to next step without further purification.

Step 2. Preparation of methyl 4-(5-fluoropyridin-3-yl)-4-oxobutanoate

To a solution of 4-(5-fluoropyridin-3-yl)-4-oxobutanoic acid (34 g, 172 mmol) in MeOH (300 mL) was added $H_2SO_4$ (12 mL, 225 mmol) and the resulting mixture was stirred at 70° C. for 12 h. The mixture was directly concentrated. The residue was dissolved in DCM (100 mL), water (50 mL) and added sat. $NaHCO_3$ until the pH-8, then extracted with DCM (100 mL×3). The combined organic layers were dried over $Na_2SO_4$, filtered and concentrated. The residue was purified by flash silica gel chromatography (ethyl acetate/petroleum ether) to give methyl 4-(5-fluoropyridin-3-yl)-4-oxobutanoate. $^1$H NMR (400 MHz, $CDCl_3$) δ 9.03 (s, 1H), 8.67 (d, J=2.8 Hz, 1H), 7.92-7.99 (m, 1H), 3.72 (s, 3H), 3.33 (t, J=6.4 Hz, 2H), 2.81 (t, J=6.4 Hz, 2H).

Step 3. Preparation of 5-(5-fluoropyridin-3-yl)pyrrolidin-2-one

To a solution of methyl 4-(5-fluoropyridin-3-yl)-4-oxobutanoate (9 g, 42.6 mmol) in MeOH (150 mL) was added ammonium acetate (9.85 g, 128 mmol), $NaBH_3CN$ (8.03 g, 128 mmol) and the mixture was stirred at 80° C. for 12 h. The reaction solution was concentrated and the residue purified by flash silica gel chromatography (ethyl acetate/ethanol) to give 5-(5-fluoropyridin-3-yl)pyrrolidin-2-one. $^1$H NMR (400 MHz, $CD_3OD$) δ 8.35-8.46 (m, 2H), 7.66 (td, J=2.0, 9.6 Hz, 1H), 4.90-4.94 (m, 1H), 2.60-2.74 (m, 1H), 2.43-2.50 (m, 2H), 1.91-2.03 (m, 1H).

Step 4. Preparation of 5-(5-fluoropyridin-3-yl)pyrrolidine-2-thione

To a solution of 5-(5-fluoropyridin-3-yl)pyrrolidin-2-one (4.1 g, 22.75 mmol) in toluene (40 mL) was added Lawesson's reagent (4.60 g, 11.4 mmol) and the resulting mixture was stirred at 110° C. for 12 h. The reaction solution was directly concentrated and the residue was purified by flash silica gel chromatography (ethyl acetate/petroleum ether) to give 5-(5-fluoropyridin-3-yl)pyrrolidine-2-thione. $^1$H NMR (400 MHz, $CD_3OD$) δ 8.46 (d, J=2.4 Hz, 1H), 8.40 (s, 1H), 7.64 (td, J=2.0, 9.2 Hz, 1H), 5.16 (t, J=7.2 Hz, 1H), 2.88-3.09 (m, 2H), 2.72 (dtd, J=5.6, 8.4, 13.25 Hz, 1H), 2.03-2.14 (m, 1H).

Step 5. Preparation of 3-fluoro-5-(5-(methylthio)-3,4-dihydro-2H-pyrrol-2-yl)pyridine To a solution of 5-(5-fluoropyridin-3-yl)pyrrolidine-2-thione (4.0 g, 20.4 mmol) in THF (70 mL) was added MeI (1.91 mL, 30.6 mmol) and the resulting mixture was stirred at 20° C. for 12 h. The reaction solution was concentrated. The residue was washed with sat. $NaHCO_3$ (40 mL) and the aqueous phase was extracted with DCM (20 mL×3). The combined organic layers were dried over $Na_2SO_4$, filtered, and concentrated to give 3-fluoro-5-(5-(methylthio)-3,4-dihydro-2H-pyrrol-2-yl)pyridine, which was used in the next step without further purification.

Step 6. Preparation of methyl 2-(2-(5-fluoropyridin-3-yl)-3,4-dihydro-2H-pyrrol-5-yl)hydrazine-1-carboxylate To a solution of 3-fluoro-5-(5-(methylthio)-3,4-dihydro-2H-pyrrol-2-yl)pyridine (3.8 g, 18.1 mmol) in MeOH (60 mL) was added methyl hydrazinecarboxylate (2.44 g, 27.1 mmol) and the resulting mixture was stirred at 80° C. for 5 h. The reaction solution was directly concentrated and the residue was purified by flash silica gel chromatography (MeOH/DCM) to give methyl 2-(2-(5-fluoropyridin-3-yl)-3,4-dihydro-2H-pyrrol-5-yl)hydrazine-1-carboxylate. $^1$H NMR (400 MHz, $CDCl_3$) δ 8.37-8.44 (m, 2H), 7.43-7.51 (m, 1H), 4.88 (t, J=7.2 Hz, 1H), 3.66 (s, 3H), 2.65-2.79 (m, 2H), 2.53 (dt, J=6.4, 12.8 Hz, 1H), 1.84-1.97 (m, 1H).

Step 7. Preparation of 5-(5-fluoropyridin-3-yl)-2,5,6,7-tetrahydro-3H-pyrrolo[2,1-c][1,2,4]triazol-3-one To a solution of methyl 2-(2-(5-fluoropyridin-3-yl)-3,4-dihydro-2H-pyrrol-5-yl)hydrazine-1-carboxylate (3.7 g, 14.67 mmol) in DMF (250 mL) was stirred at 145° C. for 12 h. The reaction solution was concentrated. The residue was purified by flash silica gel chromatography (EtOAc/EtOH) to give 5-(5-fluoropyridin-3-yl)-2,5,6,7-tetrahydro-3H-pyrrolo[2,1-c][1,2,4]triazol-3-one. $^1$H NMR (400 MHz, $CD_3OD$) δ 8.46 (d, J=2.4 Hz, 1H), 8.41 (s, 1H), 7.64 (td, J=2.0, 9.2 Hz, 1H), 5.34 (dd, J=5.6, 8.0 Hz, 1H), 3.06-3.18 (m, 1H), 2.93-3.03 (m, 1H), 2.83-2.93 (m, 1H), 2.53-2.47 (m, 1H).

Step 8. Chiral Separation to Afford I-4A

The mixture of 5-(5-fluoropyridin-3-yl)-2,5,6,7-tetrahydro-3H-pyrrolo[2,1-c][1,2,4]triazol-3-one (1.8 g, 8.17 mmol) enantiomers were resolved by Chiral-SFC (Method Column DAICEL CHIRALPAK AD (250 mm×50 mm, 10 um)); Condition 0.1% $NH_3H_2O$/EtOH) to give (R)-5-(5-fluoropyridin-3-yl)-2,5,6,7-tetrahydro-3H-pyrrolo[2,1-c][1,2,4]triazol-3-one (806 mg) (ee=99%) and I-4A ((S)-5-(5-fluoropyridin-3-yl)-2,5,6,7-tetrahydro-3H-pyrrolo[2,1-c][1,2,4]triazol-3-one) (ee=100%).

(R)-5-(5-fluoropyridin-3-yl)-2,5,6,7-tetrahydro-3H-pyrrolo[2,1-c][1,2,4]triazol-3-one $^1$H NMR (500 MHz, $CD_3OD$) δ 8.45 (d, J=2.5 Hz, 1H), 8.41 (s, 1H), 7.63 (td, J=2.0, 9.5 Hz, 1H), 5.34 (dd, J=5.5, 8.0 Hz, 1H), 3.12 (dddd, J=6.0, 8.0, 9.0, 13.47 Hz, 1H), 2.94-3.02 (m, 1H), 2.84-2.92 (m, 1H), 2.50 (tdd, J=6.0, 9.0, 13.5 Hz, 1H).

(S)-5-(5-fluoropyridin-3-yl)-2,5,6,7-tetrahydro-3H-pyrrolo[2,1-c][1,2,4]triazol-3-one (I-4A)

$^1$H NMR (500 MHz, $CD_3OD$) δ 8.45 (d, J=2.5 Hz, 1H), 8.41 (s, 1H), 7.63 (td, J=2.0, 9.5 Hz, 1H), 5.34 (dd, J=5.5, 8.0 Hz, 1H), 3.12 (dddd, J=5.5, 8.0, 9.0, 13.47 Hz, 1H), 2.94-3.02 (m, 1H), 2.84-2.92 (m, 1H), 2.50 (tdd, J=6.0, 9.0, 13.5 Hz, 1H).

Preparation of Intermediate I-5A ((S)-5-(3-fluorophenyl)-2,5,6,7-tetrahydro-3H-pyrrolo[2,1-c][1,2,4]triazol-3-one)

Intermediate I-5A was prepared from pyrrolidine-2,5-dione as outlined below.

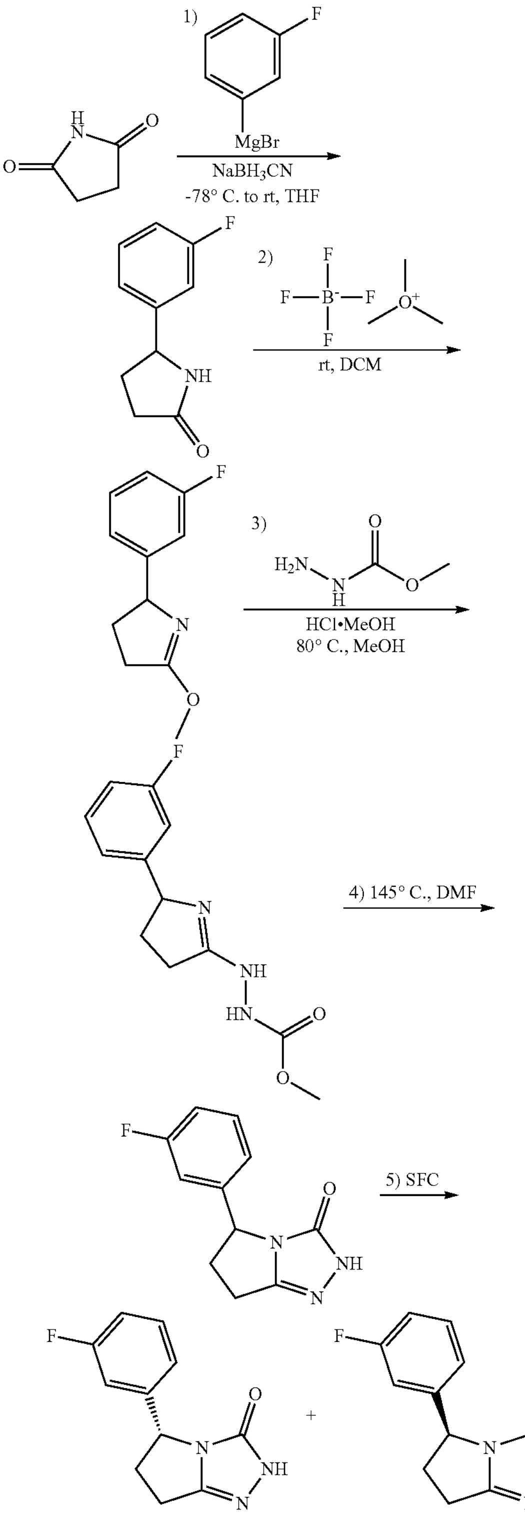

I-5A

Step 1. Preparation of 5-(3-fluorophenyl)pyrrolidin-2-one (3-Fluorophenyl) magnesium bromide (323 mL, 323 mmol) was added to pyrrolidine-2,5-dione (16 g, 161 mmol)

at −78° C. under $N_2$ by syringe dropwise. After the addition was completed, the reaction was allowed to warm up to 25° C. and reacted for another 16 h. Then $NaBH_3CN$ (10.2 g, 161 mmol) was added to the mixture and reacted for another 3 h. 6 M HCl was added and the pH was adjusted to 3. It was reacted for another 1 h. Aqueous NaOH was added to adjust the pH to neutral. The reaction mixture was extracted with EtOAc (80 mL×3). The combined organic phases were washed with brine (50 mL), dried over anhydrous $Na_2SO_4$, filtered and concentrated under reduced pressure. The residue was purified by flash silica gel chromatography (hexanes/ethyl acetate) to give 5-(3-fluorophenyl) pyrrolidin-2-one. Calculated $C_{10}H_{11}FNO$ $[M+H]^+$, 180; Found 180.

Step 2. Preparation of 2-(3-fluorophenyl)-5-methoxy-3,4-dihydro-2H-pyrrole

A mixture of 5-(3-fluorophenyl) pyrrolidin-2-one (10 g, 55.8 mmol) and trimethyloxonium tetrafluoroborate (10.7 g, 72.5 mmol) in DCM (100 mL) was stirred at 25° C. for 16 h to give a brown mixture. Aqueous $NaHCO_3$ was added to adjust the pH to neutral. The organic layer was separated and the aqueous was re-extracted with DCM (30 mL×3) and the combined organic layers were washed with brine (30 mL×2), dried over anhydrous $Na_2SO_4$, filtered and concentrated under reduced pressure to give crude 2-(3-fluorophenyl)-5-methoxy-3,4-dihydro-2H-pyrrole, which was used directly. Calculated $C_{11}H_{13}FNO$ $[M+H]^+$, 194; Found 194.

Step 3. Preparation of methyl 2-(2-(3-fluorophenyl)-3,4-dihydro-2H-pyrrol-5-yl) hydrazine-1-carboxylate A mixture of 2-(3-fluorophenyl)-5-methoxy-3,4-dihydro-2H-pyrrole (10 g, 51.8 mmol) and methyl hydrazinecarboxylate (6.06 g, 67.3 mmol) in MeOH (80 mL) and HCl (2 mL, 4 M in MeOH) was stirred at 80° C. for 6.5 h to give a solution. The solvent was evaporated and the residue was purified by flash silica gel chromatography (ethyl acetate/petroleum ether) to give methyl 2-(2-(3-fluorophenyl)-3,4-dihydro-2H-pyrrol-5-yl) hydrazine-1-carboxylate. Calculated $C_{12}H_{15}FN_3O_2[M+H]^+$, 252; Found 252.

Step 4. Preparation of 5-(3-fluorophenyl)-2,5,6,7-tetrahydro-3H-pyrrolo[2,1-c][1,2,4]triazol-3-one A mixture of methyl 2-(2-(3-fluorophenyl)-3,4-dihydro-2H-pyrrol-5-yl) hydrazine-1-carboxylate (1.3 g, 5.17 mmol) in DMF (100 mL) was stirred in 145° C. for 3 h under $N_2$. Then the reaction mixture was concentrated to give a solid. The solid was suspended in EtOAc and the turbid liquid was filtered and concentrated to give 5-(3-fluorophenyl)-2,5,6,7-tetrahydro-3H-pyrrolo[2,1-c][1,2,4]triazol-3-one. Calculated $C_{11}H_{11}FN_3O$ $[M+H]^+$, 220; Found 220.

Step 5. Preparation of 5-(3-fluorophenyl)-2,5,6,7-tetrahydro-3H-pyrrolo[2,1-c][1,2,4]triazol-3-one 5-(3-Fluorophenyl)-2,5,6,7-tetrahydro-3H-pyrrolo[2,1-c][1,2,4]triazol-3-one (3.7 g, 16.9 mmol) was separated by SFC (Method Column DAICEL CHIRALCEL OD (250 mm×50 mm, 10 um); Condition 0.1% $NH_3H_2O$/EtOH) to give (R)-5-(3-fluorophenyl)-2,5,6,7-tetrahydro-3H-pyrrolo[2,1-c][1,2,4]triazol-3-one (ee=99.6%) and I-5A ((S)-5-(3-fluorophenyl)-2,5,6,7-tetrahydro-3H-pyrrolo[2,1-c][1,2,4]triazol-3-one) (ee=98.9%).

(R)-5-(3-fluorophenyl)-2,5,6,7-tetrahydro-3H-pyrrolo[2,1-c][1,2,4]triazol-3-one $^1H$ NMR (400 MHz, $CD_3OD$) δ 7.35-7.43 (m, 1H), 6.97-7.08 (m, 3H), 5.23 (dd, J=4.4, 8.0 Hz, 1H), 3.00-3.11 (m, 1H), 2.85-2.95 (m, 1H), 2.76-2.85 (m, 1H), 2.34-2.46 (m, 1H).

(S)-5-(3-fluorophenyl)-2,5,6,7-tetrahydro-3H-pyrrolo[2,1-c][1,2,4]triazol-3-one (I-5A)

$^1H$ NMR (400 MHz, $CD_3OD$) δ 7.32-7.43 (m, 1H), 6.96-7.07 (m, 3H), 5.23 (dd, J=4.4, 8.0 Hz, 1H), 3.00-3.11 (m, 1H), 2.86-2.95 (m, 1H), 2.76-2.85 (m, 1H), 2.34-2.46 (m, 1H).

Preparation of Intermediate I-6A ((S)-5-(5-chloropyridin-3-yl)-2,5,6,7-tetrahydro-3H-pyrrolo[2,1-c][1,2,4]triazol-3-one)

Intermediate I-6A was prepared from pyrrolidine-2,5-dione and 3-bromo-5-chloropyridine as outlined below.

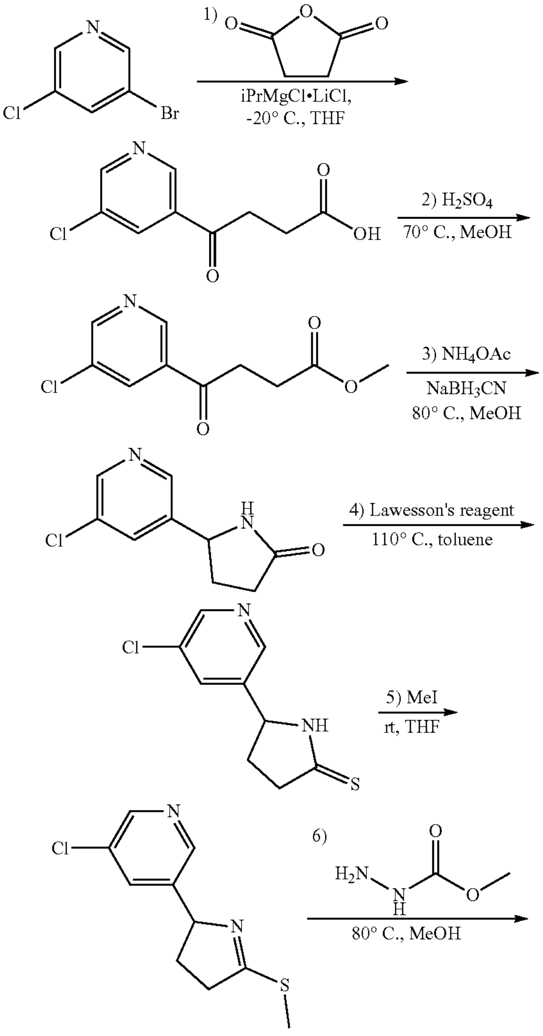

-continued

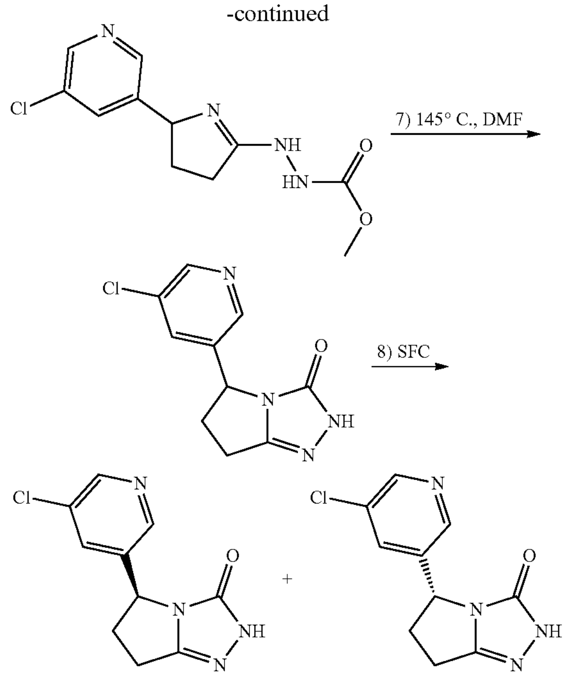

I-6A

Step 1. Preparation of 4-(5-chloropyridin-3-yl)-4-oxobutanoic acid

Isopropylmagnesium chloride (48.0 mL, 52.0 mmol) was added to a solution of 3-bromo-5-chloropyridine (10 g, 52.0 mmol) in THF (100 mL) via syringe over 5 min in 0° C. After stirring for 1 h, this mixture was added to a solution of dihydrofuran-2,5-dione (6.76 g, 67.6 mmol) in THF (100 mL) via cannula over a period of 30 min in −20° C. and then stirred at −20° C. for 3 h. The pH was adjusted to around 9 by progressively adding solution $NaHCO_3$. The aqueous phase was acidified with aq. HCl and extracted with EtOAc (100 mL×5). The combined organic layers were dried over $NaSO_4$ and concentrated into crude product 4-(5-chloropyridin-3-yl)-4-oxobutanoic acid. Calculated $C_9H_9ClNO_3$ $[M+H]^+$, 214; Found 214.

Step 2. Preparation of methyl 4-(5-chloropyridin-3-yl)-4-oxobutanoate

The crude 4-(5-chloropyridin-3-yl)-4-oxobutanoic acid (8 g, 37.5 mmol) was added in MeOH (80 mL). This mixture was stirred for 12 h. After stirring for 3 h, the pH was adjusted to around 9 by progressively adding solution $NaHCO_3$. The combined aqueous layers were extracted with DCM (50 mL×3) to remove neutral impurities. The combined organic layers were dried over $NaSO_4$ and concentrated. The solvent was evaporated and the residue was purified by flash silica gel chromatography (hexanes/ethyl acetate) to give methyl 4-(5-chloropyridin-3-yl)-4-oxobutanoate. Calculated $C_{10}H_{11}ClNO_3$ $[M+H]^+$, 228; Found 228.

Step 3. Preparation of 5-(5-chloropyridin-3-yl)pyrrolidin-2-one

To a solution of methyl 4-(5-chloropyridin-3-yl)-4-oxobutanoate (3.4 g, 14.9 mmol) in MeOH (50 mL) was added ammonium acetate (3.45 g, 44.8 mmol), $NaBH_3CN$ (2.82 g, 44.8 mmol) and the mixture was stirred at 80° C. for 12 h. The combined aqueous layers were extracted with DCM (30 mL×4) to remove neutral impurities. The combined organic layers were dried over $Na_2SO_4$ and concentrated. The organic phase was concentrated and the residue was purified by flash silica gel chromatography (EtOAc/EtOH) to give 5-(5-chloropyridin-3-yl)pyrrolidin-2-one. Calculated $C_9H_{10}ClN_2O$ $[M+H]^+$, 197; Found 197.

Step 4. Preparation of 5-(5-chloropyridin-3-yl)pyrrolidine-2-thione

To a solution of 5-(5-chloropyridin-3-yl)pyrrolidin-2-one (700 mg, 3.56 mmol) in toluene (15 ml) was added Lawesson's reagent (720 mg, 1.78 mmol) and the resulting mixture was stirred at 110° C. for 12 h. The reaction solution was directly concentrated and the residue was purified by flash silica gel chromatography (ethyl acetate/petroleum ether) to give 5-(5-chloropyridin-3-yl)pyrrolidine-2-thione. Calculated $C_9H_{10}ClN_2S$ $[M+H]^+$, 213; Found 213.

Step 5. Preparation of 3-chloro-5-(5-(methylthio)-3,4-dihydro-2H-pyrrol-2-yl)pyridine To a solution of 5-(5-chloropyridin-3-yl)pyrrolidine-2-thione (1.45 g, 6.82 mmol) in THF (20 ml) was added iodomethane (1.20 mL, 19.2 mmol) and the resulting mixture was stirred at 20° C. for 12 h. The reaction solution was concentrated to give crude product 3-chloro-5-(5-(methylthio)-3,4-dihydro-2H-pyrrol-2-yl)pyridine, which was used in the next step without further purification. Calculated $C_{10}H_{12}ClN_2S$ $[M+H]^+$, 227; Found 227.

Step 6. Preparation of methyl 2-(2-(5-chloropyridin-3-yl)-3,4-dihydro-2H-pyrrol-5-yl)hydrazine-1-carboxylate To a solution of 3-chloro-5-(5-(methylthio)-3,4-dihydro-2H-pyrrol-2-yl)pyridine (1.3 g, 5.73 mmol) in MeOH (15 ml) was added methyl hydrazinecarboxylate (0.775 g, 8.60 mmol) and the resulting mixture was stirred at 80° C. for 5 h. The reaction solution was directly concentrated and the residue was purified by flash silica gel chromatography (EtOAc/EtOH) to give methyl 2-(2-(5-chloropyridin-3-yl)-3,4-dihydro-2H-pyrrol-5-yl)hydrazine-1-carboxylate. Calculated $C_{11}H_{14}ClN_4O_2$$[M+H]^+$, 269; Found 269.

Step 7. Preparation of 5-(5-chloropyridin-3-yl)-2,5,6,7-tetrahydro-3H-pyrrolo[2,1-c][1,2,4]triazol-3-one To a solution of methyl 2-(2-(5-chloropyridin-3-yl)-3,4-dihydro-2H-pyrrol-5-yl)hydrazine-1-carboxylate (1.1 g, 4.09 mmol) in DMF (50 ml) was stirred at 145° C. for 12 h. The reaction solution was directly concentrated. The residue was purified by flash silica gel chromatography (EtOAc/EtOH) to give 5-(5-chloropyridin-3-yl)-2,5,6,7-tetrahydro-3H-pyrrolo[2,1-c][1,2,4]triazol-3-one. Calculated $C_{10}H_{10}ClN_4O$ $[M+H]^+$, 237; Found 237.

Step 8. Chiral Separation to Afford I-6A

The mixture of 5-(5-chloropyridin-3-yl)-2,5,6,7-tetrahydro-3H-pyrrolo[2,1-c][1,2,4]triazol-3-one (700 mg, 2.96 mmol) enantiomers were resolved by Chiral-SFC (Method Column DAICEL CHIRALPAK AD (250 mm×30 mm, 10 um); Condition 0.1% $NH_3H_2O$/EtOH) to give I-6A ((S)-5-(5-chloropyridin-3-yl)-2,5,6,7-tetrahydro-3H-pyrrolo[2,1-c]

[1,2,4]triazol-3-one) (retention time=4.96 min) and (R)-5-(5-chloropyridin-3-yl)-2,5,6,7-tetrahydro-3H-pyrrolo[2,1-c][1,2,4]triazol-3-one (retention time=4.96 min).

(S)-5-(5-chloropyridin-3-yl)-2,5,6,7-tetrahydro-3H-pyrrolo[2,1-c][1,2,4]triazol-3-one (I-6A)

$^1$H NMR (400 MHz, $CD_3OD$) δ=8.54 (d, J=2.3 Hz, 1H), 8.47 (d, J=1.9 Hz, 1H), 7.86 (t, J=2.1 Hz, 1H), 5.31 (dd, J=5.6, 8.1 Hz, 1H), 3.19-3.05 (m, 1H), 3.04-2.82 (m, 2H), 2.50 (tdd, J=6.1, 9.0, 13.2 Hz, 1H).

(R)-5-(5-chloropyridin-3-yl)-2,5,6,7-tetrahydro-3H-pyrrolo[2,1-c][1,2,4]triazol-3-one $^1$H NMR (400 MHz, $CD_3OD$) δ=8.54 (d, J=2.3 Hz, 1H), 8.47 (d, J=1.9 Hz, 1H), 7.86 (t, J=2.1 Hz, 1H), 5.31 (dd, J=5.7, 8.0 Hz, 1H), 3.19-3.05 (m, 1H), 3.04-2.82 (m, 2H), 2.57-2.44 (m, 1H).

Preparation of Intermediate I-7A (methyl 3-oxo-2,5,6,7-tetrahydro-3H-pyrrolo[2,1-c][1,2,4]triazole-5-carboxylate)

Intermediate I-7A was prepared from methyl 5-oxopyrrolidine-2-carboxylate as outlined below.

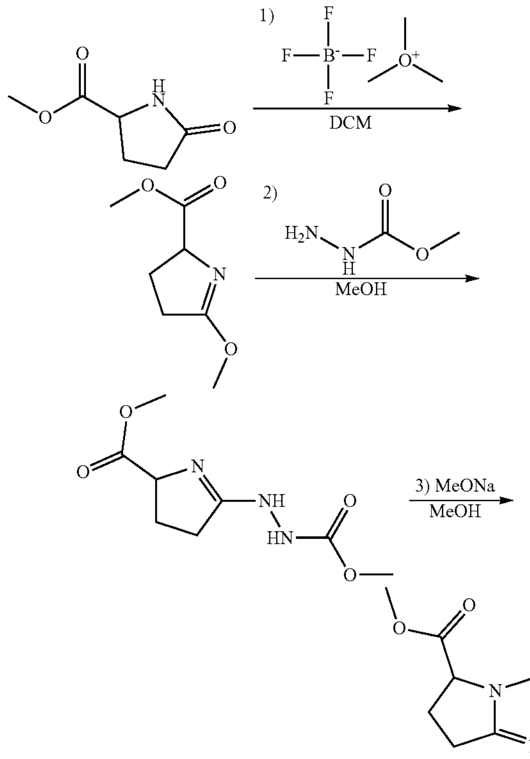

I-7A

Step 1. Preparation of methyl 5-methoxy-3,4-dihydro-2H-pyrrole-2-carboxylate

To a solution of methyl 5-oxopyrrolidine-2-carboxylate (50 g, 349 mmol) in $CH_2Cl_2$ (800 mL) was added dimethyloxonium tetrafluoroborate (70.1 g, 524 mmol) at 0° C. The mixture was stirred at 25° C. for 12 h. The mixture was quenched with sat. aq. $NaHCO_3$ (400 mL), extracted with DCM (200 mL×2). The combined organic layers were dried over $Na_2SO_4$, filtered and concentrated in vacuum to give crude methyl 5-methoxy-3,4-dihydro-2H-pyrrole-2-carboxylate, which was used to next step without further purification. Calculated $C_7H_{12}NO_3$ $[M+H]^+$, 158; Found 158.

Step 2. Preparation of methyl 5-(2-(methoxycarbonyl)hydrazinyl)-3,4-dihydro-2H-pyrrole-2-carboxylate To a solution of methyl 5-methoxy-3,4-dihydro-2H-pyrrole-2-carboxylate (55 g, 350 mmol) in MeOH (800 mL) was added methyl hydrazinecarboxylate (47.3 g, 525 mmol), HCl/MeOH (4 M) (50 mL) at 20° C. and the resulting mixture was stirred at 80° C. for 4 h. The reaction was directly concentrated and the residue was slurried with ethyl acetate and MeOH to give methyl 5-(2-(methoxycarbonyl)hydrazineyl)-3,4-dihydro-2H-pyrrole-2-carboxylate. Calculated $C_8H_{14}N_3O_4$ $[M+H]^+$, 216; Found 216. $^1$H NMR (400 MHz, $CD_3OD$) δ 4.73 (dd, J=4.8, 9.2 Hz, 1H), 3.80 (s, 3H), 3.80 (s, 3H), 2.99-3.09 (m, 2H), 2.68 (qd, J=8.8, 13.2 Hz, 1H), 2.35-2.43 (m, 1H).

Step 3. Preparation of I-7A (methyl 3-oxo-2,5,6,7-tetrahydro-3H-pyrrolo[2,1-c][1,2,4]triazole-5-carboxylate)

To a solution of methyl 5-(2-(methoxycarbonyl)hydrazineyl)-3,4-dihydro-2H-pyrrole-2-carboxylate (20.0 g, 93.0 mmol) in MeOH (400 mL) was added sodium methanolate (15.1 g, 279 mmol) and the resulting mixture was stirred at 80° C. for 8 h. To the reaction was added HCl (4.0 M in MeOH) until pH-5 and stirred at 80° C. for 2 h. The solid was filtered and the filtrate was purified by flash silica gel chromatography (MeOH/DCM) to give methyl 3-oxo-2,5,6,7-tetrahydro-3H-pyrrolo[2,1-c][1,2,4]triazole-5-carboxylate. Calculated $C_7H_{10}N_3O_3[M+H]^+$, 184; Found 184. $^1$H NMR (400 MHz, $CD_3OD$) δ 4.74 (dd, J=3.2, 9.2 Hz, 1H), 3.80 (s, 3H), 2.93-3.05 (m, 1H), 2.75-2.88 (m, 2H), 2.57-2.67 (m, 1H).

Preparation of Intermediate I-8A ((S)-5-(4-fluorophenyl)-2,5,6,7-tetrahydro-3H-pyrrolo[2,1-c][1,2,4]triazol-3-one)

Intermediate I-8A was prepared from pyrrolidine-2,5-dione as outlined below.

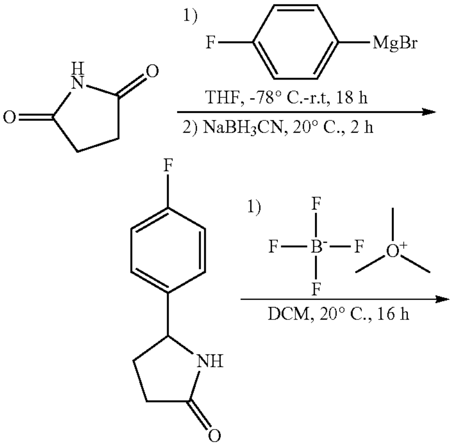

-continued

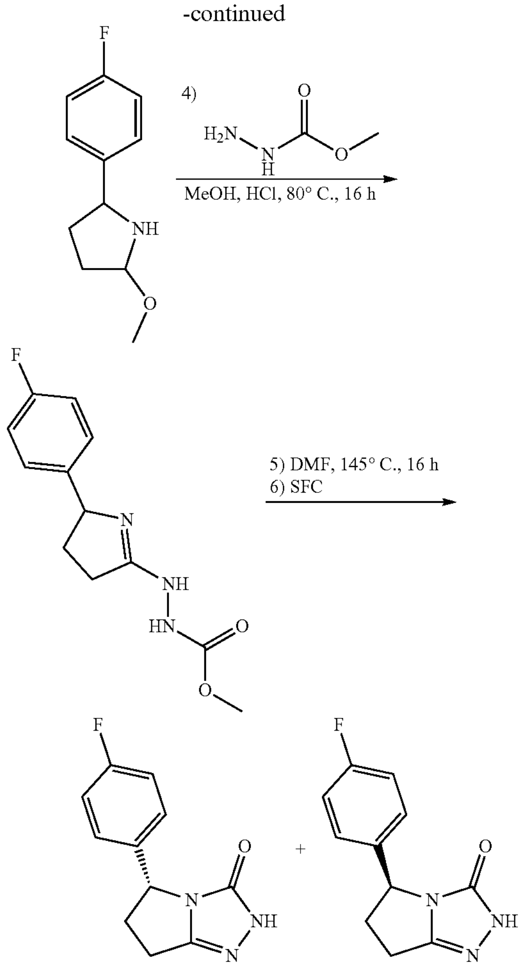

I-8A

Steps 1-2. Preparation of 5-(4-fluorophenyl)pyrrolidin-2-one (4-Fluorophenyl)magnesium bromide in THF (404 mL, 404 mmol) was added to pyrrolidine-2,5-dione (20 g, 202 mmol) at −78° C. under $N_2$ by syringe dropwise. After the addition was completed, the reaction was allowed to warm up to 25° C. and reacted for another 2.5 h. Then $NaBH_3CN$ (12.68 g, 202 mmol) was added to the mixture and reacted for another 16 h. HCl (6M in water) was added and the pH was adjusted to 3. The reaction was stirred for another 1 h. NaOH (25 mL EtOH+5 mL water) was added to adjust the pH to neutral. The reaction mixture was extracted with EtOAc (200 mL×3). The combined organic phases were washed with brine (200 mL), dried over anhydrous $Na_2SO_4$, filtered, and concentrated under reduced pressure. The residue was purified by flash silica gel chromatography (EtOAc/hexanes) to give 5-(4-fluorophenyl)pyrrolidin-2-one. Calculated $C_{10}H_{11}FNO$ $[M+H]^+$, 180; Found 180. $^1H$ NMR (400 MHz, $CDCl_3$) δ 7.31-7.24 (m, 2H), 7.10-7.02 (m, 2H), 6.30 (br s, 1H), 4.75 (t, J=7.1 Hz, 1H), 2.65-2.34 (m, 3H), 2.01-1.86 (m, 1H).

Step 3. Preparation of 2-(4-fluorophenyl)-5-methoxy-3,4-dihydro-2H-pyrrole

A mixture of 5-(4-fluorophenyl)pyrrolidin-2-one (3.2 g, 17.9 mmol) and trimethyloxonium tetrafluoroborate (3.43 g, 23.2 mmol) in DCM (10 mL) was stirred at 25° C. for 16 h. The residue was diluted in a mixture of sat. aq. $NaHCO_3$ (10 mL) and DCM (10 mL). The organic layer was separated and the aqueous layer was re-extracted with DCM (10 mL×3) and the combined organic layers were washed with brine (10 mL), dried over anhydrous $Na_2SO_4$, filtered, and concentrated under reduced pressure to give crude 2-(4-fluorophenyl)-5-methoxy-3,4-dihydro-2H-pyrrole, which was used directly in the next step without further purification. Calculated $C_{11}H_{13}FNO$ $[M+H]^+$, 194; Found 194.

Step 4. Preparation of methyl 2-(2-(4-fluorophenyl)-3,4-dihydro-2H-pyrrol-5-yl)hydrazine-1-carboxylate A mixture of 2-(4-fluorophenyl)-5-methoxy-3,4-dihydro-2H-pyrrole (2.9 g, crude) and methyl hydrazinecarboxylate (1.76 g, 19.51 mmol) in MeOH (32 mL) and HCl (4 M in MeOH, 0.5 mL) was stirred at 80° C. for 4 h. The solvent was evaporated and the residue was purified by flash silica gel chromatography (MeCN in water) to give methyl 2-(2-(4-fluorophenyl)-3,4-dihydro-2H-pyrrol-5-yl)hydrazine-1-carboxylate. Calculated $C_{12}H_{15}FN_3O_2[M+H]^+$, 252; Found 252. $^1H$ NMR (500 MHz, DMSO-$d_6$) δ 8.85 (br s, 1H), 7.45-7.28 (m, 2H), 7.18 (t, J=8.8 Hz, 2H), 7.02 (br s, 1H), 3.57 (s, 3H), 3.33 (br s, 1H), 2.48-2.39 (m, 2H), 2.37-2.28 (m, 1H), 2.37-2.28 (m, 1H), 1.76-1.58 (m, 1H).

Step 5. Preparation of 5-(4-fluorophenyl)-2,5,6,7-tetrahydro-3H-pyrrolo[2,1-c][1,2,4]triazol-3-one A mixture of methyl 2-(2-(4-fluorophenyl)-3,4-dihydro-2H-pyrrol-5-yl)hydrazine-1-carboxylate (2.2 g, 8.76 mmol) in DMF (100 mL) was stirred at 145° C. for 16 h. The solvent was evaporated and the residue was purified by flash silica gel chromatography (EtOAc in hexanes) to give 5-(4-fluorophenyl)-2,5,6,7-tetrahydro-3H-pyrrolo[2,1-c][1,2,4]triazol-3-one. Calculated $C_{11}H_{11}FN_3O$ $[M+H]^+$, 220; Found 220. $^1H$ NMR (500 MHz, DMSO-$d_6$) δ 11.26 (s, 1H), 7.35-7.26 (m, 2H), 7.24-7.14 (m, 2H), 5.17 (dd, J=4.5, 8.2 Hz, 1H), 3.00-2.88 (m, 1H), 2.87-2.78 (m, 1H), 2.77-2.68 (m, 1H), 2.31-2.21 (m, 1H).

Step 6. Chiral SFC to afford (S)-5-(4-fluorophenyl)-2,5,6,7-tetrahydro-3H-pyrrolo[2,1-c][1,2,4]triazol-3-one (I-8A)

5-(4-Fluorophenyl)-2,5,6,7-tetrahydro-3H-pyrrolo[2,1-c][1,2,4]triazol-3-one (2.5 g, 11.40 mmol) was purified by SFC (Method Column DAICEL CHIRALCEL OD (250 mm×50 mm, 10 um); Condition 0.1% $NH_3H_2O$/EtOH) to give (R)-5-(4-fluorophenyl)-2,5,6,7-tetrahydro-3H-pyrrolo[2,1-c][1,2,4]triazol-3-one (t=0.991 min) as the first eluting peak, and (S)-5-(4-fluorophenyl)-2,5,6,7-tetrahydro-3H-pyrrolo[2,1-c][1,2,4]triazol-3-one (t=1.100 min) as the second eluting peak.

(R)-5-(4-fluorophenyl)-2,5,6,7-tetrahydro-3H-pyrrolo[2,1-c][1,2,4]triazol-3-one $^1H$ NMR (500 MHz, DMSO-$d_6$) δ 11.26 (s, 1H) 7.26-7.33 (m, 2H) 7.16-7.23 (m, 2H) 5.17 (dd, J=8.01, 4.50 Hz, 1H) 2.90-2.98 (m, 1H) 2.79-2.86 (m, 1H) 2.69-2.75 (m, 1H) 2.22-2.30 (m, 1H).

(S)-5-(4-fluorophenyl)-2,5,6,7-tetrahydro-3H-pyrrolo[2,1-c][1,2,4]triazol-3-one (I-8A)

$^1H$ NMR (500 MHz, DMSO-$d_6$) δ 11.26 (s, 1H) 7.26-7.32 (m, 2H) 7.17-7.23 (m, 2H) 5.17 (dd, J=8.09, 4.58 Hz, 1H) 2.90-2.99 (m, 1H) 2.78-2.87 (m, 1H) 2.69-2.77 (m, 1H) 2.26 (qd, J=8.90, 5.04 Hz, 1H).

Preparation of Intermediate I-9A (5-(2,6-difluorophenyl)-2,5,6,7-tetrahydro-3H-pyrrolo[2,1-c][1,2,4]triazol-3-one)

Intermediate I-9A was prepared from 1-(2,6-difluorophenyl)ethan-1-one as outlined below.

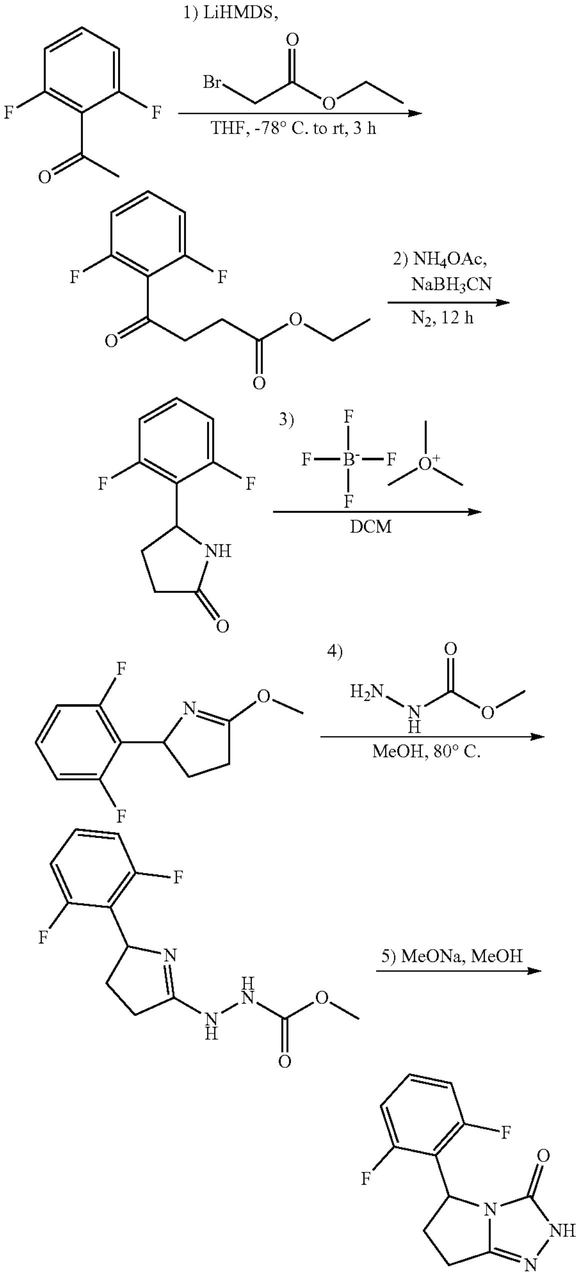

I-9A

Step 1. Preparation of ethyl 4-(2,6-difluorophenyl)-4-oxobutanoate

To a stirred solution of 1-(2,6-difluorophenyl)ethan-1-one (5 g, 32.0 mmol) in THF (150 mL) and 1,3-dimethyltetrahydropyrimidin-2(1H)-one (8.21 g, 64.0 mmol) was added lithium bis(trimethylsilyl)amide (32.0 mL, 32.0 mmol) (1 M in THF) at −78° C. After the addition was finished, the reaction was stirred at −78° C. for 30 min. Then ethyl 2-bromoacetate (3.73 mL, 33.6 mmol) was added to the above mixture in one portion at −78° C. After the addition was finished, the reaction was stirred at 20° C. for 2 h. LCMS showed the reaction was finished. The mixture was diluted with tert-butyl methyl ether (200 mL) and quenched with sat. aq. $NH_4Cl$ (200 mL). The mixture was extracted with tert-butyl methyl ether (200 mL×2). The combined organic fractions were washed with brine (200 mL), dried over anhydrous $Na_2SO_4$, filtered, and concentrated in vacuo. The residue was purified by flash silica gel chromatography (EtOAc in hexanes) to give ethyl 4-(2,6-difluorophenyl)-4-oxobutanoate. Calculated $C_{12}H_{13}F_2O_3$ $[M+H]^+$, 243; Found 243.

Step 2. Preparation of 5-(2,6-difluorophenyl)pyrrolidin-2-one

To a solution of ethyl 4-(2,6-difluorophenyl)-4-oxobutanoate (2.8 g, 11.6 mmol) in EtOH (20 mL) was added acetic acid, ammonia salt (13.4 g, 173 mmol), sodium cyanoborohydride (1.45 g, 23.1 mmol) and the reaction was stirred at 90° C. for 12 h. Water (50 mL) was added. The mixture was extracted with ethyl acetate (50 mL). The organic layer was separated and the aqueous layer was re-extracted with EtOAc (50 mL×3). The combined organic layers were washed with brine (50 mL), dried over anhydrous $Na_2SO_4$, filtered, and concentrated. The residue was purified by flash silica gel chromatography (EtOAc in hexanes) to give 5-(2,6-difluorophenyl)pyrrolidin-2-one. Calculated $C_{10}H_{10}F_2NO$ $[M+H]^+$, 198; Found 198.

Step 3. Preparation of 2-(2,6-difluorophenyl)-5-methoxy-3,4-dihydro-2H-pyrrole

To a solution of 5-(2,6-difluorophenyl)pyrrolidin-2-one (1.8 g, 9.13 mmol) in DCM (50 mL) was added trimethyloxonium tetrafluoroborate (2.03 g, 13.7 mmol) at 0° C. under $N_2$. The mixture was stirred at 25° C. for 15 h. The mixture was quenched with sat. aq. $NaHCO_3$ (50 mL), and extracted with DCM (50 mL×2). The combined organic layers were dried over $Na_2SO_4$, filtered, and concentrated in vacuum to give crude 2-(2,6-difluorophenyl)-5-methoxy-3,4-dihydro-2H-pyrrole, which was used in the next step without further purification. Calculated $C_{11}H_{12}F_2NO$ $[M+H]^+$, 212; Found 212.

Step 4. Preparation of methyl 2-(2-(2,6-difluorophenyl)-3,4-dihydro-2H-pyrrol-5-yl)hydrazine-1-carboxylate To a solution of 2-(3,5-difluorophenyl)-5-methoxy-3,4-dihydro-2H-pyrrole (1.7 g, 8.05 mmol) in MeOH (34 mL) was added methyl hydrazinecarboxylate (0.761 g, 8.45 mmol) and HCl (1 mL, 4 M in MeOH) at 20° C. and the resulting mixture was stirred at 80° C. for 2 h under $N_2$. The mixture was concentrated in vacuum, and the crude residue was washed with EtOAc and hexanes and filtered to give crude methyl 2-(2-(2,6-difluorophenyl)-3,4-dihydro-2H- pyrrol-5-yl)hydrazine-1-carboxylate, which was used in the next step without further purification. Calculated $C_{12}H_{14}F_2N_3O_2[M+H]^+$, 270; Found 270.

Step 5. Preparation of I-9A (5-(2,6-difluorophenyl)-2,5,6,7-tetrahydro-3H-pyrrolo[2,1-c][1,2,4]triazol-3-one)

To a solution of methyl 2-(2-(2,6-difluorophenyl)-3,4-dihydro-2H-pyrrol-5-yl)hydrazine-1-carboxylate (1.1 g, 4.09 mmol) in MeOH (25 mL) was added sodium methoxide (0.662 g, 12.3 mmol) and the resulting mixture was stirred at 80° C. for 8 h. The mixture was cooled to RT and acidified to pH=7 with HCl (4 M in MeOH). Then the mixture was filtered and the solid was dried by vacuum distillation to give 5-(2,6-difluorophenyl)-2,5,6,7-tetrahydro-3H-pyrrolo[2,1-c][1,2,4]triazol-3-one. Calculated $C_{11}H_{10}F_2N_3O$ $[M+H]^+$, 238; Found 238. $^1H$ NMR (400 MHz, $CD_3OD$) δ 7.36-7.49 (m, 1H), 6.94-7.12 (m, 2H), 5.60 (dd, J=5.2, 8.8 Hz, 1H), 3.08-3.21 (m, 1H), 2.87-3.06 (m, 2H), 2.54-2.66 (m, 1H).

Preparation of Intermediate I-10A (5-(3,4-difluorophenyl)-2,5,6,7-tetrahydro-3H-pyrrolo[2,1-c][1,2,4]triazol-3-one)

Intermediate I-10A was prepared from pyrrolidine-2,5-dione and (3,4-difluorophenyl) magnesium bromide as outlined below.

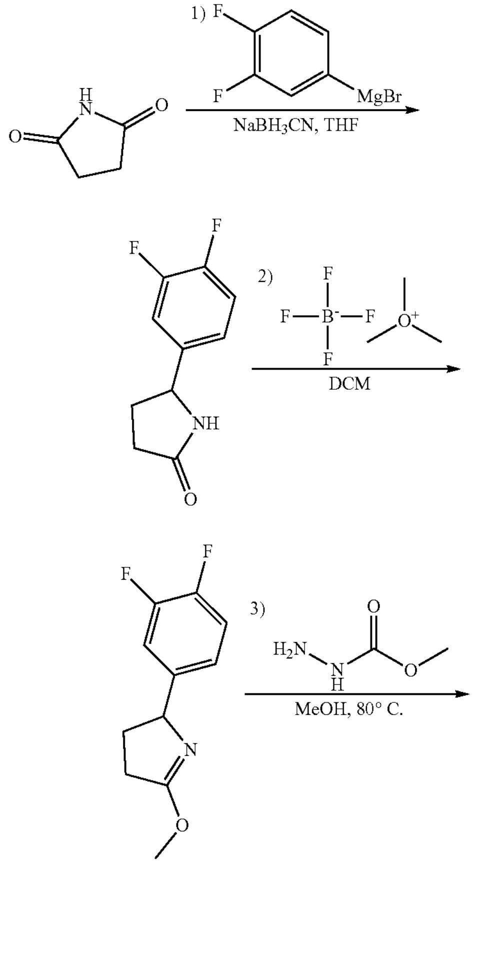

-continued

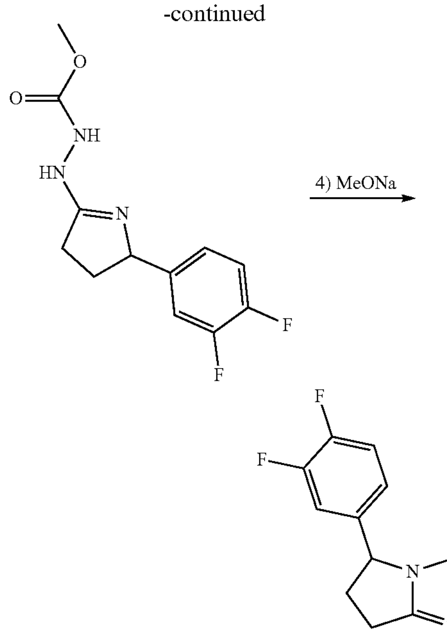

I-10A

Step 1. Preparation of 5-(3,4-difluorophenyl)pyrrolidin-2-one

To a solution of (3,4-difluorophenyl)magnesium bromide (60.6 mL, 30.3 mmol) in THF (15 mL) was added isopropylmagnesium chloride lithium chloride complex solution (17.47 mL, 22.71 mmol) at −78° C. under $N_2$. Then the reaction was stirred at −78° C. for 1 h. To another solution of pyrrolidine-2,5-dione (2.5 g, 25.2 mmol) in THF (50 mL) was added above at −78° C. under $N_2$. The mixture was stirred at 25° C. for 16 h. Then to the mixture was added $NaBH_3CN$ (1.74 g, 27.8 mmol) at 25° C. and the mixture was stirred at 25° C. for 1 h. The reaction was acidified to pH=3-4 with HCl (6 M in water), and the resulting mixture was stirred for 1 h and neutralized with NaOH (4 M in water). The mixture was quenched with water (20 mL), extracted with EtOAc (10 mL×3). The combined organic layers were dried over $Na_2SO_4$, filtered, and concentrated in vacuum, and the residue was purified by flash silica gel chromatography (EtOAc) to give 5-(3,4-difluorophenyl)pyrrolidin-2-one. Calculated $C_{10}H_{10}F_2NO$ $[M+H]^+$, 198; Found 198. $^1H$ NMR (400 MHz, $CD_3OD$) δ 7.20-7.32 (m, 2H), 7.14 (ddd, J=4.0 Hz, 1H), 4.79 (t, J=7.6 Hz, 1H), 2.53-2.66 (m, 1H), 2.38-2.47 (m, 2H), 1.85-1.97 (m, 1H).

Step 2. Preparation of 2-(3,4-difluorophenyl)-5-methoxy-3,4-dihydro-2H-pyrrole To a solution of 5-(3,4-difluorophenyl)pyrrolidin-2-one (1 g, 5.07 mmol) in DCM (10 mL) was added trimethyloxonium tetrafluoroborate (1.13 g, 7.61 mmol) at 0° C. under $N_2$. The mixture was stirred at 25° C. for 15 h. The mixture was quenched with sat. aq. $NaHCO_3$ (10 mL), and extracted with DCM (10 mL×2). The combined organic layers were dried over $Na_2SO_4$, filtered, and concentrated in vacuum to give crude 2-(3,4-difluorophenyl)-5-methoxy-3,4-dihydro-2H-pyrrole, which was used in the next step without further purification. Calculated $C_{11}H_{12}F_2NO$ $[M+H]^+$, 212; Found 212.

Step 3. Preparation of methyl 2-(2-(3,4-difluorophenyl)-3,4-dihydro-2H-pyrrol-5-yl)hydrazine-1-carboxylate To a solution of 2-(3,4-difluorophenyl)-5-methoxy-3,4-dihydro-2H-pyrrole (1 g, 4.73 mmol) in MeOH (10 mL) was added methyl hydrazinecarboxylate (0.448 g, 4.97 mmol) and HCl (2 mL, 4 M in MeOH) at 20° C. and the resulting mixture was stirred at 80° C. for 12 h. The reaction was directly concentrated and the residue was purified by recrystallization to give methyl 2-(2-(3,4-difluorophenyl)-3,4-dihydro-2H-pyrrol-5-yl)hydrazine-1-carboxylate. Calculated $C_{12}H_{14}F_2N_3O_2[M+H]^+$, 270; Found 270. $^1$H NMR (400 MHz, $CD_3OD$) δ 7.28-7.38 (m, 2H), 7.20 (br d, J=8.8 Hz, 1H), 5.17 (t, J=7.6 Hz, 1H), 3.78-3.81 (m, 3H), 3.07-3.15 (m, 2H), 2.73-2.84 (m, 1H), 2.10-2.21 (m, 1H)

Step 4. Preparation of I-10A

To a solution of methyl 2-(2-(3,4-difluorophenyl)-3,4-dihydro-2H-pyrrol-5-yl)hydrazine-1-carboxylate (1.1 g, 4.09 mmol) in MeOH (20 mL) was added sodium methoxide (0.662 g, 12.3 mmol) and the resulting mixture was stirred at 80° C. for 8 h. The mixture was cooled to RT and acidified to pH=7 with HCl (4 M in MeOH). Then the mixture was filtered and the solid was dried by vacuum distillation to give 5-(3,4-difluorophenyl)-2,5,6,7-tetrahydro-3H-pyrrolo[2,1-c][1,2,4]triazol-3-one. Calculated $C_{11}H_{10}F_2N_3O$ $[M+H]^+$, 238; Found 238. $^1$H NMR (500 MHz, $CD_3OD$) δ 7.20-7.32 (m, 2H), 7.09 (ddd, J=4.5 Hz, 1H), 5.22 (dd, J=5.5 Hz, 1H), 3.02-3.13 (m, 1H), 2.90-2.98 (m, 1H), 2.79-2.88 (m, 1H), 2.43 (tdd, J=13.5 Hz, 1H), 1.90-2.08 (m, 1H).

Preparation of Intermediate I-11A (5-(4-chlorophenyl)-2,5,6,7-tetrahydro-3H-pyrrolo[2,1-c][1,2,4]triazol-3-one)

Intermediate I-11A was prepared from pyrrolidine-2,5-dione as outlined below.

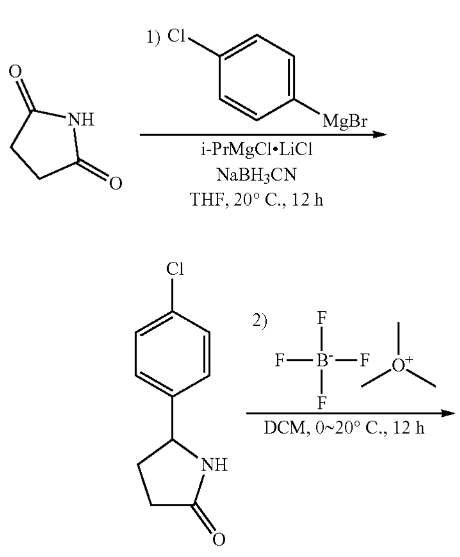

-continued

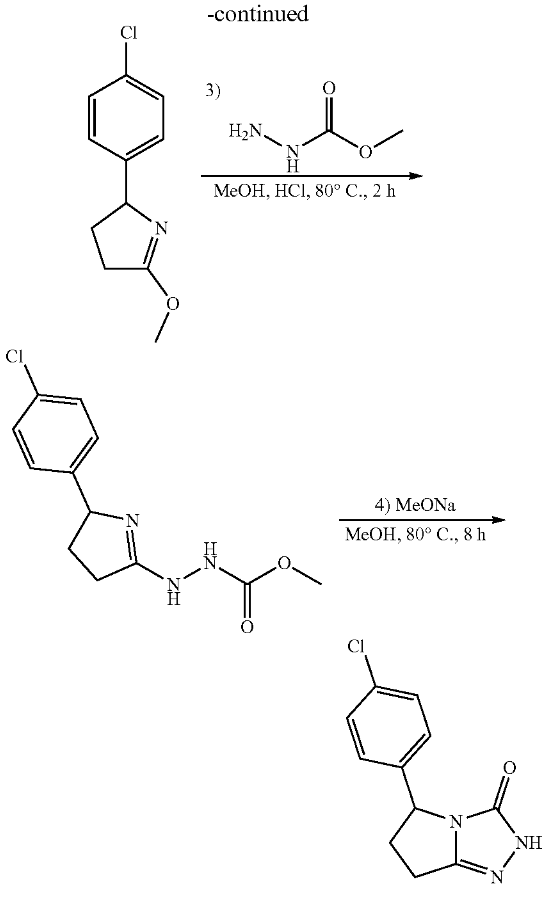

I-11A

Step 1. Preparation of 5-(4-chlorophenyl)pyrrolidin-2-one

To a solution of (4-chlorophenyl) magnesium bromide (60.6 mL, 60.6 mmol) in THF (200 mL) was added isopropylmagnesium chloride lithium chloride complex solution (34.9 mL, 45.4 mmol) at 0° C. under $N_2$. Then the reaction was stirred at 0° C. for 1 h. To another solution of pyrrolidine-2,5-dione (5 g, 50.5 mmol) in THF (100 mL) was added above at −78° C. under $N_2$. The mixture was stirred at 25° C. for 16 h. Then to the mixture was added $NaBH_3CN$ (3.49 g, 55.5 mmol) at 25° C. and the mixture was stirred at 25° C. for 1 h. The reaction was acidified to pH=3-4 with HCl (6 M in water), and the resulting mixture was stirred for 1 h and neutralized with NaOH (4 M in water). The mixture was quenched with water (500 mL), and extracted with EtOAc (500 mLx3). The combined organic layers were dried over $Na_2SO_4$, filtered, and concentrated in vacuum, and the residue was purified by flash silica gel chromatography (EtOAc) to give 5-(4-chlorophenyl)pyrrolidin-2-one. $^1$H NMR ($CDCl_3$, 400 MHz) δ 7.31-7.37 (m, 2H), 7.20-7.26 (m, 2H), 4.73 (t, J=7.2 Hz, 1H), 2.49-2.62 (m, 1H), 2.30-2.46 (m, 2H), 1.83-1.98 ppm (m, 1H).

Step 2. Preparation of 2-(4-chlorophenyl)-5-methoxy-3,4-dihydro-2H-pyrrole

To a solution of 5-(4-chlorophenyl)pyrrolidin-2-one (12 g, 61.3 mmol) in DCM (300 mL) was added trimethyloxonium tetrafluoroborate (13.6 g, 92 mmol) at 0° C. under $N_2$.

The mixture was stirred at 25° C. for 15 h. The mixture was quenched with sat. aq. $NaHCO_3$ (50 mL), and extracted with DCM (50 mL×2). The combined organic layers were dried over $Na_2SO_4$, filtered, and concentrated in vacuum to give crude 2-(4-chlorophenyl)-5-methoxy-3,4-dihydro-2H-pyrrole, which was used in the next step without further purification. Calculated $C_{11}H_{13}ClNO$ $[M+H]^+$, 210; Found 210.

Step 3. Preparation of methyl 2-(2-(4-chlorophenyl)-3,4-dihydro-2H-pyrrol-5-yl)hydrazine-1-carboxylate To a solution of 2-(4-chlorophenyl)-5-methoxy-3,4-dihydro-2H-pyrrole (6 g, 28.6 mmol) in MeOH (200 mL) was added methyl hydrazinecarboxylate (3.35 g, 37.2 mmol) and HCl (15 mL, 4 M in MeOH) at 20° C. and the resulting mixture was stirred at 80° C. for 6 h under $N_2$. The mixture was concentrated under reduced pressure, and the residue was then washed with EtOAc/PE (1:1) to give methyl 2-(2-(4-chlorophenyl)-3,4-dihydro-2H-pyrrol-5-yl)hydrazine-1-carboxylate. Calculated $C_{12}H_{15}ClN_3O_2[M+H]^+$, 268; Found 268.

Step 4. Preparation of I-11A

To a solution of methyl 2-(2-(4-chlorophenyl)-3,4-dihydro-2H-pyrrol-5-yl)hydrazine-1-carboxylate (5.9 g, 22.0 mmol) in MeOH (150 mL) was added sodium methoxide (3.57 g, 66.1 mmol) and the resulting mixture was stirred at 80° C. for 8 h. The mixture was cooled to RT and acidified to pH=7 with HCl (4 M in MeOH). Then the mixture was filtered and the solid was dried by vacuum distillation to give 5-(4-chlorophenyl)-2,5,6,7-tetrahydro-3H-pyrrolo[2,1-c][1,2,4]triazol-3-one. Calculated $C_{11}H_{11}ClN_3O$ $[M+H]^+$, 236; Found 236.

Preparation of Intermediate I-12A (5-(2,4-difluorophenyl)-2,5,6,7-tetrahydro-3H-pyrrolo[2,1-c][1,2,4]triazol-3-one)

Intermediate I-12A was prepared from 1-(2,4-difluorophenyl)ethan-1-one as outlined below.

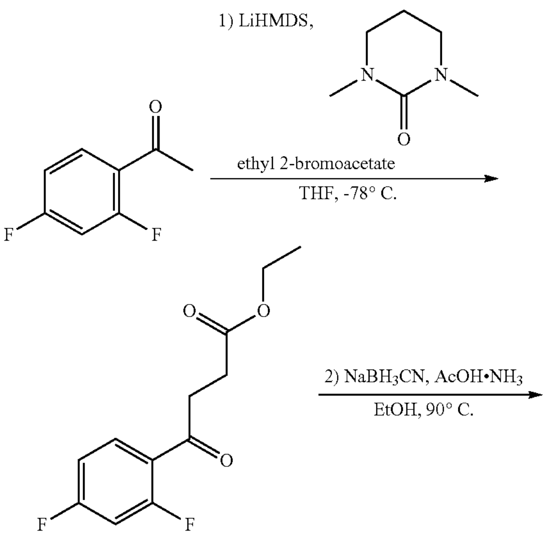

-continued

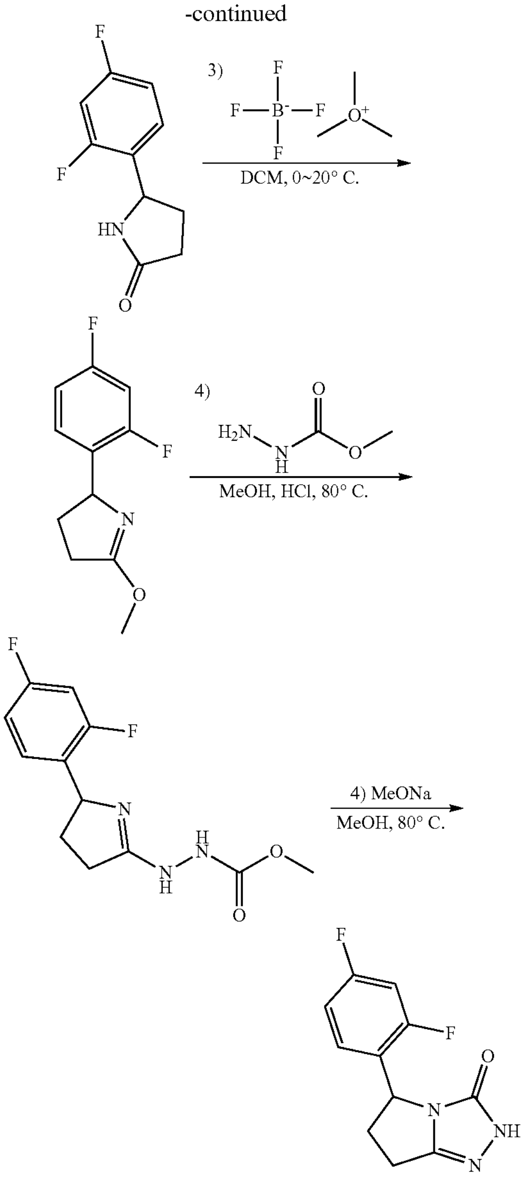

I-12A

Step 1. Preparation of ethyl 4-(2,4-difluorophenyl)-4-oxobutanoate

To a stirred solution of 1-(2,4-difluorophenyl)ethan-1-one (10 g, 64.0 mmol) in THF (300 mL) and 1,3-dimethyltetrahydropyrimidin-2(1H)-one (16.4 g, 128 mmol) was added lithium bis(trimethylsilyl)amide (64.0 mL, 64.0 mmol, 1 M in THF) at −78° C. After the addition was finished, the reaction was stirred at −78° C. for 30 min. Then ethyl 2-bromoacetate (7.46 mL, 67.3 mmol) was added in one portion at −78° C. After the addition was finished, the reaction was stirred at 20° C. for 2 h. The mixture was diluted with tert-butyl methyl ether (200 mL) and quenched with sat. aq. $NH_4Cl$ (200 mL). The mixture was extracted with tert-butyl methyl ether (200 mL×2). The combined organic fractions were washed with brine (200 mL), dried over anhydrous $Na_2SO_4$, filtered, and concentrated in vacuo. The residue was purified by flash silica gel chromatography (EtOAc/hexanes) to give ethyl 4-(2,4-difluorophenyl)-4-oxobutanoate. Calculated $C_{12}H_{13}F_2O_3$ $[M+H]^+$, 243; Found 243.

Step 2. Preparation of 5-(2,4-difluorophenyl)pyrrolidin-2-one

To a solution of ethyl 4-(2,4-difluorophenyl)-4-oxobutanoate (2.5 g, 10.3 mmol) in EtOH (100 mL) was added acetic acid, ammonia salt (11.9 g, 155 mmol), sodium cyanoborohydride (1.30 g, 20.6 mmol) and the reaction mixture was stirred at 90° C. for 12 h. Water (100 mL) was added. The mixture was extracted with ethyl acetate (100 mL). The organic layer was separated and the aqueous was re-extracted with EtOAc (100 mL×3). The combined organic layers were washed with brine (100 mL), dried over anhydrous $Na_2SO_4$, filtered, and concentrated. The residue was purified by flash silica gel chromatography (EtOAc/hexanes) to give 5-(2,4-difluorophenyl)pyrrolidin-2-one. Calculated $C_{10}H_{10}F_2NO$ $[M+H]^+$, 198; Found 198.

Step 3. Preparation of 2-(2,4-difluorophenyl)-5-methoxy-3,4-dihydro-2H-pyrrole To a solution of 5-(2,4-difluorophenyl)pyrrolidin-2-one (2 g, 10.1 mmol) in DCM (50 mL) was added trimethyloxonium tetrafluoroborate (2.25 g, 15.21 mmol) at 0° C. under $N_2$. The mixture was stirred at 25° C. for 15 h. The mixture was quenched with sat. aq. $NaHCO_3$ (50 mL), and extracted with DCM (50 mL×3). The combined organic layers were dried over $Na_2SO_4$, filtered, and concentrated in vacuum to give crude 2-(2,4-difluorophenyl)-5-methoxy-3,4-dihydro-2H-pyrrole, which was used in the next step without further purification. Calculated $C_{11}H_{12}F_2NO$ $[M+H]^+$, 212; Found 212.

Step 4. Preparation of methyl 2-(2-(2,4-difluorophenyl)-3,4-dihydro-2H-pyrrol-5-yl)hydrazine-1-carboxylate To a solution of 2-(2,4-difluorophenyl)-5-methoxy-3,4-dihydro-2H-pyrrole (2 g, 9.47 mmol) in MeOH (50 mL) was added methyl hydrazinecarboxylate (0.896 g, 9.94 mmol) and HCl (1 mL, 4 M in MeOH) at 20° C. and the resulting mixture was stirred at 80° C. for 3 h under $N_2$. The mixture was concentrated in vacuum, and the residue was purified by flash silica gel chromatography (EtOAc in hexanes) to give methyl 2-(2-(2,4-difluorophenyl)-3,4-dihydro-2H-pyrrol-5-yl)hydrazine-1-carboxylate. Calculated $C_{12}H_{14}F_2N_3O_2$$[M+H]^+$, 270; Found 270.

Step 5. Preparation of 5-(2,4-difluorophenyl)-2,5,6,7-tetrahydro-3H-pyrrolo[2,1-c][1,2,4]triazol-3-one (I-12A)

To a solution of methyl 2-(2-(2,4-difluorophenyl)-3,4-dihydro-2H-pyrrol-5-yl)hydrazine-1-carboxylate (900 mg, 3.34 mmol) in MeOH (20 mL) was added sodium methoxide (542 mg, 10.0 mmol) and the resulting mixture was stirred at 80° C. for 8 h. The residue was purified by RP-HPLC (Column Boston Green ODS 150×30 mm×5 um; Condition water (TFA)-ACN) to give 5-(2,4-difluorophenyl)-2,5,6,7-tetrahydro-3H-pyrrolo[2,1-c][1,2,4]triazol-3-one. Calculated $C_{11}H_{10}F_2N_3O$ $[M+H]^+$, 238; Found 238.

Preparation of Intermediate I-13A ((S)-5-(3-(trifluoromethyl)phenyl)-2,5,6,7-tetrahydro-3H-pyrrolo[2,1-c][1,2,4]triazol-3-one)

Intermediate I-13A was prepared from 1-bromo-3-(trifluoromethyl)benzene and pyrrolidine-2,5-dione as outlined below.

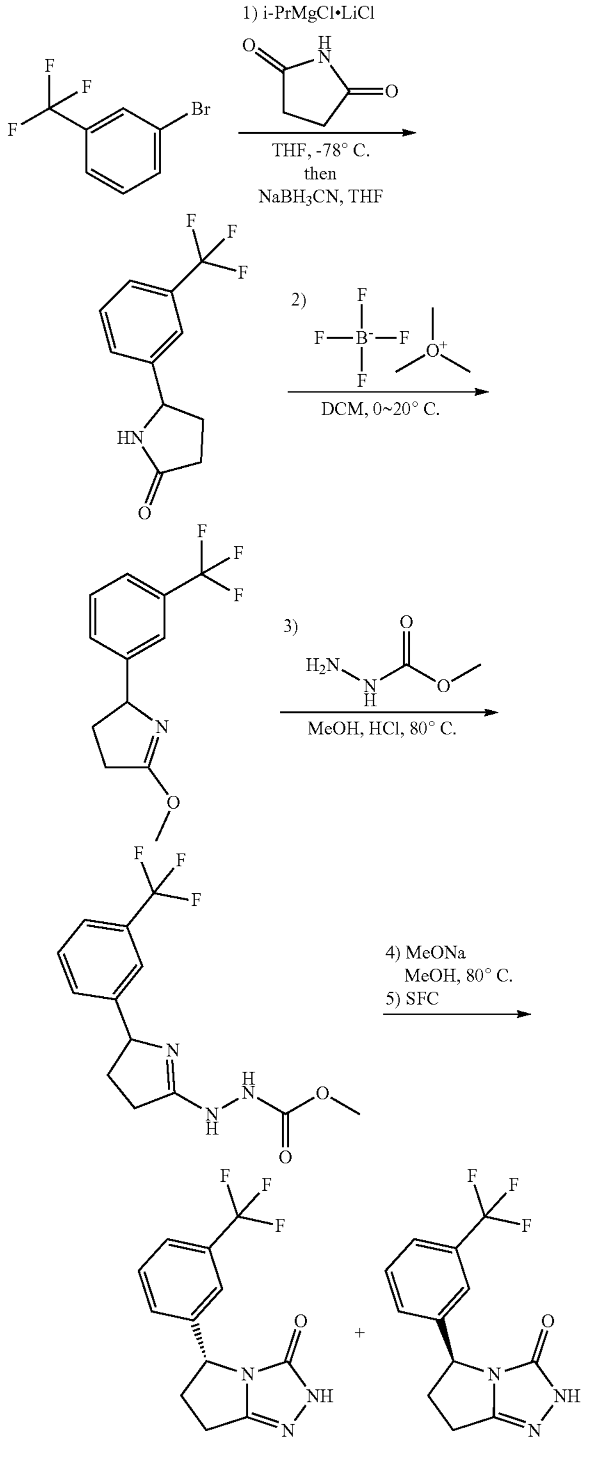

I-13A

Step 1. Preparation of 5-(3-(trifluoromethyl)phenyl)pyrrolidin-2-one

To a first solution of 1-bromo-3-(trifluoromethyl)benzene (4.54 g, 20.2 mmol) in THF (40 mL) was added i-PrMgCl·LiCl (21.7 mL, 28.3 mmol) at 0° C. under $N_2$. Then the reaction was stirred at 25° C. for 1 h. To a second solution of pyrrolidine-2,5-dione (2 g, 20.2 mmol) in THF (60 mL) was added i-PrMgCl·LiCl (14.0 mL, 18.2 mmol) at 0° C. under $N_2$, the reaction was stirred at 0° C. for 1 h. To the second mixture was added the first solution at −78° C. The resulting mixture was stirred at 25° C. for 16 h. Then to the mixture was added $NaBH_3CN$ (1.40 g, 22.2 mmol) at 25° C. and the mixture was stirred at 25° C. for 1 h. The reaction was acidified to pH=3-4 with HCl (6 M in water), and was stirred for 1 h and basified with NaOH (4 M in water). The mixture was quenched with water (500 mL), extracted with EtOAc (500 mL×3). The combined organic layers were dried over $Na_2SO_4$, filtered, and concentrated in vacuum, and the residue was purified by flash silica gel chromatography (EtOAc/hexanes) to give 5-(3-(trifluoromethyl)phenyl)pyrrolidin-2-one. Calculated $C_{11}H_{11}F_3NO$ $[M+H]^+$, 230; Found 230. $^1H$ NMR (500 MHz, $CDCl_3$) δ 7.43-7.63 (m, 4H), 4.83 (t, J=7.17 Hz, 1H), 2.56-2.68 (m, 1H), 2.38-2.50 (m, 2H), 1.90-2.00 (m, 1H).

Step 2. Preparation of 5-methoxy-2-(3-(trifluoromethyl)phenyl)-3,4-dihydro-2H-pyrrole To a solution of 5-(3-(trifluoromethyl)phenyl)pyrrolidin-2-one (2.1 g, 9.16 mmol) in DCM (40 mL) was added trimethyloxonium tetrafluoroborate (2.03 g, 13.7 mmol) at 0° C. under $N_2$. The mixture was stirred at 25° C. for 12 h. The mixture was quenched with sat. aq. $NaHCO_3$ (80 mL), and extracted with DCM (30 mL×2). The combined organic layers were dried over $Na_2SO_4$, filtered, and concentrated in vacuum to give crude 5-methoxy-2-(3-(trifluoromethyl)phenyl)-3,4-dihydro-2H-pyrrole, which was used in the next step without further purification. Calculated $C_{12}H_{13}F_3NO$ $[M+H]^+$, 244; Found 244.

Step 3. Preparation of methyl 2-(2-(3-(trifluoromethyl)phenyl)-3,4-dihydro-2H-pyrrol-5-yl)hydrazine-1-carboxylate To a solution of 5-methoxy-2-(3-(trifluoromethyl)phenyl)-3,4-dihydro-2H-pyrrole (2 g, 8.22 mmol) in MeOH (40 mL) was added methyl hydrazinecarboxylate (0.815 g, 9.04 mmol) at 20° C. and the resulting mixture was stirred at 80° C. for 12 h. The reaction mixture was concentrated and the residue was purified by flash silica gel chromatography (EtOAc/hexanes) to give methyl 2-(2-(3-(trifluoromethyl)phenyl)-3,4-dihydro-2H-pyrrol-5-yl)hydrazine-1-carboxylate. Calculated $C_{13}H_{15}F_3N_3O_2[M+H]^+$, 302; Found 302.

Step 4. Preparation of 5-(3-(trifluoromethyl)phenyl)-2,5,6,7-tetrahydro-3H-pyrrolo[2,1-c][1,2,4]triazol-3-one To a solution of methyl 2-(2-(3-(trifluoromethyl)phenyl)-3,4-dihydro-2H-pyrrol-5-yl)hydrazine-1-carboxylate (1.3 g, 4.32 mmol) in MeOH (15 mL) was added sodium methoxide (0.70 g, 13.0 mmol) and the resulting mixture was stirred at 80° C. for 8 h. The mixture was cooled to RT and acidified to pH=7 with HCl (4 M in MeOH). Then the mixture was filtered, washed with water (80 mL), and the solid was dried by vacuum distillation to give 5-(3-(trifluoromethyl)phenyl)-2,5,6,7-tetrahydro-3H-pyrrolo[2,1-c][1,2,4]triazol-3-one. Calculated $C_{12}H_{11}F_3N_3O$ $[M+H]^+$, 270; Found 270. $^1H$ NMR (400 MHz, DMSO-$d_6$) δ 7.67-7.72 (m, 1H), 7.59-7.66 (m, 2H), 7.51-7.59 (m, 1H), 5.29 (dd, J=5.01, 8.11 Hz, 1H), 2.99 (dtd, J=6.32, 8.67, 13.05 Hz, 1H), 2.71-2.91 (m, 2H), 2.27-2.38 (m, 1H).

Step 5. Chiral separation towards isolation of (S)-5-(3-(trifluoromethyl)phenyl)-2,5,6,7-tetrahydro-3H-pyrrolo[2,1-c][1,2,4]triazol-3-one (I-13A)

The racemic mixture of 5-(3-(trifluoromethyl)phenyl)-2,5,6,7-tetrahydro-3H-pyrrolo[2,1-c][1,2,4]triazol-3-one (900 mg, 3.34 mmol) was separated by Chiral-SFC (Method Column DAICEL CHIRALCEL OD-H (250 mm×30 mm, 5 um); Condition 0.1% $NH_3H_2O$/IPA) to afford (R)-5-(3-(trifluoromethyl)phenyl)-2,5,6,7-tetrahydro-3H-pyrrolo[2,1-c][1,2,4]triazol-3-one (t=2.878 min) as the first eluting peak, and (S)-5-(3-(trifluoromethyl)phenyl)-2,5,6,7-tetrahydro-3H-pyrrolo[2,1-c][1,2,4]triazol-3-one (t=3.317 min) as the second eluting peak.

(R)-5-(3-(trifluoromethyl)phenyl)-2,5,6,7-tetrahydro-3H-pyrrolo[2,1-c][1,2,4]triazol-3-one Calculated $C_{12}H_{11}F_3N_3O$ $[M+H]^+$, 270; Found 270.

(S)-5-(3-(trifluoromethyl)phenyl)-2,5,6,7-tetrahydro-3H-pyrrolo[2,1-c][1,2,4]triazol-3-one (I-13A)

Calculated $C_{12}H_{11}F_3N_3O$ $[M+H]^+$, 270; Found 270.

Preparation of Intermediate I-14A (5-(4-(trifluoromethyl)phenyl)-2,5,6,7-tetrahydro-3H-pyrrolo[2,1-c][1,2,4]triazol-3-one)

Intermediate I-14A was prepared from 1-bromo-4-(trifluoromethyl)benzene and pyrrolidine-2,5-dione as outlined below.

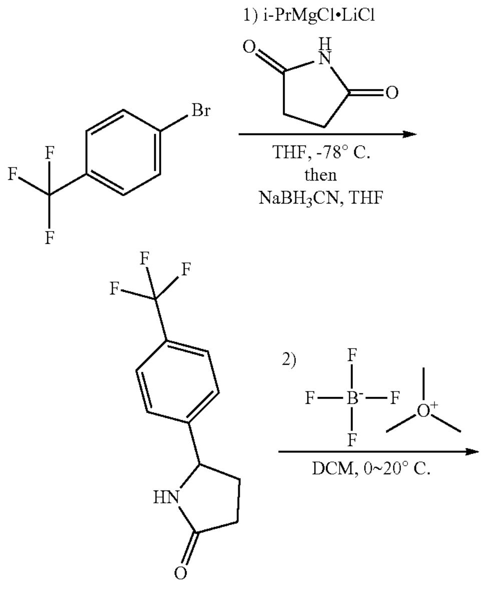

-continued

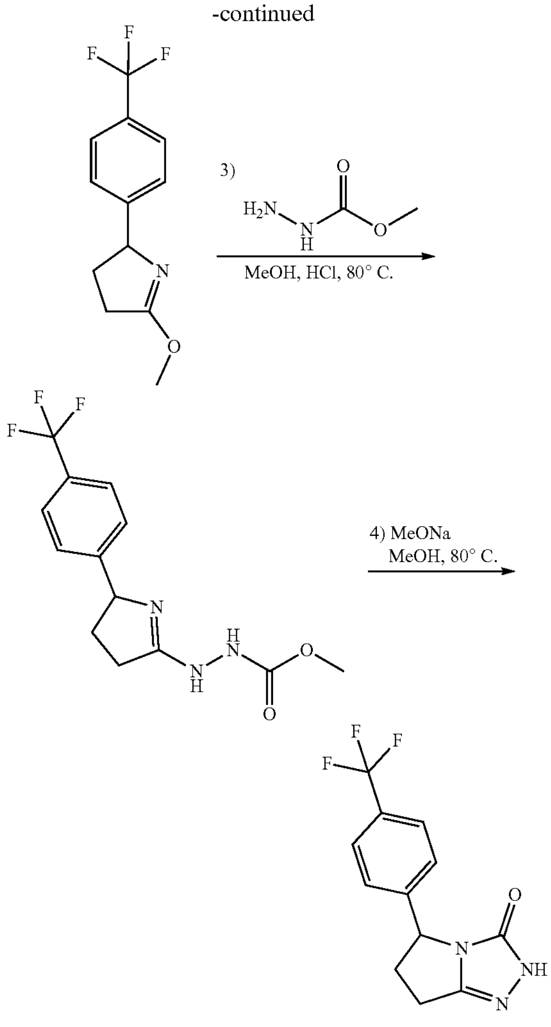

I-14A

Step 1. Preparation of 5-(4-(trifluoromethyl)phenyl)pyrrolidin-2-one

To a first solution of 1-bromo-4-(trifluoromethyl)benzene (9.08 g, 40.4 mmol) in THF (70 mL) was added i-PrMgCl·LiCl (43.5 mL, 56.5 mmol) at 0° C. under $N_2$. Then the reaction was stirred at 25° C. for 1 h. To a second solution of pyrrolidine-2,5-dione (4 g, 40.4 mmol) in THF (70 mL) was added i-PrMgCl·LiCl (27.9 mL, 36.3 mmol) at 0° C. under $N_2$, the reaction was stirred at 0° C. for 1 h. To the second mixture was added the first solution at −78° C. The mixture was stirred at 25° C. for 16 h. Then to the mixture was added $NaBH_3CN$ (3.04 g, 48.4 mmol) at 25° C. and the mixture was stirred at 25° C. for 1 h. The reaction was acidified to pH=3-4 with HCl (6 M in water), and was stirred for 1 h and neutralized with NaOH (4 M in water). The mixture was quenched with water (500 mL), and extracted with EtOAc (500 mL×3). The combined organic layers were dried over $Na_2SO_4$, filtered, and concentrated in vacuum, and the residue was purified by flash silica gel chromatography (EtOAc) to give 5-(4-(trifluoromethyl)phenyl)pyrrolidin-2-one. Calculated $C_{11}H_{11}F_3NO$ $[M+H]^+$, 230; Found 230. $^1H$ NMR (400 MHz, $CD_3OD$) δ ppm 1.21 (dd, J=4.53, 2.28 Hz, 2H) 1.98 (d, J=2.15 Hz, 2H) 4.06 (d, J=6.92 Hz, 1H) 7.28-7.91 (m, 4H) 8.51-8.54 (m, 1H).

Step 2. Preparation of 5-methoxy-2-(4-(trifluoromethyl)phenyl)-3,4-dihydro-2H-pyrrole To a solution of 5-(4-(trifluoromethyl)phenyl)pyrrolidin-2-one (900 mg, 3.93 mmol) in DCM (20 mL) was added trimethyloxonium tetrafluoroborate (1450 mg, 9.82 mmol) at 0° C. under $N_2$. The mixture was stirred at 25° C. for 15 h. The mixture was quenched with sat. aq. $NaHCO_3$ (80 mL), and extracted with DCM (30 mL×2). The combined organic layers were dried over $Na_2SO_4$, filtered, and concentrated in vacuum to give crude 5-methoxy-2-(4-(trifluoromethyl)phenyl)-3,4-dihydro-2H-pyrrole, which was used in the next step without further purification. Calculated $C_{12}H_{13}F_3NO$ $[M+H]^+$, 244; Found 244.

Step 3. Preparation of methyl 2-(2-(4-(trifluoromethyl)phenyl)-3,4-dihydro-2H-pyrrol-5-yl)hydrazine-1-carboxylate To a solution of 5-methoxy-2-(4-(trifluoromethyl)phenyl)-3,4-dihydro-2H-pyrrole (3.18 g, 13.1 mmol) in MeOH (50 mL) was added methyl hydrazinecarboxylate (1.24 g, 13.7 mmol) and HCl (2 mL, 4 M in MeOH) at 20° C. and the resulting mixture was stirred at 80° C. for 3 h under $N_2$. The mixture was concentrated in vacuum, and the residue was purified by flash silica gel chromatography (EtOAc/hexanes) to give methyl 2-(2-(4-(trifluoromethyl)phenyl)-3,4-dihydro-2H-pyrrol-5-yl)hydrazine-1-carboxylate. Calculated $C_{13}H_{15}F_3N_3O_2[M+H]^+$, 302; Found 302.

Step 4. Preparation of 5-(4-(trifluoromethyl)phenyl)-2,5,6,7-tetrahydro-3H-pyrrolo[2,1-c][1,2,4]triazol-3-one To a solution of methyl 2-(2-(4-(trifluoromethyl)phenyl)-3,4-dihydro-2H-pyrrol-5-yl)hydrazine-1-carboxylate (715 mg, 2.37 mmol) in MeOH (10 mL) was added sodium methanolate (385 mg, 7.12 mmol) and the resulting mixture was stirred at 80° C. for 8 h. The mixture was cooled to RT and acidified to pH=7 with HCl (4 M in MeOH). The resulting mixture was filtered, and the filtrate was purified by RP-HPLC (column: Boston Green ODS 150×30 mm×5 um, mobile phase A-B: water (0.01% TFA)-ACN) to give I-14A, 5-(4-(trifluoromethyl)phenyl)-2,5,6,7-tetrahydro-3H-pyrrolo[2,1-c][1,2,4]triazol-3-one. Calculated $C_{12}H_{11}F_3N_3O$ $[M+H]^+$, 270; Found 270.

Preparation of Intermediate I-15A (5-(3,5-difluoro-4-methylphenyl)-2,5,6,7-tetrahydro-3H-pyrrolo[2,1-c][1,2,4]triazol-3-one)

Intermediate I-15A was prepared from 5-bromo-1,3-difluoro-2-methylbenzene and pyrrolidine-2,5-dione as outlined below.

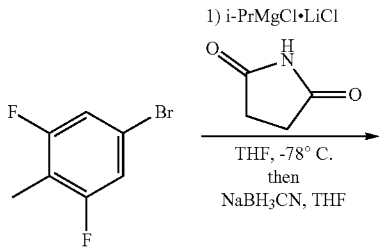

-continued

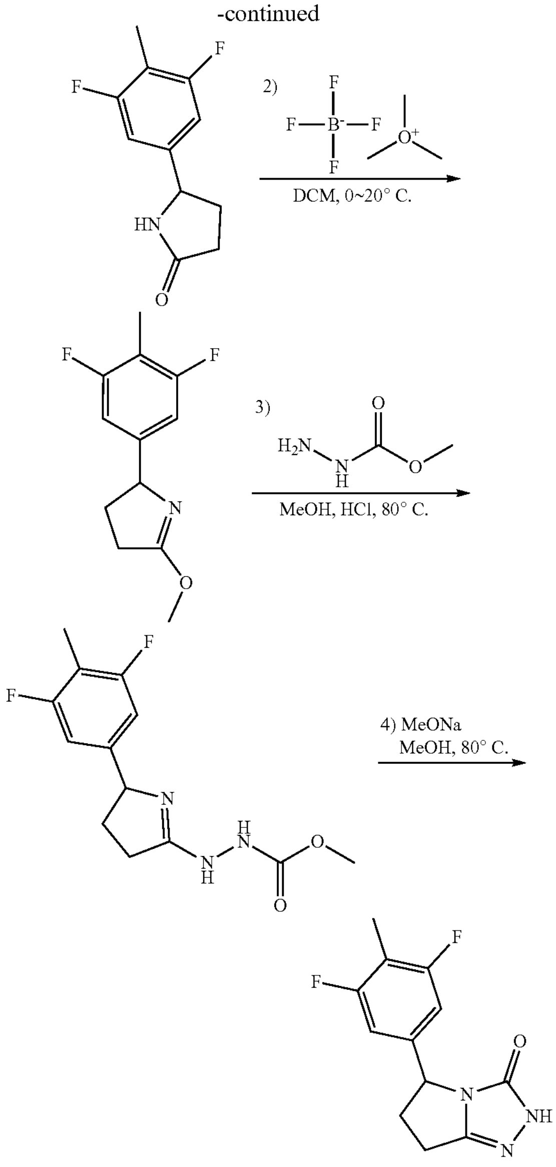

I-15A

Step 1. Preparation of 5-(3,5-difluoro-4-methylphenyl)pyrrolidin-2-one

To a first solution of 5-bromo-1,3-difluoro-2-methylbenzene (1250 mg, 6.06 mmol) in THF (10 mL) was added i-PrMgCl·LiCl (6.52 mL, 8.48 mmol) at 0° C. under $N_2$. Then the reaction was stirred at 25° C. for 1 h. To the second solution of pyrrolidine-2,5-dione (600 mg, 6.06 mmol) in THF (15 mL) was added i-PrMgCl·LiCl (4.19 mL, 5.45 mmol) at 0° C. under $N_2$, the reaction was stirred at 0° C. for 1 h. Then to the second mixture was added the first solution at −78° C. The reaction was warmed to 25° C. and stirred at 25° C. for 12 h. Then $NaBH_3CN$ (419 mg, 6.66 mmol) was added and the resulting mixture was stirred for 1 h. The reaction mixture was acidified with HCl (6 M in water) until pH-3 and stirred for 1 h. Then NaOH (4M in water) was added to adjust the pH to neutral. The reaction mixture was extracted with EtOAc (10 mL×3). The combined organic layers were washed with brine (20 mL), dried over $Na_2SO_4$, filtered, and concentrated. The residue was purified by flash silica gel chromatography (EtOAc/hexanes) to give 5-(3,5-difluoro-4-methylphenyl)pyrrolidin-2-one. Calculated $C_{11}H_{12}F_2NO$ $[M+H]^+$, 212; Found 212. $^1H$ NMR (400 MHz, $CD_3OD$) δ 6.82-6.95 (m, 2H), 4.77 (t, J=7.09 Hz, 1H), 2.54-2.66 (m, 1H), 2.36-2.44 (m, 2H), 2.16 (t, J=1.55 Hz, 3H), 1.82-1.96 (m, 1H).

Step 2. Preparation of 2-(3,5-difluoro-4-methylphenyl)-5-methoxy-3,4-dihydro-2H-pyrrole To a solution of 5-(3,5-difluoro-4-methylphenyl)pyrrolidin-2-one (150 mg, 0.710 mmol) in DCM (3 mL) was added dimethyloxonium tetrafluoroborate (143 mg, 1.07 mmol) at 0° C. The mixture was stirred at 30° C. for 12 h. The mixture was quenched with sat. aq. $NaHCO_3$ (10 mL), and extracted with DCM (5 mL×2). The combined organic layers were washed with brine (10 mL), dried over $Na_2SO_4$, filtered, and concentrated in vacuum to give crude 2-(3,5-difluoro-4-methylphenyl)-5-methoxy-3,4-dihydro-2H-pyrrole, which was used in the next step without further purification. Calculated $C_{12}H_{14}F_2NO$ $[M+H]^+$, 226; Found 226.

Step 3. Preparation of methyl 2-(2-(3,5-difluoro-4-methylphenyl)-3,4-dihydro-2H-pyrrol-5-yl)hydrazine-1-carboxylate To a solution of 2-(3,5-difluoro-4-methylphenyl)-5-methoxy-3,4-dihydro-2H-pyrrole (160 mg, 0.710 mmol) in MeOH (3 ml) was added methyl hydrazinecarboxylate (96 mg, 1.07 mmol) at 20° C. and the resulting mixture was stirred at 80° C. for 12 h. The reaction mixture was concentrated, and the residue was added to EtOAc (10 mL), and the resulting mixture was stirred for 10 min, and filtered to give methyl 2-(2-(3,5-difluoro-4-methylphenyl)-3,4-dihydro-2H-pyrrol-5-yl)hydrazine-1-carboxylate. Calculated $C_{13}H_{16}F_2N_3O_2$ $[M+H]^+$, 284; Found 284. $^1H$ NMR (400 MHz, $CD_3OD$) δ 6.93-7.04 (m, 2H), 5.15 (t, J=7.27 Hz, 1H), 3.76-3.86 (m, 3H), 3.06-3.15 (m, 2H), 2.73-2.85 (m, 1H), 2.18 (s, 3H), 2.09-2.17 (m, 1H).

Step 4. Preparation of I-15A

To a solution of methyl 2-(2-(3,5-difluoro-4-methylphenyl)-3,4-dihydro-2H-pyrrol-5-yl)hydrazine-1-carboxylate (110 mg, 0.388 mmol) in MeOH (3 mL) was added sodium methanolate (62.9 mg, 1.16 mmol) at 20° C. and the resulting mixture was stirred at 80° C. for 12 h. The reaction mixture was added HCl (0.3 mL, 4 M in MeOH) to pH ~6, then filtered, and the filtrate was purified by RP-HPLC (Method Column: Boston Green ODS (150×30 mm×5 um); Condition mobile phase A-B: water (0.01% TFA)-ACN) to give 5-(3,5-difluoro-4-methylphenyl)-2,5,6,7-tetrahydro-3H-pyrrolo[2,1-c][1,2,4]triazol-3-one. Calculated $C_{12}H_{12}F_2N_3O$ $[M+H]^+$, 252; Found 252.

Preparation of Intermediate I-16A (5-(3,5-difluorophenyl)-6-methyl-2,5,6,7-tetrahydro-3H-pyrrolo[2,1-c][1,2,4]triazol-3-one)

Intermediate I-16A was prepared from 1-(3,5-difluorophenyl)propan-1-one as outlined below.

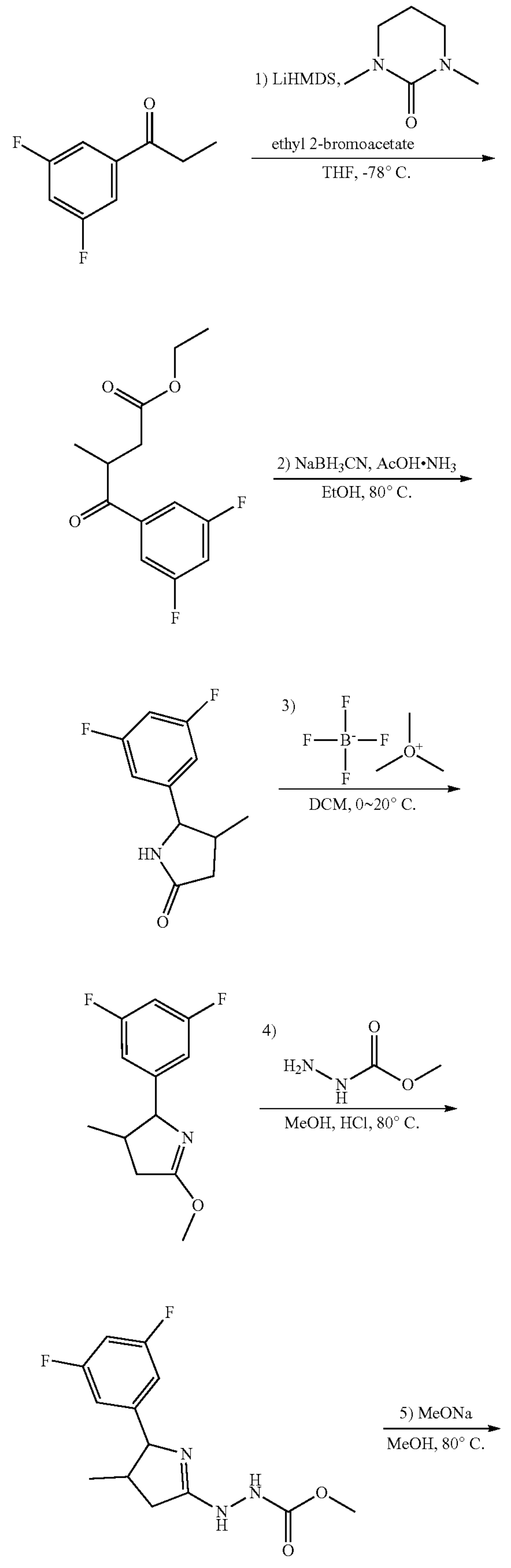

-continued

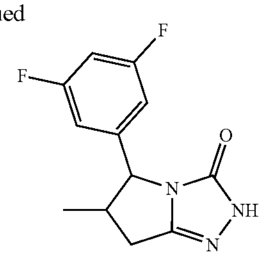

I-16A

Step 1. Preparation of ethyl 4-(3,5-difluorophenyl)-3-methyl-4-oxobutanoate

To a stirred solution of 1-(3,5-difluorophenyl)propan-1-one (5 g, 29.4 mmol) in THF (30 mL) was added 1,3-dimethyltetrahydropyrimidin-2(1H)-one (7.53 g, 58.8 mmol), LHMDS (29.4 mL, 29.4 mmol) at −78° C. under $N_2$. After the addition was finished, the reaction was stirred at −78° C. for 30 min. Then ethyl 2-bromoacetate (3.44 mL, 30.9 mmol) was added to the above mixture in one portion at −78° C. After the addition was finished, the reaction was stirred at 20° C. for 2 h. The mixture was diluted with tert-butyl methyl ether (10 mL) and quenched with saturated aqueous $NH_4Cl$ (20 mL). The mixture was extracted with tert-butyl methyl ether (30 mL×2). The combined organic fractions were washed with brine (10 mL), dried over anhydrous $Na_2SO_4$, filtered, and concentrated. The residue was purified by flash silica gel chromatography (EtOAc in hexanes) to give ethyl 4-(3,5-difluorophenyl)-3-methyl-4-oxobutanoate. Calculated $C_{13}H_{15}F_2O_3$ $[M+H]^+$, 257; Found 257.

Step 2. Preparation of 5-(3,5-difluorophenyl)-4-methylpyrrolidin-2-one

To a solution of ethyl 4-(3,5-difluorophenyl)-3-methyl-4-oxobutanoate (5.4 g, 21.07 mmol) in EtOH (30 ml) was added acetic acid, ammonia salt (8.12 g, 105 mmol), sodium cyanoborohydride (2.65 g, 42.1 mmol) and the reaction was stirred at 80° C. for 12 h. Water (50 mL) was added. The mixture was extracted with ethyl acetate (50 mL). The organic layer was separated and the aqueous was re-extracted with EtOAc (50 mL×3). The combined organic layers were washed with brine (50 mL), dried over anhydrous $Na_2SO_4$, filtered, and concentrated. The residue was purified by flash silica gel chromatography (EtOAc in hexanes) to give 5-(3,5-difluorophenyl)-4-methylpyrrolidin-2-one. Calculated $C_{11}H_{12}F_2NO$ $[M+H]^+$, 212; Found 212.

Step 3. Preparation of 2-(3,5-difluorophenyl)-5-methoxy-3-methyl-3,4-dihydro-2H-pyrrole To a solution of 5-(3,5-difluorophenyl)-4-methylpyrrolidin-2-one (2.1 g, 9.94 mmol) in DCM (30 mL) was added trimethyloxonium tetrafluoroborate (2.21 g, 14.9 mmol) at 0° C. under $N_2$. The mixture was stirred at 25° C. for 15 h. The mixture was quenched with saturated aqueous $NaHCO_3$ (10 mL), extracted with DCM (10 mL×2). The combined organic layers were dried over $Na_2SO_4$, filtered, and concentrated in vacuum to give crude 2-(3,5-difluorophenyl)-5-methoxy-3-methyl-3,4-dihydro-2H-pyrrole, which was used in the next step without further purification. Calculated $C_{12}H_{14}F_2NO$ $[M+H]^+$, 226; Found 226.

Step 4. Preparation of methyl 2-(2-(3,5-difluorophenyl)-3-methyl-3,4-dihydro-2H-pyrrol-5-yl)hydrazine-1-carboxylate To a solution of 2-(3,5-difluorophenyl)-5-methoxy-3-methyl-3,4-dihydro-2H-pyrrole (2 g, 8.88 mmol) in MeOH (10 mL) was added methyl hydrazinecarboxylate (0.840 g, 9.32 mmol) and HCl (2 mL, 4 M in MeOH) at 20° C. and the resulting mixture was stirred at 80° C. for 12 h. The reaction was directly concentrated and the residue was purified by recrystallization to give methyl 2-(2-(3,5-difluorophenyl)-3-methyl-3,4-dihydro-2H-pyrrol-5-yl)hydrazine-1-carboxylate. Calculated $C_{13}H_{16}F_2N_3O_2[M+H]^+$, 284; Found 284.

Step 5. Preparation of I-16A (5-(3,5-difluorophenyl)-6-methyl-2,5,6,7-tetrahydro-3H-pyrrolo[2,1-c][1,2,4]triazol-3-one)

To a solution of methyl 2-(2-(3,5-difluorophenyl)-3-methyl-3,4-dihydro-2H-pyrrol-5-yl)hydrazine-1-carboxylate (1.5 g, 5.30 mmol) in MeOH (2 mL) was added sodium methoxide (0.858 g, 15.89 mmol) and the resulting mixture was stirred at 80° C. for 8 h. The mixture was cooled to RT and acidified to pH=7 with HCl (4 M in MeOH). The mixture was concentrated and the residue was purified by recrystallization to give I-16A. Calculated $C_{12}H_{12}F_2N_3O$ $[M+H]^+$, 252; Found 252.

Preparation of Intermediate I-17A ((S)-5-(3,5-difluorophenyl)-5,6,7,8-tetrahydro-[1,2,4]triazolo[4,3-a]pyridin-3(2H)-one)

Intermediate I-17A was prepared from 1-bromo-3,5-difluorobenzene and piperidine-2,6-dione as outlined below.

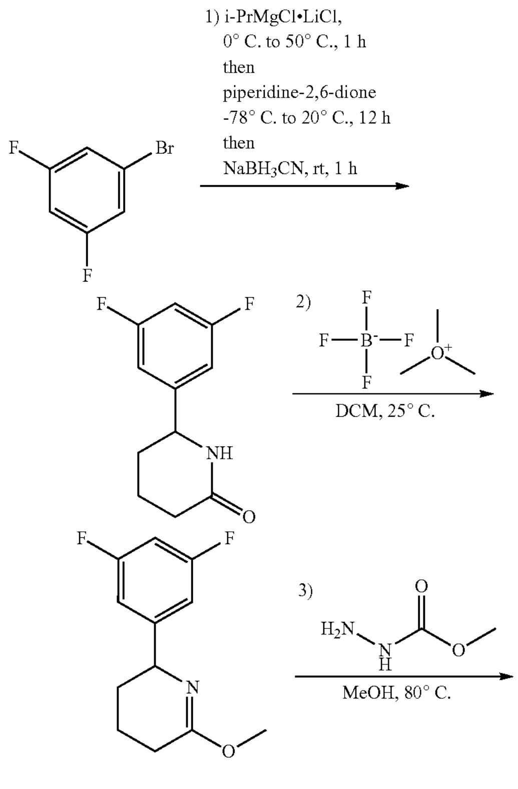

-continued

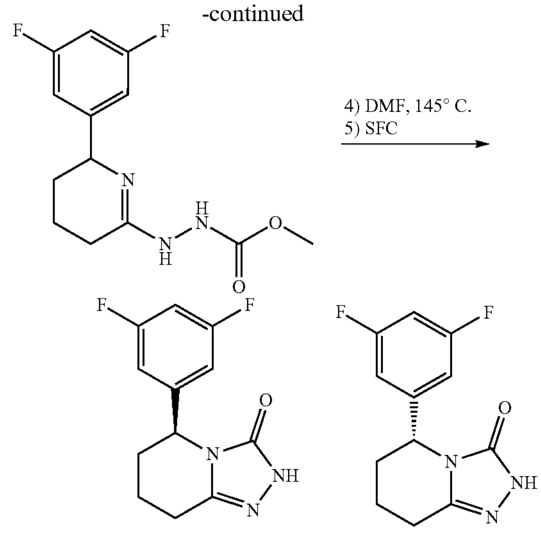

I-17A

Step 1. Preparation of 6-(3,5-difluorophenyl)piperidin-2-one

To a solution of 1-bromo-3,5-difluorobenzene (5.12 g, 26.5 mmol) in THF (50 mL) was added iPrMgCl·LiCl (1.3 M in THF) (34.0 mL, 44.2 mmol) at 0° C. and the mixture was stirred at 50° C. for 1 h. Then to the mixture was added piperidine-2,6-dione (2 g, 17.7 mmol) in DCM (2 mL) at −78° C. The mixture was stirred at 20° C. for 12 h. To the mixture was added $NaBH_3CN$ (1.33 g, 21.2 mmol) at 20° C., then the mixture was stirred at 25° C. for 1 h. The reaction was acidified to pH=3-4 with HCl (6 M), then the mixture was stirred for 30 mins and neutralized with aq. NaOH (3 M). The mixture was quenched with sat. $NH_4Cl$ (200 mL) and extracted with DCM (100 mL×3). The combined organic layers were washed with brine (50 mL), dried over $Na_2SO_4$, filtered and concentrated. The residue was added to ethyl acetate (20 mL) and stirred for 0.5 h. Filtered the solid to give 6-(3,5-difluorophenyl)piperidin-2-one. Calculated $C_{11}H_{12}F_2NO$ $[M+H]^+$, 212; Found 212.

Step 2. Preparation of 2-(3,5-difluorophenyl)-6-methoxy-2,3,4,5-tetrahydropyridine To a solution of 6-(3,5-difluorophenyl)piperidin-2-one (500 mg, 2.37 mmol) in DCM (10 mL) was added dimethyloxonium tetrafluoroborate (475 mg, 3.55 mmol) at 25° C. The mixture was stirred at 25° C. for 12 h. The mixture was quenched with sat. aq. $NaHCO_3$ (20 mL), extracted with DCM (10 mL×2). The combined organic layers were dried over $Na_2SO_4$, filtered and concentrated in vacuum to give crude 2-(3,5-difluorophenyl)-6-methoxy-2,3,4,5-tetrahydropyridine, which was used in the next step without further purification. Calculated $C_{12}H_{14}F_2NO$ $[M+H]^+$, 226; Found 226.

Step 3. Preparation of methyl 2-(6-(3,5-difluorophenyl)-3,4,5,6-tetrahydropyridin-2-yl)hydrazine-1-carboxylate To a solution of 2-(3,5-difluorophenyl)-6-methoxy-2,3,4,5-tetrahydropyridine (490 mg, 2.175 mmol) in MeOH (10 ml) was added methyl hydrazinecarboxylate (294 mg, 3.26 mmol) at 20° C. and the resulting mixture was stirred at 80° C. for 12 h. The reaction was directly concentrated and the residue was purified by flash silica gel chromatography (MeOH/DCM) to give methyl 2-(6-(3,5-difluorophenyl)-3,4,5,6-tetrahydropyridin-2-yl)hydrazine-1-carboxylate. Calculated $C_{13}H_{16}F_2N_3O_2[M+H]^+$, 284; Found 284.

Steps 4-5. Preparation of Intermediate I-17A

A solution of methyl 2-(6-(3,5-difluorophenyl)-3,4,5,6-tetrahydropyridin-2-yl)hydrazine-1-carboxylate (300 mg, 1.06 mmol) in DMF (15 mL) was stirred at 145° C. for 12 h. The reaction solution was directly concentrated to give 5-(3,5-difluorophenyl)-5,6,7,8-tetrahydro-[1,2,4]triazolo[4,3-a]pyridin-3(2H)-one (220 mg, 0.841 mmol). 5-(3,5-difluorophenyl)-5,6,7,8-tetrahydro-[1,2,4]triazolo[4,3-a]pyridin-3(2H)-one was resolved by Chiral-SFC (Method Column DAICEL CHIRALCEL OD (250 mm×30 mm, 10 um); Condition 0.1% $NH_3H_2O$/EtOH) to give 5-(3,5-difluorophenyl)-5,6,7,8-tetrahydro-[1,2,4]triazolo[4,3-a]pyridin-3(2H)-one (ee %=97.6%) and 5-(3,5-difluorophenyl)-5,6,7,8-tetrahydro-[1,2,4]triazolo[4,3-a]pyridin-3(2H)-one (ee %=97.3%).

(S)-5-(3,5-difluorophenyl)-5,6,7,8-tetrahydro-[1,2,4]triazolo[4,3-a]pyridin-3(2H)-one (I-17A)

$^1H$ NMR (400 MHz, $CD_3OD$) δ 6.87 (tt, J=2.35, 9.00 Hz, 1H), 6.67-6.77 (m, 2H), 5.13 (t, J=5.09 Hz, 1H), 2.79-2.91 (m, 1H), 2.65-2.78 (m, 1H), 2.29 (dddd, J=2.74, 6.06, 10.86, 13.99 Hz, 1H), 2.01 (tdd, J=3.42, 6.55, 13.99 Hz, 1H), 1.63-1.88 (m, 2H).

(R)-5-(3,5-difluorophenyl)-5,6,7,8-tetrahydro-[1,2,4]triazolo[4,3-a]pyridin-3(2H)-one $^1H$ NMR (400 MHz, $CD_3OD$) δ 6.87 (tt, J=2.20, 9.15 Hz, 1H), 6.68-6.76 (m, 2H), 5.13 (t, J=5.28 Hz, 1H), 2.79-2.89 (m, 1H), 2.65-2.77 (m, 1H), 2.29 (dddd, J=3.13, 5.87, 11.00, 14.04 Hz, 1H), 2.01 (tdd, J=3.33, 6.65, 14.09 Hz, 1H), 1.64-1.87 (m, 2H).

Preparation of Intermediate I-18A (5-cyclopentyl-2,5,6,7-tetrahydro-3H-pyrrolo[2,1-c][1,2,4]triazol-3-one)

Intermediate I-18A was prepared from cyclopentylmagnesium bromide and pyrrolidine-2,5-dione as outlined below.

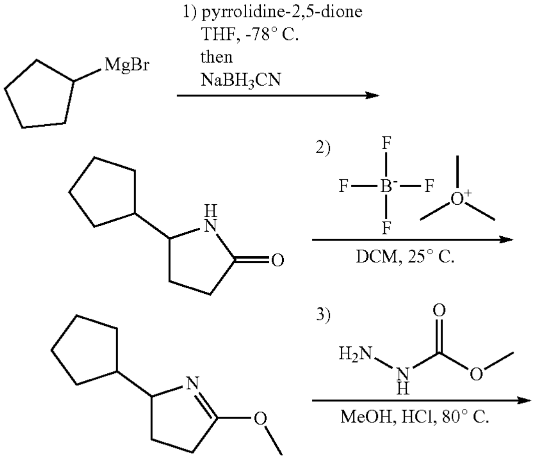

-continued

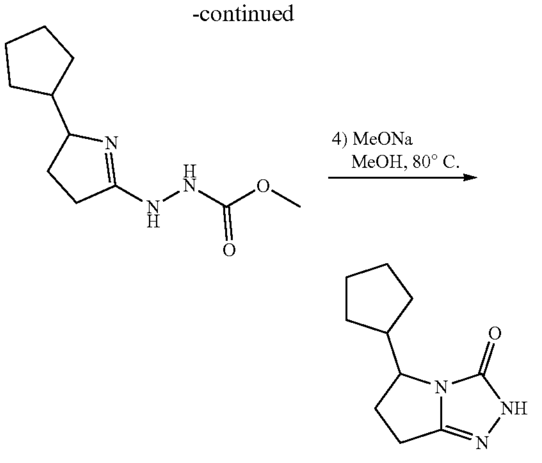

I-18A

Step 1. Preparation of 5-cyclopentylpyrrolidin-2-one

To a solution of pyrrolidine-2,5-dione (4 g, 40.4 mmol) in THF (150 mL) was added cyclopentylmagnesium bromide (121 mL, 121 mmol) dropwise by syringe at −78° C. under $N_2$. After the addition was completed, the reaction was allowed to warm up to 25° C. and react for another 16 h. Then $NaBH_3CN$ (3.04 g, 48.4 mmol) was added to the mixture and allowed to react for another 2 h. 6M HCl was added and the pH was adjusted to 4. It was stirred for another 1 h. Aq. NaOH was added to adjust the pH to neutral. The reaction mixture was extracted with EtOAc (100 mL×3). The combined organic phases were washed with brine (100 mL), dried over anhydrous $Na_2SO_4$, filtered and concentrated under reduced pressure. The mixture was purified by flash silica gel chromatography (hexanes/ethyl acetate) to give 5-cyclopentylpyrrolidin-2-one. Calculated $C_9H_{16}NO$ $[M+H]^+$, 154; Found 154.

Step 2. Preparation of 2-cyclopentyl-5-methoxy-3,4-dihydro-2H-pyrrole

To a solution of 5-cyclopentylpyrrolidin-2-one (520 mg, 3.39 mmol) in DCM (20 mL) was added trimethyloxonium tetrafluoroborate (753 mg, 5.09 mmol) at 0° C. under $N_2$. The mixture was stirred at 25° C. for 12 h. The mixture was quenched with sat. $NaHCO_3$ (800 mL) until there were no bubbles, extracted with DCM (300 mL×2). The combined organic layers were dried over $Na_2SO_4$, filtered and concentrated in vacuum to give crude 2-cyclopentyl-5-methoxy-3,4-dihydro-2H-pyrrole, which was used in the next step without further purification. Calculated $C_{10}H_{18}NO$ $[M+H]^+$, 168; Found 168.

Step 3. Preparation of methyl 2-(2-cyclopentyl-3,4-dihydro-2H-pyrrol-5-yl)hydrazine-1-carboxylate To a solution of 2-cyclopentyl-5-methoxy-3,4-dihydro-2H-pyrrole (520 mg, 3.11 mmol) in MeOH (20 mL) was added methyl hydrazinecarboxylate (308 mg, 3.42 mmol) and HCl/MeOH (0.06 mL) at 20° C. and the resulting mixture was stirred at 80° C. for 12 h. The reaction was directly concentrated and the residue was purified by flash silica gel chromatography (ethyl acetate/petroleum ether) to give methyl 2-(2-cyclopentyl-3,4-dihydro-2H-pyrrol-5-yl) hydrazine-1-carboxylate. Calculated $C_{11}H_{20}N_3O_2[M+H]^+$, 226; Found 226.

Step 4. Preparation of I-18A

To a solution of methyl 2-(2-cyclopentyl-3,4-dihydro-2H-pyrrol-5-yl)hydrazine-1-carboxylate (200 mg, 0.888 mmol) in MeOH (6 mL) was added sodium methoxide (144 mg, 2.66 mmol) and the resulting mixture was stirred at 80° C. for 16 h. The mixture was cooled to RT and acidified to pH=7 with HCV/MeOH (4 M). Then the mixture was filtered and purified by prep. HPLC (Method Column Boston Green ODS 150x30 mmx5 um; Condition water (0.01% TFA)-CAN) to give 5-cyclopentyl-2,5,6,7-tetrahydro-3H-pyrrolo[2,1-c][1,2,4]triazol-3-one. Calculated $C_{10}H_{16}N_3O$ $[M+H]^+$, 194; Found 194. $^1H$ NMR (400 MHz, $CD_3OD$) δ 4.12-4.19 (m, 1H), 2.81 (d, J=8.1 Hz, 1H), 2.59-2.75 (m, 2H), 2.27-2.46 (m, 2H), 1.79-1.88 (m, 1H), 1.65-1.77 (m, 3H), 1.60 (ddd, J=10.4, 5.4, 2.4 Hz, 2H), 1.42 (br d, J=9.2 Hz, 2H).

Preparation of Intermediate I-19A (5-cyclohexyl-2,5,6,7-tetrahydro-3H-pyrrolo[2,1-c][1,2,4]triazol-3-one)

Intermediate I-19A was prepared from cyclohexylmagnesium bromide and pyrrolidine-2,5-dione as outlined below.

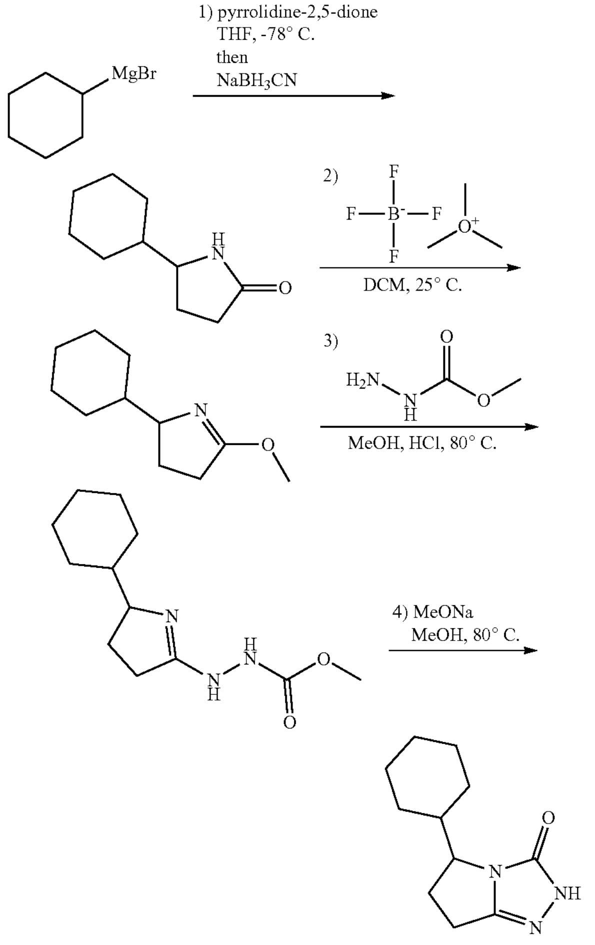

I-19A

Step 1. Preparation of 5-cyclohexylpyrrolidin-2-one

To a solution of pyrrolidine-2,5-dione (2.5 g, 25.2 mmol) in THF (100 mL) was added cyclohexylmagnesium bromide (76 mL, 76 mmol) dropwise by syringe at −78° C. under $N_2$. After the addition was completed, the reaction was allowed to warm up to 25° C. and stirred for 16 h. Then $NaBH_3CN$ (2.378 g, 37.8 mmol) was added to the mixture and allowed to stir for another 2 h. 6M HCl was added and the pH was adjusted to 4. It was stirred for another 1 h. Aqueous NaOH was added to adjust the pH to 7. The reaction mixture was extracted with EtOAc (100 mLx3). The combined organic phases were washed with brine (100 mL), dried over anhydrous $Na_2SO_4$, filtered and concentrated under reduced pressure. The mixture was purified by flash silica gel chromatography (ethyl acetate/petroleum ether) to give 5-cyclohexylpyrrolidin-2-one. Calculated $C_{10}H_{18}NO$ $[M+H]^+$, 168; Found 168.

Step 2. Preparation of 2-cyclohexyl-5-methoxy-3,4-dihydro-2H-pyrrole

To a solution of 5-cyclohexylpyrrolidin-2-one (1.3 g, 7.77 mmol) in DCM (30 mL) was added trimethyloxonium tetrafluoroborate (1.72 g, 11.7 mmol) at 0° C. under $N_2$. The mixture was stirred at 35° C. for 12 h. The mixture was quenched with sat. $NaHCO_3$ (40 mL) until there were no bubbles, extracted with DCM (20 mLx2). The combined organic layers were dried over $Na_2SO_4$, filtered and concentrated in vacuum to give crude 2-cyclohexyl-5-methoxy-3,4-dihydro-2H-pyrrole, which was used to next step without further purification. Calculated $C_{11}H_{20}NO$ $[M+H]^+$, 182; Found 182.

Step 3. Preparation of methyl 2-(2-cyclohexyl-3,4-dihydro-2H-pyrrol-5-yl)hydrazine-1-carboxylate To a solution of 2-cyclohexyl-5-methoxy-3,4-dihydro-2H-pyrrole (1.3 g, 5.74 mmol) in MeOH (20 mL) was added methyl hydrazinecarboxylate (0.620 g, 6.88 mmol) and HCl/MeOH (0.06 mL) at 20° C. and the resulting mixture was stirred at 80° C. for 12 h. The reaction was directly concentrated and the residue was purified by flash silica gel chromatography (ethyl acetate/petroleum ether) to give methyl 2-(2-cyclohexyl-3,4-dihydro-2H-pyrrol-5-yl)hydrazine-1-carboxylate. Calculated $C_{12}H_{22}N_3O_2$ $[M+H]^+$, 240; Found 240.

Step 4. Preparation of I-19A

To a solution of methyl 2-(2-cyclohexyl-3,4-dihydro-2H-pyrrol-5-yl)hydrazine-1-carboxylate (700 mg, 2.92 mmol) in MeOH (20 mL) was added sodium methoxide (474 mg, 8.77 mmol) and the resulting mixture was stirred at 80° C. for 24 h. The mixture was cooled to RT and acidified to pH=7 with HCl/MeOH (4 M). Then the mixture was filtered and purified by prep. HPLC (Method Column Boston Uni C18 150x40 mmx5 um; Condition water (0.01% TFA)-CAN) to give 5-cyclohexyl-2,5,6,7-tetrahydro-3H-pyrrolo[2,1-c][1,2,4]triazol-3-one. Calculated $C_{11}H_{18}N_3O$ $[M+H]^+$, 208; Found 208. $^1H$ NMR (500 MHz, $CD_3OD$) δ 4.06 (dt, J=8.4, 4.1 Hz, 1H), 2.66-2.80 (m, 2H), 2.51-2.60 (m, 1H), 2.41 (dt, J=8.9, 4.4 Hz, 1H), 1.98 (br d, J=4.4 Hz, 1H), 1.76-1.84 (m, 2H), 1.67-1.75 (m, 2H), 1.46-1.52 (m, 1H), 1.25-1.37 (m, 2H), 1.17-1.24 (m, 2H), 1.09 (dd, J=12.6, 3.6 Hz, 1H).

Preparation of Intermediate I-20A ((S and R)-5-(3-chlorophenyl)-2,5,6,7-tetrahydro-3H-pyrrolo[2,1-c][1,2,4]triazol-3-one)

Intermediate I-20A was prepared from pyrrolidine-2,5-dione and 3-bromo-5-chloropyridine as outlined below.

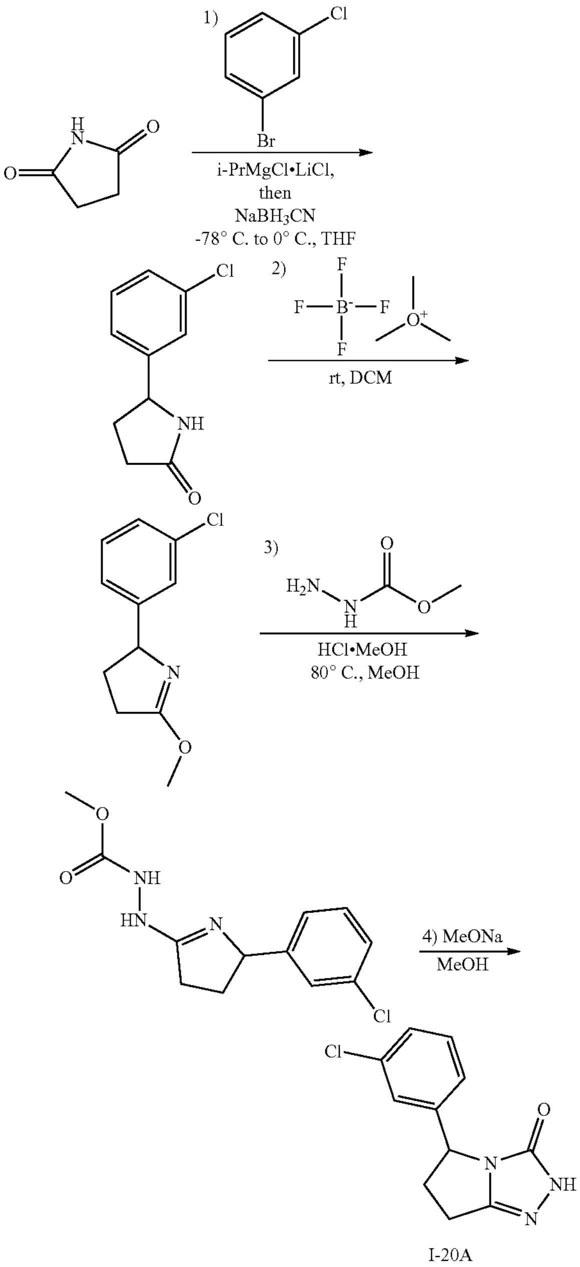

I-20A

Step 1. Preparation of 5-(3-chlorophenyl)pyrrolidin-2-one

To a solution 1 of 1-bromo-3-chlorobenzene (10.1 g, 52.5 mmol) in THF (100 mL) was added i-PrMgCl·LiCl (56.5 mL, 73.5 mmol) at 0° C. under $N_2$. Then the reaction was stirred at 25° C. for 1 h. To a solution 2 of pyrrolidine-2,5-dione (5.2 g, 52.5 mmol) in THF (200 mL) was added isopropylmagnesium(II) lithium chloride (36.3 mL, 47.2 mmol) at 0° C. under $N_2$, the reaction was stirred at 25° C. for 1 h. The first solution was added to the second solution at −78° C. under $N_2$ and stirred at 25° C. for 12 h. Then $NaBH_3CN$ (3.63 g, 57.7 mmol) was added and the reaction was stirred for 1 h. To the reaction solution was added HCl (6 M) until the PH-3 and stirred for 1 h. Aqueous NaOH (4M) was added to adjust the pH to neutral. The reaction mixture was extracted with EtOAc (300 mL×3). The combined organic layers were washed with brine (250 mL), dried over $Na_2SO_4$, filtered, and concentrated. The residue was purified by flash silica gel chromatography (12 g silica gel, eluent of 100% ethyl acetate/petroleum ether gradient to give 5-(3-chlorophenyl)pyrrolidin-2-one. Calculated $C_{10}H_{11}ClNO$ $[M+H]^+$, 196; Found 196.

Step 2. Preparation of 2-(3-chlorophenyl)-5-methoxy-3,4-dihydro-2H-pyrrole

To a solution of 5-(3-chlorophenyl)pyrrolidin-2-one (7.0 g, 35.8 mmol) in DCM (180 mL) was added trimethyloxonium tetrafluoroborate (7.94 g, 53.7 mmol) at 0° C. under $N_2$. The mixture was stirred at 25° C. for 15 h. The mixture was quenched with saturated $NaHCO_3$ (150 mL) until there were no bubbles, and extracted with DCM (200 mL×2). The combined organic layers were dried over $Na_2SO_4$, filtered, and concentrated in vacuum to give crude 2-(3-chlorophenyl)-5-methoxy-3,4-dihydro-2H-pyrrole, which was used in the next step without further purification. Calculated $C_{11}H_{13}ClNO$ $[M+H]^+$, 210; Found 210.

Step 3. Preparation of methyl 2-(2-(3-chlorophenyl)-3,4-dihydro-2H-pyrrol-5-yl)hydrazine-1-carboxylate A mixture of 2-(3-chlorophenyl)-5-methoxy-3,4-dihydro-2H-pyrrole (7.5 g, 35.8 mmol) and methyl hydrazinecarboxylate (3.22 g, 35.8 mmol) in MeOH (180 mL), HCl·MeOH (2 mL) was stirred at 80° C. for 12 h to give a yellow solution. The solvent was evaporated and the residue was purified by recrystallization to give methyl 2-(2-(3-chlorophenyl)-3,4-dihydro-2H-pyrrol-5-yl)hydrazine-1-carboxylate. Calculated $C_{12}H_{15}ClN_3O_2[M+H]^+$, 268; Found 268.

Step 4. Preparation of I-20A, (S and R)-5-(3-chlorophenyl)-2,5,6,7-tetrahydro-3H-pyrrolo[2,1-c][1,2,4]triazol-3-one To a solution of methyl 2-(2-(3-chlorophenyl)-3,4-dihydro-2H-pyrrol-5-yl)hydrazine-1-carboxylate (5.0 g, 18.7 mmol) in MeOH (100 mL) was added Sodium methylate (3.03 g, 56.0 mmol) and the resulting mixture was stirred at 80° C. for 8 h. The mixture was cooled to room temperature and acidified to pH=7 with HCV/MeOH (4 M). Then the mixture was filtered and the solid was dried by vacuum distillation to give I-20A, (S and R)-5-(3-chlorophenyl)-2,5,6,7-tetrahydro-3H-pyrrolo[2,1-c][1,2,4]triazol-3-one. Calculated $C_{11}H_{11}ClN_3O$ $[M+H]^+$, 236; Found 236.

Preparation of I-21A (5-(pyrazin-2-yl)-2,5,6,7-tetrahydro-3H-pyrrolo[2,1-c][1,2,4]triazol-3-one)

Intermediate I-21A was prepared from pyrazine-2-carbaldehyde as outlined below.

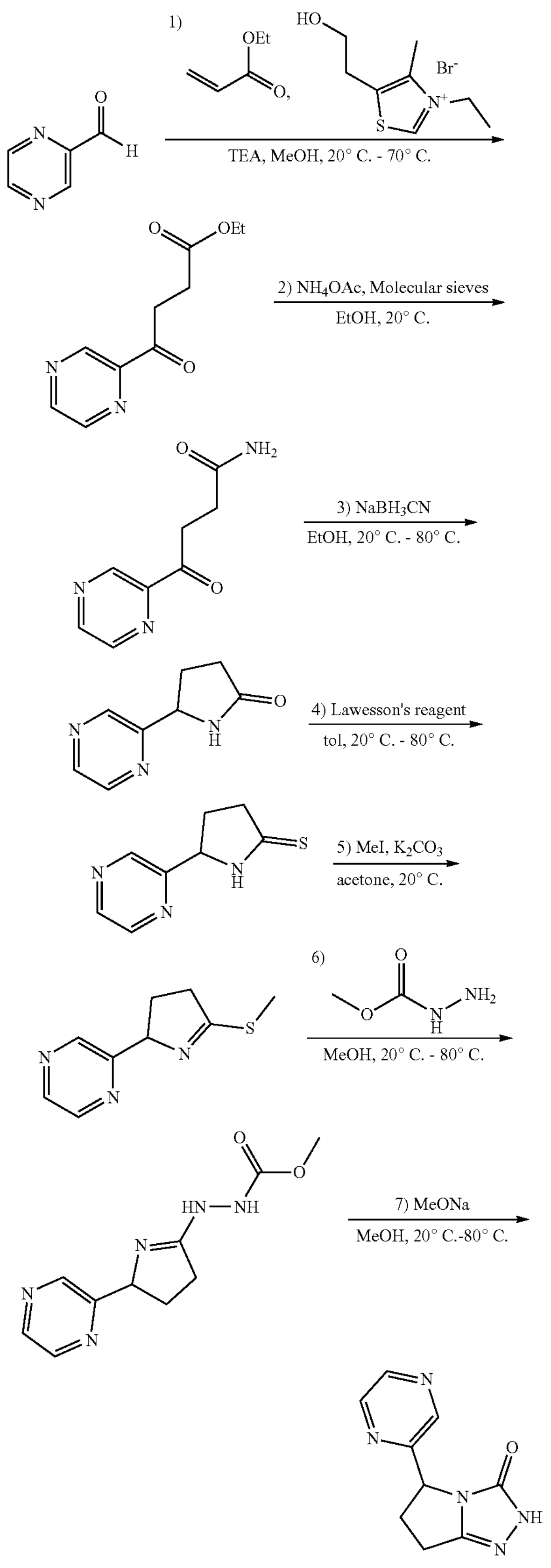

I-21A

Step 1. Preparation of ethyl 4-oxo-4-(pyrazin-2-yl)butanoate

Two reactions of identical scale were carried out in parallel:

To a solution of pyrazine-2-carbaldehyde (180 g, 1.67 mol) in MeOH (1.80 L) at 20° C. was added ethyl acrylate (205 g, 2.05 mol), 3-ethyl-5-(2-hydroxyethyl)-4-methylthiazolium bromide (83.9 g, 0.33 mol), and TEA (505 g, 5.00 mol). The mixture was a heated to 70° C. and stirred for 1 h. The two batches were combined and worked up together. The suspension was filtered and the filter cake was washed with EtOAc. The filtrate was washed with saturated $NH_4Cl$ (1.00 L) and the aqueous layer was extracted with EtOAc (1.00 L×4). The organic layer was washed with saturated $NaHCO_3$ (1.00 L), brine (0.50 L) and dried over $Na_2SO_4$. The organic layer was dried under reduced pressure and the crude residue was purified by flash column chromatography (petroleum ether/EtOAc). The fractions containing the desired product were pooled and concentrated to give ethyl 4-oxo-4-(pyrazin-2-yl)butanoate. $^1H$ (400 MHz, $CDCl_3$) δ 9.13 (s, 1H), 8.69 (d, J=2.00 Hz, 1H), 8.58 (d, J=0.80 Hz, 1H), 4.04-4.09 (m, 2H), 3.43 (t, J=6.40 Hz, 2H), 2.68 (d, J=6.80 Hz, 2H), 1.17 (t, J=7.20 Hz, 2H).

Steps 2-3. Preparation of 5-(pyrazin-2-yl)pyrrolidin-2-one

To a solution of ethyl 4-oxo-4-(pyrazin-2-yl)butanoate (160 g, 768 mmol) in EtOH (1.04 L) at 20° C. was added ammonium acetate (592 g, 7.68 mol) and molecular sieves (320 g, 1.32 mol). The resulting mixture was stirred at 20° C. for 12 h. The reaction is concentrated to dryness and the resulting brown liquid was used in the next step without further purification.

The subsequent step was carried out in two reactions of identical scale in parallel:

4-oxo-4-(pyrazin-2-yl)butanamide (138 g, 768 mmol) in EtOH (960 mL) at 20° C. was added $NaBH_3CN$ (145 g, 2.31 mol) and the resulting mixture was stirred at 80° C. for 5 h. The two batches were combined and worked up together. The suspension was filtered and the filter cake was washed with EtOH (500 mL). The filtrate was concentrated under reduced pressure. The crude residue was purified by flash column chromatography (petroleum ether/30% EtOAc: EtOH). The fractions containing the desired product mass were pooled and concentrated, the resulting residue was dissolved the residue in DCM (1.00 L). The solution was filtered and the filter cake was washed with DCM (200 mL). The filtrate was concentrated to give 5-(pyrazin-2-yl)pyrrolidin-2-one. $^1H$ NMR (400 MHz, $CDCl_3$) δ 8.62-8.64 (m, 2H), 8.58 (d, J=2.40 Hz, 1H), 8.14 (s, 1H), 4.79-4.82 (m, 1H), 2.49-2.50 (m, 1H), 2.23-2.30 (m, 2H), 1.98-2.21 (m, 1H).

Step 4. Preparation of 5-(pyrazin-2-yl)pyrrolidine-2-thione

To a solution of 5-(pyrazin-2-yl)pyrrolidin-2-one (77.0 g, 472 mmol) in toluene (3.85 L) at 20° C. was added Lawesson's reagent (95.4 g, 236 mmol). The resulting mixture was stirred at 80° C. for 0.5 h. The reaction was concentrated under reduced pressure and purified by flash column chromatography (petroleum ether/30% EtOAc:EtOH). The fractions containing the desired product mass were pooled and concentrated to give 5-(pyrazin-2-yl)pyrrolidine-2-thione. $^1H$ NMR (400 MHz, $CDCl_3$) δ 8.61 (d, J=1.20 Hz, 1H), 8.46 (t, J=1.60 Hz, 1H), 8.40 (d, J=2.40 Hz, 1H), 7.74-7.77 (m, 1H), 5.20 (t, J=7.20 Hz, 1H), 4.17-4.21 (m, 1H), 2.70-2.79 (m, 2H), 2.52-2.55 (m, 1H), 2.46 (s, 3H), 2.06-2.10 (m, 2H).

Step 5. Preparation of 2-(5-(methylthio)-3,4-dihydro-2H-pyrrol-2-yl)pyrazine

To a solution of 5-(pyrazin-2-yl)pyrrolidine-2-thione (84.0 g, 469 mmol) in acetone (494 mL) at 20° C. was added the $K_2CO_3$ (194 g, 1.41 mol). The mixture was stirred at 20° C. for 1 h. MeI (133 g, 937 mmol, 58.3 mL) was added dropwise and the reaction was stirred at 20° C. for 11 h. The reaction was filtered and the filter cake was washed with acetone (200 mL). The filtrate was concentrated under reduced pressure and the crude residue was purified by column chromatography (petroleum ether/30% EtOAc:EtOH). The fractions containing the desired product mass were pooled and concentrated to give 2-(5-(methylthio)-3,4-dihydro-2H-pyrrol-2-yl)pyrazine. $^1H$ NMR (400 MHz, $CDCl_3$) δ 8.61 (d, J=1.20 Hz, 1H), 8.46 (t, J=0.8 Hz, 1H), 8.40 (d, J=2.40 Hz, 1H), 7.74-7.77 (m, 1H), 5.20 (t, J=7.20 Hz, 1H), 4.17-4.21 (m, 1H), 2.70-2.79 (m, 2H), 2.52-2.55 (m, 1H), 2.46 (s, 3H), 2.06-2.10 (m, 2H).

Steps 6-7. Preparation of I-21A

Two reactions of identical scale were carried out in parallel:

To a solution of 2-(5-(methylthio)-3,4-dihydro-2H-pyrrol-2-yl)pyrazine (22.0 g, 114 mmol) in MeOH (440 mL) at 20° C. was added methyl hydrazinecarboxylate (15.4 g, 171 mmol). The reaction mixture was heated to 80° C. for 2 h. The reaction was concentrated to dryness and methyl 2-(2-(pyrazin-2-yl)-3,4-dihydro-2H-pyrrol-5-yl)hydrazine-1-carboxylate was obtained and used into the next step without further purification.

The subsequent step was carried out in two reactions of identical scale in parallel:

To a solution of methyl 2-(2-(pyrazin-2-yl)-3,4-dihydro-2H-pyrrol-5-yl)hydrazine-1-carboxylate (26.0 g, 111 mmol) in MeOH (485 mL) at 20° C. was added MeONa (25.6 g, 332 mmol). The resulting mixture was stirred at 80° C. for 12 h. The two batches were combined and poured into $H_2O$ (500 mL) at room temperature. The mixture was filtered and the filter cake was washed with MeOH (200 mL). The filtrate was concentrated to give the desired crude residue which was purified by flash column chromatography (petroleum ether/30% EtOAc:EtOH) to give 5-(pyrazin-2-yl)-2,5,6,7-tetrahydro-3H-pyrrolo[2,1-c][1,2,4]triazol-3-one. After another cycle of purification by pre-HPLC (Method: Welch Xtimate C18; Condition water (TFA)-ACN) to give I-21A, 5-(pyrazin-2-yl)-2,5,6,7-tetrahydro-3H-pyrrolo[2,1-c][1,2,4]triazol-3-one. $^1H$ NMR (400 MHz, $CDCl_3$) δ 9.26 (s, 1H), 8.69 (s, 1H), 8.57 (d, J=2.40 Hz, 2H), 5.31-5.33 (m, 1H), 3.00-3.07 (m, 2H), 2.85-2.87 (m, 1H), 2.73-2.80 (m, 1H).

Preparation of Intermediate I-22A ((S and R)-5-(3,5-difluorophenyl)-5,6-dihydrothiazolo[2,3-c][1,2,4]triazol-3(2H)-one)

Intermediate I-22A was prepared from 2-amino-2-(3,5-difluorophenyl)ethan-1-ol as outlined below.

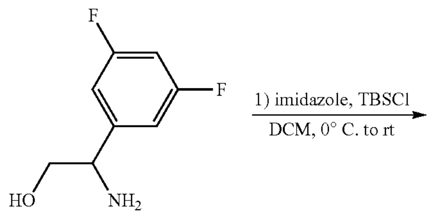

-continued

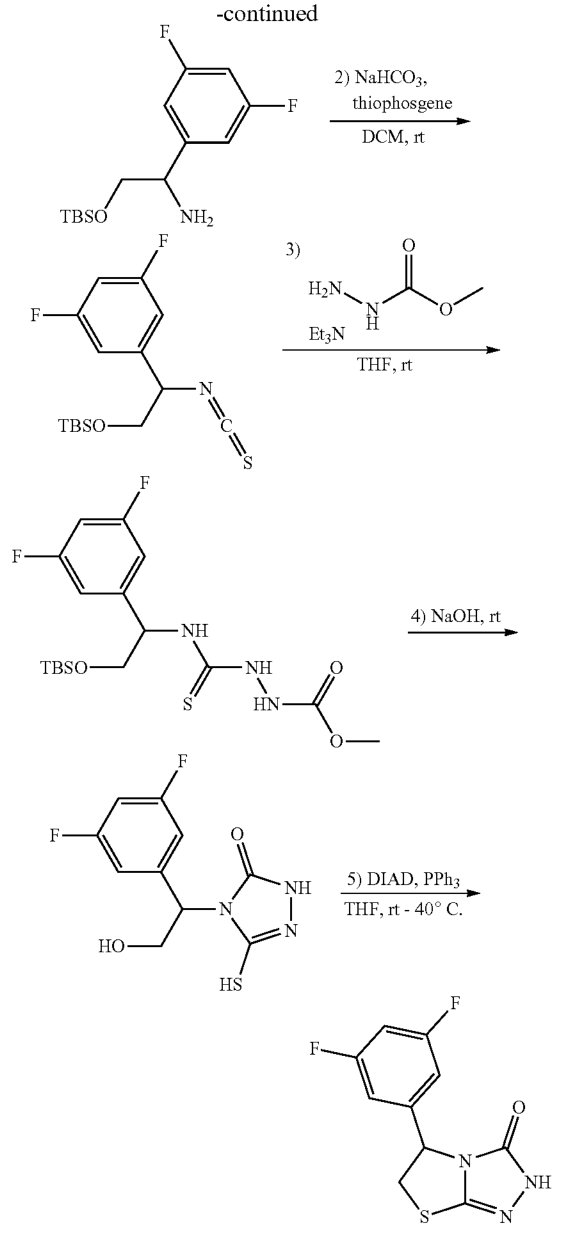

I-22A

Step 1. Preparation of 2-((tert-butyldimethylsilyl)oxy)-1-(3,5-difluorophenyl)ethan-1-amine To a mixture of 2-amino-2-(3,5-difluorophenyl)ethan-1-ol (800 mg, 4.62 mmol) in DCM (20 mL) was added imidazole (472 mg, 6.93 mmol) and TBSCl (836 mg, 5.54 mmol) at 0° C. under $N_2$. The mixture was stirred at 20° C. for 12 h. Distilled water (40 mL) was added, after stirring for 10 min, the mixture was extracted with DCM (30 mL×2), washed with brine (40 mL), the organic layer was dried over $Na_2SO_4$ and filtered. The filtrate was concentrated in vacuo. The residue was purified by flash column chromatography (4 g silica gel, eluent of 4% EtOAc/petroleum ether gradient) to give 2-((tert-butyldimethylsilyl)oxy)-1-(3,5-difluorophenyl)ethan-1-amine. Calculated $C_{14}H_{24}F_2NOSi$ $[M+H]^+$, 288; Found 288.

Step 2. Preparation of tert-butyl(2-(3,5-difluorophenyl)-2-isothiocyanatoethoxy)dimethylsilane A solution of 2-((tert-butyldimethylsilyl)oxy)-1-(3,5-difluorophenyl)ethan-1-amine (700 mg, 2.435 mmol) in DCM (5 mL) and aqueous $NaHCO_3$ (5 ml) was stirred at 25° C. for 15 min. To the mixture was added thiophosgene (0.355 mL, 4.87 mmol) via syringe to the bottom layer at 25° C., the mixture was stirred at 25° C. for 1.5 h. The mixture was quenched with brine, and extracted with DCM (20 mL×2). The combined organic layers were dried over $Na_2SO_4$ and filtered. The filtrate was concentrated in vacuo to afford crude tert-butyl(2-(3,5-difluorophenyl)-2-isothiocyanatoethoxy)dimethylsilane, which was used directly in next step without further purification. Calculated $C_{15}H_{22}F_2NOSSi$ $[M+H]^+$, 330; Found 330.

Step 3. Preparation of methyl 6-(3,5-difluorophenyl)-9,9,10,10-tetramethyl-4-thioxo-8-oxa-2,3,5-triaza-9-silaundecanoate A mixture of tert-butyl(2-(3,5-difluorophenyl)-2-isothiocyanatoethoxy)dimethylsilane (680 mg, 2.06 mmol), $Et_3N$ (0.863 mL, 6.19 mmol) and methyl hydrazinecarboxylate (223 mg, 2.477 mmol) in THF (10 mL) was stirred at 25° C. for 12 h. The mixture was concentrated in vacuo. The residue was purified by flash silica gel chromatography (8 g silica gel, eluent of 55% ethyl acetate/petroleum ether gradient) to afford methyl 6-(3,5-difluorophenyl)-9,9,10,10-tetramethyl-4-thioxo-8-oxa-2,3,5-triaza-9-silaundecanoate. Calculated $C_{17}H_{28}F_2N_3O_3SSi$ $[M+H]^+$ 420; Found 420.

Step 4. Preparation of 4-(1-(3,5-difluorophenyl)-2-hydroxyethyl)-5-mercapto-2,4-dihydro-3H-1,2,4-triazol-3-one A mixture of methyl 6-(3,5-difluorophenyl)-9,9,10,10-tetramethyl-4-thioxo-8-oxa-2,3,5-triaza-9-silaundecanoate (630 mg, 1.50 mmol) in sodium hydroxide (10 mL, 1.000 mmol) was stirred at 25° C. for 3 h. The mixture was purified by pre-HPLC (Column; Boston Green ODS, Condition; water (0.01% TFA)-CAN) to afford 4-(1-(3,5-difluorophenyl)-2-hydroxyethyl)-5-mercapto-2,4-dihydro-3H-1,2,4-triazol-3-one. Calculated $C_{10}H_{10}F_2N_3O_2S$ $[M+H]^+$ 274; Found 274.

Step 5. Preparation of I-22A, (S and R)-5-(3,5-difluorophenyl)-5,6-dihydrothiazolo[2,3-c][1,2,4]triazol-3(2H)-one To a solution of 4-(1-(3,5-difluorophenyl)-2-hydroxyethyl)-5-mercapto-2,4-dihydro-3H-1,2,4-triazol-3-one (200 mg, 0.183 mmol) and triphenylphosphane (96 mg, 0.366 mmol) in THF (4 mL) was added DIAD (0.071 mL, 0.366 mmol) at 25° C., and the mixture was stirred at 40° C. for 12 h under $N_2$ (g). The mixture was concentrated in vacuo. The residue was purified by pre-HPLC (Column; Boston Green ODS, Condition; water (0.01% TFA)-CAN) to afford I-22A, (S and R)-5-(3,5-difluorophenyl)-5,6-dihydrothiazolo[2,3-c][1,2,4]triazol-3(2H)-one. Calculated $C_{10}H_8F_2N_3OS$ $[M+H]^+$ 274; Found 274.

Preparation of Intermediate I-23A ((S and R)-5-(4-methoxyphenyl)-2,5,6,7-tetrahydro-3H-pyrrolo[2,1-c][1,2,4]triazol-3-one)

Intermediate I-23A was prepared from pyrrolidine-2,5-dione as outlined below.

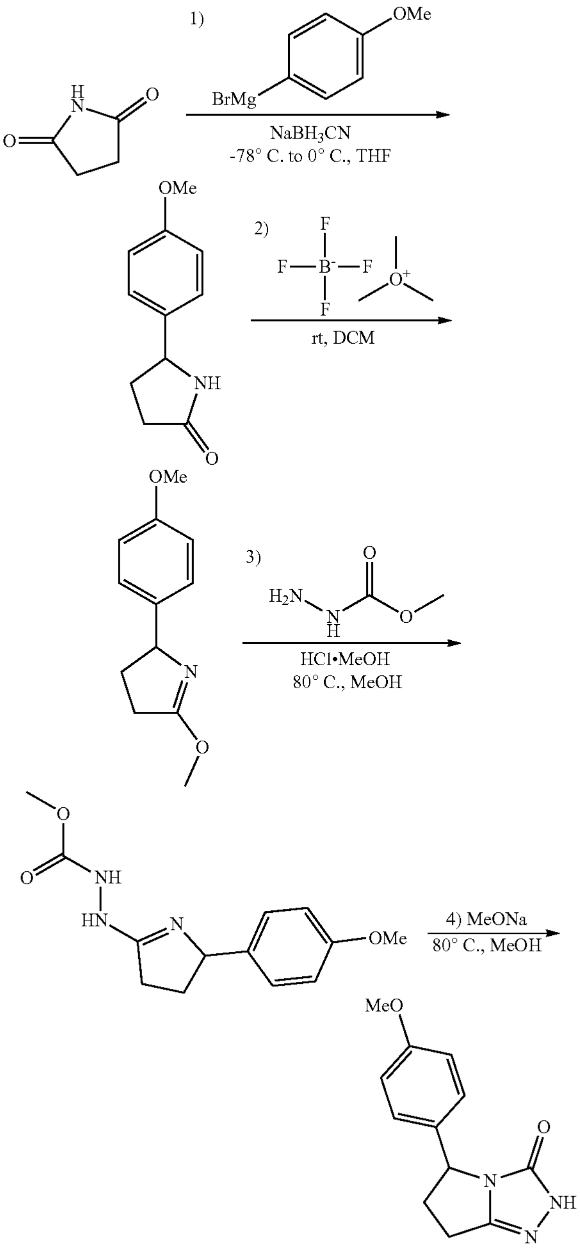

I-23A

Step 1. Preparation of 5-(4-methoxyphenyl)pyrrolidin-2-one

To a solution of pyrrolidine-2,5-dione (2 g, 20.2 mmol) in THF (100 mL) was added 4-methoxyphenylmagnesium bromide (89 mL, 44.4 mmol) by syringe dropwisely at −78° C. under $N_2$. After the addition was completed, the reaction was allowed to warm up to 25° C. and stirred for another 16 h. Then $NaBH_3CN$ (1.52 g, 24.2 mmol) was added to the mixture and stirred for another 2 h. Aqueous HCl (4M) was added and the pH was adjusted to 4. The mixture was stirred at rt for another 1 h. Aqueous NaOH (4M) was added to adjust the pH to neutral. The reaction mixture extracted with EtOAc (50 mL×2). The combined organic phases were washed with brine (100 mL), dried over anhydrous $Na_2SO_4$, filtered, and concentrated under reduced pressure. The mixture was purified by flash silica gel chromatography (40 g silica gel, eluent of 80-100% EtOAc gradient) to give 5-(4-methoxyphenyl)pyrrolidin-2-one. Calculated $C_{11}H_{14}NO_2$ $[M+H]^+$ 192; Found 192.

Step 2. Preparation of 5-methoxy-2-(4-methoxyphenyl)-3,4-dihydro-2H-pyrrole

To a solution of 5-(4-methoxyphenyl)pyrrolidin-2-one (600 mg, 3.14 mmol) in DCM (20 mL) was added trimethyloxonium tetrafluoroborate (696 mg, 4.71 mmol) at 0° C. under $N_2$. The mixture was stirred at 25° C. for 12 h. The mixture was quenched with saturated $NaHCO_3$ (20 mL) until there are no bubbles, extracted with DCM (20 mL×2). The combined organic layers were dried over $Na_2SO_4$, filtered, and concentrated in vacuum to give crude 5-methoxy-2-(4-methoxyphenyl)-3,4-dihydro-2H-pyrrole, which was used in the next step without further purification. Calculated $C_{12}H_{16}NO_2$ $[M+H]^+$ 206; Found 206.

Step 3. Preparation of methyl 2-(2-(4-methoxyphenyl)-3,4-dihydro-2H-pyrrol-5-yl)hydrazine-1-carboxylate To a solution of 5-methoxy-2-(4-methoxyphenyl)-3,4-dihydro-2H-pyrrole (600 mg, 2.92 mmol) in MeOH (20 mL) was added methyl hydrazinecarboxylate (290 mg, 3.22 mmol) and HCl/MeOH (0.06 mL) at 20° C. and the resulting mixture was stirred at 80° C. for 12 h. The reaction was directly concentrated and the residue was washed with petroleum ether/EtOAc=1:1 to give methyl 2-(2-(4-methoxyphenyl)-3,4-dihydro-2H-pyrrol-5-yl)hydrazine-1-carboxylate. Calculated $C_{13}H_{18}N_3O_3[M+H]^+$ 264; Found 264.

Step 3. Preparation of I-23A, (S and R)-5-(4-methoxyphenyl)-2,5,6,7-tetrahydro-3H-pyrrolo[2,1-c][1,2,4]triazol-3-one To a solution of methyl 2-(2-(4-methoxyphenyl)-3,4-dihydro-2H-pyrrol-5-yl)hydrazine-1-carboxylate (400 mg, 1.52 mmol) in MeOH (10 mL) was added NaOMe (410 mg, 7.60 mmol) and the resulting mixture was stirred at 80° C. for 24 h. The mixture was cooled to room temperature and acidified to pH=7 with HCl/MeOH (4 M). Then the mixture was filtered and purified by prep. HPLC (Column; Boston Uni C18, Condition; water (0.01% TFA)-ACN) to give I-23A (S and R)-5-(4-methoxyphenyl)-2,5,6,7-tetrahydro-3H-pyrrolo[2,1-c][1,2,4]triazol-3-one. Calculated $C_{12}H_{14}N_3O_2$ $[M+H]^+$ 232; Found 232.

Preparation of Intermediate I-24A ((S and R)-4-(3-oxo-2,5,6,7-tetrahydro-3H-pyrrolo[2,1-c][1,2,4]triazol-5-yl)benzonitrile)

Intermediate I-24A was prepared from I-11A as outlined below.

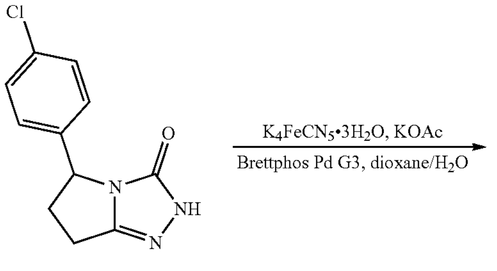

I-11A

-continued

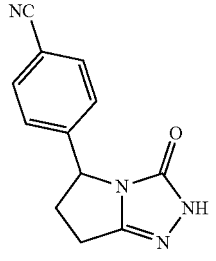

I-24A

To a stirred solution of 5-(4-chlorophenyl)-2,5,6,7-tetrahydro-3H-pyrrolo[2,1-c][1,2,4]triazol-3-one (200 mg, 0.849 mmol) in dioxane (5 mL) and water (5 mL) was added potassium ferrocyanide trihydrate (358 mg, 0.849 mmol), potassium acetate (250 mg, 2.55 mmol) and Brettphos Pd G3 (115 mg, 0.127 mmol) at 20° C. After the addition was finished, the reaction was stirred at 100° C. for 12 h under $N_2$ atmosphere. The reaction was filtered and the filtrate was concentrated to dryness. The residue was purified by Prep-HPLC (Column; Phenomenex Gemini-NX, Condition; water (7 mM $HCOONH_4$)-ACN) to give I-24A, (S and R)-4-(3-oxo-2,5,6,7-tetrahydro-3H-pyrrolo[2,1-c][1,2,4]triazol-5-yl)benzonitrile. Calculated $C_{12}H_{11}N_4O$ $[M+H]^+$ 227; Found 227.

Preparation of Intermediate I-25A ((S and R)-5-(6-methylpyrazin-2-yl)-2,5,6,7-tetrahydro-3H-pyrrolo[2,1-c][1,2,4]triazol-3-one)

Intermediate I-25A was prepared as outlined below.

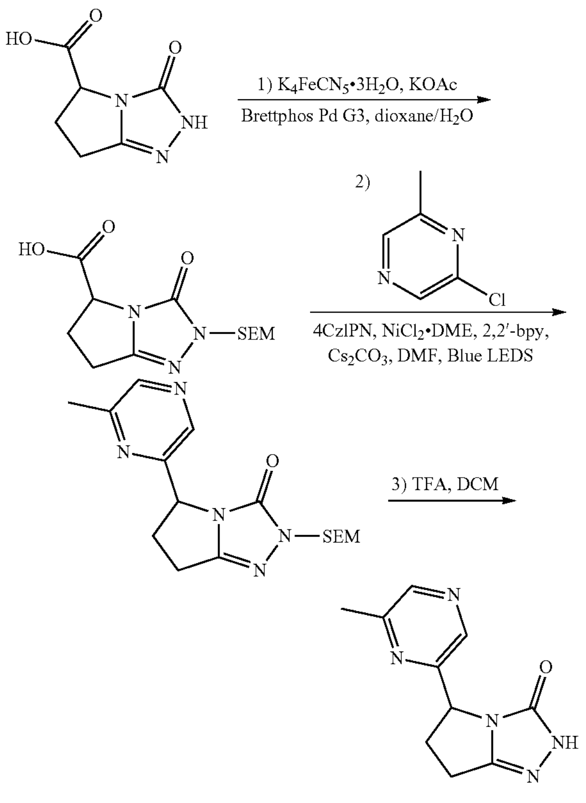

I-25A

Step 1. Preparation of methyl 3-oxo-2-((2-(trimethylsilyl)ethoxy)methyl)-2,5,6,7-tetrahydro-3H-pyrrolo[2,1-c][1,2,4]triazole-5-carboxylate To a solution of methyl 3-oxo-2,5,6,7-tetrahydro-3H-pyrrolo[2,1-c][1,2,4]triazole-5-carboxylate (5.0 g, 27.3 mmol), $Cs_2CO_3$ (13.3 g, 40.9 mmol) in DMF (136 mL) was added SEM-Cl (5.81 mL, 32.8 mmol) at 0° C. and the resulting mixture was stirred at 20° C. for 12 h. The reaction was filtered and the filtrate was concentrated to give methyl 3-oxo-2-((2-(trimethylsilyl)ethoxy)methyl)-2,5,6,7-tetrahydro-3H-pyrrolo[2,1-c][1,2,4]triazole-5-carboxylate, which was used to next step without further purification. Calculated $C_{12}H_{22}N_3O_4Si$ $[M+H]^+$ 300; Found 300.

Step 2. 5-(6-methylpyrazin-2-yl)-2-((2-(trimethylsilyl)ethoxy)methyl)-2,5,6,7-tetrahydro-3H-pyrrolo[2,1-c][1,2,4]triazol-3-one To a solution of 3-oxo-2-((2-(trimethylsilyl)ethoxy)methyl)-2,5,6,7-tetrahydro-3H-pyrrolo[2,1-c][1,2,4]triazole-5-carboxylic acid (500 mg, 1.670 mmol) in DMF (10 mL) was added 2-chloro-6-methylpyrazine (429 mg, 3.34 mmol), $Cs_2CO_3$ (816 mg, 2.505 mmol), 2,2'-bipyridine (58.7 mg, 0.376 mmol), Nickel(II) chloride ethylene glycol dimethyl ether complex (55.0 mg, 0.250 mmol), 4CzIPN (65.9 mg, 0.083 mmol) under $N_2$ and the resulting mixture was stirred for 12 h with 450 nm blue light. To the mixture was added water (50 mL) and extracted with EtOAc (20 mL×3). The combined organic layers were washed with brine (50 mL), dried over $Na_2SO_4$, filtered and concentrated. The residue was purified by flash silica gel chromatography (eluent of 100% ethyl acetate/petroleum ether gradient) to give 5-(6-methylpyrazin-2-yl)-2-((2-(trimethylsilyl)ethoxy)methyl)-2,5,6,7-tetrahydro-3H-pyrrolo[2,1-c][1,2,4]triazol-3-one. Calculated $C_{16}H_{26}N_5O_2Si$ $[M+H]^+$ 348; Found 348.

Step 3. Preparation of I-25A, (S and R)-5-(6-methylpyrazin-2-yl)-2,5,6,7-tetrahydro-3H-pyrrolo[2,1-c][1,2,4]triazol-3-one To a mixture of 5-(6-methylpyrazin-2-yl)-2-((2-(trimethylsilyl)ethoxy)methyl)-2,5,6,7-tetrahydro-3H-pyrrolo[2,1-c][1,2,4]triazol-3-one (320 mg, 0.921 mmol) in DCM (4.5 mL) was added TFA (1.5 mL) and the resulting mixture was stirred at 20° C. for 2 h. The reaction solution was directly concentrated. The residue was dissolved in MeOH (5 mL), added $NH_3$— $H_2O$ (0.5 mL) to PH-8 and stirred for 1 h. Then the solution was concentrated and the residue was purified by Prep-HPLC (Column: Boston Uni C18, Condition water (0.01% TFA)-ACN) to give I-25A, (S and R)-5-(6-methylpyrazin-2-yl)-2,5,6,7-tetrahydro-3H-pyrrolo[2,1-c][1,2,4]triazol-3-one. Calculated $C_{10}H_{12}N_5O$ $[M+H]^+$ 218; Found 218.

Preparation of Intermediates I-26A (5S,7R)-5-(3,5-difluorophenyl)-7-methyl-2,5,6,7-tetrahydro-3H-pyrrolo[2,1-c][1,2,4]triazol-3-one and I-27A (5S,7S)-5-(3,5-difluorophenyl)-7-methyl-2,5,6,7-tetrahydro-3H-pyrrolo[2,1-c][1,2,4]triazol-3-one Intermediates I-26A and I-27A were prepared from 4-(3,5-difluorophenyl)-2-methyl-4-oxobutanoic acid as outlined below.

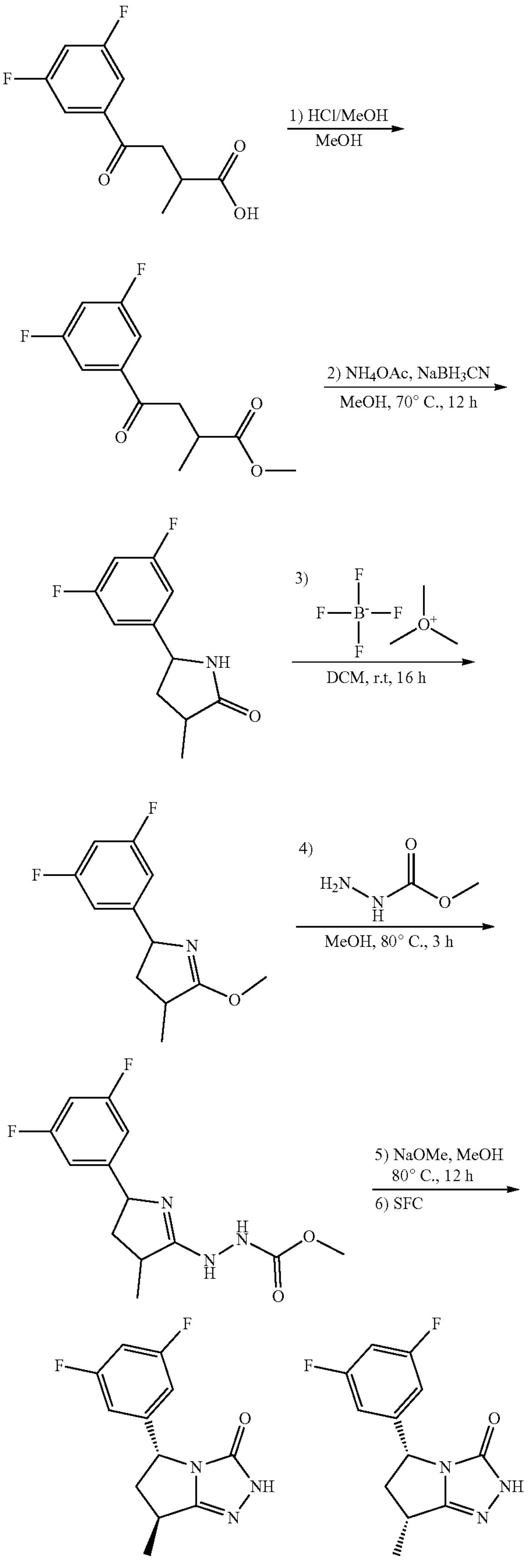

-continued

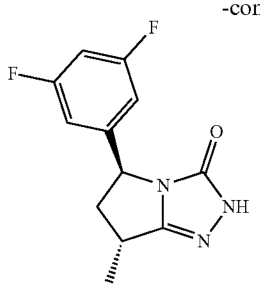

I-26A

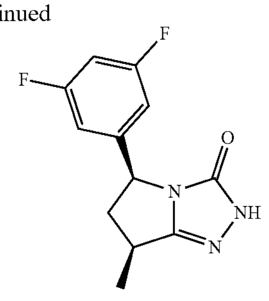

I-27A

Step 1. Synthesis of methyl 4-(3,5-difluorophenyl)-2-methyl-4-oxobutanoate

To a solution of 4-(3,5-difluorophenyl)-2-methyl-4-oxobutanoic acid (21 g, 92 mmol) in MeOH (20 ml) was added HCV/MeOH (200 ml). The resulting mixture was stirred at 25° C. for 16 h. The mixture was concentrated under reduced pressure and the resulting residue was diluted with saturated aqueous $NaHCO_3$ (150 mL) and extracted with EtOAc (3×30 mL). The combined organic layers were washed with brine (10 mL), dried over $Na_2SO_4$, filtered and concentrated under reduced pressure to give a residue. The residue was purified by silica gel chromatography (petroleum ether/ethyl acetate) to afford methyl 4-(3,5-difluorophenyl)-2-methyl-4-oxobutanoate with impurities present. The resulting material was further purified by preparative SFC (Method Column DAICEL CHIRALPAK AD; Condition MeOH (0.1% $NH_3H_2O$)) to afford methyl 4-(3,5-difluorophenyl)-2-methyl-4-oxobutanoate, combination of first and second eluting peaks. $^1$H NMR (400 MHz, MeOD) δ 7.54-7.62 (m, 2H), 7.20-7.29 (m, 1H), 3.67 (s, 3H), 3.44 (dd, J=18.24, 8.70 Hz, 1H), 3.09-3.17 (m, 1H), 2.99-3.09 (m, 1H), 1.27 (d, J=7.27 Hz, 3H).

Step 2. Synthesis of 5-(3,5-difluorophenyl)-3-methylpyrrolidin-2-one

To a solution of methyl 4-(3,5-difluorophenyl)-2-methyl-4-oxobutanoate (2.5 g, 10.3 mmol) in MeOH (25 mL) was added ammonium acetate (0.796 g, 10.3 mmol) and sodium cyanoborohydride (0.649 g, 10.3 mmol) at 0° C. under nitrogen atmosphere. The resulting mixture was brought to 70° C. for 12 h. The mixture was cooled to ambient temperature, poured into ice water (100 mL) and extracted with EtOAc (3×20 mL). The combined organic layers were washed with brine (20 mL), dried over anhydrous $Na_2SO_4$, filtered and concentrated under reduced pressure. The resulting residue was purified by silica gel chromatography (petroleum ether/ethyl acetate) to afford 5-(3,5-difluorophenyl)-3-methylpyrrolidin-2-one. Calculated $C_{11}H_{12}F_2NO$ $[M+H]^+$, 212; found 212.

Step 3. Synthesis of 2-(3,5-difluorophenyl)-5-methoxy-4-methyl-3,4-dihydro-2H-pyrrole To a solution of 5-(3,5-difluorophenyl)-3-methylpyrrolidin-2-one (1.5 g, 7.1 mmol) in DCM (15 mL) was added trimethyloxonium tetrafluoroborate (1.58 g, 10.6 mmol) at 0° C. under nitrogen. The resulting mixture was stirred at 45° C. for 16 h. The mixture was quenched by dropwise addition into saturated aqueous $NaHCO_3$ (100 mL) at 5-10° C., extracted with DCM (3×20 mL). The combined organic layers were washed with brine (20 mL), dried over $Na_2SO_4$, filtered and concentrated under reduced pressure to afford 2-(3,5-difluorophenyl)-5-methoxy-4-methyl-3,4-dihydro-2H-pyrrole, which was used in the next step without purification. Calculated $C_{12}H_{14}F_2NO$ $[M+H]^+$, 226; found 226.

Steps 4. Synthesis of methyl 2-(2-(3,5-difluorophenyl)-4-methyl-3,4-dihydro-2H-pyrrol-5-yl)hydrazine-1-carboxylate To a solution of 2-(3,5-difluorophenyl)-5-methoxy-4-methyl-3,4-dihydro-2H-pyrrole (1.6 g, 7.1 mmol) in MeOH (20 mL) was added methyl hydrazinecarboxylate (0.672 g, 7.46 mmol) at 25° C. under nitrogen. The resulting mixture was stirred at 80° C. for 3 h. The reaction was concentrated under reduced pressure to give methyl 2-(2-(3,5-difluorophenyl)-4-methyl-3,4-dihydro-2H-pyrrol-5-yl)hydrazine-1-carboxylate, which was used in the next step without purification. Calculated $C_{13}H_{16}F_2N_3O_2[M+H]^+$, 284; found 284.

Steps 5-6. Synthesis of 5-(3,5-difluorophenyl)-7-methyl-2,5,6,7-tetrahydro-3H-pyrrolo[2,1-c][1,2,4]triazol-3-one followed by SFC to afford I-26A and I-27A To a solution of methyl 2-(2-(3,5-difluorophenyl)-4-methyl-3,4-dihydro-2H-pyrrol-5-yl)hydrazine-1-carboxylate (2 g, 7.06 mmol) in MeOH (20 mL) was added sodium methylate (3.58 g, 21.2 mmol) at 0° C. under nitrogen. The resulting mixture was brought to 80° C. for 12 h. The mixture was cooled to 0° C. and acidified to pH=7 with HCl/MeOH (4 M). The mixture was filtered and the filtrate was concentrated under reduced pressure. The resulting residue was purified by preparative HPLC (Column Welch Xtimate C18 250*70 mm*10 um; conditions water ($NH_4HCO_3$)-MeCN) to afford 5-(3,5-difluorophenyl)-7-methyl-2,5,6,7-tetrahydro-3H-pyrrolo[2,1-c][1,2,4]triazol-3-one as a racemic mixture. The mixture was separated by preparative SFC (Column: DAICEL CHIRALCEL OD (250 mm×30 mm, 10 um); Condition 0.1% $NH_3H_2O$/IPA) to afford I-27A, (5S,7S)-5-(3,5-difluorophenyl)-7-methyl-2,5,6,7-tetrahydro-3H-pyrrolo[2,1-c][1,2,4]triazol-3-one as the fourth eluting peak. The second and third eluting peaks were poorly resolved. The peaks were combined and concentrated under reduced pressure and the resulting residue was repurified by preparative SFC (Column (s,s) WHELK-O1 (250 mm×30 mm, 5 um) Condition 0.1% $NH_3H_2O$/EtOH) to afford I-26A, (5S,7R)-5-(3,5-difluorophenyl)-7-methyl-2,5,6,7-tetrahydro-3H-pyrrolo[2,1-c][1,2,4]triazol-3-one as the second eluting peak.

(5S,7R)-5-(3,5-difluorophenyl)-7-methyl-2,5,6,7-tetrahydro-3H-pyrrolo[2,1-c][1,2,4]triazol-3-one (I-26A)

$^1$H NMR (400 MHz, MeOD) δ 6.83-6.97 (m, 3H), 5.29 (dd, J=3.2, 8.2, Hz, 1H) 3.32-3.38 (m, 1H), 2.58-2.79 (m, 2H), 1.34 (d, J=6.9 Hz, 3H). Calculated $C_{12}H_{12}F_2N_3O$ $[M+H]^+$, 252; found 252.

(5S,7S)-5-(3,5-difluorophenyl)-7-methyl-2,5,6,7-tetrahydro-3H-pyrrolo[2,1-c][1,2,4]triazol-3-one (I-27A)

$^1$H NMR (400 MHz, MeOD) δ 6.85-7.01 (m, 3H), 5.09-5.24 (m, 1H), 3.15-3.28 (m, 2H), 1.97-2.12 (m, 1H), 1.34 (d, J=6.5 Hz, 3H). Calculated $C_{12}H_{12}F_2N_3O$ $[M+H]^+$, 252; found 252.

Preparation of Intermediate I-28A 5-(5-fluoropyridin-2-yl)-2,5,6,7-tetrahydro-3H-pyrrolo[2,1-c][1,2,4]triazol-3-one Intermediate I-28A was prepared from 3-oxo-2-((2-(trimethylsilyl)ethoxy)methyl)-2,5,6,7-tetrahydro-3H-pyrrolo[2,1-c][1,2,4]triazole-5-carboxylic acid as outlined below.

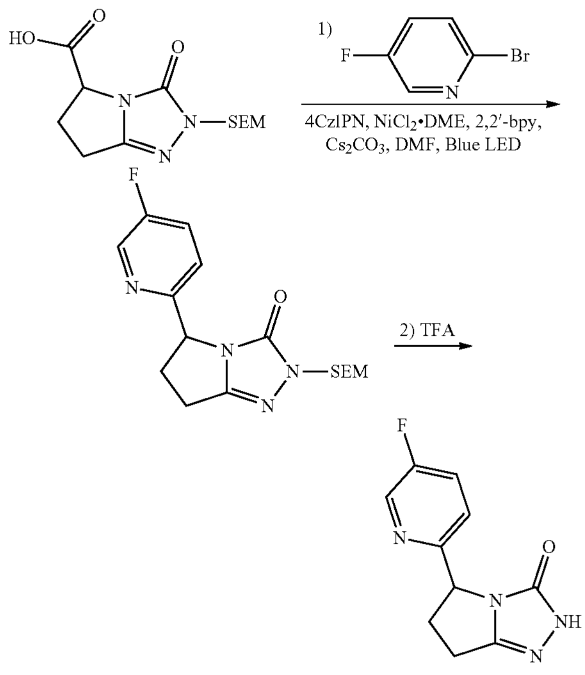

I-28A

Step 1. Synthesis of 5-(5-fluoropyridin-2-yl)-2-((2-(trimethylsilyl)ethoxy)methyl)-2,5,6,7-tetrahydro-3H-pyrrolo[2,1-c][1,2,4]triazol-3-one To a solution of 3-oxo-2-((2-(trimethylsilyl)ethoxy)methyl)-2,5,6,7-tetrahydro-3H-pyrrolo[2,1-c][1,2,4]triazole-5-carboxylic acid (700 mg, 2.34 mmol) in DMF (14 mL) was added 2-bromo-5-fluoropyridine (411 mg, 2.34 mmol), $Cs_2CO_3$ (1143 mg, 3.51 mmol), 2,2'-bipyridine (82 mg, 0.53 mmol), nickel(II) chloride ethylene glycol dimethyl ether complex (77 mg, 0.35 mmol) and 4CzIPN (92 mg, 0.12 mmol) under $N_2$. The resulting mixture was stirred for 12 h with 450 nm blue light. The mixture was purified by preparative HPLC (Column Boston Green ODS 150*30 mm*5 um; condition water (0.1% TFA)-MeCN) to afford 5-(5-fluoropyridin-2-yl)-2-((2-(trimethylsilyl)ethoxy)methyl)-2,5,6,7-tetrahydro-3H-pyrrolo[2,1-c][1,2,4]triazol-3-one. Calculated $C_{16}H_{24}FN_4O_2Si$ $[M+H]^+$, 351; found 351.

Step 2. Synthesis of I-28A 5-(5-fluoropyridin-2-yl)-2,5,6,7-tetrahydro-3H-pyrrolo[2,1-c][1,2,4]triazol-3-one To a mixture of 5-(5-fluoropyridin-2-yl)-2-((2-(trimethylsilyl)ethoxy)methyl)-2,5,6,7-tetrahydro-3H-pyrrolo[2,1-c][1,2,4]triazol-3-one (220 mg, 0.628 mmol) in DCM (6 mL) was added TFA (2 mL). The resulting mixture was stirred at ambient temperature for 2 h. The reaction was concentrated and the resulting residue was dissolved in MeOH (10 mL). Ammonium hydroxide was added until pH-8 and the resulting solution was stirred for 1 h. The solution was concentrated and the resulting residue was purified by preparative HPLC (Column Welch Xtimate C18 150*25 mm*5 um; condition water (10 mM-$NH_4HCO_3$)-MeCN) to afford I-28A, 5-(5-fluoropyridin-2-yl)-2,5,6,7-tetrahydro-3H-pyrrolo[2,1-c][1,2,4]triazol-3-one. Calculated $C_{10}H_{10}FN_4O$ $[M+H]^+$, 221; found 221.

Preparation of Intermediate I-29A 5-(3-chloro-5-fluoro-4-methylphenyl)-2,5,6,7-tetrahydro-3H-pyrrolo[2,1-c][1,2,4]triazol-3-one Intermediate I-29A was prepared from 5-bromo-1-chloro-3-fluoro-2-methylbenzene as outlined below.

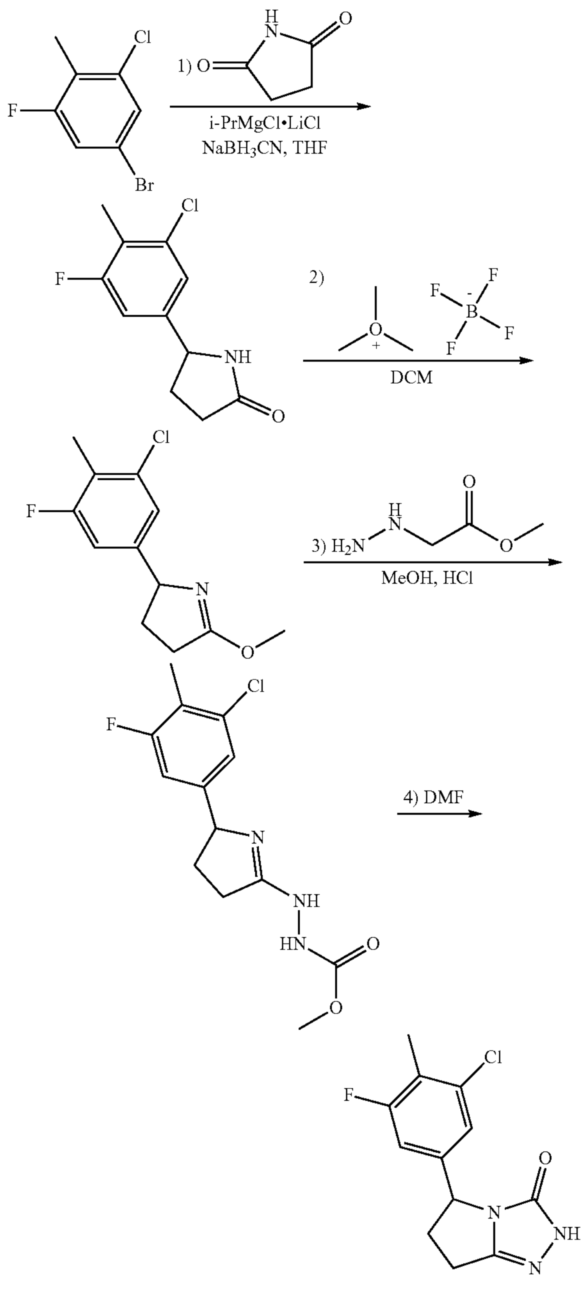

I-29A

Step 1. Synthesis of 5-(3-chloro-5-fluoro-4-methylphenyl)pyrrolidin-2-one

To a solution of 5-bromo-1-chloro-3-fluoro-2-methylbenzene (4.96 g, 22.2 mmol) in THF (100 mL) was added iPrMgCl·LiCl (1.3 M in THF) (18.63 mL, 24.22 mmol) at 0° C. under nitrogen. The resulting solution was stirred at 20° C. for 1 h. To another solution of pyrrolidine-2,5-dione (2.00 g, 20.2 mmol) in THF (100 mL) was added iPrMgCl·LiCl (1.3 M in THF) (13.97 mL, 18.17 mmol) at 0° C. under nitrogen. The resulting solution was stirred at 0° C. for 1 h. The first solution was added to the second solution at −78° C. The resulting mixture was allowed to warm to ambient temperature and stirred for 16 h. $NaBH_3CN$ (1.78 g, 28.3 mmol) was added to the reaction mixture at ambient temperature and the reaction was stirred for 1 h. The reaction was acidified to pH=3-4 with HCl (6 M), stirred for 1 h and neutralized with aqueous NaOH (4 M). The mixture was diluted with water (300 mL) and extracted with EtOAc (3×500 mL). The combined organic layers were dried over $Na_2SO_4$, filtered and concentrated under reduced pressure. The resulting residue was purified by silica gel chromatography (ethyl acetate) to afford 5-(3-chloro-5-fluoro-4-methylphenyl)pyrrolidin-2-one. Calculated $C_{11}H_{12}ClFNO$ $[M+H]^+$, 228; found 228.

Step 2. Synthesis of 2-(3-chloro-5-fluoro-4-methylphenyl)-5-methoxy-3,4-dihydro-2H-pyrrole To a solution of 5-(3-chloro-5-fluoro-4-methylphenyl) pyrrolidin-2-one (1.6 g, 7.0 mmol) in DCM (20 mL) was added trimethyloxonium tetrafluoroborate (1.559 g, 10.54 mmol) at 0° C. under nitrogen. The mixture was stirred at 40° C. for 24 h under nitrogen. The mixture was cooled to ambient temperature, quenched with saturated aqueous $NaHCO_3$ (50 mL) and extracted with DCM (2×50 mL). The combined organic layers were dried over $Na_2SO_4$, filtered and concentrated under reduced pressure to afford crude 2-(3-chloro-5-fluoro-4-methylphenyl)-5-methoxy-3,4-dihydro-2H-pyrrole, which was used in the next step without further purification. Calculated $C_{12}H_{14}ClFNO$ $[M+H]^+$, 242; found 242.

Step 3. Synthesis of methyl 2-(2-(3-chloro-5-fluoro-4-methylphenyl)-3,4-dihydro-2H-pyrrol-5-yl)hydrazine-1-carboxylate To a solution of 2-(3-chloro-5-fluoro-4-methylphenyl)-5-methoxy-3,4-dihydro-2H-pyrrole (1.1 g, 4.5 mmol) in MeOH (30 mL) was added methyl hydrazinecarboxylate (0.451 g, 5.01 mmol) and HCl/MeOH (3 mL) at ambient temperature. The resulting mixture was brought to 80° C. and stirred for 2 h under nitrogen. The mixture was concentrated under reduced pressure. The resulting residue was slurried with ethyl acetate for 15 min and filtered to give methyl 2-(2-(3-chloro-5-fluoro-4-methylphenyl)-3,4-dihydro-2H-pyrrol-5-yl)hydrazine-1-carboxylate, which was used in next step without further purification. Calculated $C_{13}H_{15}ClFN_3O_2$ $[M+H]^+$, 300; found 300.

Step 4. Synthesis of I-29A 5-(3-chloro-5-fluoro-4-methylphenyl)-2,5,6,7-tetrahydro-3H-pyrrolo[2,1-c][1,2,4]triazol-3-one A mixture of methyl 2-(2-(3-chloro-5-fluoro-4-methylphenyl)-3,4-dihydro-2H-pyrrol-5-yl)hydrazine-1-carboxylate (700 mg, 2.33 mmol) in DMF (100 mL) was stirred at 145° C. for 4 h under nitrogen. The mixture was cooled to ambient temperature, washed with ethyl acetate (10 mL), filtered and purified by preparative HPLC (Column Boston Prime C18 150*40 mm*5 um; condition water (0.1% TFA)-MeCN) to afford I-29A, 5-(3-chloro-5-fluoro-4-methylphenyl)-2,5,6,7-tetrahydro-3H-pyrrolo[2,1-c][1,2,4]triazol-3-one.

5-(3-chloro-5-fluoro-4-methylphenyl)-2,5,6,7-tetrahydro-3H-pyrrolo[2,1-c][1,2,4]triazol-3-one $^1H$ NMR (400 MHz, MeOD): δ 7.16 (s, 1H), 6.98 (dd, J=10.0, 1.6 Hz, 1H), 5.20 (dd, J=8.0, 4.8 Hz, 1H), 3.00-3.13 (m, 1H), 2.89-2.98 (m, 1H), 2.74-2.87 (m, 1H), 2.40-2.48 (m, 1H), 2.30 (d, J=2.4 Hz, 3H). Calculated $C_{12}H_{12}ClFN_3O$ $[M+H]^+$, 268; found 268.

Preparation of Intermediate I-30A

Intermediate I-30A was prepared from 4-bromo-2,6-difluorophenol as outlined below.

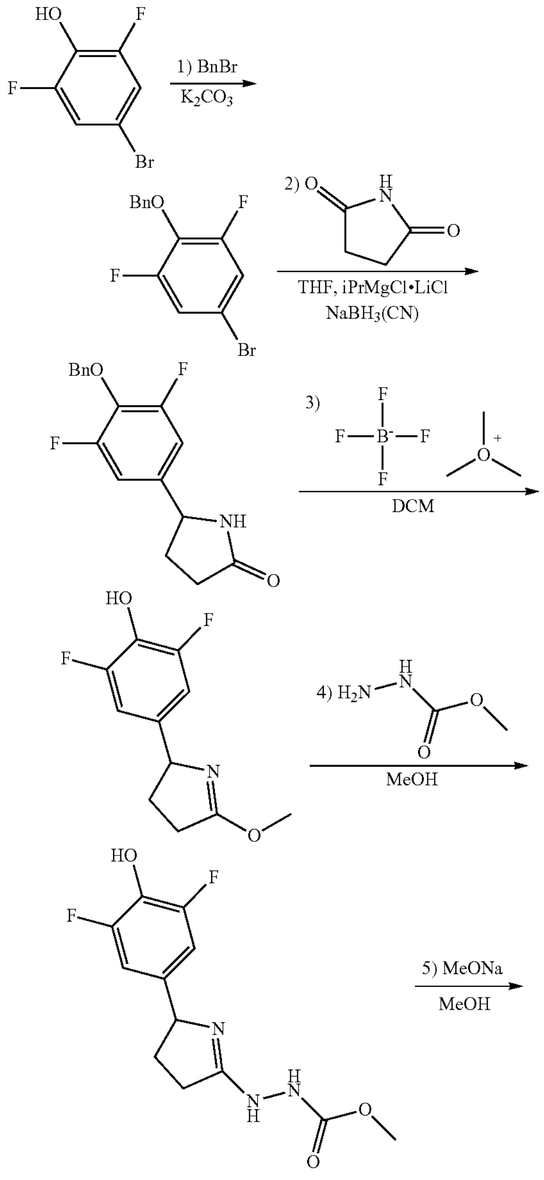

-continued

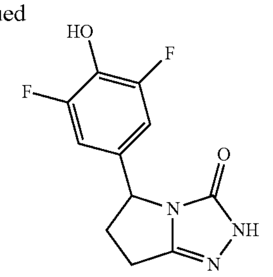

I-30A

Step 1. Preparation of 2-(benzyloxy)-5-bromo-1,3-difluorobenzene

To a solution of 4-bromo-2,6-difluorophenol (5 g, 23.92 mmol) in DMF (100 mL) was added $K_2CO_3$ (4.96 g, 35.9 mmol) and (bromomethyl)benzene (3.41 mL, 28.7 mmol) and the resulting mixture was stirred at 25° C. for 12 h. Water (500 mL) was added to the mixture, then the solution was extracted with EtOAc (80 mL*3). The combined organic layers were washed with brine (100 mL), dried over $Na_2SO_4$, filtered and concentrated. The residue was purified by flash silica gel chromatography (ISCO®; 80 g Sepa-Flash® Silica Flash Column, eluent of 2% ethyl acetate/pet. ether gradient @ 35 mL/min) to give 2-(benzyloxy)-5-bromo-1,3-difluorobenzene. $^1H$ NMR (400 MHz, $CD_3OD$) δ 7.28-7.44 (m, 5H), 7.15-7.25 (m, 2H), 5.14 (s, 2H).

Step 2. Preparation of 5-(4-(benzyloxy)-3,5-difluorophenyl)pyrrolidin-2-one

To a solution (named solution-1) of 2-(benzyloxy)-5-bromo-1,3-difluorobenzene (5.5 g, 18.39 mmol) in THF (40 mL) was added iPrMgCl·LiCl (1.3 M in THF) (21.74 mL, 28.3 mmol) at 0° C. under $N_2$. The reaction was then stirred at 45° C. for 1 h. Separately, iPrMgCl·LiCl (1.3 M in THF) (13.97 mL, 18.17 mmol) was added to a solution of pyrrolidine-2,5-dione (2 g, 20.18 mmol) in THF (40 mL) at 0° C. under $N_2$ and stirred at 0° C. for 1 h. This mixture was then cooled to −78° C. and solution-1 was added. The reaction mixture was warmed to 25° C. and stirred at 25° C. for 12 h. $NaBH_3CN$ (1.395 g, 22.20 mmol) was added and then the reaction was stirred for 1 h. HCl (6 M) was added until the pH-4 then allowed to stir for 1 h. Aqueous NaOH (4 M) was then added to adjust the pH to neutral. The reaction mixture was diluted with water (30 mL) and extracted with EtOAc (10 mL*3). The combined organic layers were washed with brine (50 mL), dried over $Na_2SO_4$, filtered and concentrated. The residue was purified by flash silica gel chromatography (ISCO®; 40 g SepaFlash® Silica Flash Column, eluent of 100% ethyl acetate/pet. ether gradient @ 35 mL/min) to give 5-(4-(benzyloxy)-3,5-difluorophenyl)pyrrolidin-2-one. Calculated $C_{17}H_{16}F_2NO_2$ $[M+H]^+$, 304; Found 304.

Step 3. Preparation of 2,6-difluoro-4-(5-methoxy-3,4-dihydro-2H-pyrrol-2-yl)phenol To a solution of 5-(4-(benzyloxy)-3,5-difluorophenyl) pyrrolidin-2-one (2.9 g, 9.56 mmol) in DCM (45 mL) was added trimethyloxonium tetrafluoroborate (2.121 g, 14.34 mmol) at 0° C. The mixture was stirred at 30° C. for 48 h. The mixture was quenched with sat. aq. $NaHCO_3$ (50 mL), then extracted with DCM (15 mL*3). The combined organic layers were washed with brine (50 mL), dried over $Na_2SO_4$, filtered and concentrated to give 2,6-difluoro-4-(5-methoxy-3,4-dihydro-2H-pyrrol-2-yl)phenol, which was used to next step without further purification. Calculated $C_{11}H_{12}F_2NO_2$ $[M+H]^+$, 228; Found 228.

Step 4. Preparation of methyl 2-(2-(3,5-difluoro-4-hydroxyphenyl)-3,4-dihydro-2H-pyrrol-5-yl)hydrazine-1-carboxylate To a solution of 2,6-difluoro-4-(5-methoxy-3,4-dihydro-2H-pyrrol-2-yl)phenol (2.1 g, 9.24 mmol) in MeOH (35 mL) was added methyl hydrazinecarboxylate (1.249 g, 13.86 mmol) at 20° C. and the resulting mixture was stirred at 80° C. for 5 h. The reaction was cooled to room temperature, concentrated, and the residue was purified by flash silica gel chromatography (ISCO®; 40 g SepaFlash® Silica Flash Column, eluent of 5% MeOH/ethyl acetate gradient @ 35 mL/min) to give methyl 2-(2-(3,5-difluoro-4-hydroxyphenyl)-3,4-dihydro-2H-pyrrol-5-yl)hydrazine-1-carboxylate. Calculated $C_{12}H_{14}F_2N_3O_3[M+H]^+$, 286; Found 286.

Step 5. Preparation of Intermediate I-30A

To a solution of methyl 2-(2-(3,5-difluoro-4-hydroxyphenyl)-3,4-dihydro-2H-pyrrol-5-yl)hydrazine-1-carboxylate (1.6 g, 5.61 mmol) in MeOH (30 mL) was added sodium methanolate (1.515 g, 28.0 mmol) and the resulting mixture was stirred at 80° C. for 12 h. The reaction was allowed to cool to room temperature then HCV/MeOH (4 M) was added until pH-5 and stirred for 10 min. The reaction mixture was concentrated and the residue was purified by flash silica gel chromatography (ISCO®; 20 g SepaFlash® Silica Flash Column, eluent of 5% MeOH/DCM gradient @ 35 mL/min) to give I-30A, 5-(3,5-difluoro-4-hydroxyphenyl)-2,5,6,7-tetrahydro-3H-pyrrolo[2,1-c][1,2,4]triazol-3-one. Calculated $C_{11}H_{10}F_2N_3O_2$ $[M+H]^+$, 254; Found 254. $^1H$ NMR (400 MHz, $CD_3OD$) δ 6.85 (d, J=7.6 Hz, 2H), 5.13 (dd, J=4.8, 7.6 Hz, 1H), 2.99-3.09 (m, 1H), 2.74-2.98 (m, 2H), 2.41 (tdd, J=5.2, 8.4, 13.2 Hz, 1H).

Preparation of Intermediate I-31A 5-(2,6-difluoro-4-methylphenyl)-2,5,6,7-tetrahydro-3H-pyrrolo[2,1-c][1,2,4]triazol-3-one Intermediate I-31A was prepared from 1-(4-bromo-2,6-difluorophenyl)ethan-1-one as outlined below.

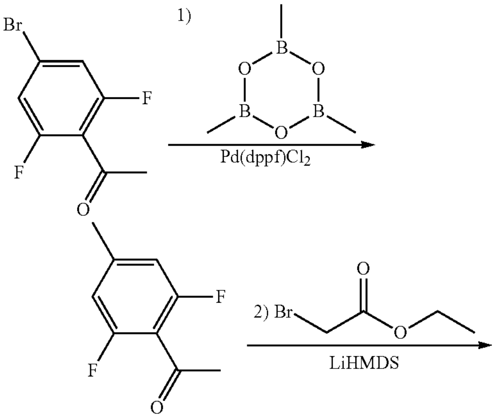

-continued

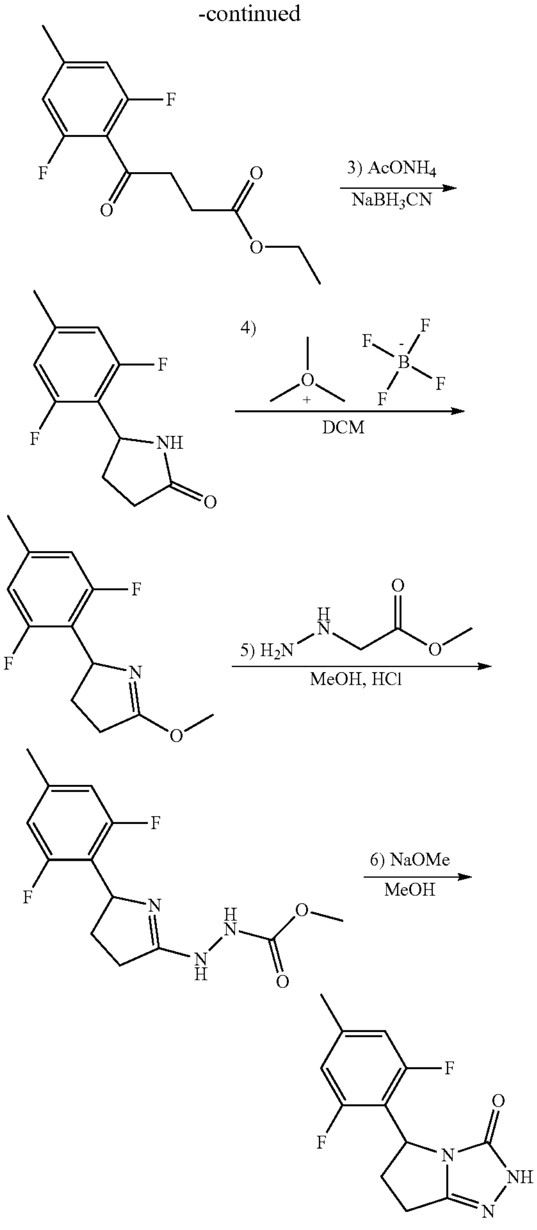

I-31A

Step 1. Synthesis of 1-(2,6-difluoro-4-methylphenyl)ethan-1-one

To a solution of 1-(4-bromo-2,6-difluorophenyl)ethan-1-one (6.0 g, 25 mmol), 2,4,6-trimethyl-1,3,5,2,4,6-trioxatriborinane (10.94 mL, 38.3 mmol) and $K_2CO_3$ (10.58 g, 77 mmol) in dioxane (10 mL) and water (1 mL) was added Pd(dppf)$Cl_2$ (1.868 g, 2.55 mmol) under nitrogen. The resulting mixture was brought to 100° C. for 12 h. The mixture was cooled to ambient temperature, diluted with water (40 mL) and extracted with EtOAc (2×20 mL). The combined organic layers were washed with brine (30 mL), dried over $Na_2SO_4$, filtered and concentrated under reduced pressure. The resulting residue was purified by silica gel chromatography (petroleum ether/ethyl acetate) to afford 1-(2,6-difluoro-4-methylphenyl)ethan-1-one. $^1$H NMR (400

MHz, $CDCl_3$) δ 6.74 (d, J=8.8 Hz, 2H), 2.55 (t, J=2.0 Hz, 3H), 2.35 (s, 3H). Calculated $C_9H_9F_2O$ $[M+H]^+$, 171; found 171.

Step 2. Synthesis of ethyl 4-(2,6-difluoro-4-methylphenyl)-4-oxobutanoate

To a stirred solution of 1-(2,6-difluoro-4-methylphenyl)ethan-1-one (3.19 g, 18.7 mmol) and 1,3-dimethyltetrahydropyrimidin-2(1H)-one (4.81 g, 37.5 mmol) in THF (20 mL) was added lithium bis(trimethylsilyl)amide (1 M in THF) (18.75 mL, 18.75 mmol) at −78° C. The mixture was stirred at −78° C. for 30 minutes then ethyl 2-bromoacetate (2.183 mL, 19.68 mmol) was added. The reaction was warmed to ambient temperature and held for 2 h. The mixture was diluted with tert-butyl methyl ether (100 mL) and quenched with saturated aq. $NH_4Cl$ (100 mL). The mixture was extracted with tert-butyl methyl ether (2×50 mL). The combined organic layers were washed with brine (100 mL), dried over $Na_2SO_4$, filtered and the filtrate was concentrated under reduced pressure. The resulting residue was purified by silica gel chromatography (petroleum ether/ethyl acetate) to afford ethyl 4-(2,6-difluoro-4-methylphenyl)-4-oxobutanoate. $^1$H NMR (400 MHz, $CDCl_3$) δ 6.62 (d, J=9.2 Hz, 2H), 3.95-4.04 (m, 2H), 3.04 (t, J=6.8 Hz, 2H), 2.58 (t, J=6.8 Hz, 2H), 2.22 (s, 3H), 1.10-1.13 (m, 3H). Calculated $C_{13}H_{15}F_2O_3$ $[M+H]^+$, 257; found 257.

Step 3. Synthesis of 5-(2,6-difluoro-4-methylphenyl)pyrrolidin-2-one

To a solution of ethyl 4-(2,6-difluoro-4-methylphenyl)-4-oxobutanoate (2.2 g, 8.6 mmol) and $AcONH_4$ (1.985 g, 25.8 mmol) in EtOH (40 mL) was added $NaBH_3$(CN) (1.349 g, 21.46 mmol) at ambient temperature. The mixture was brought to 90° C. for 12 h. The mixture was cooled to ambient temperature and concentrated under reduced pressure. The resulting residue was taken up in water (100 mL) and extracted with EtOAc (3×100 mL). The combined organic layers were dried over $Na_2SO_4$, filtered and concentrated under reduced pressure. The resulting residue was purified by silica gel chromatography (petroleum ether/ethyl acetate) to afford 5-(2,6-difluoro-4-methylphenyl)pyrrolidin-2-one. $^1$H NMR (400 MHz, $CDCl_3$) δ 6.54-6.71 (m, 2H), 5.09 (dd, J=5.2, 8.76 Hz, 1H), 2.48-2.60 (m, 2H), 2.34-2.46 (m, 1H), 2.25 (s, 3H), 2.08-2.19 (m, 1H). Calculated $C_{11}H_{12}F_2NO$ $[M+H]^+$, 212; found 212.

Step 4. Synthesis of 2-(2,6-difluoro-4-methylphenyl)-5-methoxy-3,4-dihydro-2H-pyrrole To a solution of 5-(2,6-difluoro-4-methylphenyl)pyrrolidin-2-one (700 mg, 3.31 mmol) in DCM was added trimethyloxonium tetrafluoroborate (637 mg, 4.31 mmol) at 0° C. under nitrogen. The mixture was stirred at 25° C. for 16 h. The reaction mixture was quenched with saturated $NaHCO_3$ (100 mL) and extracted with DCM (3×50 mL). The combined organic layers were washed with brine (100 mL), dried over anhydrous $Na_2SO_4$, filtered and concentrated under reduced pressure to give crude 2-(2,6-difluoro-4-methylphenyl)-5-methoxy-3,4-dihydro-2H-pyrrole, which was used in the next step without further purification. Calculated $C_{12}H_{14}F_2NO$ $[M+H]^+$, 226; found 226.

Step 5. Synthesis of methyl 2-(2-(2,6-difluoro-4-methylphenyl-3,4-dihydro-2H-pyrrol-5-yl)hydrazine-1-carboxylate To a solution of 2-(2,6-difluoro-4-methylphenyl)-5-methoxy-3,4-dihydro-2H-pyrrole (380 mg, 1.69 mmol) in MeOH (20 mL) was added methyl hydrazinecarboxylate (167 mg, 1.86 mmol) and HCl/MeOH (1 mL) at 20° C. under nitrogen. The resulting mixture was brought to 80° C. for 2 h. The mixture was cooled to ambient temperature and concentrated under reduced pressure. The resulting residue was purified by silica gel chromatography (ethyl acetate/methanol) to afford methyl 2-(2-(2,6-difluoro-4-methylphenyl)-3,4-dihydro-2H-pyrrol-5-yl)hydrazine-1-carboxylate. $^1$H NMR (400 MHz, $CD_3OD$) δ 6.92 (d, J=9.6 Hz, 2H), 5.50-5.60 (m, 1H), 4.12 (q, J=7.2 Hz, 1H), 3.77 (s, 3H), 3.11-3.24 (m, 2H), 2.76-2.88 (m, 1H), 2.38 (s, 3H). Calculated $C_{13}H_{16}F_2N_3O_2$[M+H]$^+$, 284; found 284.

Step 6. Synthesis of I-31A 5-(2,6-difluoro-4-methylphenyl)-2,5,6,7-tetrahydro-3H-pyrrolo[2,1-c][1,2,4]triazol-3-one To a solution of methyl 2-(2-(2,6-difluoro-4-methylphenyl)-3,4-dihydro-2H-pyrrol-5-yl)hydrazine-1-carboxylate (250 mg, 0.883 mmol) in MeOH (10 mL) was added sodium methanolate (143 mg, 2.65 mmol). The resulting mixture was brought to 80° C. for 5 h. The reaction mixture was cooled to ambient temperature and HCl/MeOH (4 M) was added until pH-6 and the solution was concentrated under reduced pressure. The resulting residue was dissolved in MeOH (50 mL) and filtered. The filtrate was concentrated to afford I-31A 5-(2,6-difluoro-4-methylphenyl)-2,5,6,7-tetrahydro-3H-pyrrolo[2,1-c][1,2,4]triazol-3-one. Calculated $C_{12}H_{12}F_2N_3O$ [M+H]$^+$, 252; found 252.

Preparation of Intermediate I-32A 5-(4-chloro-3-fluorophenyl)-2,5,6,7-tetrahydro-3H-pyrrolo[2,1-c][1,2,4]triazol-3-one Intermediate I-32A was prepared from 4-bromo-1-chloro-2-fluorobenzene as outlined below.

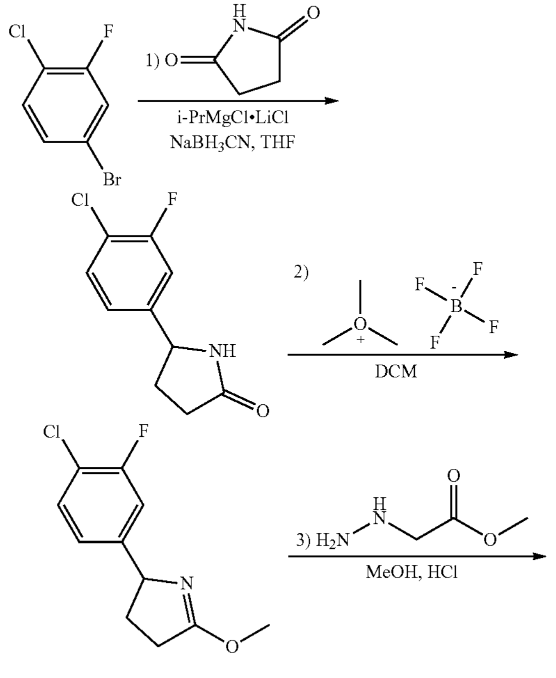

-continued

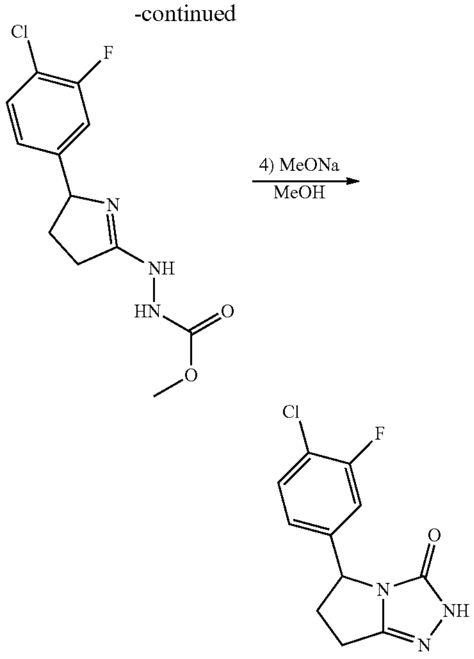

I-32A

Step 1. Synthesis of 5-(4-chloro-3-fluorophenyl)pyrrolidin-2-one

To a solution of 4-bromo-1-chloro-2-fluorobenzene (5.28 g, 25.2 mmol) in THF (100 mL) was added iPrMgCl·LiCl (1.3 M in THF) (27.2 mL, 35.3 mmol) at 0° C. under nitrogen. The resulting solution was stirred at ambient temperature for 1 h. To another solution of pyrrolidine-2,5-dione (2.5 g, 25 mmol) in THF (100 mL) was added iPrMgCl·LiCl (1.3 M in THF) (17.47 mL, 22.71 mmol) at 0° C. under nitrogen. The resulting solution was stirred at 0° C. for 1 h. The first solution was added to the second solution at −78° C. The resulting solution was warmed to ambient temperature and stirred for 12 h. $NaBH_3(CN)$ (1.744 g, 27.8 mmol) was added to the reaction mixture at ambient temperature and stirred for 1 h. The reaction was acidified to pH~3 with HCl (6 M), stirred for 1 h and neutralized with aqueous NaOH (4 M). The mixture was diluted with water (50 mL) and extracted with EtOAc (3×50 mL). The combined organic layers were washed with brine (30 mL), dried over $Na_2SO_4$, filtered and concentrated under reduced pressure. The resulting residue was purified by silica gel chromatography (petroleum ether/ethyl acetate) to afford 5-(4-chloro-3-fluorophenyl)pyrrolidin-2-one. Calculated $C_{10}H_{10}ClFNO$ [M+H]$^+$, 214; found 214.

Step 2. Synthesis of 2-(4-chloro-3-fluorophenyl)-5-methoxy-3,4-dihydro-2H-pyrrole To a solution of 5-(4-chloro-3-fluorophenyl)pyrrolidin-2-one (1.00 g, 4.68 mmol) in DCM (23.4 mL) was added trimethyloxonium tetrafluoroborate (1.039 g, 7.02 mmol) at 0° C. under nitrogen. The mixture was stirred at ambient temperature for 15 h. The mixture was quenched with saturated aqueous $NaHCO_3$ (150 mL) and extracted with DCM (2×30 mL). The combined organic layers were dried over $Na_2SO_4$, filtered and concentrated under reduced pressure to afford 2-(4-chloro-3-fluorophenyl)-5-methoxy-3,4- dihydro-2H-pyrrole, which was used in the next step without further purification. Calculated $C_{11}H_{12}ClFNO$ $[M+H]^+$, 228; found 228.

Step 3. Synthesis of methyl 2-(2-(4-chloro-3-fluorophenyl)-3,4-dihydro-2H-pyrrol-5-yl)hydrazine-1-carboxylate To a solution of 2-(4-chloro-3-fluorophenyl)-5-methoxy-3,4-dihydro-2H-pyrrole (1.00 g, 3.51 mmol) in MeOH (20 mL) was added methyl hydrazinecarboxylate (0.422 g, 4.68 mmol) and HCl/MeOH (1 mL) at ambient temperature. The resulting mixture was brought to 80° C. and stirred for 12 h. The mixture was concentrated under reduced pressure. The resulting residue was slurried with ethyl acetate for 15 min and filtered to afford methyl 2-(2-(4-chloro-3-fluorophenyl)-3,4-dihydro-2H-pyrrol-5-yl)hydrazine-1-carboxylate, which was used in the next step without further purification. Calculated $C_{12}H_{14}ClFN_3O_2$$[M+H]^+$, 286; found 286.

Step 4. Synthesis of I-32A 5-(4-chloro-3-fluorophenyl)-2,5,6,7-tetrahydro-3H-pyrrolo[2,1-c][1,2,4]triazol-3-one To a solution of methyl 2-(2-(4-chloro-3-fluorophenyl)-3,4-dihydro-2H-pyrrol-5-yl)hydrazine-1-carboxylate (1.00 g, 3.50 mmol) in MeOH (20 mL) was added sodium methanolate (0.945 g, 17.5 mmol). The resulting mixture was stirred at 80° C. for 5 h. The reaction mixture was cooled to ambient temperature and HCl/MeOH (4 M) was added until pH-6 and the solution was concentrated under reduced pressure. The resulting residue was dissolved in MeOH (50 mL) and filtered. The filtrate was concentrated to give I-32A, 5-(4-chloro-3-fluorophenyl)-2,5,6,7-tetrahydro-3H-pyrrolo[2,1-c][1,2,4]triazol-3-one. Calculated $C_{11}H_{10}ClFN_3O$ $[M+H]^+$, 254; found 254.

Preparation of Intermediate I-33A 5-(3,4,5-trifluorophenyl)-2,5,6,7-tetrahydro-3H-pyrrolo[2,1-c][1,2,4]triazol-3-one Intermediate I-33A was prepared from 5-bromo-1,2,3-trifluorobenzene as outlined below.

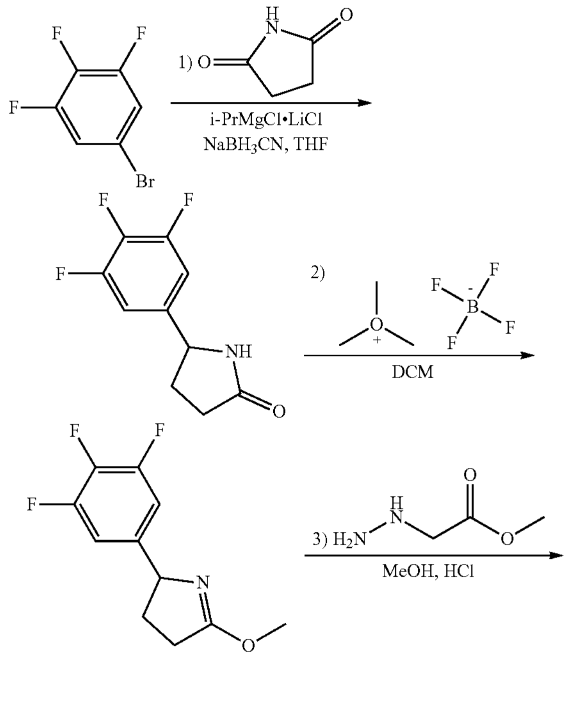

-continued

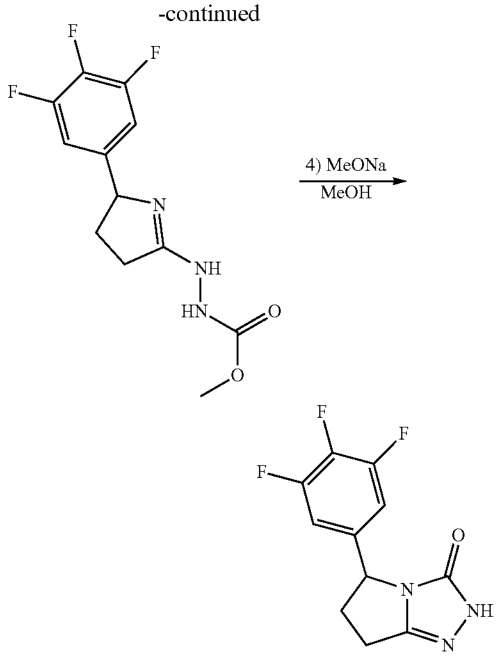

I-32A

Step 1. Synthesis of 5-(3,4,5-trifluorophenyl)pyrrolidin-2-one

To a solution (named solution-1) of 5-bromo-1,2,3-trifluorobenzene (4.90 g, 23.2 mmol) in THF (60 mL) was added iPrMgCl·LiCl (1.3 M in THF) (25 mL, 32.5 mmol) at 0° C. under nitrogen. The resulting solution was stirred at ambient temperature for 1 h. To another solution of pyrrolidine-2,5-dione (2.3 g, 23 mmol) in THF (100 mL) was added iPrMgCl·LiCl (1.3 M in THF) (16.07 mL, 20.89 mmol) at 0° C. under nitrogen. The resulting solution was stirred at 0° C. for 1 h. The first solution was added to the second solution at −78° C. The resulting solution was warmed to ambient temperature and stirred for 12 h. $NaBH_3(CN)$ (1.605 g, 25.5 mmol) was added to the reaction mixture at ambient temperature and stirred for 1 h. The reaction was acidified to pH-3 with HCl (6 M), stirred for 1 h and neutralized with aqueous NaOH (4M). The mixture was diluted with water (20 mL) and extracted with EtOAc (3×10 mL). The combined organic layers were washed with brine (20 mL), dried over $Na_2SO_4$, filtered and concentrated under reduced pressure. The resulting residue was purified by silica gel chromatography (petroleum ether/ethyl acetate) to afford 5-(3,4,5-trifluorophenyl)pyrrolidin-2-one. Calculated $C_{10}H_9F_3NO$ $[M+H]^+$, 216; found 216.

Step 2. Synthesis of 5-methoxy-2-(3,4,5-trifluorophenyl)-3,4-dihydro-2H-pyrrole

To a solution of 5-(3,4,5-trifluorophenyl)pyrrolidin-2-one (1.00 g, 4.65 mmol) in DCM (20 mL) was added trimethyloxonium tetrafluoroborate (1.031 g, 6.97 mmol) at 0° C. under nitrogen. The mixture was stirred at ambient temperature for 15 h. The mixture was quenched with saturated aqueous $NaHCO_3$ (50 mL) and extracted with DCM (2×200 mL). The combined organic layers were dried over $Na_2SO_4$, filtered and concentrated under reduced pressure to afford 5-methoxy-2-(3,4,5-trifluorophenyl)-3,4-dihydro-2H-pyrrole, which was used in the next step without further purification. Calculated $C_{11}H_{11}F_3NO$ $[M+H]^+$, 230; found 230.

Step 3. Synthesis of methyl 2-(2-(3,4,5-trifluorophenyl)-3,4-dihydro-2H-pyrrol-5-yl)hydrazine-1-carboxylate To a solution of 5-methoxy-2-(3,4,5-trifluorophenyl)-3,4-dihydro-2H-pyrrole (1.00 g, 4.36 mmol) in MeOH (30 mL) was added methyl hydrazinecarboxylate (0.413 g, 4.58 mmol) and HCl/MeOH (1 mL) at ambient temperature. The resulting mixture was brought to 80° C. and stirred for 3 h under nitrogen. The mixture was concentrated under reduced pressure. The resulting residue was purified by silica gel chromatography (petroleum ether/ethyl acetate) to afford methyl 2-(2-(3,4,5-trifluorophenyl)-3,4-dihydro-2H-pyrrol-5-yl)hydrazine-1-carboxylate. Calculated $C_{12}H_{13}F_3N_3O_2$ $[M+H]^+$, 288; found 288.

Step 4. Synthesis of I-33A 5-(3,4,5-trifluorophenyl)-2,5,6,7-tetrahydro-3H-pyrrolo[2,1-c][1,2,4]triazol-3-one To a solution of methyl 2-(2-(3,4,5-trifluorophenyl)-3,4-dihydro-2H-pyrrol-5-yl)hydrazine-1-carboxylate (1.00 g, 3.48 mmol) in MeOH (16 mL) was added sodium methanolate (0.940 g, 17.4 mmol). The resulting mixture was stirred at 80° C. for 5 h. The reaction mixture was cooled to ambient temperature and HCl/MeOH (4 M) was added until pH-6 and the solution was concentrated under reduced pressure. The resulting residue was purified by silica gel chromatography (petroleum ether/ethyl acetate) to afford I-33A, 5-(3,4,5-trifluorophenyl)-2,5,6,7-tetrahydro-3H-pyrrolo[2,1-c][1,2,4]triazol-3-one. Calculated $C_{11}H_9F_3N_3O$ $[M+H]^+$, 256; found 256.

Preparation of Intermediate I-34A

Intermediate I-34A was prepared from 5-bromo-2-chloro-1,3-difluorobenzene as outlined below.

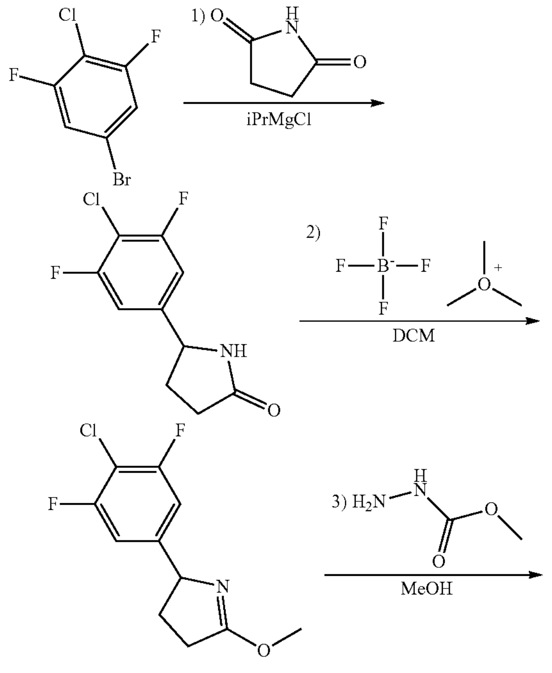

-continued

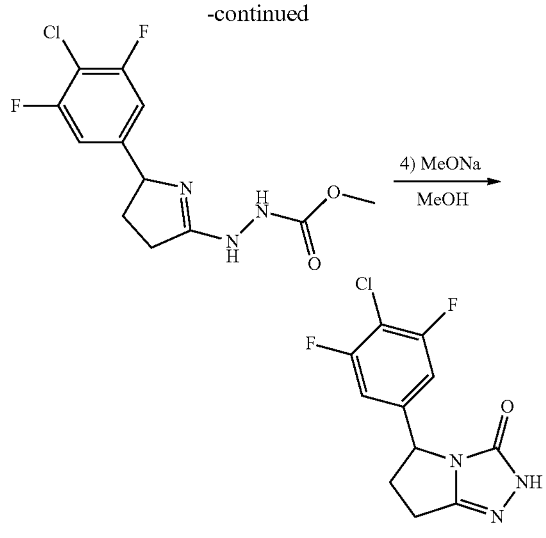

I-34A

Step 1. Preparation of 5-(4-chloro-3,5-difluorophenyl)pyrrolidin-2-one

To a solution of 5-bromo-2-chloro-1,3-difluorobenzene (10.10 g, 44.4 mmol) in THF (40 mL) was added iPrMgCl·LiCl (1.3 M in THF) (37.3 mL, 48.4 mmol) at 0° C. under $N_2$. The reaction was then stirred at 20° C. for 1 h to give mixture #1. Separately, iPrMgCl·LiCl (1.3 M in THF) (27.9 mL, 36.3 mmol) was added to another solution of pyrrolidine-2,5-dione (4 g, 40.4 mmol) in THF (40 mL) at 0° C. under $N_2$, the reaction was stirred at 0° C. for 1 h to give mixture #2. Mixture #2 was added mixture #1 at −78° C. The reaction was stirred at 25° C. for 16 h. The reaction was allowed to warm to 25° C. and $NaBH_3(CN)$ (3.81 g, 60.6 mmol) was added then stirred at 25° C. for 1 h. The reaction was acidified to pH=3-4 with HCl (6 M), stirred for 1 h and neutralized with aq. NaOH (4 M). The mixture was quenched with water (30 mL), extracted with EtOAc (50 mL×3). The combined organic layers were dried over $Na_2SO_4$, filtered and concentrated in vacuum and the residue was purified by flash silica gel chromatography (ISCO®, 40 g Agela Flash Colum, 100% EtOAc) to give 5-(4-chloro-3,5-difluorophenyl)pyrrolidin-2-one. Calculated $C_{10}H_9ClF_2NO$ $[M+H]^+$, 232; Found 232.

Step 2. Preparation of 2-(4-chloro-3,5-difluorophenyl)-5-methoxy-3,4-dihydro-2H-pyrrole A mixture of 5-(4-chloro-3,5-difluorophenyl)pyrrolidin-2-one (4.4 g, 19.00 mmol) and trimethyloxonium tetrafluoroborate (3.65 g, 24.69 mmol) in DCM (50 mL) was stirred at 40° C. for 16 h to give brown mixture. The reaction mixture was quenched with sat. $NaHCO_3$ (100 mL) and extracted with DCM (50 mL*3). The combined organic phases were washed with brine (100 mL), dried over anhydrous $Na_2SO_4$, filtered and concentrated under reduced pressure to give crude 2-(4-chloro-3,5-difluorophenyl)-5-methoxy-3,4-dihydro-2H-pyrrole. The crude product was used in the next step without further purification. Calculated $C_{11}H_{11}ClF_2NO$ $[M+18+H]^+$, 264; Found 264.

Step 3. Preparation of methyl 2-(2-(4-chloro-3,5-difluorophenyl)-3,4-dihydro-2H-pyrrol-5-yl)hydrazine-1-carboxylate To a solution of 2-(4-chloro-3,5-difluorophenyl)-5-methoxy-3,4-dihydro-2H-pyrrole (4 g, 16.28 mmol) in MeOH (60 mL) was added methyl hydrazinecarboxylate (1.613 g, 17.91 mmol) and HCl/MeOH (4 mL) at 20° C. and the resulting mixture was stirred at 80° C. for 2 h under $N_2$. The mixture was cooled to room temperature then concentrated in vacuo. The residue was purified by flash silica gel chromatography (ISCO®; 40 g SepaFlash® Silica Flash Column, eluent of DCM/EtOAc gradient @ 60 mL/min) to afford methyl 2-(2-(4-chloro-3,5-difluorophenyl)-3,4-dihydro-2H-pyrrol-5-yl) hydrazine-1-carboxylate. Calculated $C_{12}H_{13}ClF_2N_3O_2$ [M+H]$^+$, 304; Found 304.

Step 4. Preparation of I-34A

To a solution of methyl 2-(2-(4-chloro-3,5-difluorophenyl)-3,4-dihydro-2H-pyrrol-5-yl)hydrazine-1-carboxylate (100 mg, 0.329 mmol) in MeOH (5 mL) was added sodium methanolate (89 mg, 1.646 mmol) and the resulting mixture was stirred at 80° C. for 5 h. The reaction mixture was cooled to room temperature then HCl/MeOH (4 M) was added until PH-6. The solution was concentrated, the residue was dissolved in MeOH (50 mL), filtered and the filtrate was concentrated to I-34A, 5-(4-chloro-3,5-difluorophenyl)-2,5,6,7-tetrahydro-3H-pyrrolo[2,1-c][1,2,4]triazol-3-one. Calculated $C_{11}H_9ClF_2N_3O$ [M+H]$^+$, 272; Found 272. 1H NMR (400 MHz, $CD_3OD$) δ 6.71-7.15 (m, 2H), 5.20-5.26 (m, 1H), 3.02-3.13 (m, 1H), 2.89-2.99 (m, 1H), 2.78-2.88 (m, 1H), 2.78-2.88 (m, 1H), 2.38-2.50 (m, 1H).

Preparation of Intermediate I-35A

Intermediate I-35A was prepared from (R)-2-amino-2-phenylethan-1-ol as outlined below.

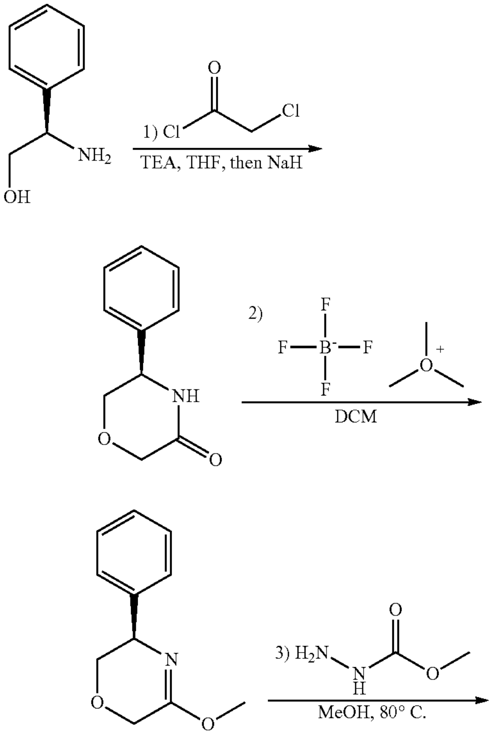

-continued

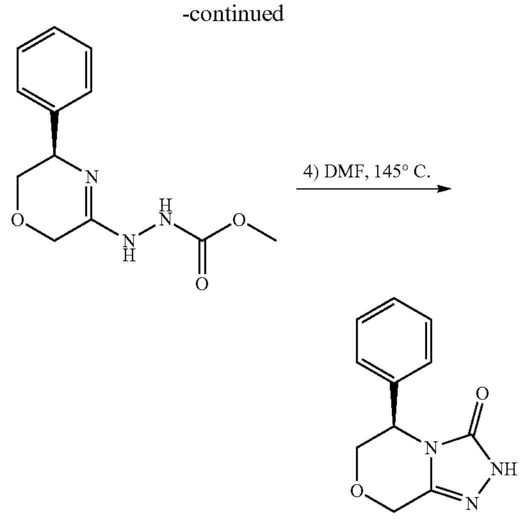

I-35A

Step 1. Preparation of (R)-5-phenylmorpholin-3-one

To a mixture of (R)-2-amino-2-phenylethan-1-ol (5 g, 36.4 mmol) and TEA (12.70 mL, 91 mmol) in THF (100 mL) was added 2-chloroacetyl chloride (2.90 mL, 36.4 mmol) at 0° C. The reaction was then allowed to stir for 2 h at 0° C. The reaction was diluted with water (50 mL) and extracted with EtOAc (20 mL*2). The combined organic layers were washed with brine (20 mL), dried over $Na_2SO_4$, filtered and concentrated. The crude product was then dissolved in THF (70 mL), NaH (1.749 g, 43.7 mmol) was added, and the resulting mixture was stirred at 20° C. for 2 h. The reaction mixture was quenched with saturated aqueous ammonium chloride solution (50 mL) and extracted with EtOAc (20 mL*2). The combined organic layers were washed with brine (20 mL), dried over $Na_2SO_4$, filtered and concentrated. The residue was purified by flash silica gel chromatography (ISCO®; 80 g SepaFlash® Silica Flash Column, eluent of 5% MeOH/DCM gradient @ 35 mL/min) to give (R)-5-phenylmorpholin-3-one. Calculated $C_{10}H_{12}NO_2$ [M+H]$^+$, 178; Found 178.

Step 2. Preparation of (R)-5-methoxy-3-phenyl-3,6-dihydro-2H-1,4-oxazine

To a solution of (R)-5-phenylmorpholin-3-one (1 g, 5.64 mmol) in DCM (20 mL) was added dimethyloxonium tetrafluoroborate (1.133 g, 8.46 mmol) at 25° C. The mixture was stirred at 25° C. for 12 h. The mixture was quenched with sat. aq. $NaHCO_3$ (30 mL), extracted with DCM (10 mL*2). The combined organic layers were dried over $Na_2SO_4$, filtered and concentrated in vacuum to give crude (R)-5-methoxy-3-phenyl-3,6-dihydro-2H-1,4-oxazine, which was used in the next step without further purification.

Step 3. Preparation of methyl (R)-2-(5-phenyl-5,6-dihydro-2H-1,4-oxazin-3-yl)hydrazine-1-carboxylate To a solution of (R)-5-methoxy-3-phenyl-3,6-dihydro-2H-1,4-oxazine (1 g crude) in MeOH (20 mL) was added methyl hydrazinecarboxylate (0.699 g, 7.76 mmol) at 20° C. and the resulting mixture was stirred at 80° C. for 12 h. The reaction was allowed to cool to room temperature, concentrated, and the residue was purified by flash silica gel chromatography (ISCO®; 12 g SepaFlash® Silica Flash Column, eluent of 3% MeOH/DCM gradient @ 35 mL/min) to give methyl (R)-2-(5-phenyl-5,6-dihydro-2H-1,4-oxazin-3-yl)hydrazine-1-carboxylate. Calculated $C_{12}H_{16}N_3O_3$ $[M+H]^+$, 250; Found 250.

Step 4. Preparation of I-35A

A solution of (R)-2-(5-phenyl-5,6-dihydro-2H-1,4-oxazin-3-yl)hydrazine-1-carboxylate (1.2 g, 4.81 mmol) in DMF (40 mL) was stirred at 145° C. for 12 h. The reaction was allowed to cool to room temperature then concentrated. Petroleum Ether (10 mL) and Ethyl Acetate (3 mL) were added to the residue and the resulting slurry was stirred for 10 mins. The mixture was filtered and the filtrate was purified by Prep-HPLC (Method Boston Green ODS, Condition water (0.01% TFA)-ACN) to give I-35A, (R)-5-phenyl-2,5,6,8-tetrahydro-3H-[1,2,4]triazolo[3,4-c][1,4]oxazin-3-one. Calculated $C_{11}H_{12}N_3O_2$ $[M+H]^+$, 218; Found 218. $^1H$ NMR (400 MHz, $CD_3OD$) δ 7.28-7.39 (m, 4H), 7.20-7.22 (m, 1H), 5.03 (t, J=3.6 Hz, 1H), 4.82 (s, 1H), 4.63-4.72 (m, 1H), 4.15-4.19 (m, 1H), 3.96-4.00 (m, 1H).

Preparation of Intermediate I-36A (5-(3,5-difluorophenyl)-2,5,6,8-tetrahydro-3H-[1,2,4]triazolo[3,4-c][1,4]oxazin-3-one Intermediate I-36A was prepared from 2-((tert-butyldimethylsilyl)oxy)acetaldehyde as outlined below.

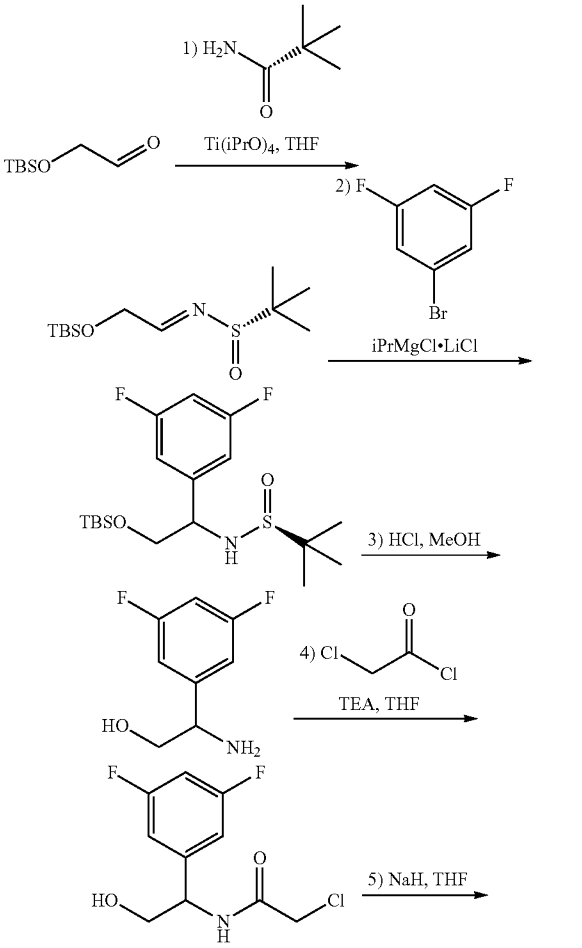

-continued

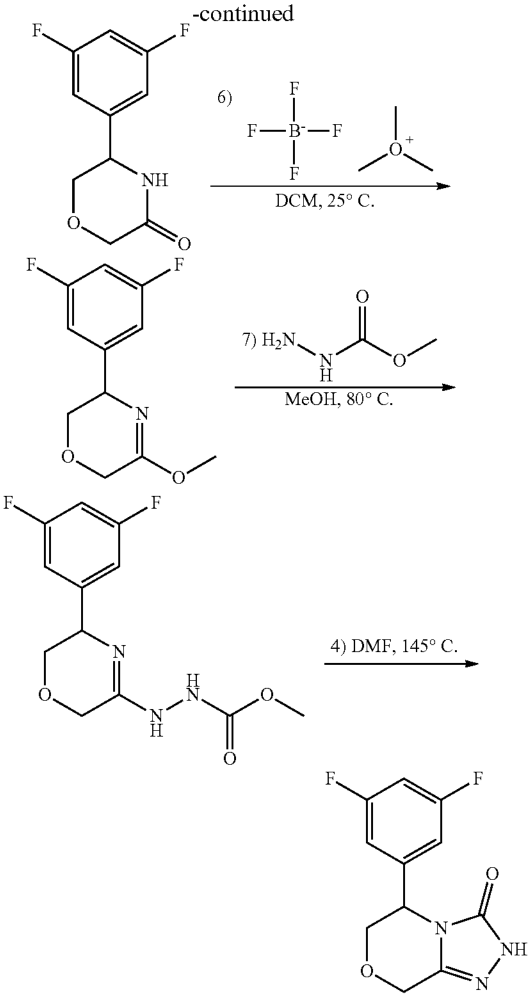

I-36A

Step 1. Preparation of (S,E)-N-(2-((tert-butyldimethylsilyl)oxy)ethylidene)-2-methylpropane-2-sulfinamide To a stirred mixture of 2-((tert-butyldimethylsilyl)oxy)acetaldehyde (10 g, 57.4 mmol) in THF (250 mL) was added (S)-2-methylpropane-2-sulfinamide (9.04 g, 74.6 mmol), $Ti(iPrO)_4$ (22.5 mL, 86 mmol) at 20° C. and the mixture was stirred at 20° C. for 12 h. The mixture was poured into brine (300 mL) and filtered. The mixture was extracted with EtOAc (100 mL×3). The combined organic layers were washed with brine (250 mL), dried over anhydrous $Na_2SO_4$, filtered and concentrated. The residue was purified by flash silica gel chromatography (0~20% EtOAc/petroleum ether) to give (S,E)-N-(2-((tert-butyldimethylsilyl)oxy)ethylidene)-2-methylpropane-2-sulfinamide. Calculated $C_{12}H_{28}NO_2SSi$ $[M+H]^+$, 278; Found 278.

Step 2. Preparation of (S)—N-(2-((tert-butyldimethylsilyl)oxy)-1-(3,5-difluorophenyl)ethyl)-2-methylpropane-2-sulfinamide To a solution of 1-bromo-3,5-difluorobenzene (8.80 g, 45.6 mmol) in THF (100 mL) was added i-PrMgCl·LiCl (47.8 mL, 62.2 mmol) at 0° C. under $N_2$ and the mixture was stirred at 40° C. for 1 h. Then the reaction mixture was added to a solution of (S,E)-N-(2-((tert-butyldimethylsilyl)oxy) ethylidene)-2-methylpropane-2-sulfinamide (11.5 g, 41.4 mmol) in THF (150 mL) at 0° C. under $N_2$. The reaction mixture was stirred at 25° C. for 5 h. The mixture was quenched with sat. $NH_4Cl$ (300 mL) and extracted with EtOAc (80 mL×3). The combined organic layers were dried over $Na_2SO_4$, filtered and concentrated in vacuum. The residue was purified by flash silica gel chromatography (100% EtOAc) to give (S)—N—((R)-2-((tert-butyldimethylsilyl)oxy)-1-(3,5-difluorophenyl)ethyl)-2-methylpropane-2-sulfinamide. Calculated $C_{18}H_{32}F_2NO_2SSi$ $[M+H]^+$, 392; Found 392.

Steps 3-4. Preparation of 2-chloro-N-(1-(3,5-difluorophenyl)-2-hydroxyethyl)acetamide A solution of (S)—N—((R)-2-((tert-butyldimethylsilyl) oxy)-1-(3,5-difluorophenyl)ethyl)-2-methylpropane-2-sulfinamide (3 g, 7.66 mmol) in HCl/MeOH (50 mL) was stirred at 25° C. for 12 h. The reaction mixture was concentrated under reduced pressure to give product 2-amino-2-(3,5-difluorophenyl)ethan-1-ol (1 g, 5.77 mmol) as a yellow oil. The crude product was used in the next step directly. To a mixture of 2-amino-2-(3,5-difluorophenyl)ethan-1-ol (1 g, 5.77 mmol) and TEA (2.01 mL, 14.4 mmol) in THF (30 mL) was added 2-chloroacetyl chloride (0.459 mL, 5.77 mmol) at 0° C. and the resulting mixture was stirred at 20° C. for 2 h. The mixture was added to water (20 mL) and extracted with EtOAc (10 mL×2). The combined organic layers were washed with brine (15 mL), dried over $Na_2SO_4$, filtered and concentrated.

The residue was purified by flash silica gel chromatography (40% EtOAc:petroleum ether) to give 2-chloro-N-(1-(3,5-difluorophenyl)-2-hydroxyethyl)acetamide. Calculated $C_{10}H_{11}ClF_2NO_2$ $[M+H]^+$, 250; Found 250.

Step 5. Preparation of 5-(3,5-difluorophenyl)morpholin-3-one

To a solution of 2-chloro-N-(1-(3,5-difluorophenyl)-2-hydroxyethyl)acetamide (560 mg, 2.243 mmol) in THF (44 mL) was added NaH (224 mg, 5.61 mmol) at 0° C. and the mixture was stirred at 20° C. for 1 h. The mixture was to added saturated aqueous $NH_4Cl$ (30 mL) and extracted with EtOAc (10 mL×2). The combined organic layers were washed with brine (20 mL), dried over $Na_2SO_4$, filtered and concentrated. The residue was purified by flash silica gel chromatography (100% ethyl acetate/petroleum ether) to give 5-(3,5-difluorophenyl)morpholin-3-one. Calculated $C_{10}H_{10}F_2NO_2$ $[M+H]^+$, 214; Found 214.

Step 6. Preparation of 3-(3,5-difluorophenyl)-5-methoxy-3,6-dihydro-2H-1,4-oxazine To a solution of 5-(3,5-difluorophenyl)morpholin-3-one (560 mg, 2.63 mmol) in DCM (10 mL) was added trimethyloxonium tetrafluoroborate (583 mg, 3.94 mmol) at 20° C. The mixture was stirred at 30° C. for 12 h. The mixture was quenched with saturated $NaHCO_3$ (20 mL), extracted with DCM (10 mL×2). The combined organic layers were washed with brine (10 mL), dried over $Na_2SO_4$, filtered and concentrated in vacuum to give crude 3-(3,5-difluorophenyl)-5-methoxy-3,6-dihydro-2H-1,4-oxazine, which was used in the next step without further purification. Calculated $C_{11}H_{12}F_2NO_2$ $[M+H+H_2O]^+$, 246; Found 246.

Step 7. Preparation of methyl 2-(5-(3,5-difluorophenyl)-5,6-dihydro-2H-1,4-oxazin-3-yl)hydrazine-1-carboxylate To a solution of 3-(3,5-difluorophenyl)-5-methoxymorpholine (580 mg, 2.53 mmol) in MeOH (10 mL) was added methyl hydrazinecarboxylate (342 mg, 3.80 mmol) at 20° C. and the resulting mixture was stirred at 80° C. for 5 h. The reaction was directly concentrated and the residue was slurried with ethyl acetate (10 mL) to give methyl 2-(5-(3,5-difluorophenyl)-5,6-dihydro-2H-1,4-oxazin-3-yl)hydrazine-1-carboxylate. Calculated $C_{12}H_{14}F_2N_3O_3[M+H]^+$, 286; Found 286.

Step 8. Preparation of I-36A

A solution of methyl 2-(5-(3,5-difluorophenyl)-5,6-dihydro-2H-1,4-oxazin-3-yl)hydrazine-1-carboxylate (480 mg, 1.68 mmol) in DMF (40 mL) was stirred at 145° C. for 12 h. The reaction solution was directly concentrated. The residue was repurified by Prep-HPLC (Method Boston Green ODS, Condition water (0.01% TFA)-ACN) to give I-36A, 5-(3,5-difluorophenyl)-2,5,6,8-tetrahydro-3H-[1,2,4]triazolo[3,4-c][1,4]oxazin-3-one. Calculated $C_{11}H_{10}F_2N_3O_2$ $[M+H]^+$, 286; Found 286. $^1H$ NMR (400 MHz, $CD_3OD$) δ 6.82-6.98 (m, 3H), 5.05 (t, J=3.6 Hz, 1H), 4.84 (s, 1H), 4.67 (d, J=15.6 Hz, 1H), 4.17 (dd, J=4.0, 12.4 Hz, 1H), 4.02 (dd, J=3.2, 12.4 Hz, 1H).

Preparation of Intermediate I-37A ((S)-5-phenyl-5,6,7,8-tetrahydro-[1,2,4]triazolo[4,3-a]pyridin-3(2H)-one)

Intermediate I-37A was prepared from piperidine-2,6-dione as outlined below.

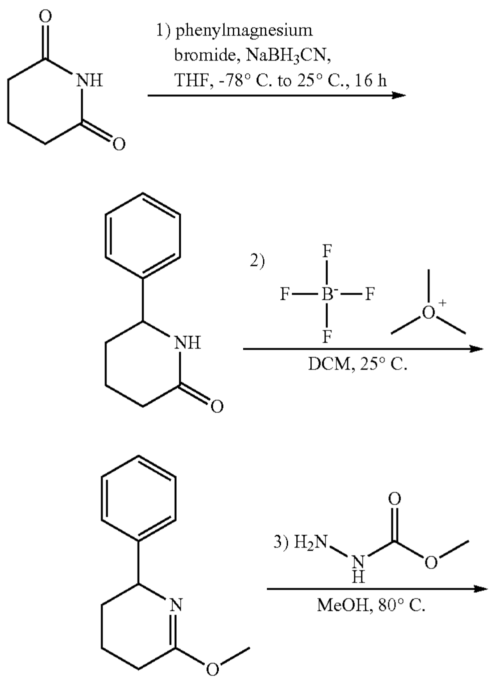

-continued

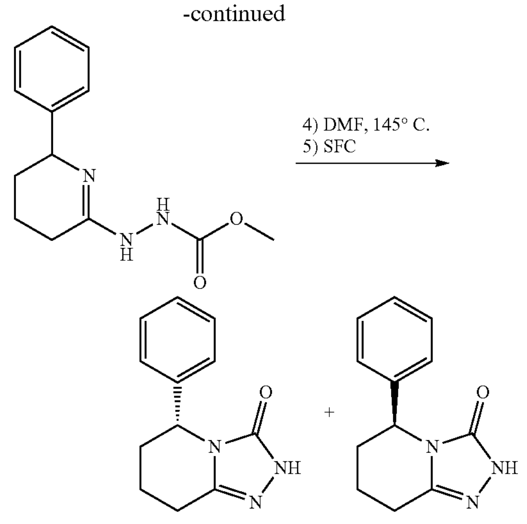

I-37A

Step 1. Preparation of 6-phenylpiperidin-2-one

To a solution of piperidine-2,6-dione (5 g, 44.2 mmol) in THF (100 mL) was added phenylmagnesium bromide (30.9 mL, 93 mmol) by syringe dropwisely at −78° C. under $N_2$. After the addition was completed, the reaction was allowed to warm up to 25° C. and stirred for 16 h. To the mixture was added $NaBH_3(CN)$ (3.06 g, 48.6 mmol) and it was stirred at 25° C. for an additional 2 h. 4 M HCl was added and the pH was adjusted to 4. The resulting mixture was stirred for 1 h. Aqueous NaOH was added to adjust the neutral pH. The mixture was quenched with water (200 mL), extracted with EtOAc (100 mL×3). The combined organic layers were dried over $Na_2SO_4$, filtered and concentrated in vacuum to give crude product as a yellow oil. It was purified by flash silica gel chromatography (100% EtOAc) to give 6-phenylpiperidin-2-one. Calculated $C_{11}H_{14}NO$ $[M+H]^+$, 176; Found 176.

Step 2. Preparation of 6-methoxy-2-phenyl-2,3,4,5-tetrahydropyridine

To a solution of 6-phenylpiperidin-2-one (2.5 g, 14.3 mmol) in $CH_2Cl_2$ (100 mL) was added dimethyloxonium tetrafluoroborate (2.87 g, 21.4 mmol) at 25° C. The mixture was stirred at 25° C. for 12 h. The mixture was quenched with saturated $NaHCO_3$ (50 mL), and extracted with DCM (50 mL×2). The combined organic layers were dried over $Na_2SO_4$, filtered and concentrated in vacuum to give crude 6-methoxy-2-phenyl-2,3,4,5-tetrahydropyridine, which was used in the next step without further purification. Calculated $C_{12}H_{16}NO$ $[M+H]^+$, 190; Found 190.

Step 3. Preparation of methyl 2-(6-phenyl-3,4,5,6-tetrahydropyridin-2-yl)hydrazine-1-carboxylate To a solution of 6-methoxy-2-phenyl-2,3,4,5-tetrahydropyridine (2.3 g, 12.2 mmol) in MeOH (65 mL) was added methyl hydrazinecarboxylate (1.64 g, 18.2 mmol) at 20° C. and the resulting mixture was stirred at 80° C. for 12 h. The reaction solution was directly concentrated. The residue was added to EtOAc (20 mL) and stirred for 0.5 h. The solid was filtered to give methyl 2-(6-phenyl-3,4,5,6-tetrahydropyridin-2-yl)hydrazine-1-carboxylate. Calculated $C_{13}H_{18}N_3O_2$ $[M+H]^+$, 248; Found 248.

Step 4 and 5. Preparation of Intermediate I-37A

A solution of methyl 2-(6-phenyl-3,4,5,6-tetrahydropyridin-2-yl)hydrazine-1-carboxylate (2.5 g, 10.1 mmol) in DMF (25 mL) was stirred at 145° C. for 12 h. The reaction solution was directly concentrated to give (±)-5-phenyl-5,6,7,8-tetrahydro-[1,2,4]triazolo[4,3-a]pyridin-3(2H)-one (2 g, 7.43 mmol). The enantiomers were separated by SFC (Method Column DAICEL CHIRALCEL OD, Condition 0.1% $NH_3H_2O$ EtOH) to give (R)-5-phenyl-5,6,7,8-tetrahydro-[1,2,4]triazolo[4,3-a]pyridin-3(2H)-one (peak 1, ee=100%) and I-37A, (S)-5-phenyl-5,6,7,8-tetrahydro-[1,2,4]triazolo[4,3-a]pyridin-3(2H)-one (peak 2, ee=100%).

(R)-5-phenyl-5,6,7,8-tetrahydro-[1,2,4]triazolo[4,3-a]pyridin-3(2H)-one $^1H$ NMR (500 MHz, $CD_3OD$) δ 7.31-7.38 (m, 2H), 7.24-7.30 (m, 1H), 7.04 (d, J=7.5 Hz, 2H), 5.18 (dd, J=3.5 Hz, 1H), 2.80-2.89 (m, 1H), 2.66-2.76 (m, 1H), 2.27 (dddd, J=2.5 Hz, 1H), 1.98-2.08 (m, 1H), 1.62-1.82 (m, 2H).

(S)-5-phenyl-5,6,7,8-tetrahydro-[1,2,4]triazolo[4,3-a]pyridin-3(2H)-one (I-37A)

$^1H$ NMR (500 MHz, $CD_3OD$) δ 7.32-7.38 (m, 2H), 7.24-7.30 (m, 1H), 7.04 (d, J=7.5 Hz, 2H), 5.18 (dd, J=3.5 Hz, 1H), 2.80-2.87 (m, 1H), 2.66-2.77 (m, 1H), 2.27 (dddd, J=3.5 Hz, 1H), 1.98-2.07 (m, 1H), 1.63-1.81 (m, 2H).

Preparation of Intermediate I-38A methyl (5S,7S)-7-fluoro-3-oxo-2,5,6,7-tetrahydro-3H-pyrrolo[2,1-c][1,2,4]triazole-5-carboxylate Intermediate I-38A was prepared from (2S,4S)-1-[(tert-butoxy)carbonyl]-4-fluoropyrrolidine-2-carboxylic acid as outlined below.

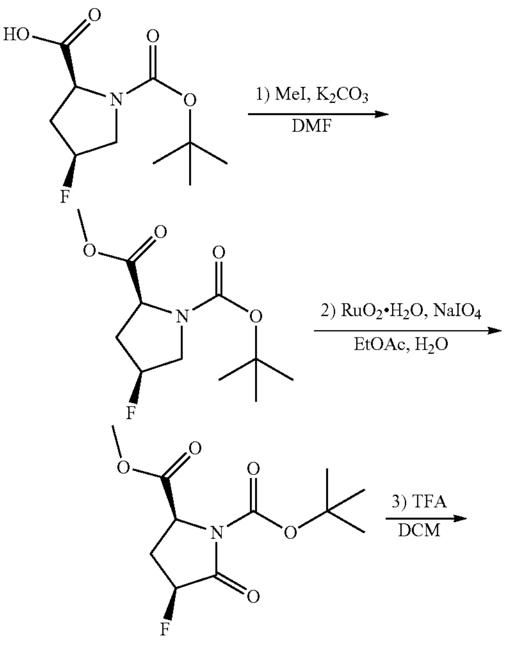

-continued

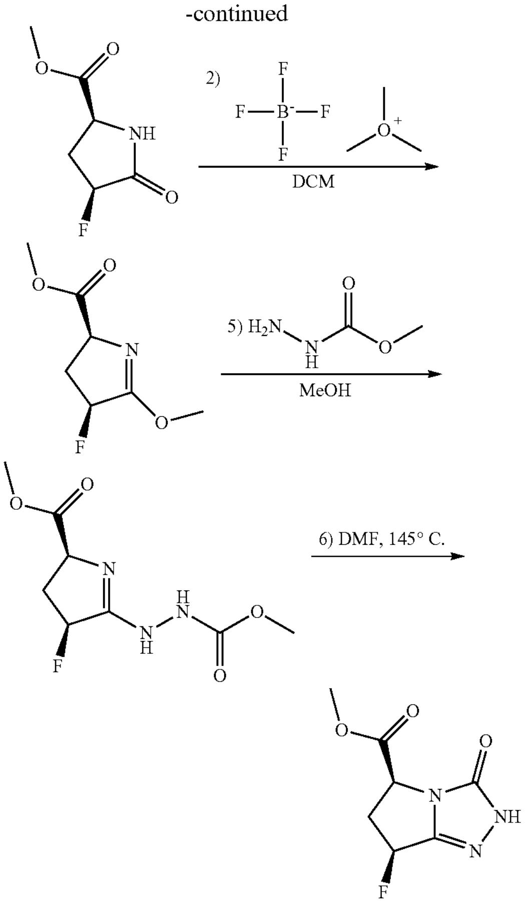

I-38A

Step 1. Preparation of 1-(tert-butyl) 2-methyl (2S, 4S)-4-fluoropyrrolidine-1,2-dicarboxylate To a solution of 1-(tert-butoxycarbonyl)-4-fluoropyrrolidine-2-carboxylic acid (10 g, 42.9 mmol) in DMF (100 mL) was added $K_2CO_3$ (11.85 g, 86 mmol) followed by iodomethane (8.01 mL, 129 mmol) at 0° C. The mixture was then stirred at 30° C. under $N_2$ atmosphere for 2 h. The mixture was poured into ice water and extracted with EtOAc twice. The combined organic layers were washed with saturated aqueous $NH_4Cl$ solution and brine, dried with anhydrous $Na_2SO_4$, filtered and concentrated to dryness. The residue was purified by chromatography on silica gel (Pet. ether:EtOAc=3:1) to afford 1-(tert-butyl) 2-methyl-4-fluoropyrrolidine-1,2-dicarboxylate. Calculated $C_{11}H_{19}FNO_4$ $[M+H]^+$, 248; Found 248.

Step 2. Preparation of 1-(tert-butyl) 2-methyl (2S, 4S)-4-fluoro-5-oxopyrrolidine-1,2-dicarboxylate A solution of sodium periodate (55.0 g, 257 mmol) and ruthenium(iii) chloride hydrate (9.66 g, 42.9 mmol) in water (450 mL) was stirred at 25° C. for 5 min. To this mixture was added 1-(tert-butyl)-2-methyl-4-fluoropyrrolidine-1,2-dicarboxylate (10.6 g, 42.9 mmol) in EtOAc (180 mL), and the reaction was stirred at 25° C. for 12 h. To the mixture was added IPA (100 mL) and the reaction was stirred at 25° C. for 3 h. The mixture was filtered and the the filtrate was extracted with EtOAc (500 mL*2), the combined organic layers were washed with brine, dried over $Na_2SO_4$, filtered, and concentrated in vacuo. The residue was purified by flash silica gel chromatography (ISCO®; 120 g SepaFlash® Silica Flash Column, eluent of 50% EtOAc/Pet. ether gradient @ 60 mL/min) to afford 1-(tert-butyl)-2-methyl-4-fluoro-5-oxopyrrolidine-1,2-dicarboxylate. Calculated $C_6H_8FNO_3$ $[M-Boc+H]^+$, 162; Found 162.

Step 3. Preparation of methyl (2S,4S)-4-fluoro-5-oxopyrrolidine-2-carboxylate

A mixture of 1-(tert-butyl)-2-methyl-4-fluoro-5-oxopyrrolidine-1,2-dicarboxylate (5 g, 19.14 mmol) in DCM (45 mL) and TFA (15 mL) was stirred at 25° C. for 1 h. The mixture was concentrated in vacuo to afford crude methyl-(2S,4S)-4-fluoro-5-oxopyrrolidine-2-carboxylate, which was used directly in next step without further purification. Calculated $C_6H_8FNO_3$ $[M+H]^+$, 162; Found 162.

Step 4. Preparation of methyl (2S,4S)-4-fluoro-5-methoxy-3,4-dihydro-2H-pyrrole-2-carboxylate A mixture of methyl-4-fluoro-5-oxopyrrolidine-2-carboxylate (3 g, 18.62 mmol) and trimethyloxonium tetrafluoroborate (3.58 g, 24.20 mmol) in DCM (30 mL) was stirred at 25° C. for 16 h to give a brown mixture. The reaction mixture was quenched with sat. $NaHCO_3$ (100 mL) and extracted with DCM (50 mL*3). The combined organic phases were washed with brine (100 mL), dried over anhydrous $Na_2SO_4$, filtered and concentrated under reduced pressure to give crude methyl-4-fluoro-5-methoxy-3,4-dihydro-2H-pyrrole-2-carboxylate. The crude was used in the next step without further purification. Calculated $C_7H_{11}FNO_3$ $[M+H]^+$, 176; Found 176.

Step 5. Preparation of methyl (2S,4S)-4-fluoro-5-(2-(methoxycarbonyl)hydrazineyl)-3,4-dihydro-2H-pyrrole-2-carboxylate To a solution of methyl-4-fluoro-5-methoxy-3,4-dihydro-2H-pyrrole-2-carboxylate (1.8 g, 10.28 mmol) in MeOH (6 mL) was added methyl hydrazinecarboxylate (1.018 g, 11.30 mmol) and HCl/MeOH (0.5 mL) at 20° C. The resulting mixture was stirred at 80° C. for 2 h under $N_2$. The reaction was cooled to room temperature and the mixture was concentrated in vacuo. The residue was purified by flash silica gel chromatography (ISCO®; 12 g SepaFlash® Silica Flash Column, eluent of 10% MeOH/EtOAc gradient @ 60 mL/min) to afford methyl 4-fluoro-5-(2-(methoxycarbonyl)hydrazineyl)-3,4-dihydro-2H-pyrrole-2-carboxylate. Calculated $C_8H_{13}FN_3O_4$ $[M+H]^+$, 234; Found 234.

Step 6. Preparation of Intermediate I-38A

A mixture of methyl (2S,4S)-4-fluoro-5-(2-(methoxycarbonyl)hydrazineyl)-3,4-dihydro-2H-pyrrole-2-carboxylate (600 mg, 2.57 mmol) in DMF (20 mL) was stirred at 145° C. for 12 h under $N_2$. The reaction was cooled to room temperature and the mixture was concentrated in vacuo. The residue was purified by flash silica gel chromatography (ISCO®; 12 g SepaFlash® Silica Flash Column, eluent of 10% MeOH/EtOAc gradient @ 60 mL/min) to afford I-38A, methyl (5S,7S)-7-fluoro-3-oxo-2,5,6,7-tetrahydro-3H-pyrrolo[2,1-c][1,2,4]triazole-5-carboxylate. Calculated $C_7H_9FN_3O_3[M+H]^+$, 202; Found 202. $^1H$ NMR (400 MHz, $CD_3OD$) δ 5.62-5.84 (m, 1H), 4.81-4.88 (m, 1H), 3.81-3.87 (m, 3H), 3.20-3.33 (m, 1H), 2.76-2.93 (m, 1H).

TABLE A
Chemical Structures of Intermediates I-1A to I-38A
| Intermediate | Structure |
| --- | --- |
| I-1A | 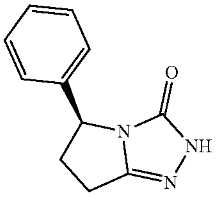 [SMILES: O=c1[nH]nc2n1[C@H](c1ccccc1)CC2] |
| I-2A | 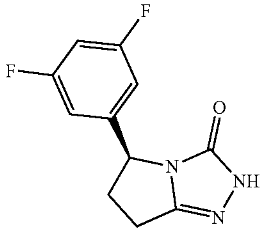 [SMILES: O=c1[nH]nc2n1[C@H](c1cc(F)cc(F)c1)CC2] |
| I-3A | 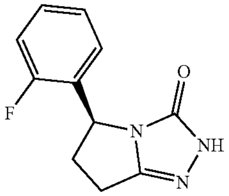 [SMILES: O=c1[nH]nc2n1[C@H](c1ccccc1F)CC2] |
| I-4A | 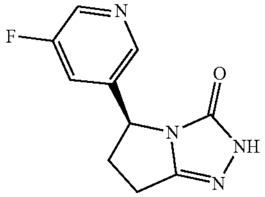 [SMILES: O=c1[nH]nc2n1[C@H](c1cncc(F)c1)CC2] |
| I-5A | 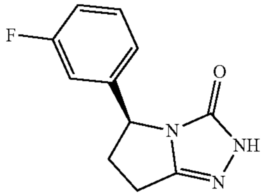 [SMILES: O=c1[nH]nc2n1[C@H](c1cccc(F)c1)CC2] |
| I-6A | 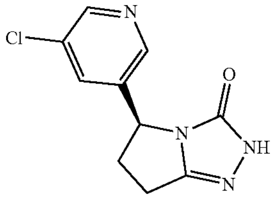 [SMILES: O=c1[nH]nc2n1[C@H](c1cncc(Cl)c1)CC2] |
| I-7A | 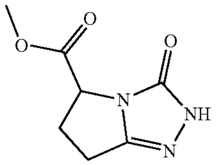 |
TABLE A-continued
Chemical Structures of Intermediates I-1A to I-38A
| Intermediate | Structure |
| --- | --- |
| I-8A | 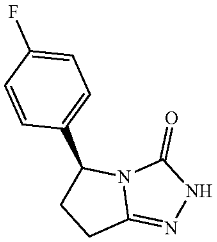 [SMILES: O=c1[nH]nc2n1[C@H](c1ccc(F)cc1)CC2] |
| I-9A | 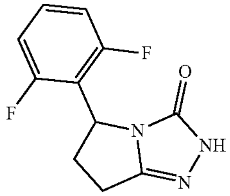 [SMILES: O=c1[nH]nc2n1C(c1c(F)cccc1F)CC2] |
| I-10A | 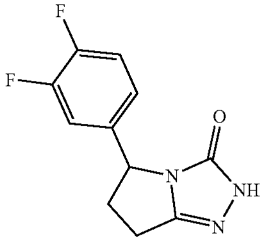 [SMILES: O=c1[nH]nc2n1C(c1ccc(F)c(F)c1)CC2] |
| I-11A | 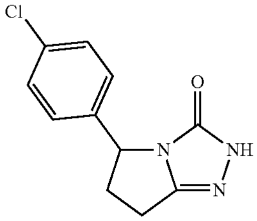 [SMILES: O=c1[nH]nc2n1C(c1ccc(Cl)cc1)CC2] |
| I-12A | 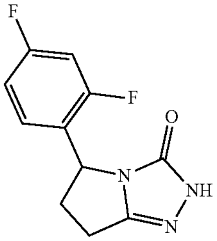 [SMILES: O=c1[nH]nc2n1C(c1ccc(F)cc1F)CC2] |
| I-13A | 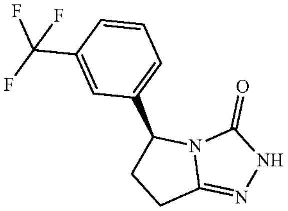 [SMILES: O=c1[nH]nc2n1[C@H](c1cccc(C(F)(F)F)c1)CC2] |

TABLE A-continued
Chemical Structures of Intermediates I-1A to I-38A
| Intermediate | Structure |
| --- | --- |
| I-14A | 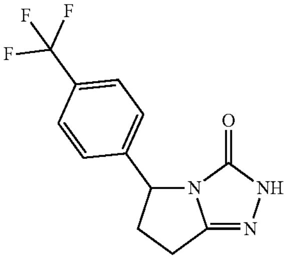 [SMILES: O=c1[nH]nc2n1C(c1ccc(C(F)(F)F)cc1)CC2] |
| I-15A | 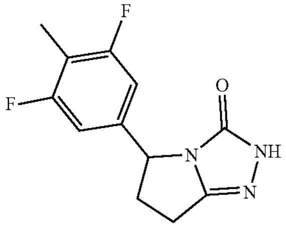 [SMILES: Cc1c(F)cc(C2CCc3n[nH]c(=O)n32)cc1F] |
| I-16A | 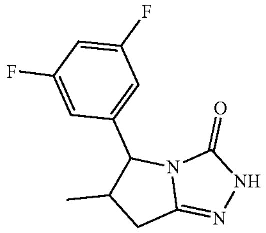 [SMILES: CC1Cc2n[nH]c(=O)n2C1c1cc(F)cc(F)c1] |
| I-17A | 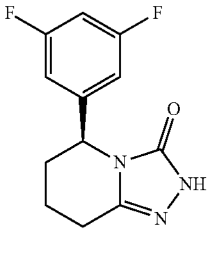 [SMILES: O=c1[nH]nc2n1[C@H](c1cc(F)cc(F)c1)CCC2] |
| I-18A | 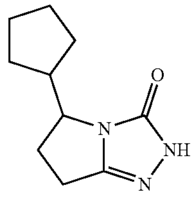 [SMILES: O=c1[nH]nc2n1C(C1CCCC1)CC2] |
| I-19A | 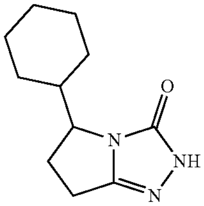 [SMILES: O=c1[nH]nc2n1C(C1CCCCC1)CC2] |
| I-20A | 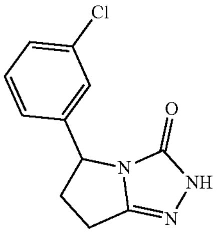 [SMILES: O=c1[nH]nc2n1C(c1cccc(Cl)c1)CC2] |
| I-21A | 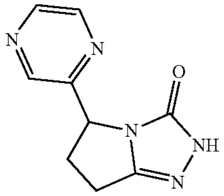 [SMILES: O=c1[nH]nc2n1C(c1cnccn1)CC2] |
| I-22A | 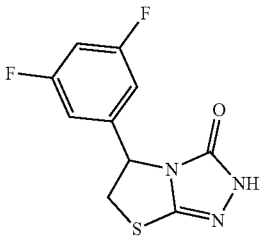 [SMILES: O=c1[nH]nc2n1C(c1cc(F)cc(F)c1)CS2] |
| I-23A | 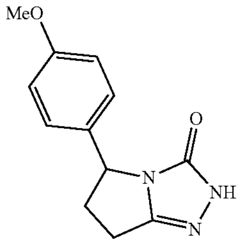 [SMILES: COc1ccc(C2CCc3n[nH]c(=O)n32)cc1] |
| I-24A | 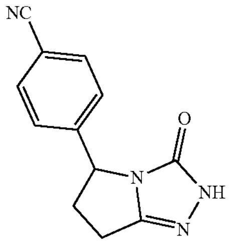 [SMILES: N#Cc1ccc(C2CCc3n[nH]c(=O)n32)cc1] |
| I-25A | 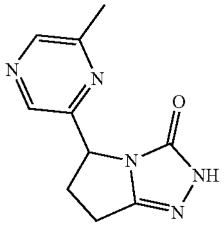 [SMILES: Cc1cncc(C2CCc3n[nH]c(=O)n32)n1] |

TABLE A-continued
Chemical Structures of Intermediates I-1A to I-38A
| Intermediate | Structure |
|---|---|
| I-26A | 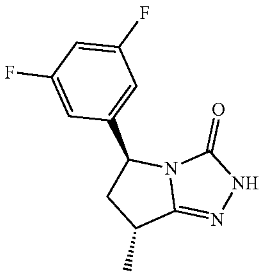 [SMILES: C[C@@H]1C[C@@H](c2cc(F)cc(F)c2)n2c1n[nH]c2=O] |
| I-27A | 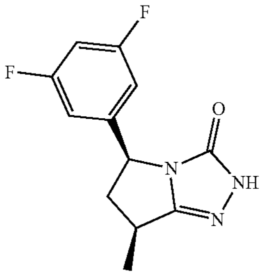 [SMILES: C[C@H]1C[C@@H](c2cc(F)cc(F)c2)n2c1n[nH]c2=O] |
| I-28A | 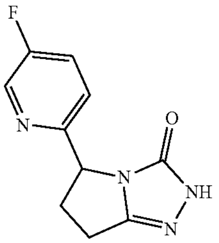 [SMILES: O=c1[nH]nc2n1C(c1ccc(F)cn1)CC2] |
| I-29A | 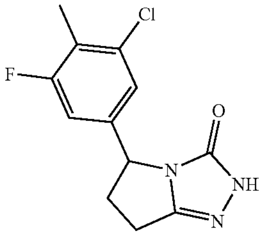 [SMILES: Cc1c(F)cc(C2CCc3n[nH]c(=O)n32)cc1Cl] |
| I-30A | 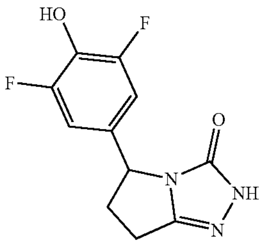 [SMILES: O=c1[nH]nc2n1C(c1cc(F)c(O)c(F)c1)CC2] |
| I-31A | 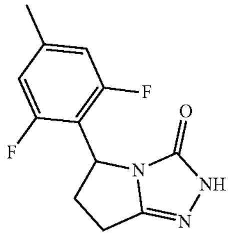 [SMILES: Cc1cc(F)c(C2CCc3n[nH]c(=O)n32)c(F)c1] |
TABLE A-continued
Chemical Structures of Intermediates I-1A to I-38A
| Intermediate | Structure |
|---|---|
| I-32A | 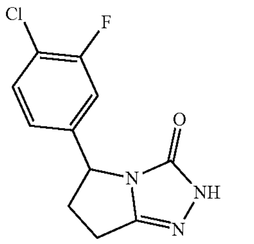 [SMILES: O=c1[nH]nc2n1C(c1ccc(Cl)c(F)c1)CC2] |
| I-33A | 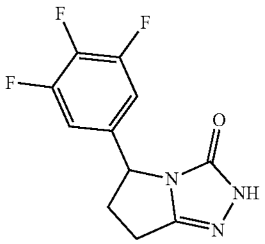 [SMILES: O=c1[nH]nc2n1C(c1cc(F)c(F)c(F)c1)CC2] |
| I-34A | 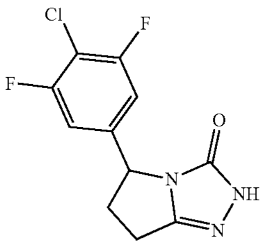 [SMILES: O=c1[nH]nc2n1C(c1cc(F)c(Cl)c(F)c1)CC2] |
| I-35A | 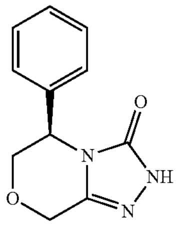 [SMILES: O=c1[nH]nc2n1[C@H](c1ccccc1)COC2] |
| I-36A | 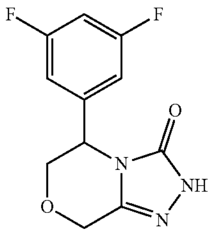 [SMILES: O=c1[nH]nc2n1C(c1cc(F)cc(F)c1)COC2] |
| I-37A | 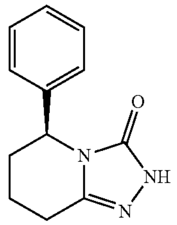 [SMILES: O=c1[nH]nc2n1[C@H](c1ccccc1)CCC2] |

TABLE A-continued

| Chemical Structures of Intermediates I-1A to I-38A | |
|---|---|
| Intermediate | Structure |
| I-38A | 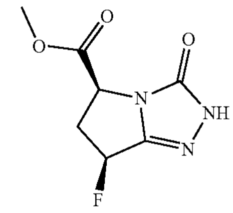 |

Synthesis of Common Intermediates (Table B)

Preparation of Intermediate I-2B3 (mesityl-l3-iodanediyl bis(3-fluorobicyclo[1.1.1]pentane-1-carboxylate)

Intermediate I-2B3 was prepared from 3-fluorobicyclo[1.1.1]pentane-1-carboxylic acid as outlined below.

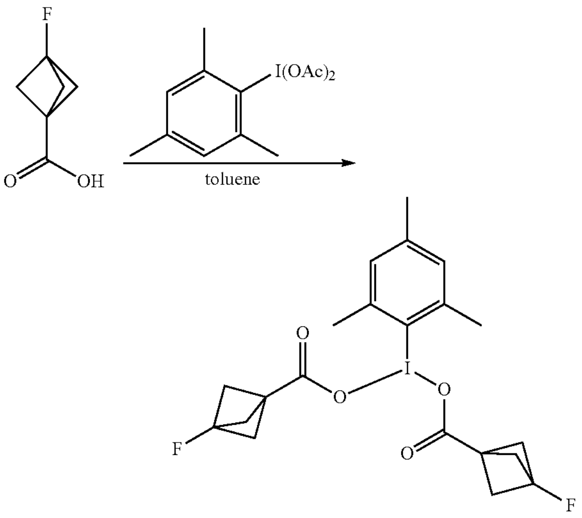

I-2B

A mixture of 3-fluorobicyclo[1.1.1]pentane-1-carboxylic acid (143 mg, 1.098 mmol) and mesityl-l3-iodanediyl diacetate (200 mg, 0.549 mmol) in toluene (15 mL) was concentrated in vacuo at 55° C., the residue was redissolved in toluene (15 mL), then concentrated in vacuo at 55° C., the residue was redissolved in toluene (15 mL), then concentrated in vacuo at 55° C. The residue was redissolved in toluene (15 mL), then concentrated in vacuo at 55° C. to afford crude mesityl-l3-iodanediyl bis(3-fluorobicyclo[1.1.1]pentane-1-carboxylate). $^1$H NMR (400 MHz, $CDCl_3$) δ 6.99-7.24 (m, 3H), 2.61-2.69 (m, 4H), 2.28-2.35 (m, 3H), 2.11-2.21 (m, 8H).

Preparation of Intermediate I-5B (mesityl-l3-iodanediyl bis(3-cyanobicyclo[1.1.1]pentane-1-carboxylate))

Intermediate I-5B was prepared from methyl 3-cyanobicyclo[1.1.1]pentane-1-carboxylate as outlined below.

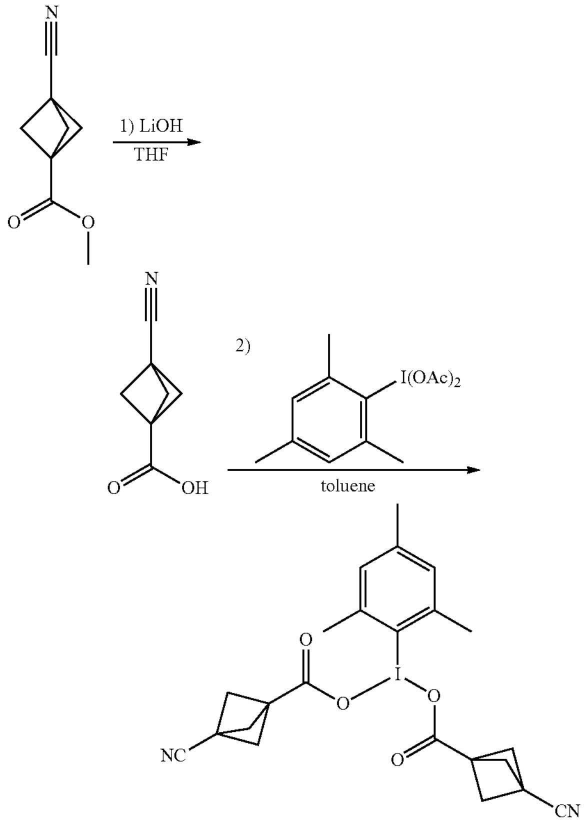

I-5B

Step 1. Preparation of 3-cyanobicyclo[1.1.1]pentane-1-carboxylic acid

To a solution of methyl 3-cyanobicyclo[1.1.1]pentane-1-carboxylate (170 mg, 1.13 mmol) in THF (3 mL) and water (1 mL) was added lithium hydroxide (81 mg, 3.37 mmol). The reaction was stirred at 20° C. for 12 h. TLC showed the starting material was consumed and new spot was found. To the reaction was added water (4 mL) and the mixture was extracted with ethyl acetate (1×2 mL). The aqueous phase was acidified with 2 M HCl to PH-4 and extracted with EtOAc (2 mL×3). The combined organic layers were dried over $Na_2SO_4$, filtered and the filtrate was concentrated in vacuo to give 3-cyanobicyclo[1.1.1]pentane-1-carboxylic acid, which was used in the next step without further purification.

Step 2. Preparation of I-5B

To a solution of 3-cyanobicyclo[1.1.1]pentane-1-carboxylic acid (100 mg, 0.730 mmol) in toluene (20 ml) was added mesityl-l3-iodanediyl diacetate (133 mg, 0.365 mmol) and the resulting mixture was concentrated on a rotary evaporator at 55° C. for four times each time with fresh toluene (20 ml). The crude product was concentrated in vacuum to give mesityl-l3-iodanediyl bis(3-cyanobicyclo[1.1.1]pentane-1-carboxylate). The crude product was used in the next step directly. $^1$H NMR (400 MHz, $CD_3OD$) δ 7.18 (s, 2H), 2.71 (s, 9H), 2.37-2.41 (m, 6H), 2.16 (br s, 6H).

Intermediates I-1B, I-3B, I-4B, and I-6B to I-19B were prepared in a fashion analogous to the procedure used to prepare I-2B using the corresponding commercially available acids and mesityl-l3-iodanediyl diacetate reagents.
TABLE B
| Chemical Structures of Intermediates I-1B to I-19B | |
|---|---|
| Intermediate | Structure |
| I-1B | 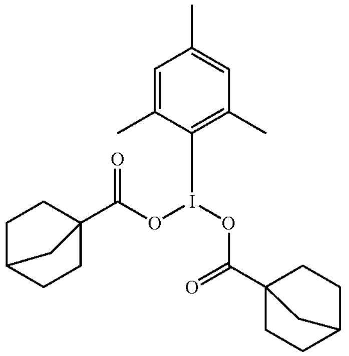 [SMILES: Cc1cc(C)c(I(OC(=O)C23CCC(CC2)C3)OC(=O)C23CCC(CC2)C3)c(C)c1] |
| I-2B | 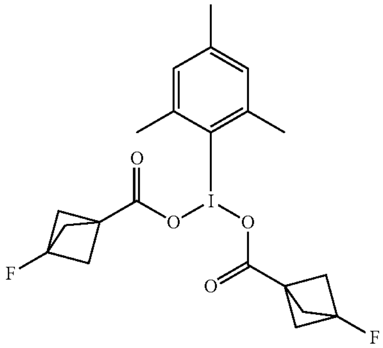 [SMILES: Cc1cc(C)c(I(OC(=O)C23CC(F)(C2)C3)OC(=O)C23CC(F)(C2)C3)c(C)c1] |
| I-3B | 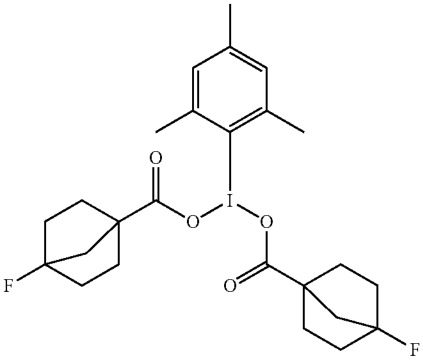 [SMILES: Cc1cc(C)c(I(OC(=O)C23CCC(F)(CC2)C3)OC(=O)C23CCC(F)(CC2)C3)c(C)c1] |
| I-4B | 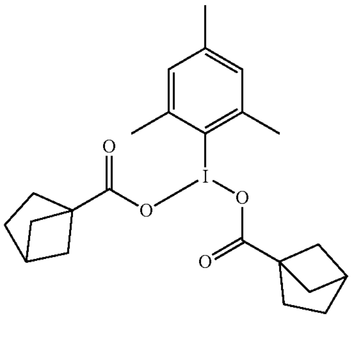 [SMILES: Cc1cc(C)c(I(OC(=O)C23CCC(C2)C3)OC(=O)C23CCC(C2)C3)c(C)c1] |
TABLE B-continued
| Chemical Structures of Intermediates I-1B to I-19B | |
|---|---|
| Intermediate | Structure |
| I-5B | 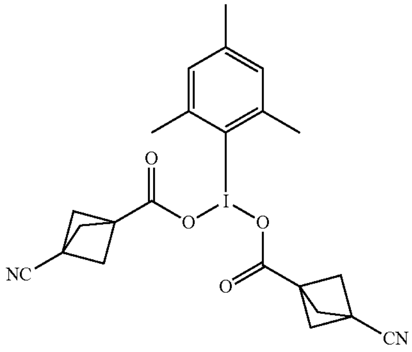 [SMILES: Cc1cc(C)c(I(OC(=O)C23CC(C#N)(C2)C3)OC(=O)C23CC(C#N)(C2)C3)c(C)c1] |
| I-6B | 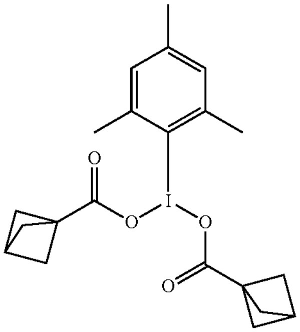 [SMILES: Cc1cc(C)c(I(OC(=O)C23CC(C2)C3)OC(=O)C23CC(C2)C3)c(C)c1] |
| I-7B | 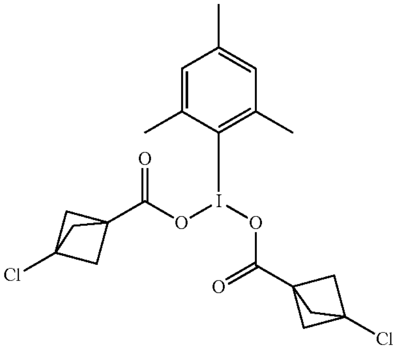 [SMILES: Cc1cc(C)c(I(OC(=O)C23CC(Cl)(C2)C3)OC(=O)C23CC(Cl)(C2)C3)c(C)c1] |
| I-8B | 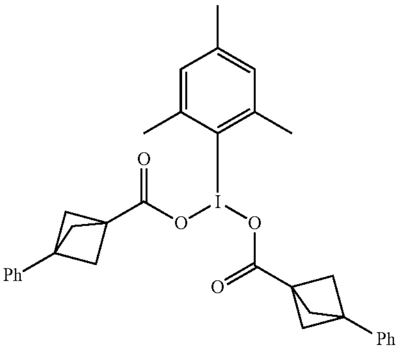 [SMILES: Cc1cc(C)c(I(OC(=O)C23CC(c4ccccc4)(C2)C3)OC(=O)C23CC(c4ccccc4)(C2)C3)c(C)c1] |

TABLE B-continued
| Chemical Structures of Intermediates I-1B to I-19B | |
|---|---|
| Intermediate | Structure |
| I-9B | 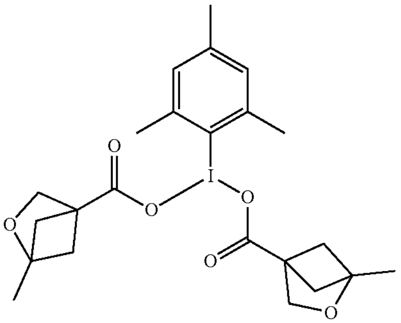 [SMILES: Cc1cc(C)c(I(OC(=O)C23COC(C)(C2)C3)OC(=O)C23COC(C)(C2)C3)c(C)c1] |
| I-10B | 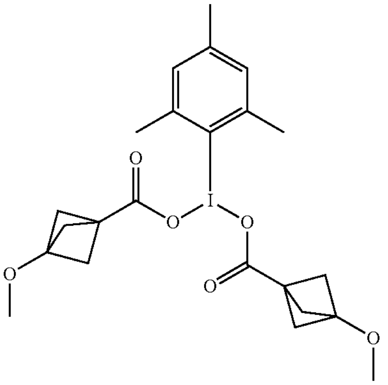 [SMILES: COC12CC(C(=O)OI(OC(=O)C34CC(OC)(C3)C4)c3c(C)cc(C)cc3C)(C1)C2] |
| I-12B | 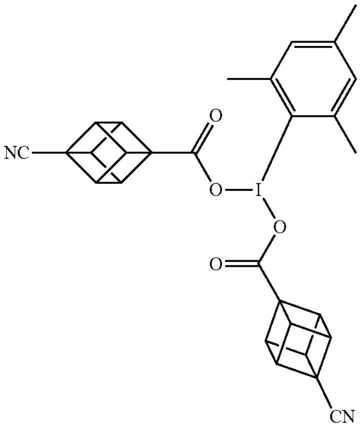 [SMILES: Cc1cc(C)c(I(OC(=O)C23C4C5C2C2C3C4C52C#N)OC(=O)C23C4C5C2C2C3C4C52C#N)c(C)c1] |
| I-11B | 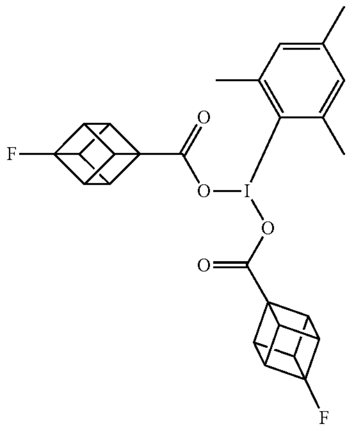 [SMILES: Cc1cc(C)c(I(OC(=O)C23C4C5C2C2C3C4C52F)OC(=O)C23C4C5C2C2C3C4C52F)c(C)c1] |
TABLE B-continued
| Chemical Structures of Intermediates I-1B to I-19B | |
|---|---|
| Intermediate | Structure |
| I-13B | 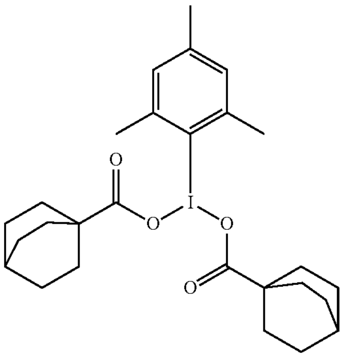 [SMILES: Cc1cc(C)c(I(OC(=O)C23CCC(CC2)CC3)OC(=O)C23CCC(CC2)CC3)c(C)c1] |
| I-14B | 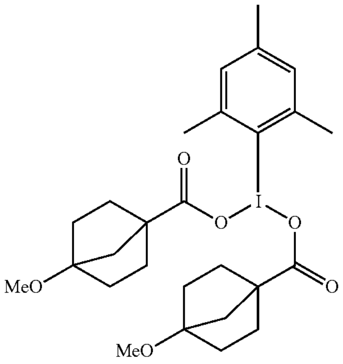 [SMILES: COC12CCC(C(=O)OI(OC(=O)C34CCC(OC)(CC3)C4)c3c(C)cc(C)cc3C)(CC1)C2] |
| I-15B | 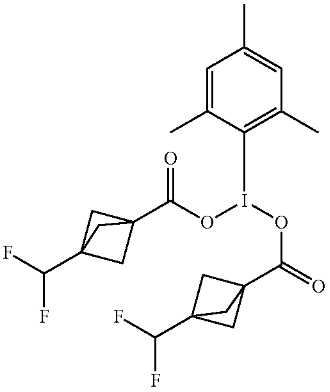 [SMILES: Cc1cc(C)c(I(OC(=O)C23CC(C(F)F)(C2)C3)OC(=O)C23CC(C(F)F)(C2)C3)c(C)c1] |
| I-16B | 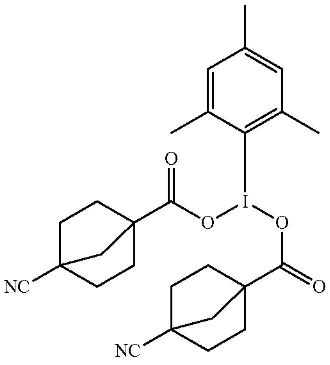 [SMILES: Cc1cc(C)c(I(OC(=O)C23CCC(C#N)(CC2)C3)OC(=O)C23CCC(C#N)(CC2)C3)c(C)c1] |

TABLE B-continued

| Chemical Structures of Intermediates I-1B to I-19B | |
|---|---|
| Intermediate | Structure |
| I-17B | 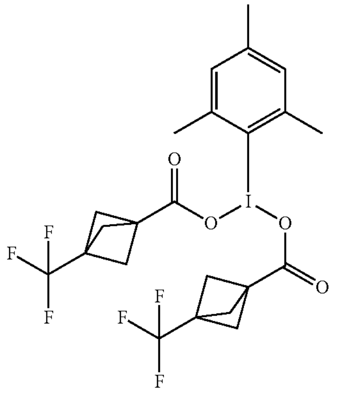 [SMILES: Cc1cc(C)c(I(OC(=O)C23CC(C(F)(F)F)(C2)C3)OC(=O)C23CC(C(F)(F)F)(C2)C3)c(C)c1] |
| I-18B | 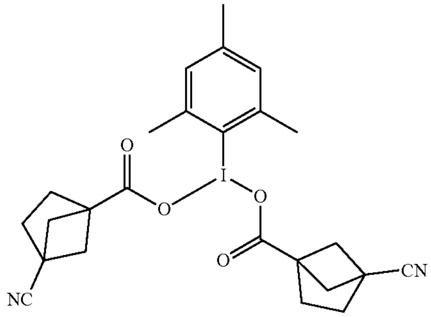 [SMILES: Cc1cc(C)c(I(OC(=O)C23CCC(C#N)(C2)C3)OC(=O)C23CCC(C#N)(C2)C3)c(C)c1] |
| I-19B | 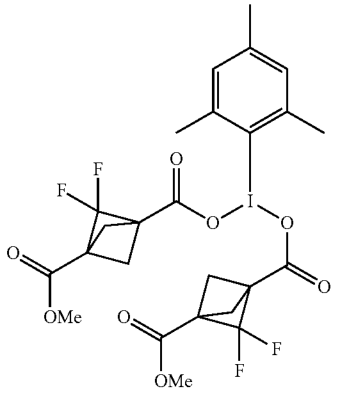 [SMILES: COC(=O)C12CC(C(=O)OI(OC(=O)C34CC(C(=O)OC)(C3)C4(F)F)c3c(C)cc(C)cc3C)(C1)C2(F)F] |

General Scheme 1.

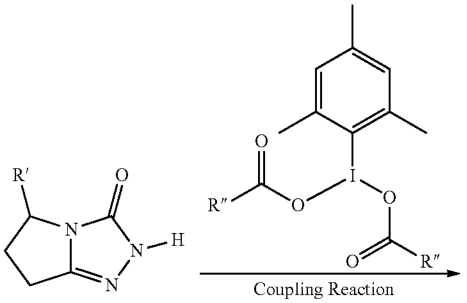

-continued

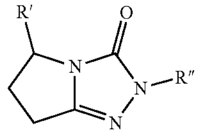

In general scheme 1, intermediates of Table A and Table B were coupled under photoredox conditions in the presence of a copper and iridium catalyst to afford the desired products listed in Table 1.

Example 1.1. Preparation of Compound 1-2 ((5S)-5-(3,5-difluorophenyl)-2-(3-fluorobicyclo[1.1.1]pentan-1-yl)-2,5,6,7-tetrahydro-3H-pyrrolo[2,1-c][1,2,4]triazol-3-one)

Compound 1-2 was prepared from intermediates I-2A and I-2B as outlined below.

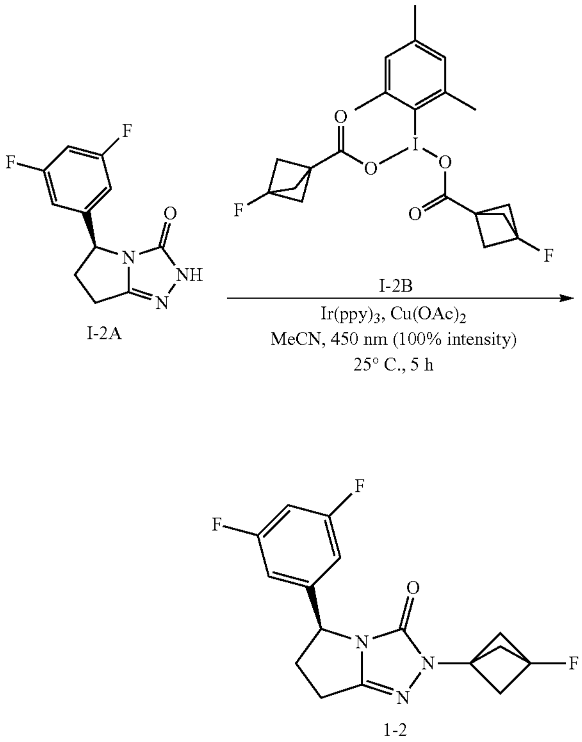

In four individual 40 mL vials were added intermediate I-2A ((S)-5-(3,5-difluorophenyl)-2,5,6,7-tetrahydro-3H-pyrrolo[2,1-c][1,2,4]triazol-3-one) (600 mg, 2.53 mmol), intermediate I-2B (mesityl-l3-iodanediyl bis(3-fluorobicyclo[1.1.1]pentane-1-carboxylate) (2550 mg, 5.06 mmol), $Ir(ppy)_3$ (tris(2-phenylpyridine)iridium) (33.1 mg, 0.051 mmol), $Cu(OAc)_2$ (331 mg, 1.27 mmol) and MeCN (25.3 mL). Each mixture was purged with nitrogen gas and then placed in a photoreactor (fan rpm 4700, stir rpm 1000, 450 nm, 100% light intensity) for 5 h. The reactions were diluted with CAN, filtered through a pad of celite then combined, and purified by flash column chromatography (60 g silica gel, ELSD, 35% EtOAc:Hex and then 70% EtOAc:Hex for desired product). The fractions containing the desired product were pooled and concentrated to dryness to give compound 1-2. The desired product can be recrystallized by dissolving with minimal amounts of EtOAc over 24-48 h. Upon filtering and washing with hexanes, the product can be isolated with >99.9% purity. Calculated $C_{16}H_{15}F_3N_3O$ $[M+H]^+$, 322; Found 322. $^1H$ NMR (499 MHz, DMSO-$d_6$) δ 7.19 (t, J=9.3 Hz, 1H), 7.05 (d, J=6.6 Hz, 2H), 5.19 (m, 1H), 2.99-2.82 (m, 2H), 2.81-2.70 (m, 1H), 2.52 (d, J=1.8 Hz, 6H), 2.35-2.24 (m, 1H).

Example 1.2. Preparation of 1-40

Compound 1-40 was prepared from intermediates I-9A and I-2B as outlined below.

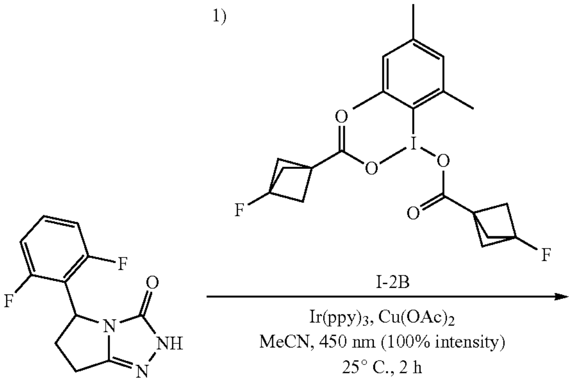

I-9A

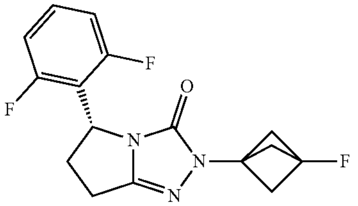

+

-continued

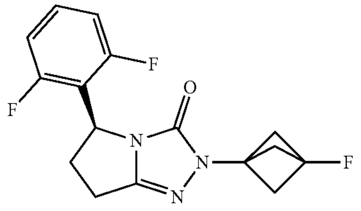

1-40

A mixture of intermediate I-9A (20 mg, 0.084 mmol), $Cu(OAc)_2$ (11.04 mg, 0.042 mmol), $Ir(ppy)_3$ (1.104 mg, 1.69 μmol) and intermediate I-2B (85 mg, 0.169 mmol) in MeCN (2 mL) was stirred at 25° C. with $N_2$ with 450 nm blue LED lamps for 2 h. LCMS showed the product was formed. The mixture was concentrated in vacuo. The residue was purified by pre-HPLC (Method Column Boston Prime C18 (150×30 mm×5 um); Condition water ($NH_3H_2O$+$NH_4HCO_3$)-ACN) to give 5-(2,6-difluorophenyl)-2-(3-fluorobicyclo[1.1.1]pentan-1-yl)-2,5,6,7-tetrahydro-3H-pyrrolo[2,1-c][1,2,4]triazol-3-one. The enantiomers were separated by SFC (Method Column DAICEL CHIRALCEL OJ (250 mm×30 mm, 10 um); Condition 0.1% $NH_3H_2O$/EtOH) to give (R)-5-(2,6-difluorophenyl)-2-(3-fluorobicyclo[1.1.1]pentan-1-yl)-2,5,6,7-tetrahydro-3H-pyrrolo[2,1-c][1,2,4]triazol-3-one (SFC-P1, ee=100%) and compound 1-40 ((S)-5-(2,6-difluorophenyl)-2-(3-fluorobicyclo[1.1.1]pentan-1-yl)-2,5,6,7-tetrahydro-3H-pyrrolo[2,1-c][1,2,4]triazol-3-one) (SFC-P2, ee=100%).

(R)-5-(2,6-difluorophenyl)-2-(3-fluorobicyclo[1.1.1]pentan-1-yl)-2,5,6,7-tetrahydro-3H-pyrrolo[2,1-c][1,2,4]triazol-3-one $^1H$ NMR (400 MHz, $CDCl_3$) δ 7.27-7.35 (m, 1H), 6.92 (t, J=8.4 Hz, 2H), 5.52 (dd, J=4.8, 8.8 Hz, 1H), 2.97-3.14 (m, 2H), 2.82-2.94 (m, 1H), 2.59 (d, J=2.0 Hz, 6H).

(S)-5-(2,6-difluorophenyl)-2-(3-fluorobicyclo[1.1.1]pentan-1-yl)-2,5,6,7-tetrahydro-3H-pyrrolo[2,1-c][1,2,4]triazol-3-one (1-40)

$^1H$ NMR (400 MHz, $CDCl_3$) δ 7.28-7.35 (m, 1H), 6.93 (t, J=8.4 Hz, 2H), 5.52 (dd, J=4.8, 8.8 Hz, 1H), 2.99-3.14 (m, 2H), 2.82-2.93 (m, 1H), 2.59 (d, J=2.0 Hz, 6H).

TABLE 1

| Compound Number | Structure | Chemical Name | Mass [M + H]+; Method |
|---|---|---|---|
| 1-1 | 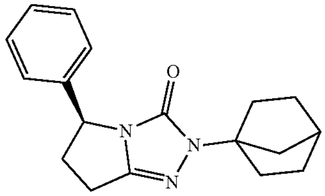 [SMILES: O=c1n(C23CCC(CC2)C3)nc2n1[C@H](c1ccccc1)CC2] | (5S)-2-(bicyclo[2.2.1]heptan-1-yl)-5-phenyl-2,5,6,7-tetrahydro-3H-pyrrolo[2,1-c][1,2,4]triazol-3-one | Calc'd 296, found 296; Ex. 1.1 |

TABLE 1-continued

| Compound Number | Structure | Chemical Name | Mass [M + H]+; Method |
|---|---|---|---|
| 1-2 | 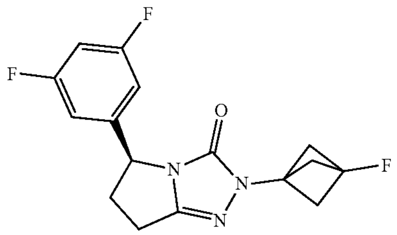 [SMILES: O=c1n(C23CC(F)(C2)C3)nc2n1[C@H](c1cc(F)cc(F)c1)CC2] | (5S)-5-(3,5-difluorophenyl)-2-(3-fluorobicyclo[1.1.1]pentan-1-yl)-2,5,6,7-tetrahydro-3H-pyrrolo[2,1-c][1,2,4]triazol-3-one | Calc'd 322, found 322; Ex. 1.1 |
| 1-3 | 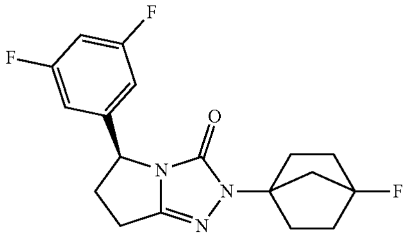 [SMILES: O=c1n(C23CCC(F)(CC2)C3)nc2n1[C@H](c1cc(F)cc(F)c1)CC2] | (5S)-5-(3,5-difluorophenyl)-2-(4-fluorobicyclo[2.2.1]heptan-1-yl)-2,5,6,7-tetrahydro-3H-pyrrolo[2,1-c][1,2,4]triazol-3-one | Calc'd 350, found 350; Ex. 1.1 |
| 1-4 | 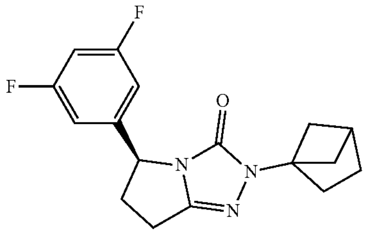 [SMILES: O=c1n(C23CCC(C2)C3)nc2n1[C@H](c1cc(F)cc(F)c1)CC2] | (5S)-2-(bicyclo[2.1.1]hexan-1-yl)-5-(3,5-difluorophenyl)-2,5,6,7-tetrahydro-3H-pyrrolo[2,1-c][1,2,4]triazol-3-one | Calc'd 318, found 318; Ex. 1.1 |
| 1-5 | 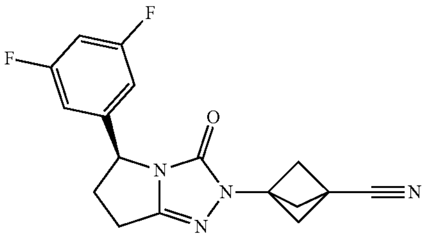 [SMILES: N#CC12CC(n3nc4n(c3=O)[C@H](c3cc(F)cc(F)c3)CC4)(C1)C2] | 3-[(5S)-5-(3,5-difluorophenyl)-3-oxo-6,7-dihydro-3H-pyrrolo[2,1-c][1,2,4]triazol-2(5H)-yl]bicyclo[1.1.1]pentane-1-carbonitrile | Calc'd 329, found 329; Ex. 1.1 |
| 1-6 | 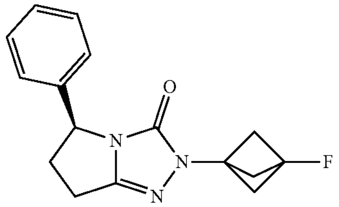 [SMILES: O=c1n(C23CC(F)(C2)C3)nc2n1[C@H](c1ccccc1)CC2] | (5S)-2-(3-fluorobicyclo[1.1.1]pentan-1-yl)-5-phenyl-2,5,6,7-tetrahydro-3H-pyrrolo[2,1-c][1,2,4]triazol-3-one | Calc'd 286, found 286; Ex. 1.1 |
| 1-7 | 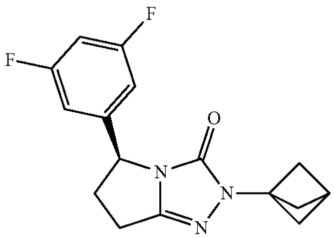 [SMILES: O=c1n(C23CC(C2)C3)nc2n1[C@H](c1cc(F)cc(F)c1)CC2] | (5S)-2-(bicyclo[1.1.1]pentan-1-yl)-5-(3,5-difluorophenyl)-2,5,6,7-tetrahydro-3H-pyrrolo[2,1-c][1,2,4]triazol-3-one | Calc'd 304, found 304; Ex. 1.1 |

TABLE 1-continued

| Compound Number | Structure | Chemical Name | Mass [M + H]+; Method |
|---|---|---|---|
| 1-8 | 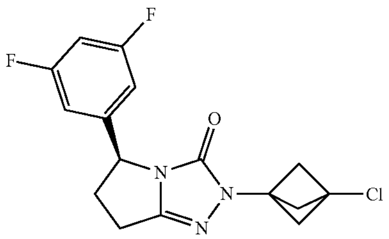 [SMILES: O=c1n(C23CC(Cl)(C2)C3)nc2n1[C@H](c1cc(F)cc(F)c1)CC2] | (5S)-2-(3-chlorobicyclo[1.1.1]pentan-1-yl)-5-(3,5-difluorophenyl)-2,5,6,7-tetrahydro-3H-pyrrolo[2,1-c][1,2,4]triazol-3-one | Calc'd 338, found 338; Ex. 1.1 |
| 1-9 | 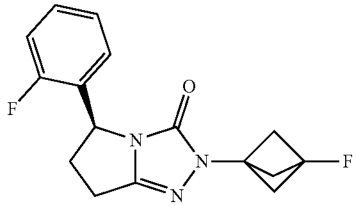 [SMILES: O=c1n(C23CC(F)(C2)C3)nc2n1[C@H](c1ccccc1F)CC2] | (5S)-2-(3-fluorobicyclo[1.1.1]pentan-1-yl)-5-(2-fluorophenyl)-2,5,6,7-tetrahydro-3H-pyrrolo[2,1-c][1,2,4]triazol-3-one | Calc'd 304, found 304; Ex. 1.1 |
| 1-10 | 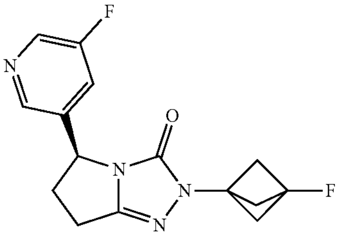 [SMILES: O=c1n(C23CC(F)(C2)C3)nc2n1[C@H](c1cncc(F)c1)CC2] | (5S)-2-(3-fluorobicyclo[1.1.1]pentan-1-yl)-5-(5-fluoropyridin-3-yl)-2,5,6,7-tetrahydro-3H-pyrrolo[2,1-c][1,2,4]triazol-3-one | Calc'd 305, found 305; Ex. 1.1 |
| 1-11 | 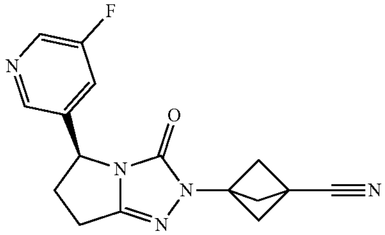 [SMILES: N#CC12CC(n3nc4n(c3=O)[C@H](c3cncc(F)c3)CC4)(C1)C2] | 3-[(5S)-5-(5-fluoropyridin-3-yl)-3-oxo-6,7-dihydro-3H-pyrrolo[2,1-c][1,2,4]triazol-2(5H)-yl]bicyclo[1.1.1]pentane-1-carbonitrile | Calc'd 312, found 312; Ex. 1.1 |
| 1-12 | 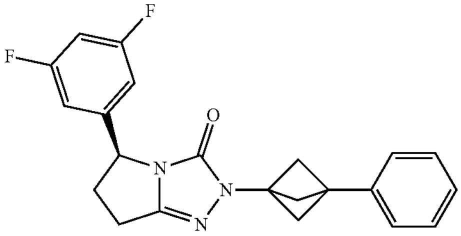 [SMILES: O=c1n(C23CC(c4ccccc4)(C2)C3)nc2n1[C@H](c1cc(F)cc(F)c1)CC2] | (5S)-5-(3,5-difluorophenyl)-2-(3-phenylbicyclo[1.1.1]pentan-1-yl)-2,5,6,7-tetrahydro-3H-pyrrolo[2,1-c][1,2,4]triazol-3-one | Calc'd 380, found 380; Ex. 1.1 |
| 1-13 | 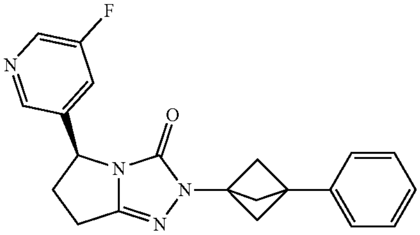 [SMILES: O=c1n(C23CC(c4ccccc4)(C2)C3)nc2n1[C@H](c1cncc(F)c1)CC2] | (5S)-5-(5-fluoropyridin-3-yl)-2-(3-phenylbicyclo[1.1.1]pentan-1-yl)-2,5,6,7-tetrahydro-3H-pyrrolo[2,1-c][1,2,4]triazol-3-one | Calc'd 363, found 363; Ex. 1.1 |

TABLE 1-continued

| Compound Number | Structure | Chemical Name | Mass [M + H]+; Method |
|---|---|---|---|
| 1-14 | 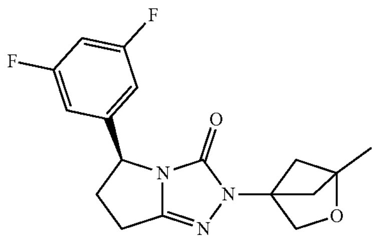 [SMILES: CC12CC(n3nc4n(c3=O)[C@H](c3cc(F)cc(F)c3)CC4)(CO1)C2] | (5S)-5-(3,5-difluorophenyl)-2-(1-methyl-2-oxabicyclo[2.1.1]hexan-4-yl)-2,5,6,7-tetrahydro-3H-pyrrolo[2,1-c][1,2,4]triazol-3-one | Calc'd 334, found 334; Ex. 1.1 |
| 1-15 | 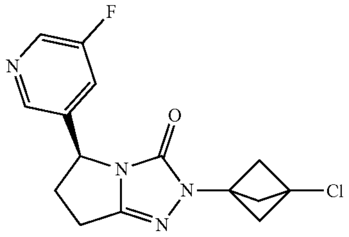 [SMILES: O=c1n(C23CC(Cl)(C2)C3)nc2n1[C@H](c1cncc(F)c1)CC2] | (5S)-2-(3-chlorobicyclo[1.1.1]pentan-1-yl)-5-(5-fluoropyridin-3-yl)-2,5,6,7-tetrahydro-3H-pyrrolo[2,1-c][1,2,4]triazol-3-one | Calc'd 321, found 321; Ex. 1.1 |
| 1-16 | 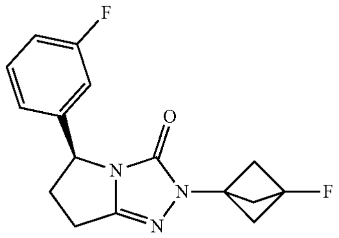 [SMILES: O=c1n(C23CC(F)(C2)C3)nc2n1[C@H](c1cccc(F)c1)CC2] | (S)-2-(3-fluorobicyclo[1.1.1]pentan-1-yl)-5-(3-fluorophenyl)-2,5,6,7-tetrahydro-3H-pyrrolo[2,1-c][1,2,4]triazol-3-one | Calc'd 304, found 304; Ex. 1.1 |
| 1-17 | 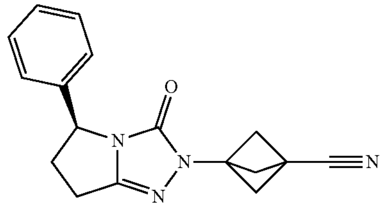 [SMILES: N#CC12CC(n3nc4n(c3=O)[C@H](c3ccccc3)CC4)(C1)C2] | 3-[(5S)-3-oxo-5-phenyl-6,7-dihydro-3H-pyrrolo[2,1-c][1,2,4]triazol-2(5H)-yl]bicyclo[1.1.1]pentane-1-carbonitrile | Calc'd 293, found 293; Ex. 1.1 |
| 1-18 | 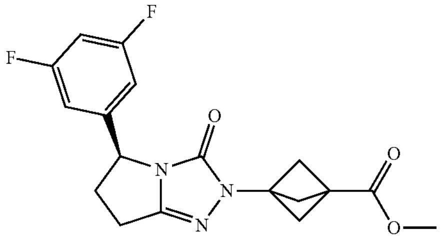 [SMILES: COC(=O)C12CC(n3nc4n(c3=O)[C@H](c3cc(F)cc(F)c3)CC4)(C1)C2] | methyl 3-[(5S)-5-(3,5-difluorophenyl)-3-oxo-6,7-dihydro-3H-pyrrolo[2,1-c][1,2,4]triazol-2(5H)-yl]bicyclo[1.1.1]pentane-1-carboxylate | Calc'd 362, found 262; Ex. 1.1 |
| 1-19 | 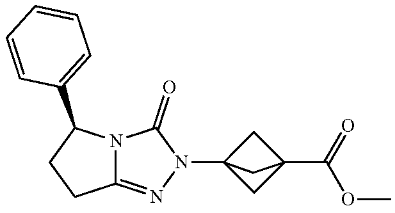 [SMILES: COC(=O)C12CC(n3nc4n(c3=O)[C@H](c3ccccc3)CC4)(C1)C2] | methyl 3-[(5S)-3-oxo-5-phenyl-6,7-dihydro-3H-pyrrolo[2,1-c][1,2,4]triazol-2(5H)-yl]bicyclo[1.1.1]pentane-1-carboxylate | Calc'd 326, found 326; Ex. 1.1 |

TABLE 1-continued

| Compound Number | Structure | Chemical Name | Mass [M + H]+; Method |
|---|---|---|---|
| 1-20 | 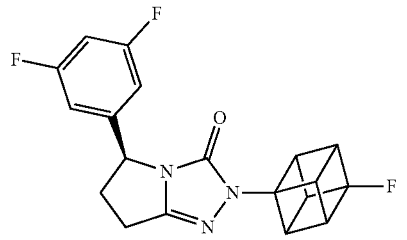 [SMILES: O=c1n(C23C4C5C2C2C3C4C52F)nc2n1[C@H](c1cc(F)cc(F)c1)CC2] | (5S)-5-(3,5-difluorophenyl)-2-(4-fluoropentacy-clo[4.2.0.0~2,5~.0~3,8~.0~4,7~]octan-1-yl)-2,5,6,7-tetrahydro-3H-pyrrolo[2,1-c][1,2,4]triazol-3-one | Calc'd 358, found 358; Ex. 1.1 |
| 1-21 | 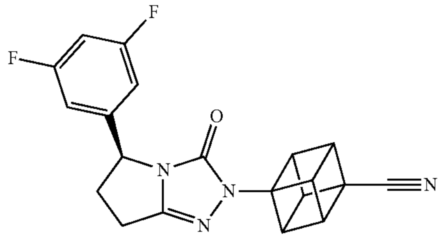 [SMILES: N#CC12C3C4C1C1C2C3C41n1nc2n(c1=O)[C@H](c1cc(F)cc(F)c1)CC2] | 4-[(5S)-5-(3,5-difluorophenyl)-3-oxo-6,7-dihydro-3H-pyrrolo[2,1-c][1,2,4]triazol-2(5H)-yl]penta-cyclo[4.2.0.0~2,5~.0~3,8~.0~4.7~]octane-1-carbonitrile | Calc'd 365, found 365; Ex. 1.1 |
| 1-22 | 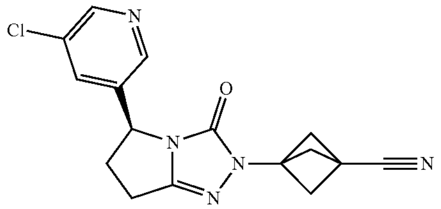 [SMILES: N#CC12CC(n3nc4n(c3=O)[C@H](c3cncc(Cl)c3)CC4)(C1)C2] | (S)-3-(5-(5-chloropyridin-3-yl)-3-oxo-6,7-dihydro-3H-pyrrolo[2,1-c][1,2,4]triazol-2(5H)-yl)bicyclo[1.1.1]pentane-1-carbonitrile | Calc'd 328, found 328; Ex. 1.1 |
| 1-23 | 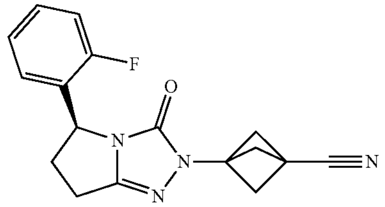 [SMILES: N#CC12CC(n3nc4n(c3=O)[C@H](c3ccccc3F)CC4)(C1)C2] | 3-[(5S)-5-(2-fluorophenyl)-3-oxo-6,7-dihydro-3H-pyrrolo[2,1-c][1,2,4]triazol-2(5H)-yl]bicyclo[1.1.1]pentane-1-carbonitrile | Calc'd 311, found 311; Ex. 1.1 |
| 1-24 | 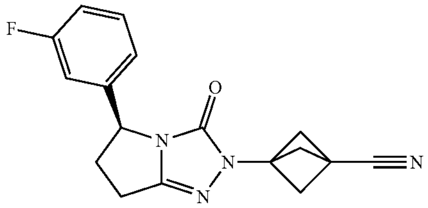 [SMILES: N#CC12CC(n3nc4n(c3=O)[C@H](c3cccc(F)c3)CC4)(C1)C2] | (S)-3-(5-(3-fluorophenyl)-3-oxo-6,7-dihydro-3H-pyrrolo[2,1-c][1,2,4]triazol-2(5H)-yl)bicyclo[1.1.1]pentane-1-caronitrile | Calc'd 311, found 311; Ex. 1.1 |
| 1-25 | 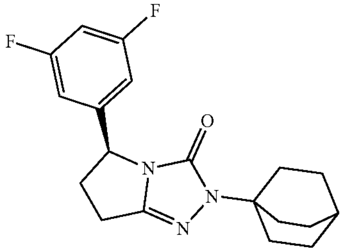 [SMILES: O=c1n(C23CCC(CC2)CC3)nc2n1[C@H](c1cc(F)cc(F)c1)CC2] | (5S)-2-(bicyclo[2.2.2]octan-1-yl)-5-(3,5-difluorophenyl)-2,5,6,7-tetrahydro-3H-pyrrolo[2,1-c][1,2,4]triazol-3-one | Calc'd 346, found 346; Ex. 1.1 |

TABLE 1-continued

| Compound Number | Structure | Chemical Name | Mass [M + H]+; Method |
|---|---|---|---|
| 1-26 | 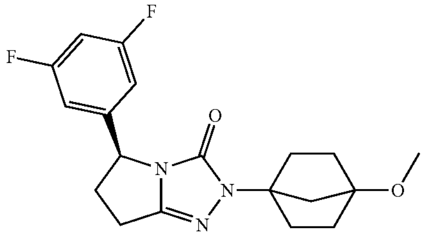 [SMILES: COC12CCC(n3nc4n(c3=O)[C@H](c3cc(F)cc(F)c3)CC4)(CC1)C2] | (5S)-5-(3,5-difluorophenyl)-2-(4-methoxybicyclo[2.2.1]heptan-1-yl)-2,5,6,7-tetrahydro-3H-pyrrolo[2,1-c][1,2,4]triazol-3-one | Calc'd 362, found 362; Ex. 1.1 |
| 1-27 | 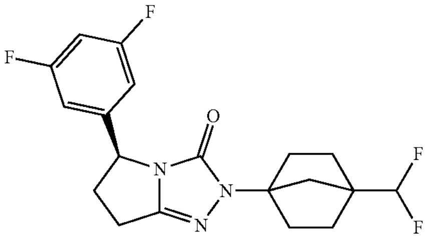 [SMILES: O=c1n(C23CCC(C(F)F)(CC2)C3)nc2n1[C@H](c1cc(F)cc(F)c1)CC2] | (5S)-2-[4-(difluoromethyl)bicyclo[2.2.1]heptan-1-yl]-5-(3,5-difluorophenyl)-2,5,6,7-tetrahydro-3H-pyrrolo[2,1-c][1,2,4]triazol-3-one | Calc'd 382, found 382; Ex. 1.1 |
| 1-28 | 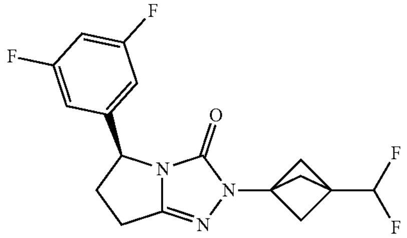 [SMILES: O=c1n(C23CC(C(F)F)(C2)C3)nc2n1[C@H](c1cc(F)cc(F)c1)CC2] | (5S)-2-[3-(difluoromethyl)bicyclo[1.1.1]pentan-1-yl]-5-(3,5-difluorophenyl)-2,5,6,7-tetrahydro-3H-pyrrolo[2,1-c][1,2,4]triazol-3-one | Calc'd 354, found 354; Ex. 1.1 |
| 1-29 | 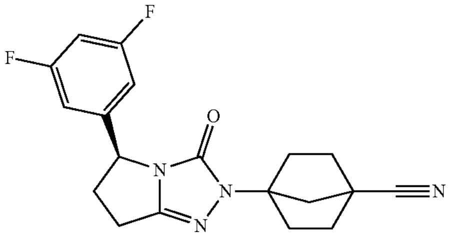 [SMILES: N#CC12CCC(n3nc4n(c3=O)[C@H](c3cc(F)cc(F)c3)CC4)(CC1)C2] | 4-[(5S)-5-(3,5-difluorophenyl)-3-oxo-6,7-dihydro-3H-pyrrolo[2,1-c][1,2,4]triazol-2(5H)-yl]bicyclo[2.2.1]heptane-1-carbonitrile | Calc'd 357, found 357; Ex. 1.1 |
| 1-30 | 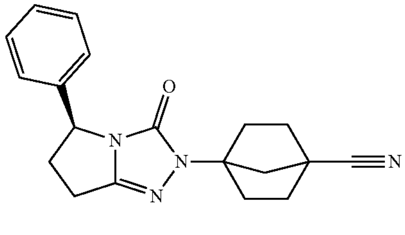 [SMILES: N#CC12CCC(n3nc4n(c3=O)[C@H](c3ccccc3)CC4)(CC1)C2] | 4-[(5S)-3-oxo-5-phenyl-6,7-dihydro-3H-pyrrolo[2,1-c][1,2,4]triazol-2(5H)-yl]bicyclo[2.2.1]heptane-1-carbonitrile | Calc'd 321, found 321; Ex. 1.1 |
| 1-31 | 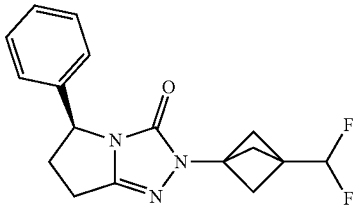 [SMILES: O=c1n(C23CC(C(F)F)(C2)C3)nc2n1[C@H](c1ccccc1)CC2] | (5S)-2-[3-(difluoromethyl)bicyclo[1.1.1]pentan-1-yl]-5-phenyl-2,5,6,7-tetrahydro-3H-pyrrolo[2,1-c][1,2,4]triazol-3-one | Calc'd 318, found 318; Ex. 1.1 |

TABLE 1-continued

| Compound Number | Structure | Chemical Name | Mass [M + H]+; Method |
|---|---|---|---|
| 1-32 | 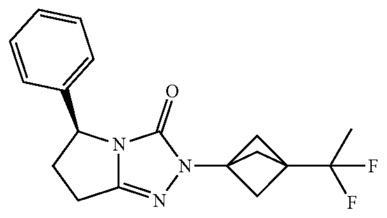 [SMILES: CC(F)(F)C12CC(n3nc4n(c3=O)[C@H](c3ccccc3)CC4)(C1)C2] | (5S)-2-[3-(1,1-difluoroethyl)bicyclo[1.1.1]pentan-1-yl]-5-phenyl-2,5,6,7-tetrahydro-3H-pyrrolo[2,1-c][1,2,4]triazol-3-one | Calc'd 332, found 332; Ex. 1.1 |
| 1-33 | 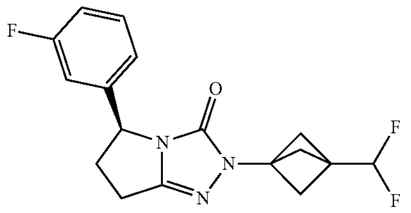 [SMILES: O=c1n(C23CC(C(F)F)(C2)C3)nc2n1[C@H](c1cccc(F)c1)CC2] | (5S)-2-[3-(difluoromethyl)bicyclo[1.1.1]pentan-1-yl]-5-(3-fluorophenyl)-2,5,6,7-tetrahydro-3H-pyrrolo[2,1-c][1,2,4]triazol-3-one | Calc'd 336, found 336; Ex. 1.1 |
| 1-34 | 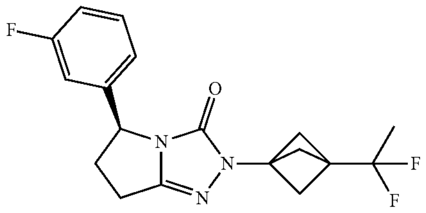 [SMILES: CC(F)(F)C12CC(n3nc4n(c3=O)[C@H](c3cccc(F)c3)CC4)(C1)C2] | (5S)-2-[3-(1,1-difluoroethyl)bicyclo[1.1.1]pentan-1-yl]-5-(3-fluorophenyl)-2,5,6,7-tetrahydro-3H-pyrrolo[2,1-c][1,2,4]triazol-3-one | Calc'd 350, found 350; Ex. 1.1 |
| 1-35 | 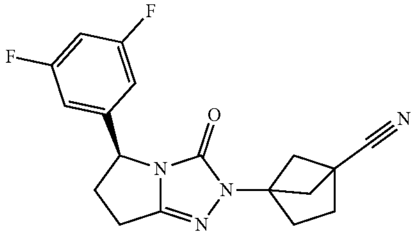 [SMILES: N#CC12CCC(n3nc4n(c3=O)[C@H](c3cc(F)cc(F)c3)CC4)(C1)C2] | 4-[(5S)-5-(3,5-difluorophenyl)-3-oxo-6,7-dihydro-3H-pyrrolo[2,1-c][1,2,4]triazol-2(5H)-yl]bicyclo[2.1.1]hexane-1-carbonitrile | Calc'd 343, found 343; Ex. 1.1 |
| 1-36 | 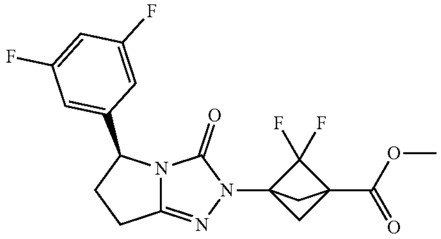 [SMILES: COC(=O)C12CC(n3nc4n(c3=O)[C@H](c3cc(F)cc(F)c3)CC4)(C1)C2(F)F] | methyl 3-[(5S)-5-(3,5-difluorophenyl)-3-oxo-6,7-dihydro-3H-pyrrolo[2,1-c][1,2,4]triazol-2(5H)-yl]-2,2-difluorobicyclo[1.1.1]pentane-1-carboxylate | Calc'd 398, found 398; Ex. 1.1 |
| 1-37 | 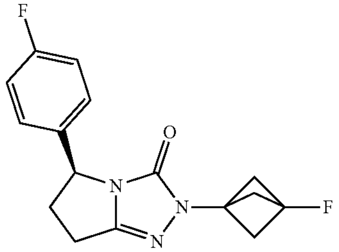 [SMILES: O=c1n(C23CC(F)(C2)C3)nc2n1[C@H](c1ccc(F)cc1)CC2] | (5S)-2-(3-fluorobicyclo[1.1.1]pentan-1-yl)-5-(4-fluorophenyl)-2,5,6,7-tetrahydro-3H-pyrrolo[2,1-c][1,2,4]triazol-3-one | Calc'd 304, found 304; Ex. 1.1 |

TABLE 1-continued

| Compound Number | Structure | Chemical Name | Mass [M + H]+; Method |
|---|---|---|---|
| 1-38 | 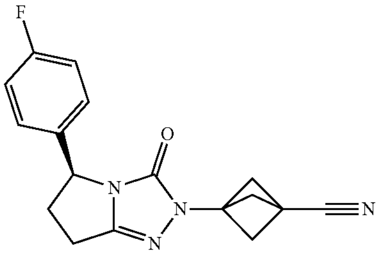 [SMILES: N#CC12CC(n3nc4n(c3=O)[C@H](c3ccc(F)cc3)CC4)(C1)C2] | 3-[(5S)-5-(4-fluorophenyl)-3-oxo-6,7-dihydro-3H-pyrrolo[2,1-c][1,2,4]triazol-2(5H)-yl]bicyclo[1.1.1]pentane-1-carbonitrile | Calc'd 311, found 311; Ex. 1.1 |
| 1-39 | 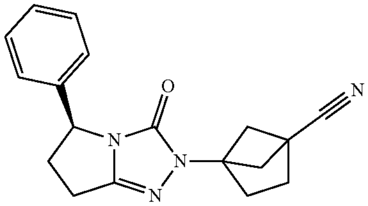 [SMILES: N#CC12CCC(n3nc4n(c3=O)[C@H](c3ccccc3)CC4)(C1)C2] | 4-[(5S)-3-oxo-5-phenyl-6,7-dihydro-3H-pyrrolo[2,1-c][1,2,4]triazol-2(5H)-yl]bicyclo[2.1.1]hexane-1-carbonitrile | Calc'd 307, found 307; Ex. 1.1 |
| 1-40 | 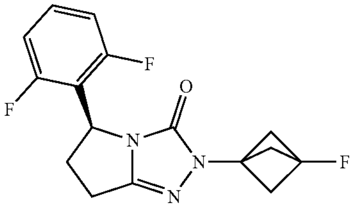 [SMILES: O=c1n(C23CC(F)(C2)C3)nc2n1[C@H](c1c(F)cccc1F)CC2] | (S)-5-(2,6-difluorophenyl)-2-(3-fluorobicyclo[1.1.1]pentan-1-yl)-2,5,6,7-tetrahydro-3H-pyrrolo[2,1-c][1,2,4]triazol-3-one | Calc'd 322, found 322; Ex. 1.2 |
| 1-41 | 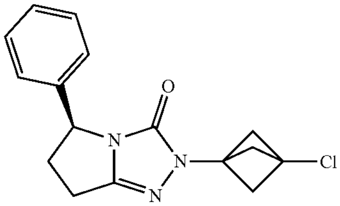 [SMILES: O=c1n(C23CC(Cl)(C2)C3)nc2n1[C@H](c1ccccc1)CC2] | (5S)-2-(3-chlorobicyclo[1.1.1]pentan-1-yl)-5-phenyl-2,5,6,7-tetrahydro-3H-pyrrolo[2,1-c][1,2,4]triazol-3-one | Calc'd 302, found 302; Ex. 1.1 |
| 1-42 | 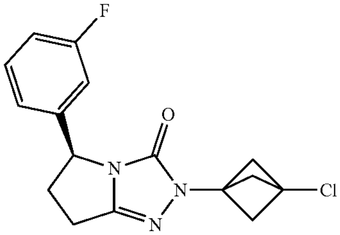 [SMILES: O=c1n(C23CC(Cl)(C2)C3)nc2n1[C@H](c1cccc(F)c1)CC2] | (S)-2-(3-chlorobicyclo[1.1.1]pentan-1-yl)-5-(3-fluorophenyl)-2,5,6,7-tetrahydro-3H-pyrrolo[2,1-c][1,2,4]triazol-3-one | Calc'd 320, found 302; Ex. 1.1 |
| 1-43 | 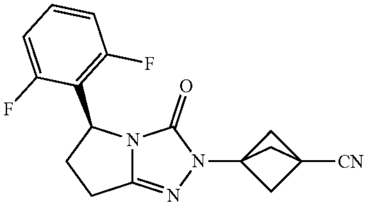 [SMILES: N#CC12CC(n3nc4n(c3=O)[C@H](c3c(F)cccc3F)CC4)(C1)C2] | (S)-3-(5-(2,6-difluorophenyl)-3-oxo-6,7-dihydro-3H-pyrrolo[2,1-c][1,2,4]triazol-2(5H)-yl)bicyclo[1.1.1]pentane-1-carbonitrile | Calc'd 329, found 329; Ex. 1.2 |

TABLE 1-continued

| Compound Number | Structure | Chemical Name | Mass [M + H]+; Method |
|---|---|---|---|
| 1-44 | 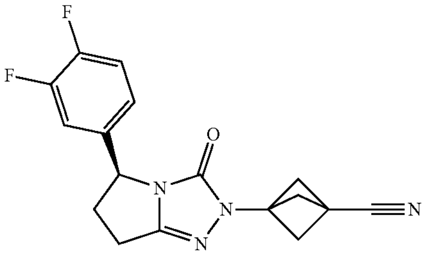 [SMILES: N#CC12CC(n3nc4n(c3=O)[C@H](c3ccc(F)c(F)c3)CC4)(C1)C2] | (S)-3-(5-(3,4-difluorophenyl)-3-oxo-6,7-dihydro-3H-pyrrolo[2,1-c][1,2,4]triazol-2(5H)-yl)bicyclo[1.1.1]pentane-1-carbonitrile | Calc'd 329, found 329; Ex. 1.2 |
| 1-45 | 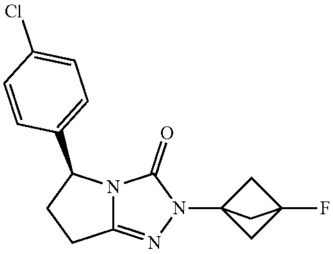 [SMILES: O=c1n(C23CC(F)(C2)C3)nc2n1[C@H](c1ccc(Cl)cc1)CC2] | (S)-5-(4-chlorophenyl)-2-(3-fluorobicyclo[1.1.1]pentan-1-yl)-2,5,6,7-tetrahydro-3H-pyrrolo[2,1-c][1,2,4]triazol-3-one | Calc'd 320, found 320; Ex. 1.2 |
| 1-46 | 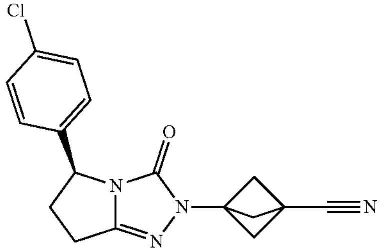 [SMILES: N#CC12CC(n3nc4n(c3=O)[C@H](c3ccc(Cl)cc3)CC4)(C1)C2] | (S)-3-(5-(4-chlorophenyl)-3-oxo-6,7-dihydro-3H-pyrrolo[2,1-c][1,2,4]triazol-2(5H)-yl)bicyclo[1.1.1]pentane-1-carbonitrile | Calc'd 327, found 327; Ex. 1.2 |
| 1-47 | 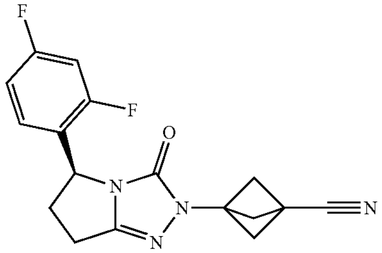 [SMILES: N#CC12CC(n3nc4n(c3=O)[C@H](c3ccc(F)cc3F)CC4)(C1)C2] | (S)-3-(5-(2,4-difluorophenyl)-3-oxo-6,7-dihydro-3H-pyrrolo[2,1-c][1,2,4]triazol-2(5H)-yl)bicyclo[1.1.1]pentane-1-carbonitrile | Calc'd 329, found 329; Ex. 1.2 |
| 1-48 | 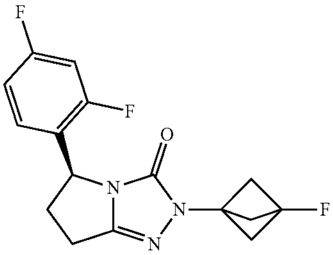 [SMILES: O=c1n(C23CC(F)(C2)C3)nc2n1[C@H](c1ccc(F)cc1F)CC2] | (S)-5-(2,4-difluorophenyl)-2-(3-fluorobicyclo[1.1.1]pentan-1-yl)-2,5,6,7-tetrahydro-3H-pyrrolo[2,1-c][1,2,4]triazol-3-one | Calc'd 322, found 322; Ex. 1.2 |
| 1-49 | 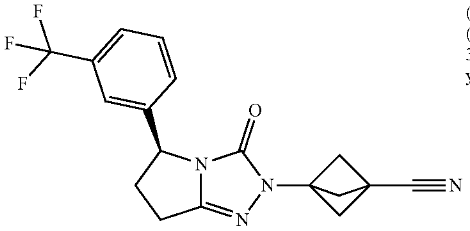 | (S)-3-(3-oxo-5-(3-(trifluoromethyl)phenyl)-6,7-dihydro-3H-pyrrolo[2,1-c][1,2,4]triazol-2(5H)-yl)bicyclo[1.1.1]pentane-1-carbonitrile | Calc'd 361, found 361; Ex. 1.1 |

TABLE 1-continued

| Compound Number | Structure | Chemical Name | Mass [M + H]+; Method |
|---|---|---|---|
| 1-50 | 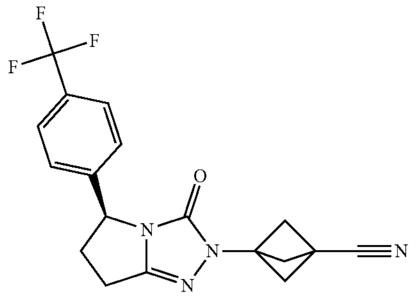 [SMILES: N#CC12CC(n3nc4n(c3=O)[C@H](c3ccc(C(F)(F)F)cc3)CC4)(C1)C2] | (S)-3-(3-oxo-5-(4-(trifluoromethyl)phenyl)-6,7-dihydro-3H-pyrrolo[2,1-c][1,2,4]triazol-2(5H)-yl)bicyclo[1.1.1]pentane-1-carbonitrile | Calc'd 361, found 361; Ex. 1.2 |
| 1-51 | 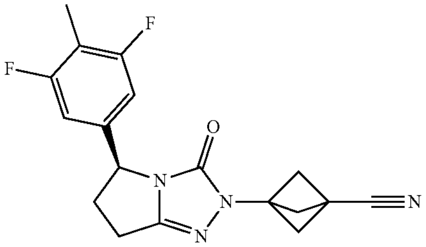 [SMILES: Cc1c(F)cc([C@@H]2CCc3nn(C45CC(C#N)(C4)C5)c(=O)n32)cc1F] | (S)-3-(5-(3,5-difluoro-4-methylphenyl)-3-oxo-6,7-dihydro-3H-pyrrolo[2,1-c][1,2,4]triazol-2(5H)-yl)bicyclo[1.1.1]pentane-1-carbonitrile | Calc'd 343, found 343; Ex. 1.2 |
| 1-52 | 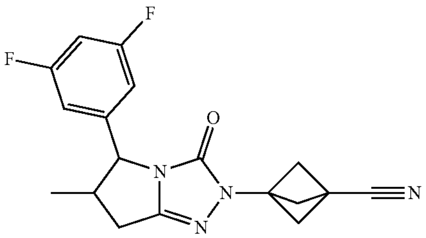 [SMILES: CC1Cc2nn(C34CC(C#N)(C3)C4)c(=O)n2C1c1cc(F)cc(F)c1] | 3-[5-(S or R)-(3,5-difluorophenyl)-6-(S or R)-methyl-3-oxo-6,7-dihydro-3H-pyrrolo[2,1-c][1,2,4]triazol-2(5H)-yl]bicyclo[1.1.1]pentane-1-carbonitrile | Calc'd 343, found 343; Ex. 1.2 |
| 1-53 | 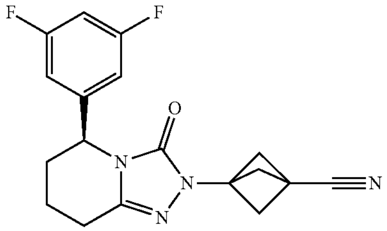 [SMILES: N#CC12CC(n3nc4n(c3=O)[C@H](c3cc(F)cc(F)c3)CCC4)(C1)C2] | (S)-3-(5-(3,5-difluorophenyl)-3-oxo-5,6,7,8-tetrahydro-[1,2,4]triazolo[4,3-a]pyridin-2(3H)-yl)bicyclo[1.1.1]pentane-1-carbonitrile | Calc'd 343, found 343; Ex. 1.1 |
| 1-54 | 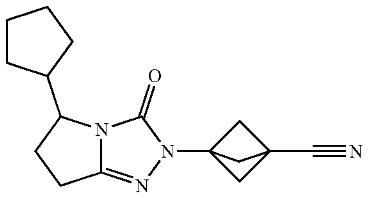 [SMILES: N#CC12CC(n3nc4n(c3=O)C(C3CCCC3)CC4)(C1)C2] | 3-(5-(S or R)-cyclopentyl-3-oxo-6,7-dihydro-3H-pyrrolo[2,1-c][1,2,4]triazol-2(5H)-yl)bicyclo[1.1.1]pentane-1-carbonitrile | Calc'd 285, found 285; Ex. 1.2 |
| 1-55 | 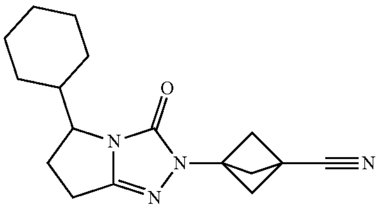 [SMILES: N#CC12CC(n3nc4n(c3=O)C(C3CCCCC3)CC4)(C1)C2] | 3-(5-(S or R)-cyclohexyl-3-oxo-6,7-dihydro-3H-pyrrolo[2,1-c][1,2,4]triazol-2(5H)-yl)bicyclo[1.1.1]pentane-1-carbonitrile | Calc'd 299, found 299; Ex. 1.2 |

TABLE 1-continued

| Compound Number | Structure | Chemical Name | Mass [M + H]+; Method |
| --- | --- | --- | --- |
| 1-56 | 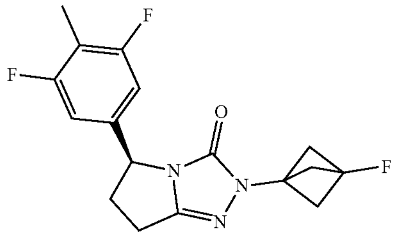 [SMILES: Cc1c(F)cc([C@@H]2CCc3nn(C45CC(F)(C4)C5)c(=O)n32)cc1F] | (S)-5-(3,5-difluoro-4-methylphenyl)-2-(3-fluorobicyclo[1.1.1]pentan-1-yl)-2,5,6,7-tetrahydro-3H-pyrrolo[2,1-c][1,2,4]triazol-3-one | Calc'd 336, found 336; Ex. 1.2 |
| 1-57 | 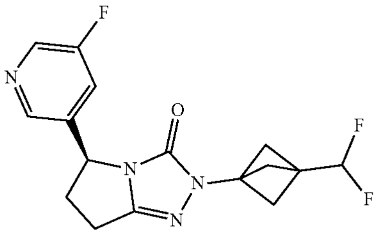 [SMILES: O=c1n(C23CC(C(F)F)(C2)C3)nc2n1[C@H](c1cncc(F)c1)CC2] | (S)-2-(3-(difluoromethyl)bicyclo[1.1.1]pentan-1-yl)-5-(5-fluoropyridin-3-yl)-2,5,6,7-tetrahydro-3H-pyrrolo[2,1-c][1,2,4]triazol-3-one | Calc'd 337, found 337; Ex. 1.1 |
| 1-58 | 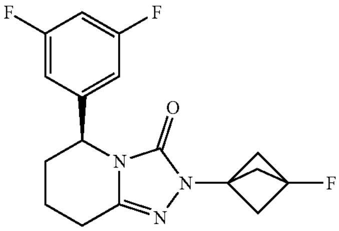 [SMILES: O=c1n(C23CC(F)(C2)C3)nc2n1[C@H](c1cc(F)cc(F)c1)CCC2] | (S)-5-(3,5-difluorophenyl)-2-(3-fluorobicyclo[1.1.1]pentan-1-yl)-5,6,7,8-tetrahydro-[1,2,4]triazolo[4,3-a]pyridin-3(2H)-one | Calc'd 336, found 336; Ex. 1.1 |
| 1-59 | 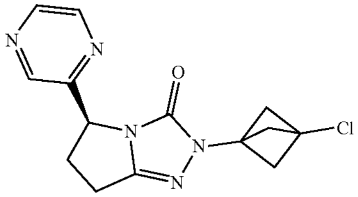 [SMILES: O=c1n(C23CC(Cl)(C2)C3)nc2n1[C@H](c1cnccn1)CC2] | (S)-2-(3-chlorobicyclo[1.1.1]pentan-1-yl)-5-(pyrazin-2-yl)-2,5,6,7-tetrahydro-3H-pyrrolo[2,1-c][1,2,4]triazol-3-one | Calc'd 304, found 304; Ex. 1.2 |
| 1-60 | 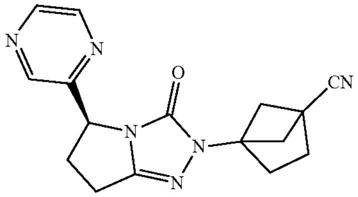 [SMILES: N#CC12CCC(n3nc4n(c3=O)[C@H](c3cnccn3)CC4)(C1)C2] | (S)-4-(3-oxo-5-(pyrazin-2-yl)-6,7-dihydro-3H-pyrrolo[2,1-c][1,2,4]triazol-2(5H)-yl)bicyclo[2.1.1]hexane-1-carbonitrile | Calc'd 309, found 309; Ex. 1.2 |
| 1-61 | 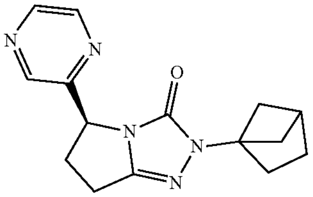 [SMILES: O=c1n(C23CCC(C2)C3)nc2n1[C@H](c1cnccn1)CC2] | (S)-2-(bicyclo[2.1.1]hexan-1-yl)-5-(pyrazin-2-yl)-2,5,6,7-tetrahydro-3H-pyrrolo[2,1-c][1,2,4]triazol-3-one | Calc'd 284, found 284 Ex. 1.2 |

TABLE 1-continued

| Compound Number | Structure | Chemical Name | Mass [M + H]+; Method |
| --- | --- | --- | --- |
| 1-62 | 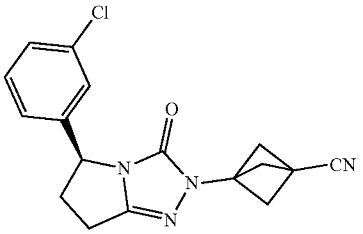 [SMILES: N#CC12CC(n3nc4n(c3=O)[C@H](c3cccc(Cl)c3)CC4)(C1)C2] | (S)-3-(5-(3-chlorophenyl)-3-oxo-6,7-dihydro-3H-pyrrolo[2,1-c][1,2,4]triazol-2(5H)-yl)bicyclo[1.1.1]pentane-1-carbonitrile | Calc'd 327, found 327 Ex. 1.2 |
| 1-63 | 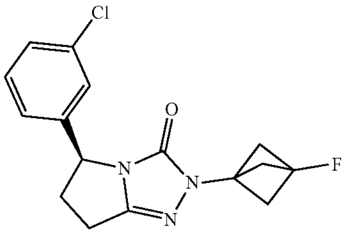 [SMILES: O=c1n(C23CC(F)(C2)C3)nc2n1[C@H](c1cccc(Cl)c1)CC2] | (S)-5-(3-chlorophenyl)-2-(3-fluorobicyclo[1.1.1]pentan-1-yl)-2,5,6,7-tetrahydro-3H-pyrrolo[2,1-c][1,2,4]triazol-3-one | Calc'd 320, found 320 Ex. 1.2 |
| 1-64 | 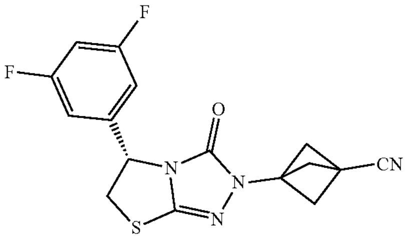 [SMILES: N#CC12CC(n3nc4n(c3=O)[C@@H](c3cc(F)cc(F)c3)CS4)(C1)C2] | (S)-3-(5-(3,5-difluorophenyl)-3-oxo-5,6-dihydrothiazolo[2,3-c][1,2,4]triazol-2(3H)-yl)bicyclo[1.1.1]pentane-1-carbonitrile | Calc'd 347, found 347 Ex. 1.2 |
| 1-65 | 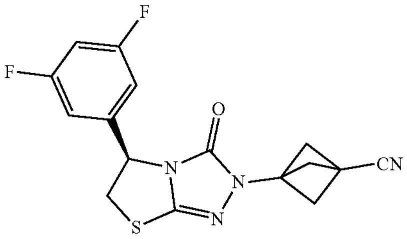 [SMILES: N#CC12CC(n3nc4n(c3=O)[C@H](c3cc(F)cc(F)c3)CS4)(C1)C2] | (R)-3-(5-(3,5-difluorophenyl)-3-oxo-5,6-dihydrothiazolo[2,3-c][1,2,4]triazol-2(3H)-yl)bicyclo[1.1.1]pentane-1-carbonitrile | Calc'd 347, found 347 Ex. 1.2 |
| 1-66 | 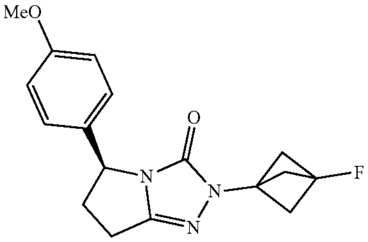 [SMILES: COc1ccc([C@@H]2CCc3nn(C45CC(F)(C4)C5)c(=O)n32)cc1] | (S)-2-(3-fluorobicyclo[1.1.1]pentan-1-yl)-5-(4-methoxyphenyl)-2,5,6,7-tetrahydro-3H-pyrrolo[2,1-c][1,2,4]triazol-3-one | Calc'd 316, found 316 Ex. 1.2 |
| 1-67 | 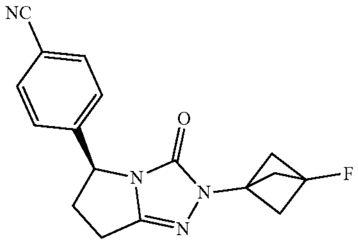 [SMILES: N#Cc1ccc([C@@H]2CCc3nn(C45CC(F)(C4)C5)c(=O)n32)cc1] | (S)-4-(2-(3-fluorobicyclo[1.1.1]pentan-1-yl)-3-oxo-2,5,6,7-tetrahydro-3H-pyrrolo[2,1-c][1,2,4]triazol-5-yl)benzonitrile | Calc'd 311, found 311 Ex. 1.2 |

TABLE 1-continued

| Compound Number | Structure | Chemical Name | Mass [M + H]+; Method |
| --- | --- | --- | --- |
| 1-68 | 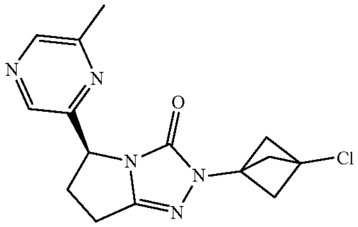 [SMILES: Cc1cncc([C@@H]2CCc3nn(C45CC(Cl)(C4)C5)c(=O)n32)n1] | (S)-2-(3-fluorobicyclo[1.1.1]pentan-1-yl)-5-(6-methylpyrazin-2-yl)-2,5,6,7-tetrahydro-3H-pyrrolo[2,1-c][1,2,4]triazol-3-one | Calc'd 318, found 318 Ex. 1.2 |
| 1-69 | 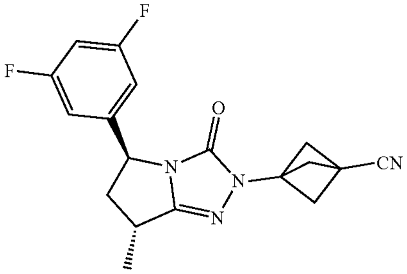 [SMILES: C[C@@H]1C[C@@H](c2cc(F)cc(F)c2)n2c1nn(C13CC(C#N)(C1)C3)c2=O] | 3-((5S,7R)-5-(3,5-difluorophenyl)-7-methyl-3-oxo-6,7-dihydro-3H-pyrrolo[2,1-c][1,2,4]triazol-2(5H)-yl)bicyclo[1.1.1]pentane-1-carbonitrile | Calc'd 343, found 343 Ex. 1.1 |
| 1-70 | 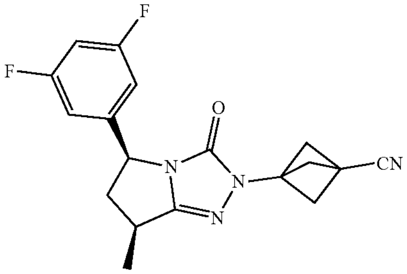 [SMILES: C[C@H]1C[C@@H](c2cc(F)cc(F)c2)n2c1nn(C13CC(C#N)(C1)C3)c2=O] | 3-((5S,7S)-5-(3,5-difluorophenyl)-7-methyl-3-oxo-6,7-dihydro-3H-pyrrolo[2,1-c][1,2,4]triazol-2(5H)-yl)bicyclo[1.1.1]pentane-1-carbonitrile | Calc'd 343, found 343 Ex. 1.1 |
| 1-71 | 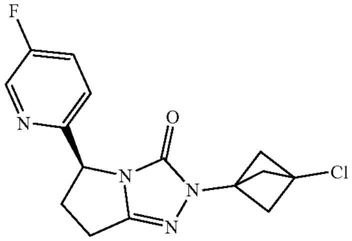 [SMILES: O=c1n(C23CC(Cl)(C2)C3)nc2n1[C@H](c1ccc(F)cn1)CC2] | (S)-2-(3-chlorobicyclo[1.1.1]pentan-1-yl)-5-(5-fluoropyridin-2-yl)-2,5,6,7-tetrahydro-3H-pyrrolo[2,1-c][1,2,4]triazol-3-one | Calc'd 321, found 321 Ex. 1.2 |
| 1-72 | 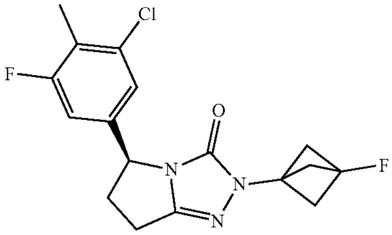 [SMILES: Cc1c(F)cc([C@@H]2CCc3nn(C45CC(F)(C4)C5)c(=O)n32)cc1Cl] | (S)-5-(3-chloro-5-fluoro-4-methylphenyl)-2-(3-fluorobicyclo[1.1.1]pentan-1-yl)-2,5,6,7-tetrahydro-3H-pyrrolo[2,1-c][1,2,4]triazol-3-one | Calc'd 352, found 352 Ex. 1.2 |
| 1-73 | 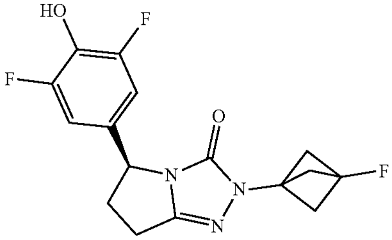 [SMILES: O=c1n(C23CC(F)(C2)C3)nc2n1[C@H](c1cc(F)c(O)c(F)c1)CC2] | (S)-5-(3,5-difluoro-4-hydroxyphenyl)-2-(3-fluorobicyclo[1.1.1]pentan-1-yl)-2,5,6,7-tetrahydro-3H-pyrrolo[2,1-c][1,2,4]triazol-3-one | Calc'd 338, found 338; Ex. 1.2 |

TABLE 1-continued

| Compound Number | Structure | Chemical Name | Mass [M + H]+; Method |
|---|---|---|---|
| 1-74 | 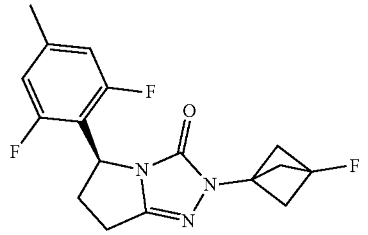 [SMILES: Cc1cc(F)c([C@@H]2CCc3nn(C45CC(F)(C4)C5)c(=O)n32)c(F)c1] | (S)-5-(2,6-difluoro-4-methylphenyl)-2-(3-fluorobicyclo[1.1.1]pentan-1-yl)-2,5,6,7-tetrahydro-3H-pyrrolo[2,1-c][1,2,4]triazol-3-one | Calc'd 336, found 336; Ex. 1.2 |
| 1-75 | 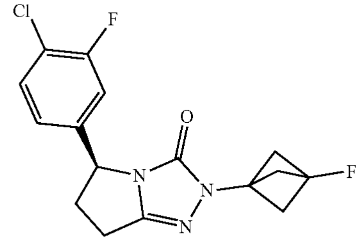 [SMILES: O=c1n(C23CC(F)(C2)C3)nc2n1[C@H](c1ccc(Cl)c(F)c1)CC2] | (S)-5-(4-chloro-3-fluorophenyl)-2-(3-fluorobicyclo[1.1.1]pentan-1-yl)-2,5,6,7-tetrahydro-3H-pyrrolo[2,1-c][1,2,4]triazol-3-one | Calc'd 338, found 338; Ex. 1.2 |
| 1-76 | 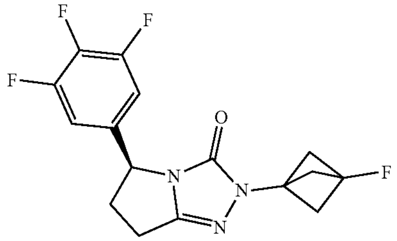 [SMILES: O=c1n(C23CC(F)(C2)C3)nc2n1[C@H](c1cc(F)c(F)c(F)c1)CC2] | (S)-2-(3-fluorobicyclo[1.1.1]pentan-1-yl)-5-(3,4,5-trifluorophenyl)-2,5,6,7-tetrahydro-3H-pyrrolo[2,1-c][1,2,4]triazol-3-one | Calc'd 340, found 340; Ex. 1.2 |
| 1-77 | 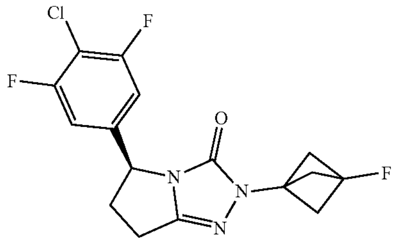 [SMILES: O=c1n(C23CC(F)(C2)C3)nc2n1[C@H](c1cc(F)c(Cl)c(F)c1)CC2] | (S)-5-(4-chloro-3,5-difluorophenyl)-2-(3-fluorobicyclo[1.1.1]pentan-1-yl)-2,5,6,7-tetrahydro-3H-pyrrolo[2,1-c][1,2,4]triazol-3-one | Calc'd 356, found 356; Ex. 1.2 |
| 1-78 | 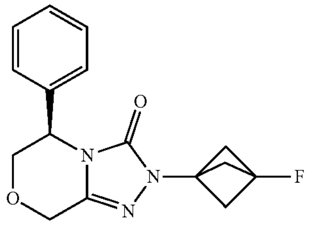 [SMILES: O=c1n(C23CC(F)(C2)C3)nc2n1[C@H](c1ccccc1)COC2] | (R)-2-(3-fluorobicyclo[1.1.1]pentan-1-yl)-5-phenyl-2,5,6,8-tetrahydro-3H-[1,2,4]triazolo[3,4-c][1,4]oxazin-3-one | Calc'd 302, found 302; Ex. 1.1 |
| 1-79 | 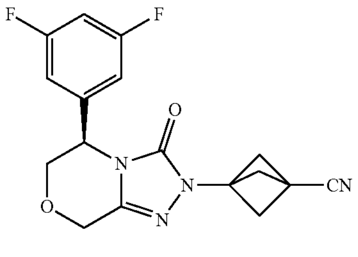 [SMILES: N#CC12CC(n3nc4n(c3=O)[C@H](c3cc(F)cc(F)c3)COC4)(C1)C2] | (R)-3-(5-(3,5-difluorophenyl)-3-oxo-5,6-dihydro-3H-[1,2,4]triazolo[3,4-c][1,4]oxazin-2(8H)-yl)bicyclo[1.1.1]pentane-1-carbonitrile | Calc'd 345, found 345; Ex. 1.2 |

TABLE 1-continued

| Compound Number | Structure | Chemical Name | Mass [M + H]+; Method |
|---|---|---|---|
| 1-80 | 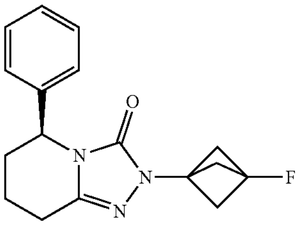 [SMILES: O=c1n(C23CC(F)(C2)C3)nc2n1[C@H](c1ccccc1)CCC2] | (S)-2-(3-fluorobicyclo[1.1.1]pentan-1-yl)-5-phenyl-5,6,7,8-tetrahydro-[1,2,4]triazolo[4,3-a]pyridin-3(2H)-one | Calc'd 300, found 300; Ex. 1.1 |

Synthesis of Common Intermediates (Table C)

Preparation of Intermediate I-1C ((S)-5-(3,5-difluorophenyl)-2-(3-(hydroxymethyl)bicyclo[1.1.1]pentan-1-yl)-2,5,6,7-tetrahydro-3H-pyrrolo[2,1-c][1,2,4]triazol-3-one Intermediate I-1C was prepared from compound 1-18 as outlined below.

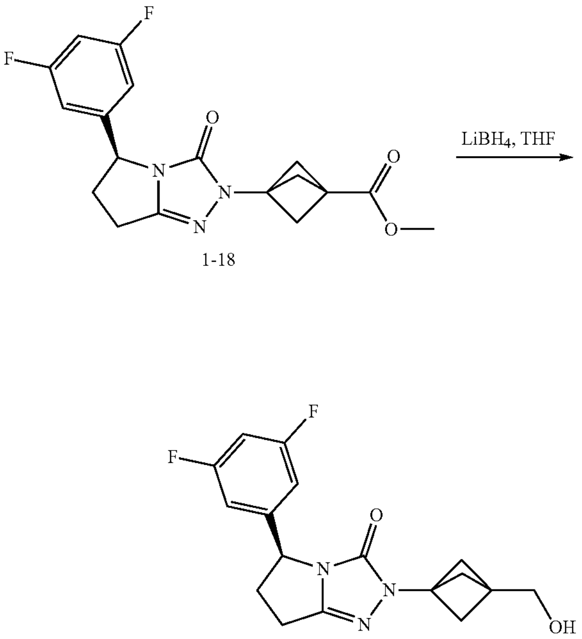

1-18

I-1C

To a solution of compound 1-18 (240 mg, 0.664 mmol) in THF (5 mL) was added lithium borohydride (0.664 mL, 1.33 mmol) dropwise at 25° C. under $N_2$, the reaction was stirred at 25° C. for 1 h. LCMS showed the reaction was complete. The mixture was added to $H_2O$ (20 mL). The mixture was extracted with EtOAc (10 mL×3). The combined organic layers were washed with brine (30 mL), dried over $Na_2SO_4$, filtered and concentrated to give intermediate I-3A (S)-5-(3,5-difluorophenyl)-2-(3-(hydroxymethyl)bicyclo[1.1.1]pentan-1-yl)-2,5,6,7-tetrahydro-3H-pyrrolo[2,1-c][1,2,4]triazol-3-one which was used directly. Calculated $C_{17}H_{18}F_2N_3O_2$ $[M+H]^+$, 334; Found 334.

Preparation of Intermediate I-2C ((S)-3-(5-(3,5-difluorophenyl)-3-oxo-6,7-dihydro-3H-pyrrolo[2,1-c][1,2,4]triazol-2(5H)-yl)bicyclo[1.1.1]pentane-1-carboxylic acid)

Intermediate I-2C was prepared from compound 1-18 as outlined below.

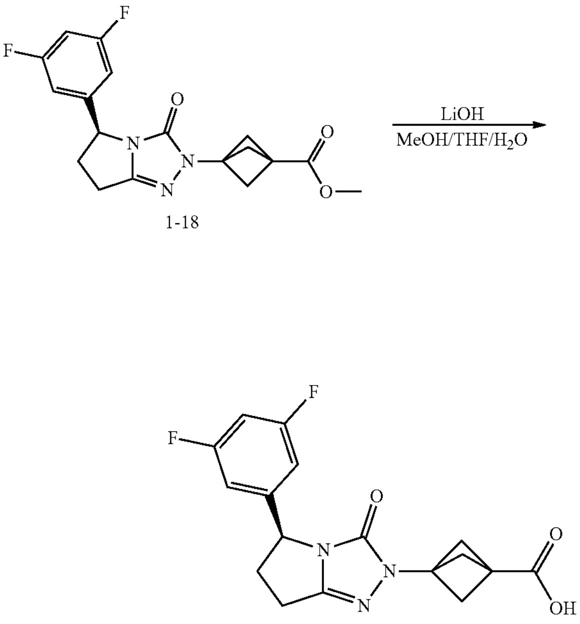

1-18

I-2C

To a solution of compound 1-18 (300 mg, 0.830 mmol) in $MeOH/THF/H_2O$(3/3/1, v/v/v) (10 mL) was added lithium hydroxide (23.86 mg, 0.996 mmol) at 25° C. and the resulting mixture was stirred at 25° C. for 16 h. Water (30 mL) and EtOAc (10 mL) were then added and the mixture was extracted with EtOAc (8 mL×2). The organic layer was discarded. The pH of the aqueous layer was adjusted to −4.0 by the addition of aq. HCl (3 M) and then extracted with EtOAc (10 mL×2). The combined organic layers were washed with brine (30 mL), dried over anhydrous $Na_2SO_4$, filtered and the filtrate was evaporated in vacuum to give intermediate I-2C (S)-3-(5-(3,5-difluorophenyl)-3-oxo-6,7-dihydro-3H-pyrrolo[2,1-c][1,2,4]triazol-2(5H)-yl)bicyclo[1.1.1]pentane-1-carboxylic acid. Calculated $C_{17}H_{16}F_2N_3O_3$$[M+H]^+$, 348; Found 348.

Preparation of Intermediate I-3C ((S)-(3-(5-(3,5-difluorophenyl)-3-oxo-6,7-dihydro-3H-pyrrolo[2,1-c][1,2,4]triazol-2(5H)-yl)bicyclo[1.1.1]pentan-1-yl) methyl methanesulfonate)

Intermediate I-3C was prepared from compound I-1C via mesylation as outlined below.

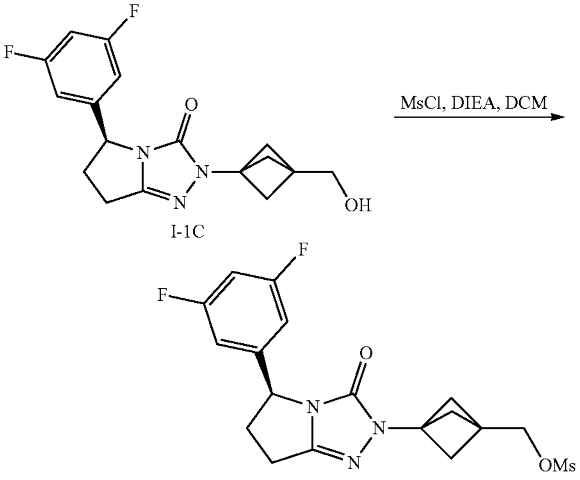

I-1C

I-3C

To a solution of intermediate I-1C (35 mg, 0.100 mmol) in DCM (2 mL) was added DIEA (0.035 mL, 0.199 mmol) and Ms-Cl (0.014 mL, 0.175 mmol) at 0° C., the mixture was stirred at 25° C. for 1 h. LCMS showed the reaction was complete. Water (10 mL) and DCM (10 mL) was added and the mixture was extracted with DCM (3x6 mL), dried over $Na_2SO_4$, filtered, and concentrated to give crude product which was purified by prep-TLC ($SiO_2$, Pet. ether/EtOAc) to give I-3C (S)-(3-(5-(3,5-difluorophenyl)-3-oxo-6,7-dihydro-3H-pyrrolo[2,1-c][1,2,4]triazol-2(5H)-yl)bicyclo[1.1.1]pentan-1-yl)methyl methanesulfonate. Calculated $C_{18}H_{20}F_2N_3O_4S$ $[M+H]^+$, 412; Found 412.

TABLE C

| Chemical Structures of Intermediates I-1C to I-3C | |
|---|---|
| Intermediate | Structure |
| I-1C | 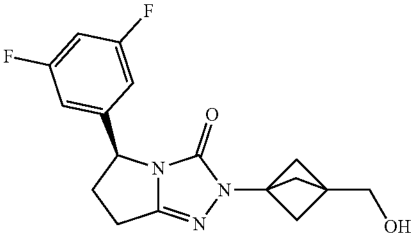 [SMILES: O=c1n(C23CC(CO)(C2)C3)nc2n1[C@H](c1cc(F)cc(F)c1)CC2] |
| I-2C | 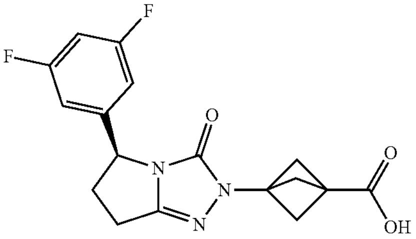 [SMILES: O=C(O)C12CC(n3nc4n(c3=O)[C@H](c3cc(F)cc(F)c3)CC4)(C1)C2] |

TABLE C-continued

| Chemical Structures of Intermediates I-1C to I-3C | |
|---|---|
| Intermediate | Structure |
| I-3C | 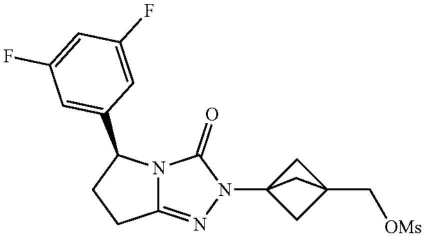 [SMILES: CS(=O)(=O)OCC12CC(n3nc4n(c3=O)[C@H](c3cc(F)cc(F)c3)CC4)(C1)C2] |

Example 2.1. Preparation of Compound 2-1 ((5S)-5-(3,5-difluorophenyl)-2-[3-(methoxymethyl)bicyclo[1.1.1]pentan-1-yl]-2,5,6,7-tetrahydro-3H-pyrrolo[2,1-c][1,2,4]triazol-3-one)

Compound 2-1 was prepared from intermediate I-1C as outlined below.

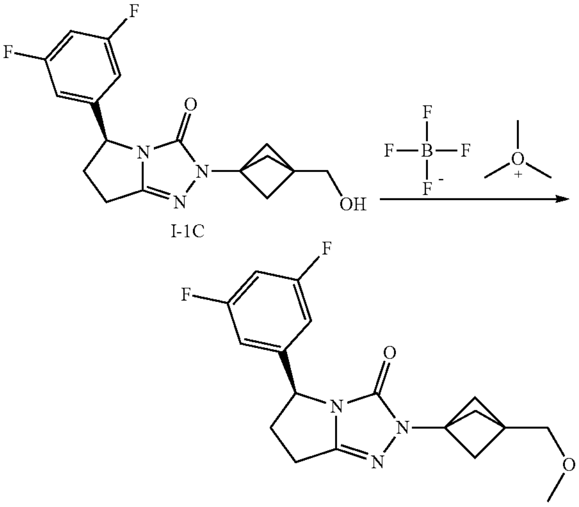
I-1C 2-1

To a solution of I-1C (50 mg, 0.150 mmol) in $CH_2Cl_2$ (2 mL) was added dimethyloxonium tetrafluoroborate (26.1 mg, 0.195 mmol) at 25° C. The mixture was stirred at 25° C. for 16 h. The mixture was quenched with sat. aq. $NaHCO_3$ (10 mL) and extracted with DCM (6 mLx3). The combined organic layers were dried over $Na_2SO_4$, filtered and concentrated in vacuum to give crude oil which was purified by prep-HPLC (Method Column Boston Green ODS 150 mmx30 mmx5 um; Condition water (TFA)-ACN) to afford compound 2-1 ((5S)-5-(3,5-difluorophenyl)-2-[3-(methoxymethyl)bicyclo[1.1.1]pentan-1-yl]-2,5,6,7-tetrahydro-3H-pyrrolo[2,1-c][1,2,4]triazol-3-one. Calculated $C_{18}H_{20}F_2N_3O_2$ $[M+H]^+$, 348; Found 348. $^1H$ NMR (400 MHz, $CD_3OD$) δ 6.87-6.97 (m, 3H), 5.21 (dd, J=4.8, 8.0 Hz, 1H), 3.53 (s, 2H), 3.36 (s, 3H), 2.78-3.10 (m, 3H), 2.35-2.45 (m, 1H), 2.19 (s, 6H).

Example 2.2. Preparation of Compound 2-2 ((S)-3-(5-(3,5-difluorophenyl)-3-oxo-6,7-dihydro-3H-pyrrolo[2,1-c][1,2,4]triazol-2(5H)-yl)-N-(thiophen-2-ylmethyl)bicyclo[1.1.1]pentane-1-carboxamide)

Compound 2-2 was prepared from intermediate I-2C as outlined below.

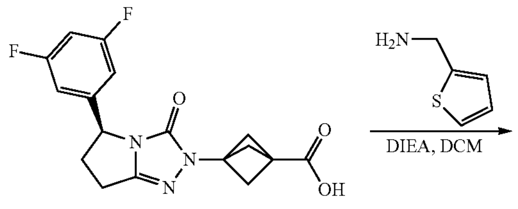

I-2C

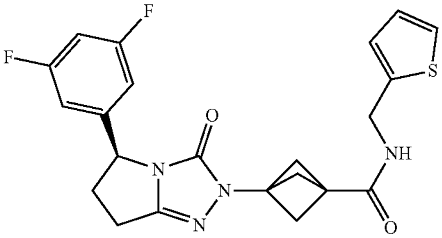

2-2

A 0.3M DMSO stock solution of I-2C (10 μL, 3 μmol) was added into a 384 well plate followed by a 0.5M DMSO solution of thiophen-2-ylmethanamine (24 μL, 12 μmol). Next a 0.8M solution of n-propylphosphonic anhydride in DMF (7.5 μL, 6 μmol) was added and the reaction plate was sealed and agitated at RT overnight. After 16 h, the reaction was diluted with DMSO to 100 μL, filtered and purified via RP-HPLC (Method Column XBridge BEH C18 OBD prep column, 130A, 5 um, 10 mm×50 mm; Condition 0.16% TFA, 20% to 55% ACN in $H_2O$) to obtain compound 2-2. Calculated $C_{22}H_{21}F_2N_4O_2S$ $[M+H]^+$, 443; Found 443.

Example 2.3. Preparation of Compound 2-4 ((S)-2-(3-(5-(3,5-difluorophenyl)-3-oxo-6,7-dihydro-3H-pyrrolo[2,1-c][1,2,4]triazol-2(5H)-yl)bicyclo[1.1.1]pentan-1-yl)acetonitrile)

Compound 2-4 was prepared from intermediate I-3C as outlined below.

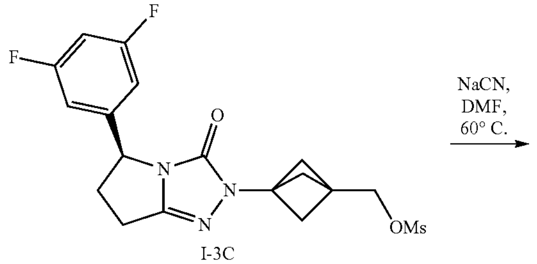

I-3C

-continued

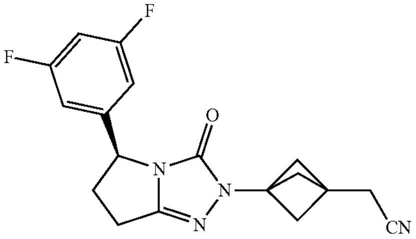

2-4

To a solution of intermediate I-2C (23 mg, 0.056 mmol) in DMF (1 mL) was added cyanosodium (20 mg, 0.408 mmol) at 20° C. The resulting mixture was stirred at 60° C. for 16 h. LCMS showed the reaction was complete. $H_2O$ (10 mL) and EtOAc (10 mL) was added. The aqueous layer was extracted with EtOAc (5 mL×2). The combined organic layers were dried over $Na_2SO_4$, filtered and concentrated to give a residue. The residue was purified by prep-HPLC (Instrument Eh; Method Column Welch Xtimate C18 150 mm×25 mm×5 um; Condition water ($NH_4HCO_3$)-ACN) to give compound 2-4. Calculated $C_{18}H_{17}F_2N_4O$ $[M+H]^+$, 343; Found 343. $^1H$ NMR (400 MHz, $CD_3OD$) δ 6.84-7.00 (m, 3H), 5.21 (dd, J=4.8, 8.0 Hz, 1H), 2.90-3.10 (m, 2H), 2.87 (s, 2H), 2.78-2.86 (m, 1H), 2.35-2.49 (m, 1H), 2.24-2.32 (m, 6H).

Example 2.4. Preparation of Compound 2-5 ((S)-2-(3-acetylbicyclo[1.1.1]pentan-1-yl)-5-(3,5-difluorophenyl)-2,5,6,7-tetrahydro-3H-pyrrolo[2,1-c][1,2,4]triazol-3-one)

Compound 2-5 was prepared from intermediate I-2C as outlined below.

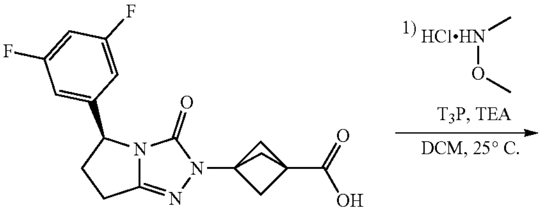

I-2C

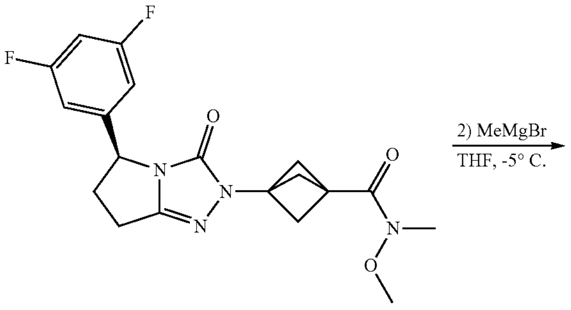

-continued

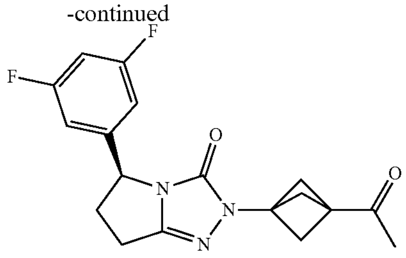

2-5

Step 1. Preparation of (S)-3-(5-(3,5-difluorophenyl)-3-oxo-6,7-dihydro-3H-pyrrolo[2,1-c][1,2,4]triazol-2(5H)-yl)-N-methoxy-N-methylbicyclo[1.1.1]pentane-1-carboxamide To a solution of I-2C (220 mg, 0.633 mmol) in DCM (6 mL) was added TEA (0.309 mL, 2.217 mmol) and N,O-dimethylhydroxylamine hydrochloride (93 mg, 0.950 mmol) at 25° C. The mixture was cooled to 0° C., 1-propanephosphonic anhydride solution (685 mg, 1.08 mmol) was added slowly under $N_2$. The resulting mixture was stirred at 25° C. for 16 h. Water (30 mL) and EtOAc (10 mL) were added. The mixture was extracted with EtOAc (10 mL×2), washed with brine (30 mL), dried over anhydrous $Na_2SO_4$, filtered and the filtrate was evaporated in vacuum to give a residue which was purified by flash silica gel chromatography (ethyl acetate/petroleum ether) to give (S)-3-(5-(3,5-difluorophenyl)-3-oxo-6,7-dihydro-3H-pyrrolo[2,1-c][1,2,4]triazol-2(5H)-yl)-N-methoxy-N-methylbicyclo[1.1.1]pentane-1-carboxamide. Calculated $C_{19}H_{21}F_2N_4O_3$ $[M+H]^+$, 391; Found 391.

Step 2. Preparation of Compound 2-5

To a solution of (S)-3-(5-(3,5-difluorophenyl)-3-oxo-6,7-dihydro-3H-pyrrolo[2,1-c][1,2,4]triazol-2(5H)-yl)-N-methoxy-N-methylbicyclo[1.1.1]pentane-1-carboxamide (230 mg, 0.589 mmol) in THF (8 mL) was added methylmagnesium bromide (0.236 mL, 0.707 mmol) at −5° C. and the resulting mixture was stirred at −5° C. for 2 h. The mixture was allowed to warm to 25° C. slowly, and the reaction was stirred at 25° C. for 16 h. Sat. $NH_4Cl$ (20 mL) and EtOAc (10 mL) were added, the mixture was extracted with EtOAc (8 mL×2), washed with brine (20 mL), dried over anhydrous $Na_2SO_4$, filtered and the filtrate was evaporated in vacuum to give an oil which was purified by prep-TLC ($SiO_2$, Pet. ether/EtOAc=1/2) to give compound 2-5. Calculated $C_{18}H_{18}F_2N_3O_2$ $[M+H]^+$, 346; Found 346. $^1H$ NMR (400 MHz, $CDCl_3$) δ 6.71-6.81 (m, 3H), 5.12 (dd, J=4.4, 8.0 Hz, 1H), 2.76-3.07 (m, 3H), 2.55 (s, 6H), 2.42 (tdd, J=4.8, 8.4a, 13.2 Hz, 1H), 2.20 (s, 3H).

TABLE 2

| Compound Number | Structure | Chemical Name | Mass [M + H]+; Method |
|---|---|---|---|
| 2-1 | 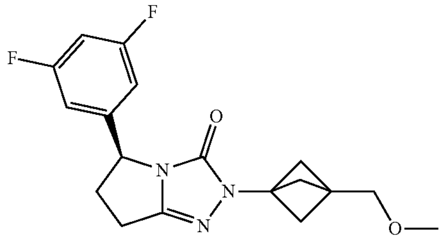 [SMILES: COCC12CC(n3nc4n(c3=O)[C@H](c3cc(F)cc(F)c3)CC4)(C1)C2] | (5S)-5-(3,5-difluorophenyl)-2-[3-(methoxymethyl)bicyclo[1.1.1]pentan-1-yl]-2,5,6,7-tetrahydro-3H-pyrrolo[2,1-c][1,2,4]triazol-3-one | Calc'd 348, found 348; Ex.2.1 |
| 2-2 | 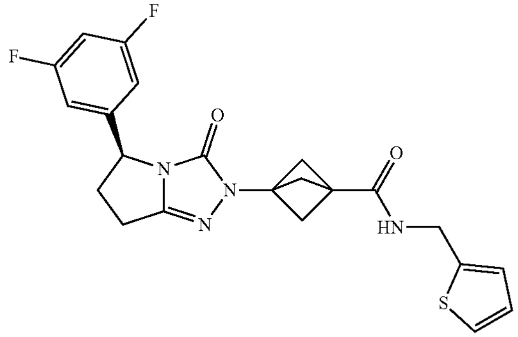 [SMILES: O=C(NCc1cccs1)C12CC(n3nc4n(c3=O)[C@H](c3cc(F)cc(F)c3)CC4)(C1)C2] | 3-[(5S)-5-(3,5-difluorophenyl)-3-oxo-6,7-dihydro-3H-pyrrolo[2,1-c][1,2,4]triazol-2(5H)-yl]-N-[(thiophen-2-yl)methyl]bicyclo[1.1.1]pentane-1-carboxamide | Calc'd 443, found 443; Ex.2.2 |

TABLE 2-continued

| Compound Number | Structure | Chemical Name | Mass [M + H]+; Method |
|---|---|---|---|
| 2-3 | 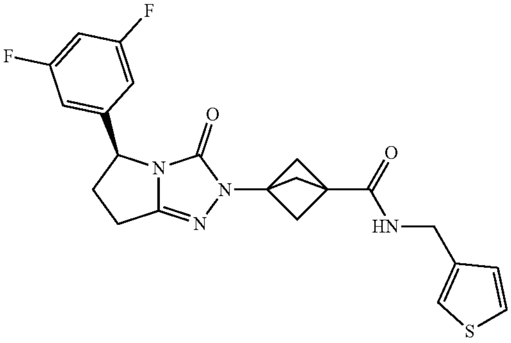 [SMILES: O=C(NCc1ccsc1)C12CC(n3nc4n(c3=O)[C@H](c3cc(F)cc(F)c3)CC4)(C1)C2] | 3-[(5S)-5-(3,5-difluorophenyl)-3-oxo-6,7-dihydro-3H-pyrrolo[2,1-c][1,2,4]triazol-2(5H)-yl]-N-[(thiophen-3-yl)methyl]bicyclo[1.1.1]pentane-1-carboxamide | Calc'd 443, found 443; Ex.2.2 |
| 2-4 | 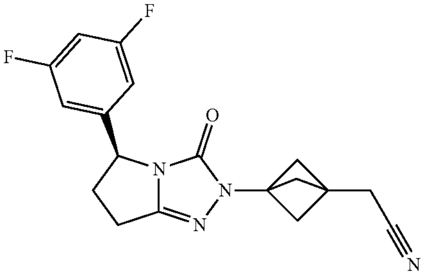 [SMILES: N#CCC12CC(n3nc4n(c3=O)[C@H](c3cc(F)cc(F)c3)CC4)(C1)C2] | (S)-2-(3-(5-(3,5-difluorophenyl)-3-oxo-6,7-dihydro-3H-pyrrolo[2,1-c][1,2,4]triazol-2(5H)-yl)bicyclo[1.1.1]pentan-1-yl)acetonitrile | Calc'd 343, found 343; Ex.2.3 |
| 2-5 | 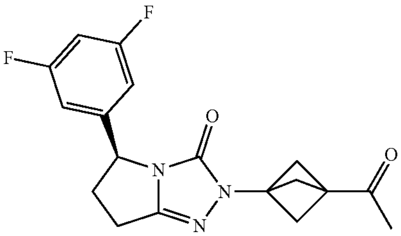 [SMILES: CC(=O)C12CC(n3nc4n(c3=O)[C@H](c3cc(F)cc(F)c3)CC4)(C1)C2] | (5S)-2-(3-acetylbicyclo[1.1.1]pentan-1-yl)-5-(3,5-difluorophenyl)-2,5,6,7-tetrahydro-3H-pyrrolo[2,1-c][1,2,4]triazol-3-one | Calc'd 346, found 346; Ex.2.4 |

Example 3.1. Preparation of Compound 3-1

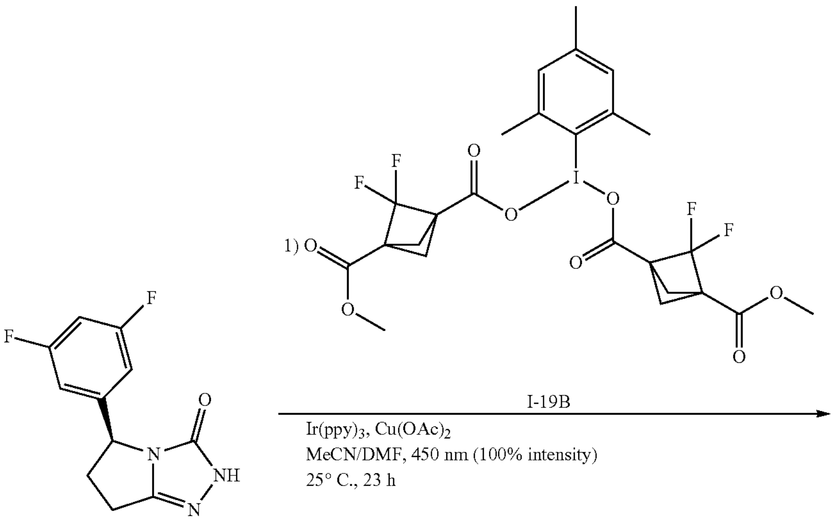

I-2A

-continued

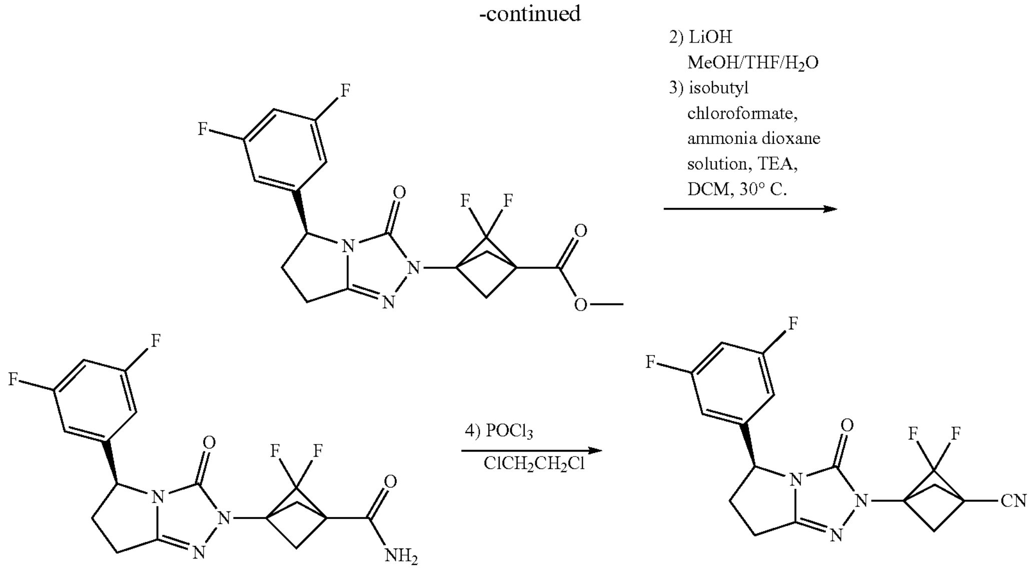

3-1

Step 1. Preparation of methyl (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carboxylate In a glovebox, two 20 mL red cap vials containing intermediate I-2A (80 mg, 0.337 mmol) were charged with I-19B (568 mg, 0.675 mmol), $Ir(ppy)_3$ (2.21 mg, 3.37 μmol), and $Cu(OAc)_2$ (22.1 mg, 0.084 mmol). The vials were brought into the glovebox, followed by addition of DMF (5620 μL) and MeCN (5620 μL) to form a homogeneous solution, then sealed, and brought outside of the glovebox. The reaction mixture was irradiated at 450 nm (100% intensity) for 23 h. The reaction mixture was directly purified using silica gel flash column chromatography (Ethyl acetate/EtOH/hexanes) to yield a crude mixture containing product, which was submitted for EKB purification (TFA as a modifier). The sample was lyophilized to afford (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carboxylate. Calculated $C_{18}H_{16}F_4N_3O_3[M+H]^+$, 398; Found 398.

Step 2. Preparation of (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carboxylic acid To a 20 mL red cap vial containing (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carboxylate (61 mg, 0.154 mmol) were charged MeOH (658 μL), MeOH (658 μL), and LiOH (219 μL, 0.219 mmol) at RT. The reaction mixture was stirred at RT for 2 h. The reaction mixture was carefully quenched with 2N HCl (110 uL) to ~pH 3, and extracted three times with EtOAc. The combined organic phases were dried over $MgSO_4$, filtered, and concentrated to yield crude (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carboxylic acid, which was used directly without further purification. Calculated $C_{17}H_{14}F_4N_3O_3[M+H]^+$, 384; Found 384.

Step 3. Preparation of (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carboxamide To a stirred solution of (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carboxylic acid (58 mg, 0.151 mmol) in DCM (408 μL) was charged isobutyl chloroformate (21.7 μL, 0.166 mmol) at 0° C., followed by addition of TEA (42.2 μL, 0.303 mmol) in one portion. The reaction mixture was stirred for 30 min at 0° C., followed by the addition of ammonia solution (in dioxane) (3030 μL, 1.51 mmol) at 0° C., and the resulting mixture was stirred for additional 1 h. reaction mixture was directly purified by silica gel flash column chromatography (ethyl acetate/EtOH/hexanes) to yield (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carboxamide. Calculated $C_{17}H_{15}F_4N_4O_2[M+H]^+$, 383; Found 383.

Step 4. Preparation of (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carbonitrile To a 20 mL red cap vial containing (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carboxamide (55 mg, 0.144 mmol) was charged $C_1CH_2CH_2C_1$ (2800 μL), followed by $POCl_3$ (500 μL, 5.36 mmol) in one portion, and the reaction mixture was stirred at 90° C. for 4 h. The reaction mixture was directly purified by silica gel flash column chromatography (ethyl acetate/EtOH/hexanes) to yield (S)-3-(5-(3,5-difluorophenyl)-3-oxo-6,7-dihydro-3H-pyrrolo[2,1-c][1,2,4]triazol-2(5H)-yl)-2,2-difluorobicyclo[1.1.1]pentane-1-carbonitrile after lyophilization. Calculated $C_{17}H_{13}F_4N_4O$ [M+H]$^+$, 365; Found 365.

Example 3.2. Preparation of Compound 3-3

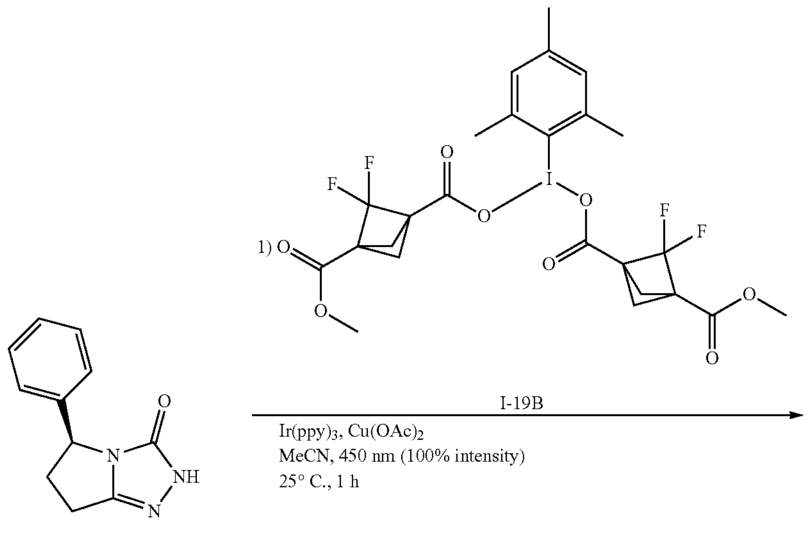

I-1A

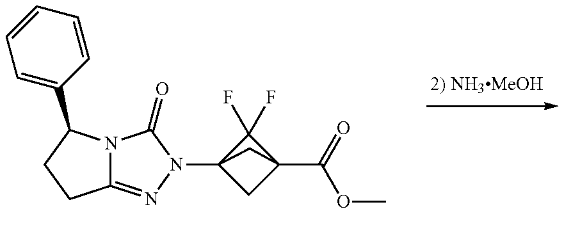

3-2

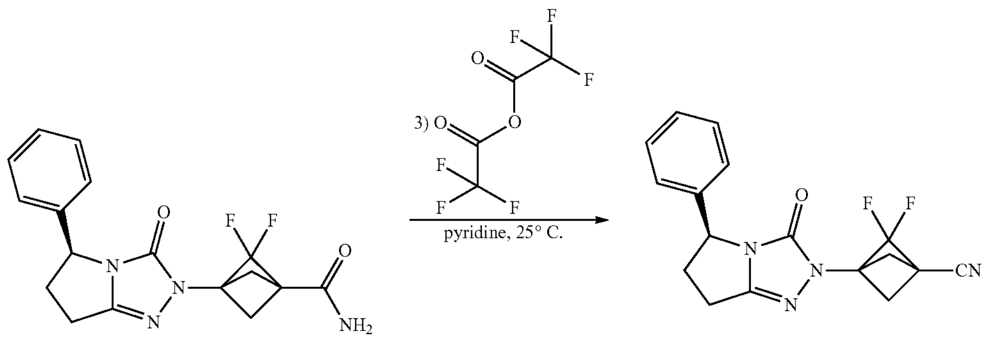

3-3

Step 1. Preparation of methyl (S)-2,2-difluoro-3-(3-oxo-5-phenyl-6,7-dihydro-3H-pyrrolo[2,1-c][1,2,4]triazol-2(5H)-yl)bicyclo[1.1.1]pentane-1-carboxylate 3-2

A mixture of intermediate I-1A (60 mg, 0.298 mmol), $Cu(OAc)_2$ (39.0 mg, 0.149 mmol), $Ir(ppy)_3$ (3.90 mg, 5.96 μmol) and I-19B (391 mg, 0.596 mmol) in MeCN (5960 μL) was stirred at 25° C. under $N_2$ with 450 nm blue LED lamps for 1 h. The mixture was concentrated in vacuo. Then the residue was purified by pre-HPLC (Method Column Boston Green ODS 150×30 mm×5 um; Condition water (0.01% TFA)-CAN) to give methyl (S)-2,2-difluoro-3-(3-oxo-5-phenyl-6,7-dihydro-3H-pyrrolo[2,1-c][1,2,4]triazol-2(5H)-yl)bicyclo[1.1.1]pentane-1-carboxylate (3-2). Calculated $C_{18}H_{18}F_2N_3O_3$ $[M+H]^+$, 362; Found 362. $^1H$ NMR (400 MHz, $CDCl_3$): δ 7.31-7.43 (m, 3H), 7.22 (d, J=6.9 Hz, 2H), 5.20 (dd, J=7.7, 4.4 Hz, 1H), 3.80 (s, 3H), 2.93-3.05 (m, 2H), 2.81-2.91 (m, 3H), 2.47-2.53 (m, 1H), 2.37-2.44 (m, 2H).

Step 2. Preparation of (S)-2,2-difluoro-3-(3-oxo-5-phenyl-6,7-dihydro-3H-pyrrolo[2,1-c][1,2,4]triazol-2(5H)-yl)bicyclo[1.1.1]pentane-1-carboxamide A solution of methyl (S)-2,2-difluoro-3-(3-oxo-5-phenyl-6,7-dihydro-3H-pyrrolo[2,1-c][1,2,4]triazol-2(5H)-yl)bicyclo[1.1.1]pentane-1-carboxylate (45 mg, 0.125 mmol) in $NH_3$-MeOH (7 M) (2 mL) was stirred at 60° C. for 12 h. The mixture was concentrated in vacuo to give crude (S)-2,2-difluoro-3-(3-oxo-5-phenyl-6,7-dihydro-3H-pyrrolo[2,1-c][1,2,4]triazol-2(5H)-yl)bicyclo[1.1.1]pentane-1-carboxamide. Calculated $C_{17}H_{17}F_2N_4O_2[M+H]^+$, 347; Found 347.

Step 3. Preparation of Compound 3-3

To a solution of (S)-2,2-difluoro-3-(3-oxo-5-phenyl-6,7-dihydro-3H-pyrrolo[2,1-c][1,2,4]triazol-2(5H)-yl)bicyclo[1.1.1]pentane-1-carboxamide (45 mg, 0.130 mmol) in pyridine (2 mL) was added 2,2,2-trifluoroacetic anhydride (109 mg, 0.520 mmol) and the mixture was stirred at 25° C. for 1 h. The mixture was concentrated in vacuo and purified by pre-HPLC (Method Column Boston Prime C18 150×30 mm×5 um; Condition water (10 mM-$NH_4HCO_3$)-ACN) to give compound 3-3. Calculated $C_{17}H_{15}F_2N_4O$ $[M+H]^+$, 329; Found 329. $^1H$ NMR (400 MHz, $CDCl_3$): δ 7.32-7.43 (m, 3H), 7.20-7.25 (m, 2H), 5.17 (dd, J=7.6, 4.4 Hz, 1H), 2.99-3.06 (m, 1H), 2.98 (s, 2H), 2.91-2.97 (m, 1H), 2.80-2.90 (m, 1H), 2.53-2.60 (m, 2H), 2.51 (dd, J=9.2, 4.4 Hz, 1H).

TABLE 3

| Compound Number | Structure | Chemical Name | Mass [M + H]+; Method |
|---|---|---|---|
| 3-1 | 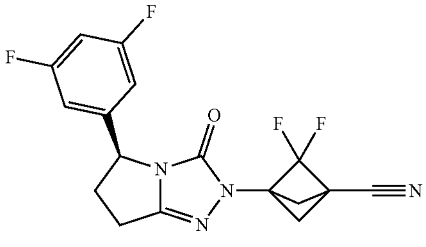 [SMILES: N#CC12CC(n3nc4n(c3=O)[C@H](c3cc(F)cc(F)c3)CC4)(C1)C2(F)F] | 3-[(5S)-5-(3,5-difluorophenyl)-3-oxo-6,7-dihydro-3H-pyrrolo[2,1-c][1,2,4]triazol-2(5H)-yl]-2,2-difluorobicyclo[1.1.1]pentane-1-carbonitrile | Calc'd 365, found 365; Ex.3.1 |
| 3-2 | 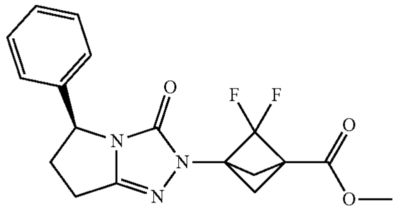 [SMILES: COC(=O)C12CC(n3nc4n(c3=O)[C@H](c3ccccc3)CC4)(C1)C2(F)F] | methyl (S)-2,2-difluoro-3-(3-oxo-5-phenyl-6,7-dihydro-3H-pyrrolo[2,1-c][1,2,4]triazol-2(5H)-yl)bicyclo[1.1.1]pentane-1-carboxylate | Calc'd 362, found 362; Ex.3.2 |
| 3-3 | 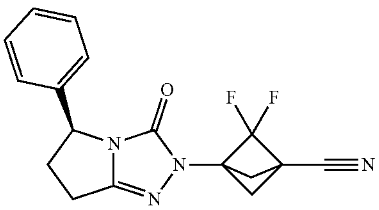 [SMILES: N#CC12CC(n3nc4n(c3=O)[C@H](c3ccccc3)CC4)(C1)C2(F)F] | 2,2-difluoro-3-[(5S)-3-oxo-5-phenyl-6,7-dihydro-3H-pyrrolo[2,1-c][1,2,4]triazol-2(5H)-yl]bicyclo[1.1.1]pentane-1-carbonitrile | Calc'd 329, found 329; Ex.3.2 |

Preparation of Intermediate I-1D ((S)-(3-(5-(3,5-difluorophenyl)-3-oxo-6,7-dihydro-3H-pyrrolo[2,1-c][1,2,4]triazol-2(5H)-yl)bicyclo[1.1.1]pentan-1-yl) methyl methanesulfonate)

Intermediate I-1D was prepared from intermediate I-7A as outlined below.

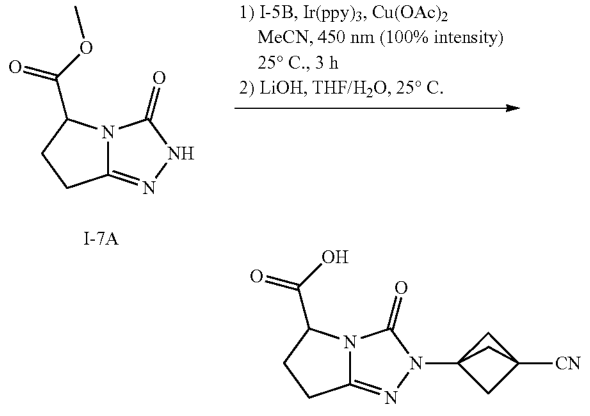

I-7A

I-1D

Step 1. Preparation of methyl 2-(3-cyanobicyclo[1.1.1]pentan-1-yl)-3-oxo-2,5,6,7-tetrahydro-3H-pyrrolo[2,1-c][1,2,4]triazole-5-carboxylate A vial was charged with intermediate I-7A (325 mg, 1.77 mmol), I-5B (1840 mg, 3.55 mmol), $Ir(ppy)_3$ (23.2 mg, 0.035 mmol), $Cu(OAc)_2$ (232 mg, 0.887 mmol) and MeCN (17 mL). The mixture was purged with nitrogen gas and then placed in a photoreactor (fan rpm 4700, stir rpm 1000, 450 nm, 100% light intensity) for 3 h. The reaction were diluted with MeCN and filtered through a pad of celite. The resulting mixture was purified by flash column chromatography (12 g silica gel, ELSD, 35% EtOAc:Hex, then 70% EtOAc:Hex, and then 100% EtOAc:Hex for desired product). The fractions containing the desired product were pooled and concentrated to dryness to give methyl 2-(3-cyanobicyclo[1.1.1]pentan-1-yl)-3-oxo-2,5,6,7-tetrahydro-3H-pyrrolo[2,1-c][1,2,4]triazole-5-carboxylate. Calculated $C_{13}H_{15}N_4O_3$ $[M+H]^+$, 275; Found 275.

Step 2. Preparation of 2-(3-cyanobicyclo[1.1.1]pentan-1-yl)-3-oxo-2,5,6,7-tetrahydro-3H-pyrrolo[2,1-c][1,2,4]triazole-5-carboxylic acid To a mixture of methyl 2-(3-cyanobicyclo[1.1.1]pentan-1-yl)-3-oxo-2,5,6,7-tetrahydro-3H-pyrrolo[2,1-c][1,2,4]triazole-5-carboxylate (195 mg, 0.711 mmol) in THF/WATER=3/1 was added LiOH (51.1 mg, 2.133 mmol). The mixture was stirred at RT for 1 h. The mixture was dissolved in water (20 mL) and DCM (20 mL). The organic layer was separated and the aqueous layer was added HCl until pH<7. The aqueous layer was re-extracted with DCM (20 mL×2), the combined organic layers were washed with brine (5 mL×2), dried over anhydrous $Na_2SO_4$, filtered and concentrated under reduced pressure to give 2-(3-cyanobicyclo[1.1.1]pentan-1-yl)-3-oxo-2,5,6,7-tetrahydro-3H-pyrrolo[2,1-c][1,2,4]triazole-5-carboxylic acid. Calculated $C_{12}H_{13}N_4O_3$ $[M+H]^+$, 261; Found 261.

Intermediate I-2D was prepared in a fashion analogous to the procedure used to prepare I-1D from I-7A and I-2B. Intermediate I-3D was prepared in a fashion analogous to the procedure used to prepare I-1D from I-38A and I-2B.

TABLE D

| Intermediate | Structure |
|---|---|
| I-1D | 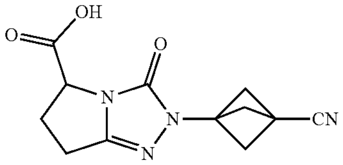 [SMILES: N#CC12CC(n3nc4n(c3=O)C(C(=O)O)CC4)(C1)C2] |
| I-2D | 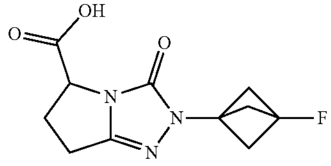 [SMILES: O=C(O)C1CCc2nn(C34CC(F)(C3)C4)c(=O)n21] |
| I-3D | 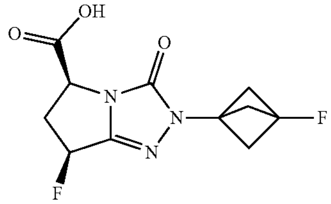 [SMILES: O=C(O)[C@@H]1C[C@H](F)c2nn(C34CC(F)(C3)C4)c(=O)n21] |

General Scheme 2a.

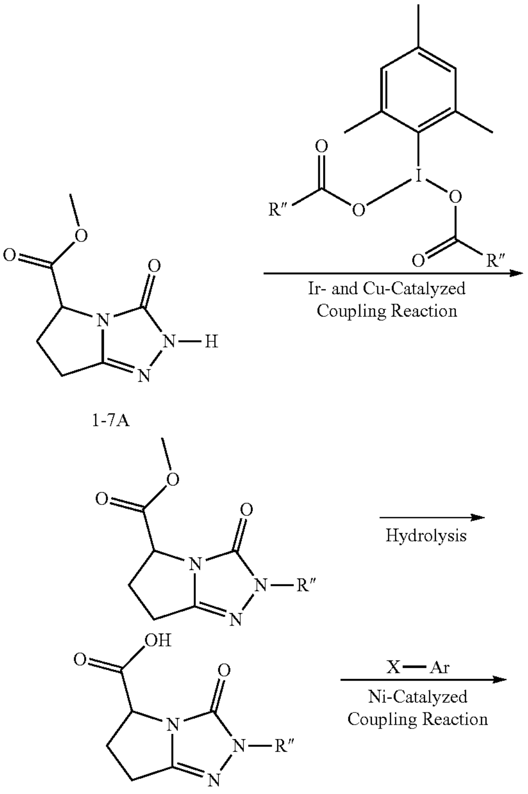

1-7A

-continued

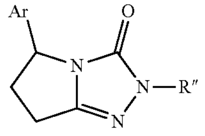

In general scheme 2a, intermediate I-7A and intermediates of Table B were coupled under photoredox conditions in the presence of a copper and iridium catalyst. The subsequent product undergoes hydrolysis to afford the corresponding acid. Treatment with the desired aryl halide under Ni-catalyzed conditions affords the desired products listed in Table 4.

General Scheme 2b.

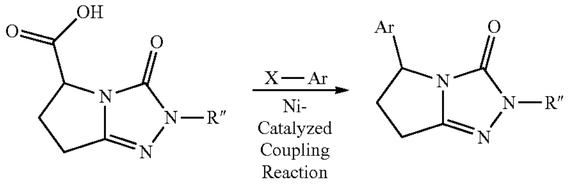

In general scheme 2b, treatment of intermediates from Table D with the desired aryl halides under Ni-catalyzed conditions affords the products listed in Table 4.

Example 4.1. Preparation of Compound 4-2

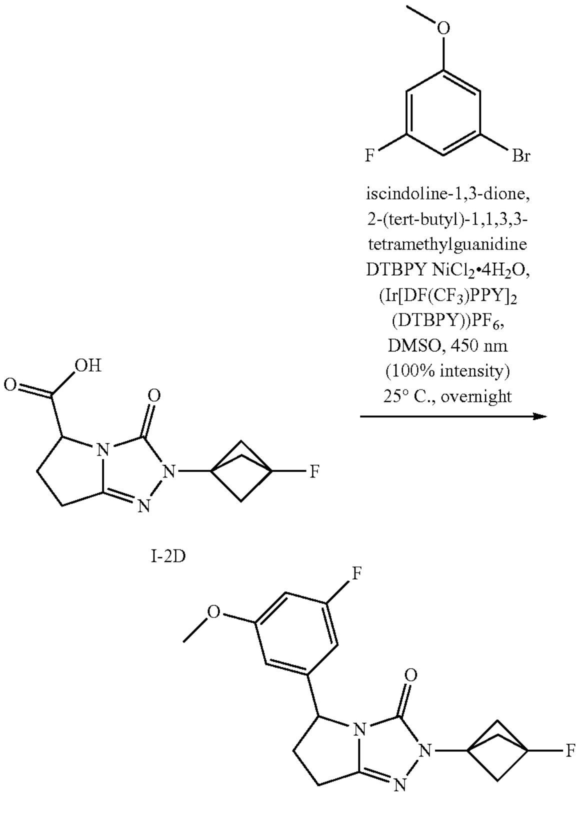

I-2D 4-2

To a 2 dram vial charged with I-2D (12.7 mg, 0.05 mmol), 1-bromo-3-fluoro-5-methoxybenzene (15.4 mg, 0.075 mmol), isoindoline-1,3-dione (7.4 mg, 0.05 mmol), DTBPY $NiCl_2 \cdot 4H_2O$ (4.7 mg, 0.01 mmol), 2-(tert-butyl)-1,1,3,3-tetramethylguanidine (17.1 mg, 0.1 mmol) and $(Ir[DF(CF_3)PPY]_2(DTBPY))PF_6$ (1.1 mg, 1.0 μmol) was added DMSO (1.25 mL). The reaction mixture was degassed by bubbling nitrogen through the solution while stirring for 15 min. The reaction mixture was then irradiated in the PennOC/Merck photoreactor with 100% LED power, 2500 rpm fan, and 630 rpm stirring for 18 h with 450 nm LED light. The reaction was then filtered and purified by reverse phase chromatography (MeCN/water with 0.1% TFA) to afford 4-2 (±)-5-(3-fluoro-5-methoxyphenyl)-2-(3-fluorobicyclo[1.1.1]pentan-1-yl)-2,5,6,7-tetrahydro-3H-pyrrolo[2,1-c][1,2,4]triazol-3-one. Calculated $C_{17}H_{18}F_2N_3O_2$ $[M+H]^+$, 334; found, 334.

Example 4.2. Preparation of Compound 4-7 ((S)-3-(3-oxo-5-(p-tolyl)-6,7-dihydro-3H-pyrrolo[2,1-c][1,2,4]triazol-2(5H)-yl)bicyclo[1.1.1]pentane-1-carbonitrile)

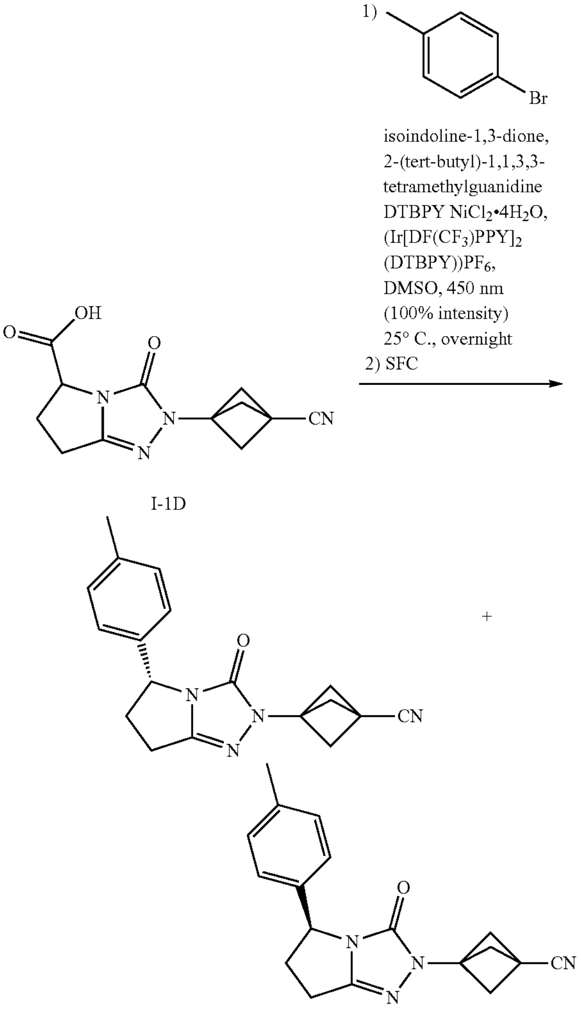

I-1D 4-7

Steps 1-2. Preparation of 3-(3-oxo-5-(p-tolyl)-6,7-dihydro-3H-pyrrolo[2,1-c][1,2,4]triazol-2(5H)-yl) bicyclo[1.1.1]pentane-1-carbonitrile Followed by SFC to Afford 4-7

To a 2 dram vial charged with I-1D (30 mg, 0.115 mmol), 1-bromo-4-methylbenzene (29.6 mg, 0.173 mmol), isoindoline-1,3-dione (17.0 mg, 0.115 mmol), DTBPY $NiCl_2 \cdot 4H_2O$ (9.18 mg, 0.023 mmol), 1-bromo-4-methylbenzene (29.6 mg, 0.173 mmol), 2-(tert-butyl)-1,1,3,3-tetramethylguanidine (39.5 mg, 0.231 mmol) and $(Ir[DF(CF_3)PPY]_2(DTBPY))PF_6$ (2.59 mg, 2.31 μmol) was added DMSO (2880 μL). The reaction mixture was degassed by bubbling nitrogen through the solution while stirring for 15 min. The reaction mixture was then irradiated in the PennOC/Merck photoreactor with 100% LED power, 1000 rpm fan, and 4700 rpm stirring for 14 h with 450 nm LED light. The reaction was diluted with DCM and $H_2O$ and was transferred to a sep funnel and shaken up. The resulting mixture was extracted with DCM 3×, dried over $Na_2SO_4$ and then concentrated to dryness. The product was purified by flash column chromatography (24 g silica gel, ELSD, 5% EtOAc: Hex, then 45% EtOAc:Hex then 75% EtOAc:Hex for desired product). The fractions containing the desired product mass were pooled and concentrated. Product 3-(3-oxo-5-(p-tolyl)-6,7-dihydro-3H-pyrrolo[2,1-c][1,2,4]triazol-2(5H)-yl)bicyclo[1.1.1]pentane-1-carbonitrile was isolated as a racemic mixture. The enantiomers were separated by SFC purification (Column & Dimensions: OJ-H, 21×250 mm, 5 um Condition: 10% MeOH w/0.1% $NH_4OH$) to give (R)-3-(3-oxo-5-(p-tolyl)-6,7-dihydro-3H-pyrrolo[2,1-c][1,2,4]triazol-2(5H)-yl)bicyclo[1.1.1]pentane-1-carbonitrile (retention time=2.95 min) and 4-7 (S)-3-(3-oxo-5-(p-tolyl)-6,7-dihydro-3H-pyrrolo[2,1-c][1,2,4]triazol-2(5H)-yl)bicyclo[1.1.1]pentane-1-carbonitrile (retention time=4.26 min).

(R)-3-(3-oxo-5-(p-tolyl)-6,7-dihydro-3H-pyrrolo[2,1-c][1,2,4]triazol-2(5H)-yl)bicyclo[1.1.1]pentane-1-carbonitrile $^1H$ NMR (499 MHz, DMSO-$d_6$) δ 7.17 (d, J=7.9 Hz, 2H), 7.11 (d, J=7.9 Hz, 2H), 5.11 (m, 1H), 2.87 (m, 2H), 2.79-2.69 (m, 1H), 2.65 (s, 6H), 2.28 (s, 3H), 2.23 (m, 1H).

(S)-3-(3-oxo-5-(p-tolyl)-6,7-dihydro-3H-pyrrolo[2,1-c][1,2,4]triazol-2(5H)-yl)bicyclo[1.1.1]pentane-1-carbonitrile, (4-7)

$^1H$ NMR (499 MHz, DMSO-$d_6$) δ 7.17 (d, J=7.8 Hz, 2H), 7.11 (d, J=7.9 Hz, 2H), 5.17-5.06 (m, 1H), 2.97-2.79 (m, 2H), 2.80-2.68 (m, 1H), 2.65 (s, 6H), 2.28 (s, 3H), 2.23 (m, 1H).

Example 4.3. Preparation of Compound 4-16 (S)-2-(3-fluorobicyclo[1.1.1]pentan-1-yl)-5-(5-(trifluoromethyl)pyrazin-2-yl)-2,5,6,7-tetrahydro-3H-pyrrolo[2,1-c][1,2,4]triazol-3-one

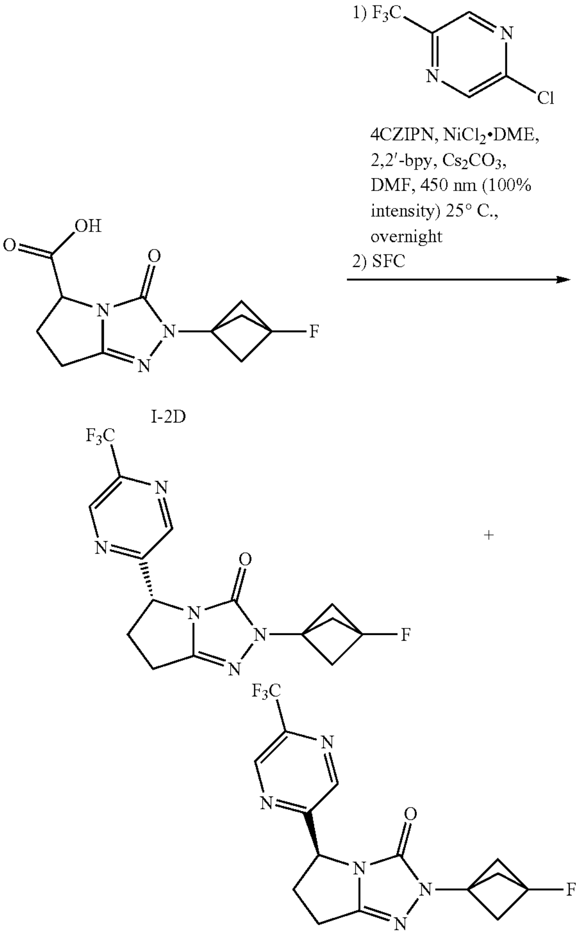

I-2D 4-16

Steps 1-2. Preparation of 2-(3-fluorobicyclo[1.1.1]pentan-1-yl)-5-(5-(trifluoromethyl)pyrazin-2-yl)-2,5,6,7-tetrahydro-3H-pyrrolo[2,1-c][1,2,4]triazol-3-one followed by SFC to afford 4-16

To a solution of I-2D (30 mg, 0.118 mmol) in DMF (1 mL) was added 2-chloro-5-(trifluoromethyl)pyrazine (40 mg, 0.219 mmol), $Cs_2CO_3$ (107 mg, 0.329 mmol), 2,2'-bipyridine (5.13 mg, 0.033 mmol), Nickel(II) chloride ethylene glycol dimethyl ether complex (4.81 mg, 0.022 mmol), and 4CZIPN (4.32 mg, 5.48 μmol) under $N_2$. The resulting mixture was then irradiated with 450 nm blue light while stirring for 12 h. The reaction was filtered and the filtrate was purified by Prep-HPLC (Prep HPLC condition: Preparative HPLC on EB instrument fitted with Boston Green ODS 150*30 mm*5 um using the mobile phase A-B:

water (0.01% TFA)-ACN, Gradient: 35-55% B, 0-10 min; 100% B, 10-12 min, 10% B, 12-14 min. FlowRate: 25 mL/min) to give 2-(3-fluorobicyclo[1.1.1]pentan-1-yl)-5-(5-(trifluoromethyl)pyrazin-2-yl)-2,5,6,7-tetrahydro-3H-pyrrolo[2,1-c][1,2,4]triazol-3-one as a racemic mixture. The enantiomers were resolved by Chiral-SFC (Instrument SFC-21 Method REGIS (s,s) WHELK-O1 (250 mm*30 mm, 5 um) Condition 25% EtOH w/0.1% $NH_4OH$) to give (R)-2-(3-fluorobicyclo[1.1.1]pentan-1-yl)-5-(5-(trifluoromethyl)pyrazin-2-yl)-2,5,6,7-tetrahydro-3H-pyrrolo[2,1-c][1,2,4]triazol-3-one (retention time=2.10 min) and 4-16, (S)-2-(3-fluorobicyclo[1.1.1]pentan-1-yl)-5-(5-(trifluoromethyl)pyrazin-2-yl)-2,5,6,7-tetrahydro-3H-pyrrolo[2,1-c][1,2,4]triazol-3-one (retention time=2.90 min).

(R)-2-(3-fluorobicyclo[1.1.1]pentan-1-yl)-5-(5-(trifluoromethyl)pyrazin-2-yl)-2,5,6,7-tetrahydro-3H-pyrrolo[2,1-c][1,2,4]triazol-3-one $^1H$ NMR (400 MHz, $CD_3OD$) δ 9.02 (s, 1H), 8.88 (s, 1H), 5.52 (dd, J=4.0, 8.4 Hz, 1H), 3.04-3.14 (m, 1H), 2.85-3.02 (m, 2H), 2.65 (tdd, J=4.4, 8.8, 13.2 Hz, 1H), 2.55 (d, J=2.0 Hz, 6H)

(S)-2-(3-fluorobicyclo[1.1.1]pentan-1-yl)-5-(5-(trifluoromethyl)pyrazin-2-yl)-2,5,6,7-tetrahydro-3H-pyrrolo[2,1-c][1,2,4]triazol-3-one (4-16)

$^1H$ NMR (400 MHz, $CD_3OD$) δ 9.02 (s, 1H), 8.88 (d, J=0.8 Hz, 1H), 5.52 (dd, J=4.0, 8.4 Hz, 1H), 3.04-3.15 (m, 1H), 2.84-3.04 (m, 2H), 2.65 (tdd, J=4.4, 8.8, 13.2 Hz, 1H), 2.55 (d, J=2.0 Hz, 6H)

TABLE 4

| Compound Number | Structure | Chemical Name | Mass [M + H]+; Method |
|---|---|---|---|
| 4-1 | 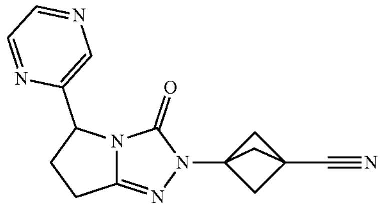 [SMILES: N#CC12CC(n3nc4n(c3=O)C(c3cnccn3)CC4)(C1)C2] | (±)-3-(3-oxo-5-(pyrazin-2-yl)-6,7-dihydro-3H-pyrrolo[2,1-c][1,2,4]triazol-2(5H)-yl)bicyclo[1.1.1]pentane-1-carbonitrile | Calc'd 295, found 295; Ex.4.1 |
| 4-2 | 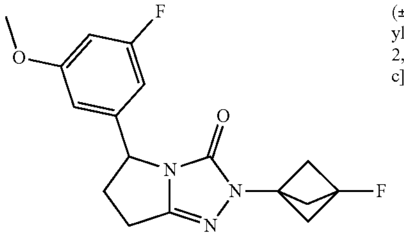 | (±)-2-(3-fluorobicyclo[1.1.1]pentan-1-yl)-5-(3-fluoro-5-methoxyphenyl)-2,5,6,7-tetrahydro-3H-pyrrolo[2,1-c][1,2,4]triazol-3-one | Calc'd 334, found 334; Ex.4.1 |
| 4-3 | 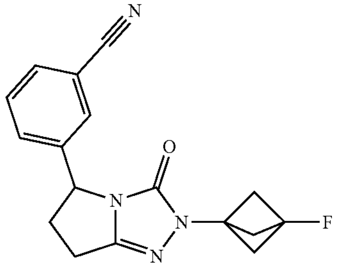 [SMILES: N#Cc1cccc(C2CCc3nn(C45CC(F)(C4)C5)c(=O)n32)c1] | (±)-3-[2-(3-fluorobicyclo[1.1.1]pentan-1-yl)-3-oxo-2,5,6,7-tetrahydro-3H-pyrrolo[2,1-c][1,2,4]triazol-5-yl]benzonitrile | Calc'd 311, found 311; Ex.4.1 |
| 4-4 | 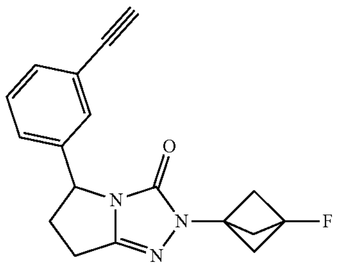 [SMILES: C#Cc1cccc(C2CCc3nn(C45CC(F)(C4)C5)c(=O)n32)c1] | (±)-5-(3-ethynylphenyl)-2-(3-fluorobicyclo[1.1.1]pentan-1-yl)-2,5,6,7-tetrahydro-3H-pyrrolo[2,1-c][1,2,4]triazol-3-one | Calc'd 310, found 310; Ex.4.1 |

TABLE 4-continued

| Compound Number | Structure | Chemical Name | Mass [M + H]+; Method |
|---|---|---|---|
| 4-5 | 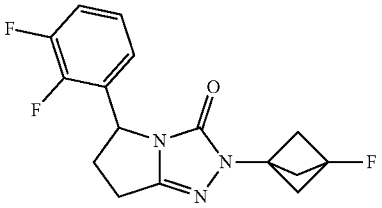 [SMILES: O=c1n(C23CC(F)(C2)C3)nc2n1C(c1cccc(F)c1F)CC2] | (±)-5-(2,3-difluorophenyl)-2-(3-fluorobicyclo[1.1.1]pentan-1-yl)-2,5,6,7-tetrahydro-3H-pyrrolo[2,1-c][1,2,4]triazol-3-one | Calc'd 322, found 322; Ex.4.1 |
| 4-6 | 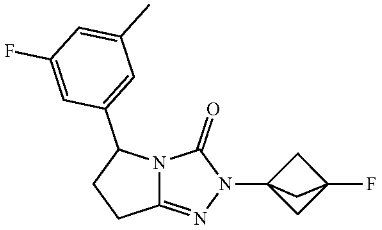 [SMILES: Cc1cc(F)cc(C2CCc3nn(C45CC(F)(C4)C5)c(=O)n32)c1] | (±)-2-(3-fluorobicyclo[1.1.1]pentan-1-yl)-5-(3-fluoro-5-methylphenyl)-2,5,6,7-tetrahydro-3H-pyrrolo[2,1-c][1,2,4]triazol-3-one | Calc'd 318, found 318; Ex.4.1 |
| 4-7 | 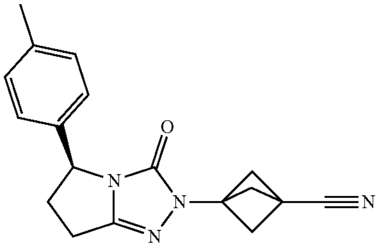 [SMILES: Cc1ccc([C@@H]2CCc3nn(C45CC(C#N)(C4)C5)c(=O)n32)cc1] | (S)-3-(3-oxo-5-(p-tolyl)-6,7-dihydro-3H-pyrrolo[2,1-c][1,2,4]triazol-2(5H)-yl)bicyclo[1.1.1]pentane-1-carbonitrile | Calc'd 307, found 307; Ex.4.2 |
| 4-8 | 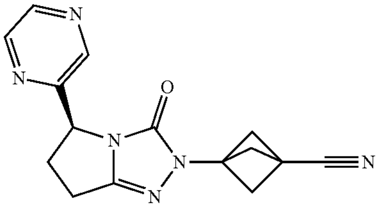 [SMILES: N#CC12CC(n3nc4n(c3=O)[C@H](c3cnccn3)CC4)(C1)C2] | (S)-3-(3-oxo-5-(pyrazin-2-yl)-6,7-dihydro-3H-pyrrolo[2,1-c][1,2,4]triazol-2(5H)-yl)bicyclo[1.1.1]pentane-1-carbonitrile | Calc'd 295, found 295; Ex.4.2 |
| 4-9 | 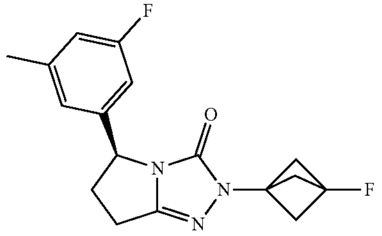 [SMILES: Cc1cc(F)cc([C@@H]2CCc3nn(C45CC(F)(C4)C5)c(=O)n32)c1] | (S)-5-(3-fluoro-5-methylphenyl)-2-(3-fluorobicyclo[1.1.1]pentan-1-yl)-2,5,6,7-tetrahydro-3H-pyrrolo[2,1-c][1,2,4]triazol-3-one | Calc'd 318, found 318; Ex.4.2 |
| 4-10 | 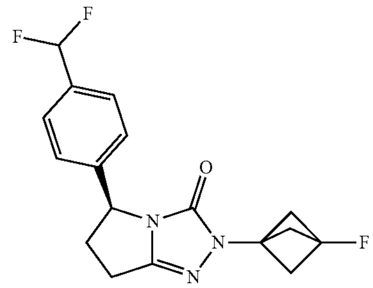 [SMILES: O=c1n(C23CC(F)(C2)C3)nc2n1[C@H](c1ccc(C(F)F)cc1)CC2] | (S)-5-(4-(difluoromethyl)phenyl)-2-(3-fluorobicyclo[1.1.1]pentan-1-yl)-2,5,6,7-tetrahydro-3H-pyrrolo[2,1-c][1,2,4]triazol-3-one | Calc'd 336, found 336; Ex.4.2 |

TABLE 4-continued

| Compound Number | Structure | Chemical Name | Mass [M + H]+; Method |
|---|---|---|---|
| 4-11 | 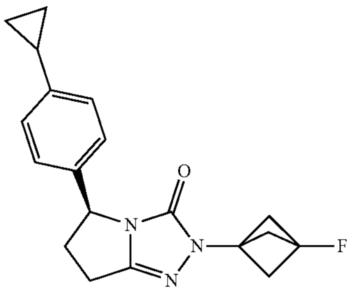 [SMILES: O=c1n(C23CC(F)(C2)C3)nc2n1[C@H](c1ccc(C3CC3)cc1)CC2] | (S)-5-(4-cyclopropylphenyl)-2-(3-fluorobicyclo[1.1.1]pentan-1-yl)-2,5,6,7-tetrahydro-3H-pyrrolo[2,1-c][1,2,4]triazol-3-one | Calc'd 326, found 326; Ex.4.2 |
| 4-12 | 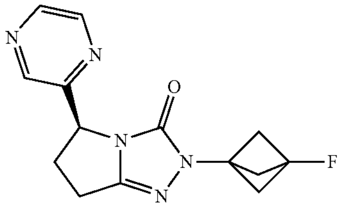 [SMILES: O=c1n(C23CC(F)(C2)C3)nc2n1[C@H](c1cnccn1)CC2] | (S)-2-(3-fluorobicyclo[1.1.1]pentan-1-yl)-5-(pyrazin-2-yl)-2,5,6,7-tetrahydro-3H-pyrrolo[2,1-c][1,2,4]triazol-3-one | Calc'd 288, found 288; Ex.4.2 |
| 4-13 | 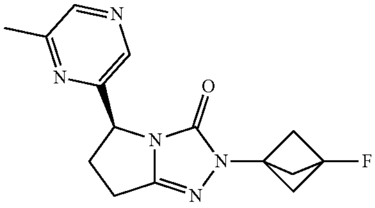 [SMILES: Cc1cncc([C@@H]2CCc3nn(C45CC(F)(C4)C5)c(=O)n32)n1] | (S)-2-(3-fluorobicyclo[1.1.1]pentan-1-yl)-5-(6-methylpyrazin-2-yl)-2,5,6,7-tetrahydro-3H-pyrrolo[2,1-c][1,2,4]triazol-3-one | Calc'd 302, found 302; Ex.4.2 |
| 4-14 | 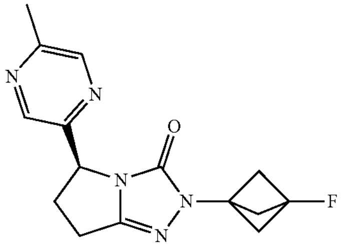 [SMILES: Cc1cnc([C@@H]2CCc3nn(C45CC(F)(C4)C5)c(=O)n32)cn1] | (S)-2-(3-fluorobicyclo[1.1.1]pentan-1-yl)-5-(5-methylpyrazin-2-yl)-2,5,6,7-tetrahydro-3H-pyrrolo[2,1-c][1,2,4]triazol-3-one | Calc'd 302, found 302; Ex.4.2 |
| 4-15 | 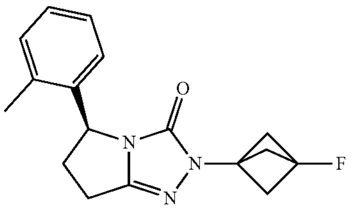 [SMILES: Cc1ccccc1[C@@H]1CCc2nn(C34CC(F)(C3)C4)c(=O)n21] | (S)-2-(3-fluorobicyclo[1.1.1]pentan-1-yl)-5-(o-tolyl)-2,5,6,7-tetrahydro-3H-pyrrolo[2,1-c][1,2,4]triazol-3-one | Calc'd 300, found 300; Ex.4.2 |
| 4-16 | 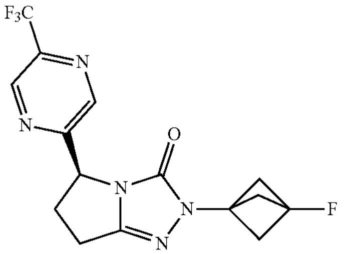 [SMILES: O=c1n(C23CC(F)(C2)C3)nc2n1[C@H](c1cnc(C(F)(F)F)cn1)CC2] | (S)-2-(3-fluorobicyclo[1.1.1]pentan-1-yl)-5-(5-(trifluoromethyl)pyrazin-2-yl)-2,5,6,7-tetrahydro-3H-pyrrolo[2,1-c][1,2,4]triazol-3-one | Calc'd 356, found 356; Ex.4.3 |

TABLE 4-continued

| Compound Number | Structure | Chemical Name | Mass [M + H]+; Method |
| --- | --- | --- | --- |
| 4-17 | 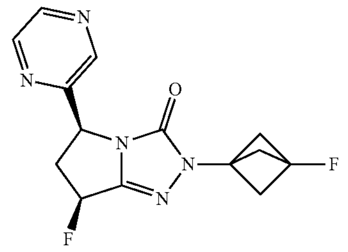 [SMILES: O=c1n(C23CC(F)(C2)C3)nc2n1[C@H](c1cnccn1)C[C@@H]2F] | (5S,7S)-7-fluoro-2-(3-fluorobicyclo[1.1.1]pentan-1-yl)-5-(pyrazin-2-yl)-2,5,6,7-tetrahydro-3H-pyrrolo[2,1-c][1,2,4]triazol-3-one | Calc'd 306, found 306; Ex.4.3 |

General Scheme 3

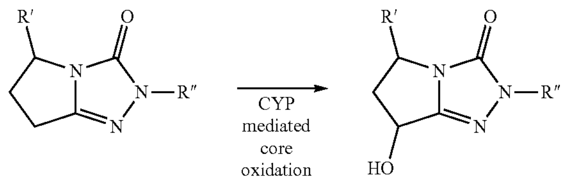

Example 5.1. Preparation of Compounds 5-1 and 5-2

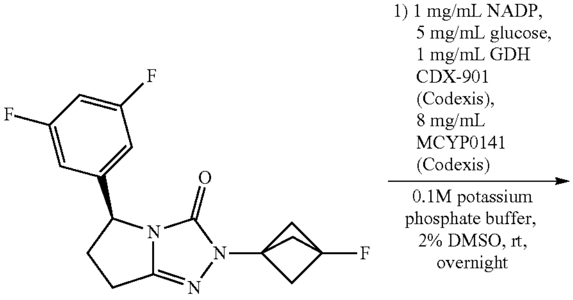

1-2

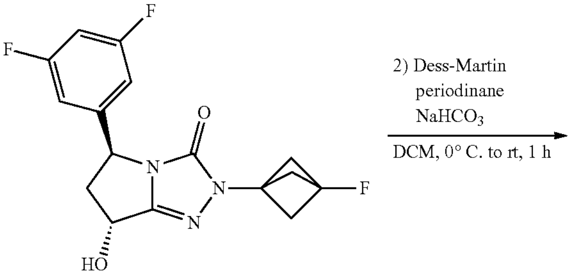

5-1

-continued

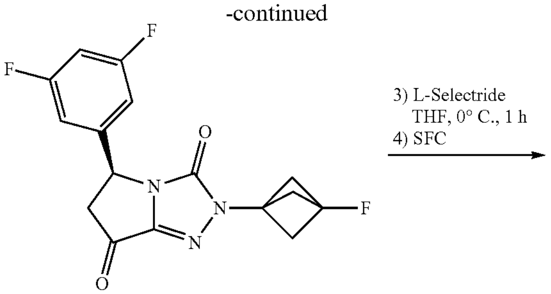

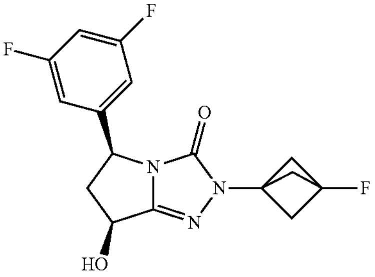

5-2

Step 1. Preparation of Compound 5-1

Four 75 mg scale reactions were set up identically in individual containers: A 250 erlenmeyer flask was charged with glucose (600 mg), NADP (120 mg), and GDH CDX-901 (120 mg), 120 mL of 0.1 M potassium phosphate buffer solution (pH=9.0) was added. Compound 1-2 (75 mg, 0.233 mmol) was dissolved in 2.4 mL of DMSO and added to the mixture. Finally 960 mg of MCYP0141 was added to the erlenmeyer and the reaction mixture was placed on a shaker overnight. The reactions were combined into a separatory funnel and extracted with 1:3 IPA/EtOAc (5×). The product was washed with brine, dried over sodium sulfate, diluted with MeOH (2 mL), filtered, and purified by reverse phase chromatography (15-70% MeCN/water with 0.1% $NH_4OH$) to give exclusively 5-1 (5S,7R)-5-(3,5-difluorophenyl)-2-(3-fluorobicyclo[1.1.1]pentan-1-yl)-7-hydroxy-2,5,6,7-tetrahydro-3H-pyrrolo[2,1-c][1,2,4]triazol-3-one. Calculated $C_{16}H_{15}F_3N_3O_2[M+H]^+$, 338; Found 338. $^1H$ NMR (499 MHz, DMSO-d6) δ 7.20 (t, J=9.3 Hz, 1H), 7.11 (d, J=6.8 Hz, 2H), 6.06 (d, J=5.7 Hz, 1H), 5.33 (t, J=6.8 Hz, 1H), 5.10-4.96 (m, 1H), 2.74-2.66 (m, 1H), 2.65-2.56 (m, 1H), 2.55 (d, J=1.7 Hz, 6H).

Step 2. Preparation of (S)-5-(3,5-difluorophenyl)-2-(3-fluorobicyclo[1.1.1]pentan-1-yl)-5,6-dihydro-3H-pyrrolo[2,1-c][1,2,4]triazole-3,7(2H)-dione To a solution of 5-1 (210 mg, 0.623 mmol) in DCM (6230 µL) was added $NaHCO_3$ (418 mg, 4.98 mmol). The mixture was cooled to 0° C. and then added Dess-Martin periodinane (528 mg, 1.25 mmol) in one portion. The reaction was then allowed to stir at RT until no starting material is observed (1 h). The reaction was quenched with sat. sodium bicarbonate, extracted with DCM, filtered over sodium sulfated and then concentrated to dryness to give (S)-5-(3,5-difluorophenyl)-2-(3-fluorobicyclo[1.1.1]pentan-1-yl)-5,6-dihydro-3H-pyrrolo[2,1-c][1,2,4]triazole-3,7(2H)-dione which was used as a crude without further purification. Calculated $C_{16}H_{13}F_3N_3O_2[M+H]^+$, 336; Found 336.

Steps 3-4. Preparation of Compound 5-2

A solution of (S)-5-(3,5-difluorophenyl)-2-(3-fluorobicyclo[1.1.1]pentan-1-yl)-5,6-dihydro-3H-pyrrolo[2,1-c][1,2,4]triazole-3,7(2H)-dione (209 mg, 0.623 mmol) in THF (6230 µL) was cooled to 0° C. and then added L-Selectride (748 µL, 0.748 mmol). The reaction was allowed to stir at 0° C. for 1 h. To the reaction was added water slowly. The crude reaction was extracted with DCM, the combined organic layer was washed with brine and dried over $Na_2SO_4$. The product was purified by flash column chromatography (5% EtOAc:Hex then 35% EtOAc:Hex). The desired product was isolated through SFC purification (Column & Dimensions: (R,R)-Whelk-O, 21×250 mm, 5 um; Condition 15% MeOH w/0.1% $NH_4OH$) to give compound 5-2. Calculated $C_{16}H_{15}F_3N_3O_2[M+H]^+$, 338; Found 338. $^1H$ NMR (499 MHz, DMSO-$d_6$) δ 7.19 (t, J=9.3 Hz, 1H), 7.10 (d, J=6.7 Hz, 2H), 6.17 (d, J=4.6 Hz, 1H), 5.13 (dd, J=8.2, 4.5 Hz, 1H), 4.92 (s, 1H), 3.29-3.13 (m, 1H), 2.54 (d, J=1.8 Hz, 6H), 2.12 (dt, J=13.9, 4.1 Hz, 1H).

TABLE 5

| Compound Number | Structure | Chemical Name | Mass [M + H]+ method |
|---|---|---|---|
| 5-1 | 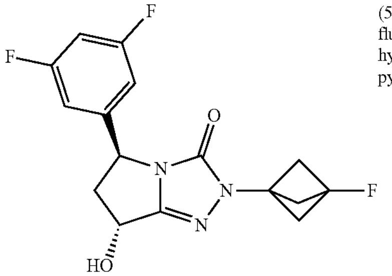 | (5S,7R)-5-(3,5-difluorophenyl)-2-(3-fluorobicyclo[1.1.1]pentan-1-yl)-7-hydroxy-2,5,6,7-tetrahydro-3H-pyrrolo[2,1-c][1,2,4]triazol-3-one | Calc'd 338, found 338; Ex.5.1 |
| 5-2 | 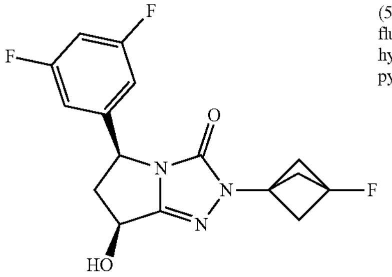 | (5S,7S)-5-(3,5-difluorophenyl)-2-(3-fluorobicyclo[1.1.1]pentan-1-yl)-7-hydroxy-2,5,6,7-tetrahydro-3H-pyrrolo[2,1-c][1,2,4]triazol-3-one | Calc'd 338, found 338; Ex.5.1 |

General Scheme 4

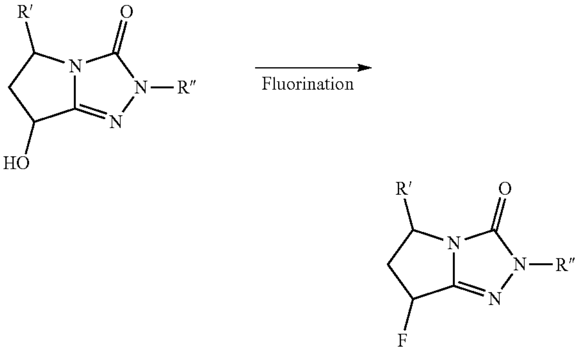

Example 6.1. Preparation of Compounds 6-1 and 6-2

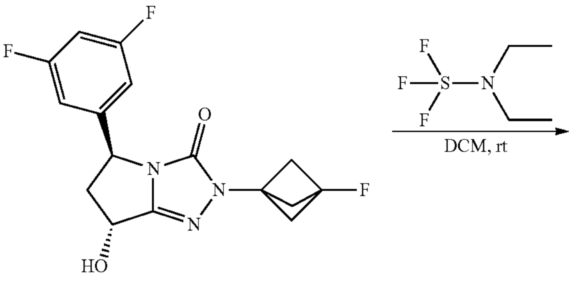

5-1

-continued

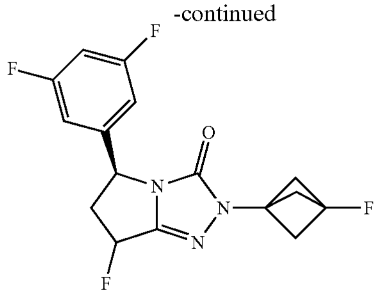

+

6-1

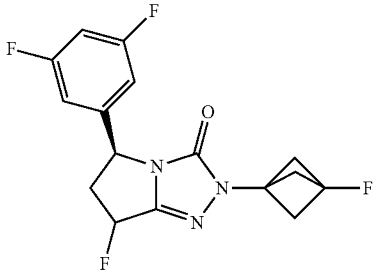

6-2

Diethylaminosulfur trifluoride (19.0 μL, 0.145 mmol) was added to a solution of 5-1 (24.5 mg, 0.073 mmol) in DCM (1450 μL) at 25° C. LCMS showed complete consumption of the starting material. The reaction was diluted with DCM and quenched with sat. sodium bicarbonate, extracted with DCM, dried over $Na_2SO_4$, filtered, and concentrated. The product was purified by flash column chromatography (ELSD, 12 g, gold silica gel, 40% EtOAc:Hex for peak 1 and 80% EtOAc:Hex for peak 2). The fractions were pooled and concentrated. Fraction one 6-1 (5S)-5-(3,5-difluorophenyl)-7-(S or R)-fluoro-2-(3-fluorobicyclo[1.1.1]pentan-1-yl)-2,5,6,7-tetrahydro-3H-pyrrolo[2,1-c][1,2,4]triazol-3-one and fraction two 6-2 (5S)-5-(3,5-difluorophenyl)-7-(S or R)-fluoro-2-(3-fluorobicyclo[1.1.1]pentan-1-yl)-2,5,6,7-tetrahydro-3H-pyrrolo[2,1-c][1,2,4]triazol-3-one were isolated.

(5S)-5-(3,5-difluorophenyl)-7-(S or R)-fluoro-2-(3-fluorobicyclo[1.1.1]pentan-1-yl)-2,5,6,7-tetrahydro-3H-pyrrolo[2,1-c][1,2,4]triazol-3-one (6-1)

$^1$H NMR (499 MHz, DMSO-$d_6$) δ 7.34-7.10 (m, 3H), 5.99 (dd, J=55.6, 5.9 Hz, 1H), 5.47 (t, J=7.1 Hz, 1H), 3.08 (ddd, J=22.7, 15.2, 6.9 Hz, 1H), 2.74 (ddt, J=32.7, 14.3, 6.6 Hz, 1H), 2.57 (s, 6H).

(5S)-5-(3,5-difluorophenyl)-7-(S or R)-fluoro-2-(3-fluorobicyclo[1.1.1]pentan-1-yl)-2,5,6,7-tetrahydro-3H-pyrrolo[2,1-c][1,2,4]triazol-3-one (6-2)

$^1$H NMR (499 MHz, DMSO-$d_6$) δ 7.23 (t, J=9.3 Hz, 1H), 7.04 (d, J=6.8 Hz, 2H), 5.92 (dd, J=55.5, 6.1 Hz, 1H), 5.34 (d, J=8.6 Hz, 1H), 3.50-3.30 (m, 1H), 2.63-2.49 (s, 7H).

TABLE 6

| Compound Number | Structure | Chemical Name | Mass [M + H]+ method |
|---|---|---|---|
| 6-1 | 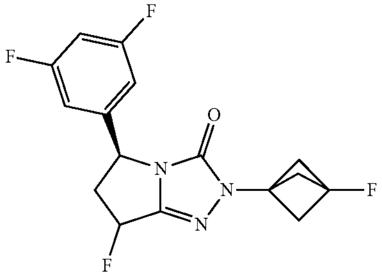 [SMILES: O=c1n(C23CC(F)(C2)C3)nc2n1[C@H](c1cc(F)cc(F)c1)CC2F] | (5S)-5-(3,5-difluorophenyl)-7-(S or R)-fluoro-2-(3-fluorobicyclo[1.1.1]pentan-1-yl)-2,5,6,7-tetrahydro-3H-pyrrolo[2,1-c][1,2,4]triazol-3-one | Calc'd 340, found 340; Ex.6.1 |
| 6-2 | 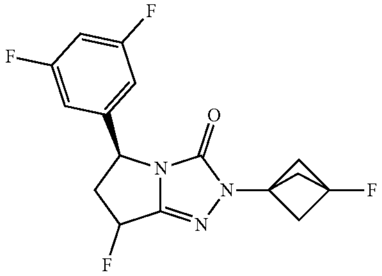 [SMILES: O=c1n(C23CC(F)(C2)C3)nc2n1[C@H](c1cc(F)cc(F)c1)CC2F] | (5S)-5-(3,5-difluorophenyl)-7-(S or R)-fluoro-2-(3-fluorobicyclo[1.1.1]pentan-1-yl)-2,5,6,7-tetrahydro-3H-pyrrolo[2,1-c][1,2,4]triazol-3-one | Calc'd 340, found 340; Ex.6.1 |

TABLE 6-continued

| Compound Number | Structure | Chemical Name | Mass [M + H]+ method |
| --- | --- | --- | --- |
| 6-3 | 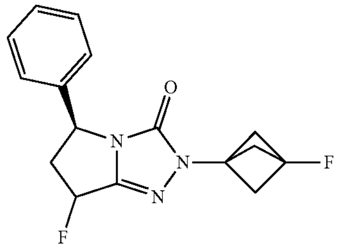 [SMILES: O=c1n(C23CC(F)(C2)C3)nc2n1[C@H](c1ccccc1)CC2F] | (5S)-7-(S or R)-fluoro-2-(3-fluorobicyclo[1.1.1]pentan-1-yl)-5-phenyl-2,5,6,7-tetrahydro-3H-pyrrolo[2,1-c][1,2,4]triazol-3-one | Calc'd 304, found 304; Ex.6.1 |
| 6-4 | 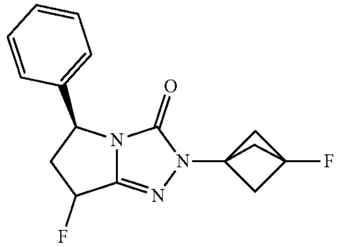 [SMILES: O=c1n(C23CC(F)(C2)C3)nc2n1[C@H](c1ccccc1)CC2F] | (5S)-7-(S or R)-fluoro-2-(3-fluorobicyclo[1.1.1]pentan-1-yl)-5-phenyl-2,5,6,7-tetrahydro-3H-pyrrolo[2,1-c][1,2,4]triazol-3-one | Calc'd 304, found 304; Ex.6.1 |
| 6-5 | 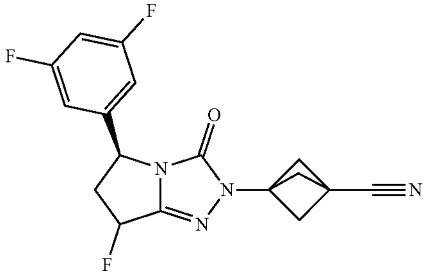 [SMILES: N#CC12CC(n3nc4n(c3=O)[C@H](c3cc(F)cc(F)c3)CC4F)(C1)C2] | 3-[(5S)-5-(3,5-difluorophenyl)-7-(S or R)-fluoro-3-oxo-6,7-dihydro-3H-pyrrolo[2,1-c][1,2,4]triazol-2(5H)-yl]bicyclo[1.1.1]pentane-1-carbonitrile | Calc'd 347, found 347; Ex.6.1 |
| 6-6 | 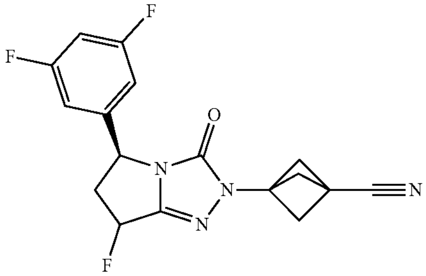 [SMILES: N#CC12CC(n3nc4n(c3=O)[C@H](c3cc(F)cc(F)c3)CC4F)(C1)C2] | 3-[(5S)-5-(3,5-difluorophenyl)-7-(S or R)-fluoro-3-oxo-6,7-dihydro-3H-pyrrolo[2,1-c][1,2,4]triazol-2(5H)-yl]bicyclo[1.1.1]pentane-1-carbonitrile | Calc'd 347, found 347; Ex.6.1 |
| 6-7 | 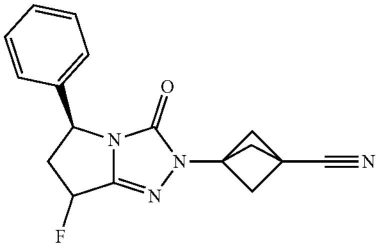 [SMILES: N#CC12CC(n3nc4n(c3=O)[C@H](c3ccccc3)CC4F)(C1)C2] | 3-[(5S)-7-(S or R)-fluoro-3-oxo-5-phenyl-6,7-dihydro-3H-pyrrolo[2,1-c][1,2,4]triazol-2(5H)-yl]bicyclo[1.1.1]pentane-1-carbonitrile | Calc'd 311, found 311; Ex.6.1 |

TABLE 6-continued

| Compound Number | Structure | Chemical Name | Mass [M + H]+ method |
|---|---|---|---|
| 6-8 | 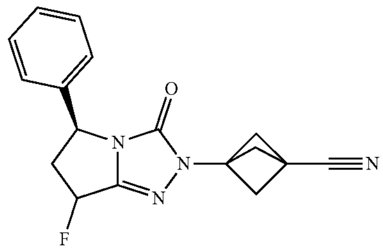 [SMILES: N#CC12CC(n3nc4n(c3=O)[C@H](c3ccccc3)CC4F)(C1)C2] | 3-[(5S)-7-(S or R)-fluoro-3-oxo-5-phenyl-6,7-dihydro-3H-pyrrolo[2,1-c][1,2,4]triazol-2(5H)-yl]bicyclo[1.1.1]pentane-1-carbonitrile | Calc'd 311, found 311; Ex.6.1 |
| 6-9 | 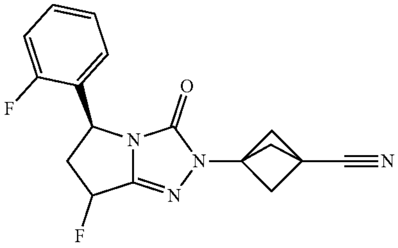 [SMILES: N#CC12CC(n3nc4n(c3=O)[C@H](c3ccccc3F)CC4F)(C1)C2] | 3-[(5S)-7-(S or R)-fluoro-5-(2-fluorophenyl)-3-oxo-6,7-dihydro-3H-pyrrolo[2,1-c][1,2,4]triazol-2(5H)-yl]bicyclo[1.1.1]pentane-1-carbonitrile | Calc'd 329, found 329; Ex.6.1 |
| 6-10 | 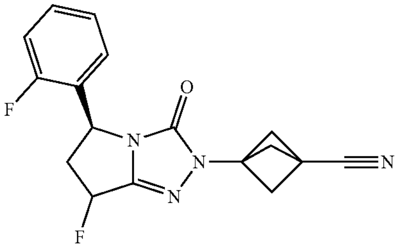 [SMILES: N#CC12CC(n3nc4n(c3=O)[C@H](c3ccccc3F)CC4F)(C1)C2] | 3-[(5S)-7-(S or R)-fluoro-5-(2-fluorophenyl)-3-oxo-6,7-dihydro-3H-pyrrolo[2,1-c][1,2,4]triazol-2(5H)-yl]bicyclo[1.1.1]pentane-1-carbonitrile | Calc'd 329, found 329; Ex.6.1 |

Example 7.1. Preparation of Compound 7-1

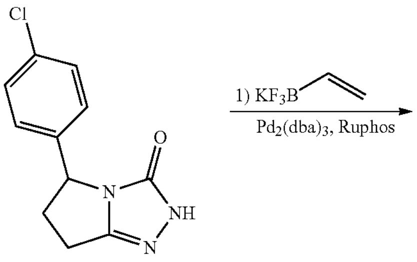

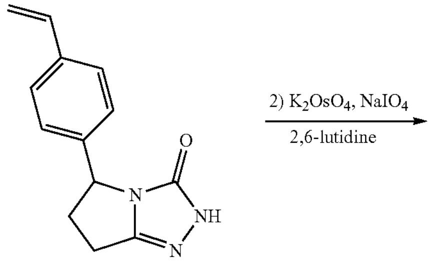

-continued

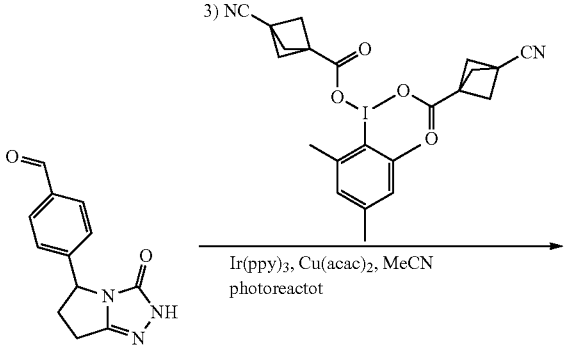

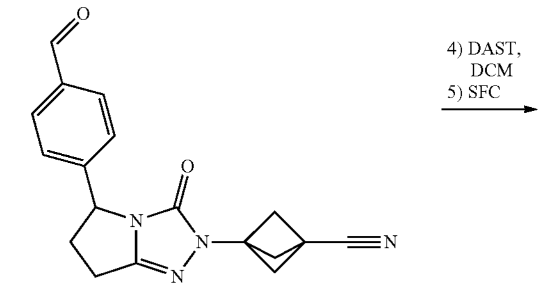

-continued

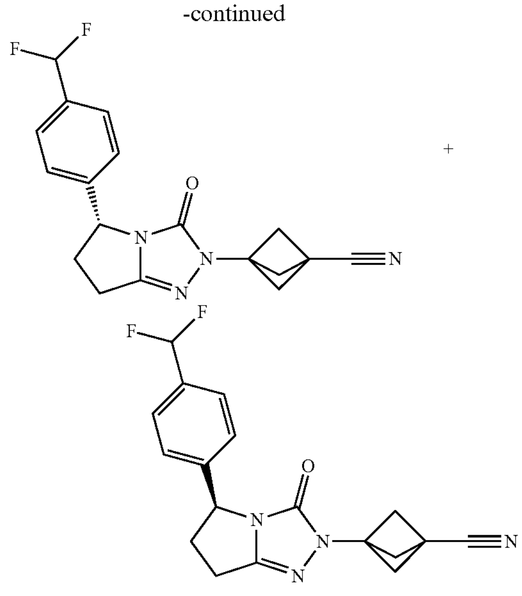

7-1

Step 1. Preparation of 5-(4-vinylphenyl)-2,5,6,7-tetrahydro-3H-pyrrolo[2,1-c][1,2,4]triazol-3-one To a solution of I-11A (2 g, 8.49 mmol), potassium vinyltrifluoroborate (1.364 g, 10.18 mmol), $Cs_2CO_3$ (8.30 g, 25.5 mmol), and RuPhos (0.792 g, 1.697 mmol) in 1,4-Dioxane (30 mL) and water (3 mL) was added $Pd_2(dba)_3$ (0.777 g, 0.849 mmol) under $N_2$. The resulting mixture was then heated to 100° C. and stirred for 12 h. The mixture was allowed to cool to room temperature. Water (40 mL) was added and the mixture was extracted with EtOAc (15 mL*3). The combined organic layers were washed with brine (30 mL), dried over $Na_2SO_4$, filtered and concentrated. The residue was purified by flash silica gel chromatography (ISCO®; 40 g SepaFlash® Silica Flash Column, eluent of 80% ethyl acetate/pet. ether gradient @ 35 mL/min) to give 5-(4-vinylphenyl)-2,5,6,7-tetrahydro-3H-pyrrolo[2,1-c][1,2,4]triazol-3-one. Calculated $C_{13}H_{14}N_3O$ $[M+H]^+$, 228; Found 228.

Step 2. Preparation of 4-(3-oxo-2,5,6,7-tetrahydro-3H-pyrrolo[2,1-c][1,2,4]triazol-5-yl)benzaldehyde To a solution of 5-(4-vinylphenyl)-2,5,6,7-tetrahydro-3H-pyrrolo[2,1-c][1,2,4]triazol-3-one (810 mg, 3.56 mmol) in 1,4-Dioxane (20 mL) and water (3.5 mL) was added 2,6-Lutidine (917 mg, 8.55 mmol), $K_2OsO_4$ (26.3 mg, 0.071 mmol), and $NaIO_4$ (3049 mg, 14.26 mmol). The resulting mixture was stirred at 20° C. for 2 h. Water (30 mL) was added to the reaction then the mixture was extracted with EtOAc (10 mL*3). The combined organic layers were washed with brine (20 mL), dried over $Na_2SO_4$, filtered and concentrated. The residue was purified by Prep-HPLC (Prep HPLC condition: Preparative HPLC on EM instrument fitted with Waters Xbridge BEH C18 100*40*10u using the mobile phase A-B: water (10 mM-NH4HCO3)-ACN, Gradient: 0-0% B, 0-11 min; 100% B, 11-13 min, 10% B, 13-15 min. FlowRate: 50 mL/min) to give 4-(3-oxo-2,5,6,7-tetrahydro-3H-pyrrolo[2,1-c][1,2,4]triazol-5-yl)benzaldehyde. Calculated $C_{12}H_{12}N_3O_2$ $[M+H]^+$, 230; Found 230.

Step 3. Preparation of 3-(5-(4-formylphenyl)-3-oxo-6,7-dihydro-3H-pyrrolo[2,1-c][1,2,4]triazol-2(5H)-yl)bicyclo[1.1.1]pentane-1-carbonitrile To a solution of 4-(3-oxo-2,5,6,7-tetrahydro-3H-pyrrolo[2,1-c][1,2,4]triazol-5-yl)benzaldehyde (130 mg, 0.567 mmol), mesityl-l3-iodanediyl bis(3-cyanobicyclo[1.1.1]pentane-1-carboxylate) (235 mg, 0.454 mmol), and copper (ii) acetylacetonate (74.2 mg, 0.284 mmol) in MeCN (20 mL) was added tris(2-phenylpyridine)iridium (7.43 mg, 0.011 mmol) under $N_2$. The resulting mixture was stirred for 2 h under 450 nm LED light irradiation. The reaction was filtered and the filtrate was purified by Prep-HPLC (Prep HPLC condition: Preparative HPLC on EJ instrument fitted with Boston Green ODS 150*30 mm*5 um using the mobile phase A-B: water (0.01% TFA)-ACN, Gradient: 28-58% B, 0-10 min; 100% B, 10-12 min, 10% B, 12-14 min. Flow-Rate: 25 mL/min) to give 3-(5-(4-formylphenyl)-3-oxo-6,7-dihydro-3H-pyrrolo[2,1-c][1,2,4]triazol-2(5H)-yl)bicyclo[1.1.1]pentane-1-carbonitrile. Calculated $C_{18}H_{17}N_4O_2$ $[M+H]^+$, 321; Found 321.

Steps 4-5. Preparation of 3-(5-(4-(difluoromethyl)phenyl)-3-oxo-6,7-dihydro-3H-pyrrolo[2,1-c][1,2,4]triazol-2(5H)-yl)bicyclo[1.1.1]pentane-1-carbonitrile followed by SFC to afford 7-1

To a solution of 3-(5-(4-formylphenyl)-3-oxo-6,7-dihydro-3H-pyrrolo[2,1-c][1,2,4]triazol-2(5H)-yl)bicyclo[1.1.1]pentane-1-carbonitrile (70 mg, 0.219 mmol) in DCM (2 mL) was added DAST (0.087 mL, 0.656 mmol) at 0° C. The resulting mixture was then stirred at 20° C. for 3 h. The mixture was quenched with sat. aq. $NaHCO_3$ (5 mL) and extracted with DCM (3 mL*2). The combined organic layers were washed with brine (5 mL), dried over $Na_2SO_4$, filtered and concentrated. The residue was purified by Prep-HPLC (Prep HPLC condition: Preparative HPLC on EJ instrument fitted with Boston Green ODS 150*30 mm*5 um using the mobile phase A-B: water (0.01% TFA)-ACN, Gradient: 39-69% B, 0-10 min; 100% B, 10-12 min, 10% B, 12-14 min. FlowRate: 25 mL/min) to give 3-(5-(4-(difluoromethyl)phenyl)-3-oxo-6,7-dihydro-3H-pyrrolo[2,1-c][1,2,4]triazol-2(5H)-yl)bicyclo[1.1.1]pentane-1-carbonitrile as a mixture of enantiomers. The enantiomers were resolved by Chiral-SFC (Instrument SFC-22 Method DAICEL CHIRALPAK AD (250 mm*30 mm, 10 um) Condition 40% EtOH to give (R)-3-(5-(4-(difluoromethyl)phenyl)-3-oxo-6,7-dihydro-3H-pyrrolo[2,1-c][1,2,4]triazol-2(5H)-yl)bicyclo[1.1.1]pentane-1-carbonitrile (retention time=1.047 min) and 7-1, (S)-3-(5-(4-(difluoromethyl)phenyl)-3-oxo-6,7-dihydro-3H-pyrrolo[2,1-c][1,2,4]triazol-2(5H)-yl)bicyclo[1.1.1]pentane-1-carbonitrile (retention time=1.206 min).

(R)-3-(5-(4-(difluoromethyl)phenyl)-3-oxo-6,7-dihydro-3H-pyrrolo[2,1-c][1,2,4]triazol-2(5H)-yl)bicyclo[1.1.1]pentane-1-carbonitrile $^1H$ NMR (400 MHz, $CDCl_3$) δ 7.54 (d, J=8.0 Hz, 2H), 7.31 (d, J=8.0 Hz, 2H), 6.46-6.82 (m, 1H), 6.46-6.82 (m, 1H), 5.18 (dd, J=4.4, 8.0 Hz, 1H), 2.96-3.07 (m, 1H), 2.78-2.96 (m, 2H), 2.74 (s, 6H), 2.46 (tdd, J=4.8, 8.4, 13.2 Hz, 1H)

(S)-3-(5-(4-(difluoromethyl)phenyl)-3-oxo-6,7-dihydro-3H-pyrrolo[2,1-c][1,2,4]triazol-2(5H)-yl)bicyclo[1.1.1]pentane-1-carbonitrile $^1H$ NMR (400 MHz, $CDCl_3$) δ 7.54 (d, J=8.4 Hz, 2H), 7.32 (d, J=8.0 Hz, 2H), 6.48-6.81 (m, 1H), 5.19 (dd, J=4.4, 8.0 Hz, 1H), 2.96-3.09 (m, 1H), 2.78-2.96 (m, 2H), 2.75 (s, 6H), 2.46 (tdd, J=4.8, 8.4, 13.2 Hz, 1H)

TABLE 7

| Compound Number | Structure | Chemical Name | Mass [M + H]+; Method |
|---|---|---|---|
| 7-1 | 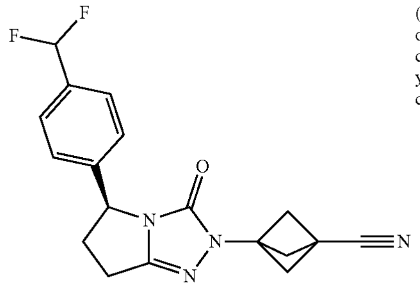 | (S)-3-(5-(4-(difluoromethyl)phenyl)-3-oxo-6,7-dihydro-3H-pyrrolo[2,1-c][1,2,4]triazol-2(5H)-yl)bicyclo[1.1.1]pentane-1-carbonitrile | Calc'd 343, found 343; Ex.7.1 |

RIPK1-ADP-Glo Enzymatic Assay

The enzymatic activity of RIPK1 is measured using an assay derived from ADP-Glo kit (TMPromega), which provides a luminescent-based ADP detection system. Specifically, the ADP generated by RIPK1 kinase is proportionally detected as luminescent signals in a homogenous fashion. In this context, the assessment of the inhibitory effect of small molecules (EC50) is measured by the effectiveness of the compounds to inhibit the ATP to ADP conversion by RIPK1.

In this assay, the potency ($EC_{50}$) of each compound was determined from a ten-point (1:3 serial dilution; top compound concentration of 100000 nM) titration curve using the following outlined procedure. To each well of a white ProxiPlus 384 well-plate, 30 nL of compound (1% DMSO in final assay volume of 3 μL) was dispensed, followed by the addition of 2 μL of 1× assay buffer (25 mM Hepes 7.3, 20 mM $MgCl_2$, 50 mM NaCl, 1 mM DTT, 0.005% Tween20, and 0.02% BSA) containing 37.5 nM of GST-RIPK1 (recombinant GST-RIPK1 kinase domain (residues 1-327) enzyme produced from baculovirus-transfected Sf21 cells: MW 62 kDa). Plates were placed in an ambient temperature humidified chamber for a 30 min pre-incubation with compound. Subsequently, each reaction was initiated by the addition of 1 μL 1× assay buffer containing 900 μM ATP and 3 μM dephosphorylated-MBP substrate. The final reaction in each well of 3 μL consists of 25 nM of GST-RIPK1, 300 μM ATP, and 3 μM dephosphorylated-MBP. Kinase reactions were allowed to proceed for 150 min prior to adding ADP-Glo reagents per Promega's outlined kit protocol. Dose-response curves were generated by plotting percent effect (% product conversion; Y-axis) vs. Log 10 compound concentrations (X-axis). $EC_{50}$ values were calculated using a non-linear regression, four-parameters sigmoidal dose-response model.

Potency Table

| Compound Number | RIPK1 $EC_{50}$ (nM) | Compound Number | RIPK1 $EC_{50}$ (nM) |
|---|---|---|---|
| 1-1 | 21.6 | 1-61 | 696.1 |
| 1-2 | 22.8 | 1-62 | 98.6 |
| 1-3 | 34.8 | 1-63 | 68.1 |
| 1-4 | 31.1 | 1-64 | 394.9 |
| 1-5 | 14.8 | 1-65 | 21.1 |
| 1-6 | 51.2 | 1-66 | 85.8 |
| 1-7 | 98.4 | 1-67 | 278.7 |
| 1-8 | 21.8 | 1-68 | 59.52 |
| 1-9 | 26.1 | 1-69 | 262.7 |
| 1-10 | 272 | 1-70 | 68.5 |

-continued

Potency Table

| Compound Number | RIPK1 $EC_{50}$ (nM) | Compound Number | RIPK1 $EC_{50}$ (nM) |
|---|---|---|---|
| 1-11 | 300 | 1-71 | 161.5 |
| 1-12 | 49.1 | 1-72 | 21.2 |
| 1-13 | 514 | 1-73 | 28.2 |
| 1-14 | 152 | 1-74 | 20.9 |
| 1-15 | 111 | 1-75 | 17.1 |
| 1-16 | 23.1 | 1-76 | 27.5 |
| 1-17 | 36.9 | 1-77 | 16.7 |
| 1-18 | 114 | 1-78 | 93.9 |
| 1-19 | 289 | 1-79 | 107.6 |
| 1-20 | 38.5 | 1-80 | 73.3 |
| 1-21 | 141 | 3-1 | 20.0 |
| 1-22 | 485 | 3-2 | 143.0 |
| 1-23 | 31.8 | 3-3 | 45.0 |
| 1-24 | 29.7 | 4-1 | 385 |
| 1-25 | 685 | 4-2 | 259 |
| 1-26 | 377 | 4-3 | 426 |
| 1-27 | 537 | 4-4 | 495 |
| 1-28 | 25.9 | 4-5 | 53.8 |
| 1-29 | 68.0 | 4-6 | 44.1 |
| 1-30 | 87.4 | 4-7 | 49.5 |
| 1-31 | 36.8 | 4-8 | 165 |
| 1-32 | 36.4 | 4-9 | 17.0 |
| 1-33 | 30.4 | 4-10 | 62.9 |
| 1-34 | 26.9 | 4-11 | 108 |
| 1-35 | 49.7 | 4-12 | 84.0 |
| 1-36 | 61.9 | 4-13 | 79.8 |
| 1-37 | 65.6 | 4-14 | 198 |
| 1-38 | 160 | 4-15 | 340.9 |
| 1-39 | 47.0 | 4-16 | 495.7 |
| 1-40 | 34.0 | 4-17 | 38.8 |
| 1-41 | 32.9 | 5-1 | 78.3 |
| 1-42 | 18.5 | 5-2 | 25.7 |
| 1-43 | 57.7 | 6-1 | 116 |
| 1-44 | 67.7 | 6-2 | 18.4 |
| 1-45 | 37.7 | 6-3 | 157 |
| 1-46 | 44.0 | 6-4 | 21.9 |
| 1-47 | 86.4 | 6-5 | 274 |
| 1-48 | 54.4 | 6-6 | 20.5 |
| 1-49 | 874 | 6-7 | 505 |
| 1-50 | 250 | 6-8 | 21.8 |
| 1-51 | 16.1 | 6-9 | 68.9 |
| 1-52 | 601 | 6-10 | 18.1 |
| 1-53 | 109 | 7-1 | 90.2 |
| 1-54 | 340 | | |
| 1-55 | 103 | | |
| 1-56 | 15.75 | | |
| 1-57 | 368.9 | | |
| 1-58 | 45.9 | | |
| 1-59 | 53.9 | | |
| 1-60 | 511.6 | | |

What is claimed is:

1. A compound of Formula I:

(I)

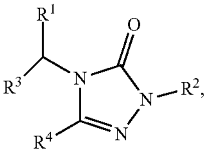

or a pharmaceutically acceptable salt thereof, wherein:

$R^1$ is selected from $C_3$-$C_6$cycloalkyl, aryl and heteroaryl, wherein each of the $C_3$-$C_6$cycloalkyl, aryl and heteroaryl is optionally substituted with one to four substituents independently selected from:

(1) halogen;

(2) —CN;

(3) —$C_1$-$C_6$alkyl, optionally substituted with one to four substituents independently selected from halogen and —CN;

(4) —$C_2$-$C_6$alkynyl;

(5) —$C_3$-$C_6$cycloalkyl;

(6) —O—$C_1$-$C_6$alkyl; and (7) —OH $R^2$ is selected from $C_3$-$C_{10}$cycloalkyl and heterocycloalkyl wherein each of the $C_3$-$C_{10}$cycloalkyl and heterocycloalkyl is optionally substituted with one to four substituents independently selected from:

(1) halogen;

(2) —CN;

(3) —$C_1$-$C_6$alkyl, optionally substituted with one to four substituents independently selected from halogen, —CN, —OH, —O—$C_1$-$C_6$alkyl, and a heteroaryl;

(4) —O—$C_1$-$C_6$alkyl, optionally substituted with one to four substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NR^bR^c$, wherein each of $R^b$ and $R^c$ is independently selected from hydrogen and —$C_1$-$C_6$alkyl optionally substituted with an heteroaryl; and (6) aryl, optionally substituted with one to three halogens; and $R^3$ and $R^4$ together with the atoms to which they are attached, form a 5- or 6-membered ring fused to the triazole ring, wherein the 5- or 6-membered ring optionally comprises additional heteroatoms selected from N, O, and S and is optionally substituted with one to four substituents independently selected from halogen, —OH, and —$C_1$-$C_6$alkyl.

2. The compound of claim 1, or a pharmaceutically acceptable salt thereof, wherein:

$R^1$ is selected from —$C_4$-$C_6$cycloalkyl, phenyl and heteroaryl, wherein the heteroaryl is selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl;

wherein the —$C_4$-$C_6$cycloalkyl, phenyl and heteroaryl is optionally substituted with one to three substituents selected from:

(1) halogen;

(2) —CN;

(3) —$CH_3$, optionally substituted with one to three substituents independently selected from halogen and —CN;

(4) —$CH_2CH_3$, optionally substituted with one to three substituents independently selected from halogen and —CN;

(5) ethynyl;

(6) cyclopropyl;

(7) —O—$CH_3$; and (8) —O—$CH_2CH_3$.

3. The compound of claim 1, or a pharmaceutically acceptable salt thereof, wherein:

$R^1$ is selected from cyclobutyl, cyclopentyl, cyclohexyl, phenyl, pyridyl, and pyrazinyl, wherein the cyclobutyl, cyclopentyl, phenyl, pyridyl, and pyrazinyl is optionally substituted with one to three substituents selected from:

(1) halogen;

(2) —CN;

(3) —$CH_3$, optionally substituted with one to three substituents independently selected from halogen and —CN;

(4) ethynyl;

(5) cyclopropyl; and (6) —O—$CH_3$.

4. The compound of claim 1, or a pharmaceutically acceptable salt thereof, wherein:

$R^1$ is phenyl, optionally substituted with one to three substituents selected from:

(1) halogen;

(2) —CN; and (3) —$CH_3$, optionally substituted with one to three substituents independently selected from halogen and —CN.

5. The compound of claim 1, or a pharmaceutically acceptable salt thereof, wherein:

$R^2$ is selected from $C_3$-$C_{10}$cycloalkyl and heterocycloalkyl wherein:

the $C_3$-$C_{10}$cycloalkyl is selected from

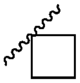, 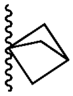, 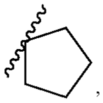, 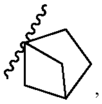, 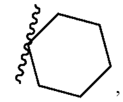, 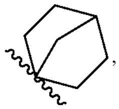, 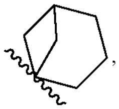, 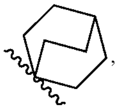, and 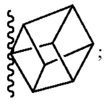;

the heterocycloalkyl is selected from

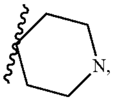, 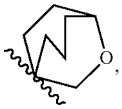, 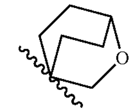, 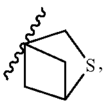, 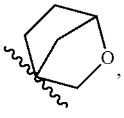, 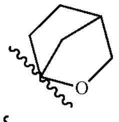, 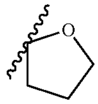, 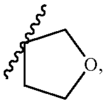, 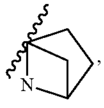, and 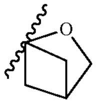;

wherein each of the $C_3$-$C_{10}$cycloalkyl and heterocycloalkyl is optionally substituted with one to three substituents independently selected from:

(1) halogen;

(2) —CN;

(3) —$C_1$-$C_4$alkyl, optionally substituted with one to three substituents independently selected from halogen, —CN, —OH, and —O—$C_1$-$C_4$alkyl;

(4) —O—$C_1$-$C_4$alkyl, optionally substituted with one to three substituents independently selected from halogen and —CN;

(5) —C(O)—$R^a$, wherein $R^a$ is selected from —OH, —$C_1$-$C_6$alkyl, —O—$C_1$-$C_6$alkyl, and —$NHR^c$, and $R^c$ is selected from hydrogen and —$C_1$-$C_4$alkyl optionally substituted with an heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl; and (6) phenyl, optionally substituted with one to three halogens.

6. The compound of claim 1, or a pharmaceutically acceptable salt thereof, wherein:

$R^2$ is selected from

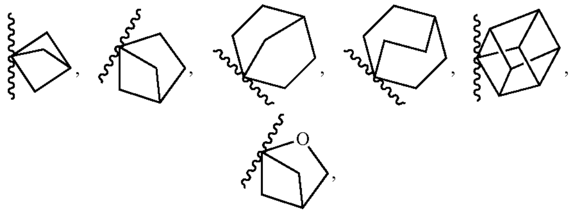

wherein each of the

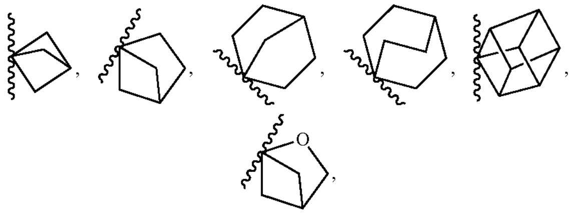

is optionally substituted with one to three substituents independently selected from:

(1) halogen;

(2) —CN;

(3) —$CH_3$, optionally substituted with one to three substituents independently selected from halogen, —CN, —OH and —O—$CH_3$;

(4) —O—$CH_3$, optionally substituted with one to three substituents independently selected from halogen and —CN;

(5) —C(O)—$R^a$, wherein $R^a$ is selected from —OH, —$CH_3$, —O—$CH_3$, and —$NHR^c$, wherein $R^c$ is selected from hydrogen and —$CH_3$ optionally substituted with a thienyl; and (6) phenyl, optionally substituted with one to three halogens.

7. The compound of claim 1, or a pharmaceutically acceptable salt thereof, wherein:

$R^2$ is

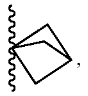

optionally substituted with one to three substituents independently selected from:

(1) halogen;

(2) —CN;

(3) —$CH_3$, optionally substituted with one to three substituents independently selected from halogen, —CN, —OH and —O—$CH_3$;

(4) —C(O)OMe;

(5) —C(O)—$NHCH_2$-thienyl; and (6) phenyl.

8. The compound of claim 1, or a pharmaceutically acceptable salt thereof, wherein: $R^3$ and $R^4$ together with the atoms to which they are attached, form a 5-membered aliphatic ring fused to the triazole ring, wherein the 5-membered aliphatic ring is optionally substituted with one to four substituents independently selected from halogen, —OH, —$CH_3$, —$CH_2CH_3$, and —$CH_2CH_2CH_3$.

9. The compound of claim 1 of Formula Ia:

(Ia)

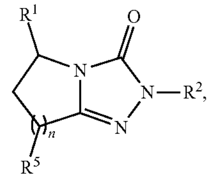

or a pharmaceutically acceptable salt thereof, wherein:

n is 1 or 2;

$R^1$ is selected from $C_3$-$C_6$cycloalkyl, aryl and heteroaryl, wherein each of the $C_3$-$C_6$cycloalkyl, aryl and heteroaryl is optionally substituted with one to three substituents independently selected from:

(1) halogen;

(2) —CN;

(3) —$C_1$-$C_6$alkyl, optionally substituted with one to four substituents independently selected from halogen and —CN;

(4) —$C_2$-$C_6$alkynyl;

(5) —$C_3$-$C_6$cycloalkyl; and (6) —O—$C_1$-$C_6$alkyl;

$R^2$ is selected from $C_3$-$C_{10}$cycloalkyl and heterocycloalkyl wherein each of the $C_3$-$C_{10}$cycloalkyl and heterocycloalkyl is optionally substituted with one to four substituents independently selected from:

(1) halogen;

(2) —CN;

(3) —$C_1$-$C_6$alkyl, optionally substituted with one to four substituents independently selected from halogen, —CN, —OH, —O—$C_1$-$C_6$alkyl, and a heteroaryl;

(4) —O—$C_1$-$C_6$alkyl, optionally substituted with one to four substituents independently selected from halogen and —CN;

(5) —C(O)—$R^a$, wherein $R^a$ is selected from —OH, —$C_1$-$C_6$alkyl, —O—$C_1$-$C_6$alkyl, and —$NR^bR^c$, wherein each of each of $R^b$ and $R^c$ is independently selected from hydrogen and —$C_1$-$C_6$alkyl optionally substituted with an heteroaryl; and (6) aryl, optionally substituted with one to three halogens; and each occurrence of $R^5$ is independently selected from hydrogen, halogen, —$C_1$-$C_6$alkyl and —OH.

10. The compound of claim 9, or a pharmaceutically acceptable salt thereof, wherein n is 1.

11. The compound of claim 10, or a pharmaceutically acceptable salt thereof, wherein:

$R^1$ is selected from —$C_4$-$C_6$cycloalkyl, phenyl and heteroaryl, wherein the heteroaryl is selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl;

wherein the —$C_4$-$C_6$cycloalkyl, phenyl and heteroaryl is optionally substituted with one to three substituents selected from:

(1) halogen;

(2) —CN;

(3) —$CH_3$, optionally substituted with one to three substituents independently selected from halogen and —CN;

(4) —$CH_2CH_3$, optionally substituted with one to three substituents independently selected from halogen and —CN;

(5) ethynyl;

(6) cyclopropyl;

(7) —O—$CH_3$; and (8) —O—$CH_2CH_3$.

12. The compound of claim 10, or a pharmaceutically acceptable salt thereof, wherein:

$R^1$ is selected from cyclobutyl, cyclopentyl, cyclohexyl, phenyl, pyridyl and pyrazinyl, wherein the cyclobutyl, cyclopentyl, cyclohexyl, phenyl, pyridyl and pyrazinyl is optionally substituted with one to three substituents selected from:

(1) halogen;

(2) —CN;

(3) —$CH_3$, optionally substituted with one to three substituents independently selected from halogen and —CN;

(4) ethynyl;

(5) cyclopropyl; and (6) —O—$CH_3$.

13. The compound of claim 10, or a pharmaceutically acceptable salt thereof, wherein:

$R^2$ is selected from $C_3$-$C_{10}$cycloalkyl and heterocycloalkyl wherein:

the $C_3$-$C_{10}$cycloalkyl is selected from

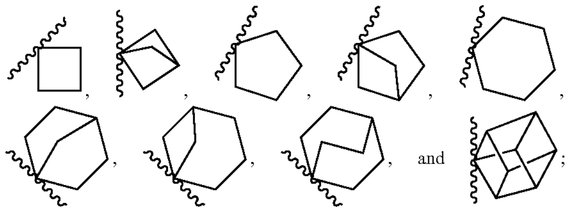

and the heterocycloalkyl is selected from

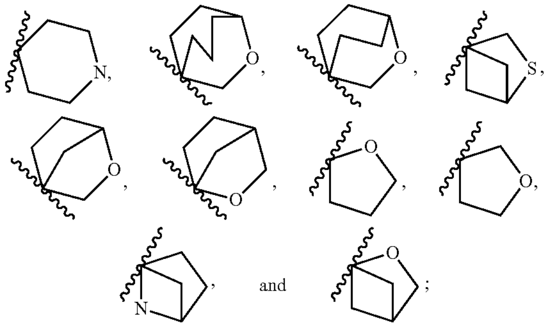

wherein each of the $C_3$-$C_{10}$cycloalkyl and heterocycloalkyl is optionally substituted with one to three substituents independently selected from:

(1) halogen;

(2) —CN;

(3) —$C_1$-$C_4$alkyl, optionally substituted with one to three substituents independently selected from halogen, —CN, —OH, and —O—$C_1$-$C_4$alkyl;

(4) —O—$C_1$-$C_4$alkyl, optionally substituted with one to four substituents independently selected from halogen and —CN;

(5) —C(O)—$R^a$, wherein is $R^a$ is selected from —OH, —$C_1$-$C_6$alkyl, —O—$C_1$-$C_6$alkyl, and —$NHR^c$, wherein $R^c$ is selected from hydrogen and —$C_1$-$C_4$alkyl optionally substituted with an heteroaryl selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl; and (6) phenyl, optionally substituted with one to three halogens.

14. The compound of claim 10, or a pharmaceutically acceptable salt thereof, wherein:

$R^2$ is selected from

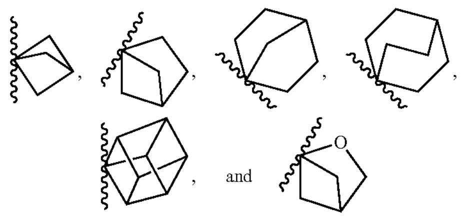

wherein each of the

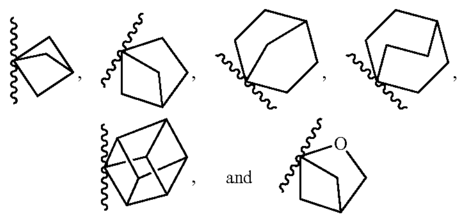

is optionally substituted with one to three substituents independently selected from:

(1) halogen;
(2) —CN;
(3) —$CH_3$, optionally substituted with one to three substituents independently selected from halogen, —CN, —OH and —O—$CH_3$;
(4) —O—$CH_3$, optionally substituted with one to three substituents independently selected from halogen and —CN;
(5) —C(O)—$R^a$, wherein is $R^a$ is selected from —OH, —$CH_3$, —O—$CH_3$, and —$NHR^c$; and $R^c$ is selected from hydrogen and —$CH_3$ optionally substituted with a thienyl; and
(6) phenyl, optionally substituted with one to three halogens.

15. The compound of claim 10, or a pharmaceutically acceptable salt thereof, wherein:

$R^1$ is selected from —$C_4$-$C_6$cycloalkyl, phenyl and heteroaryl, wherein the heteroaryl is selected from pyridyl, oxazolyl, imidazolyl, triazolyl, furyl, triazinyl, thienyl, pyrimidyl, pyrazinyl, pyridazinyl, indolizinyl, cinnolinyl, phthalazinyl, quinazolinyl, naphthyridinyl, quinoxalinyl, purinyl, benzimidazolyl, quinolyl and isoquinolyl;

wherein the —$C_4$-$C_6$cycloalkyl, phenyl and heteroaryl is optionally substituted with one to three substituents selected from:
(1) halogen;
(2) —CN;
(3) —$CH_3$, optionally substituted with one to three substituents independently selected from halogen and —CN;
(4) —$CH_2CH_3$, optionally substituted with one to three substituents independently selected from halogen and —CN;
(5) ethynyl;
(6) cyclopropyl;
(7) —O—$CH_3$; and
(8) —O—$CH_2CH_3$;

$R^2$ is selected from

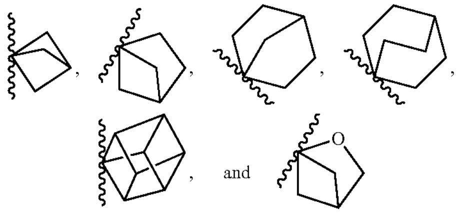

, , , , , and wherein each of the

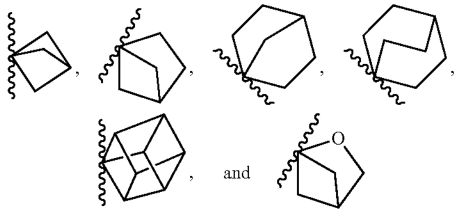

, , , , , and is optionally substituted with one to three substituents independently selected from:
(1) halogen;
(2) —CN;

(3) —$CH_3$, optionally substituted with one to three substituents independently selected from halogen, —CN, —OH and —O—$CH_3$;
(4) —O—$CH_3$, optionally substituted with one to three substituents independently selected from halogen and —CN;
(5) —C(O)—$R^a$, wherein is $R^a$ is selected from —OH, —$CH_3$, —O—$CH_3$, and —$NHR^c$; and $R^c$ is selected from hydrogen and —$CH_3$ optionally substituted with a thienyl; and
(6) phenyl, optionally substituted with one to three halogens; and $R^5$ is selected from hydrogen, halogen, —$C_1$-$C_4$alkyl and —OH.

16. The compound of claim 10, or a pharmaceutically acceptable salt thereof, wherein:

$R^1$ is phenyl, optionally substituted with one to three substituents selected from:
(1) halogen;
(2) —CN;
(3) —$CH_3$, optionally substituted with one to three substituents independently selected from halogen and —CN;
(4) cyclopropyl; and
(5) —O—$CH_3$;

$R^2$ is

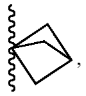

, optionally substituted with one to three substituents independently selected from:
(1) halogen;
(2) —CN; and
(3) —$CH_3$, optionally substituted with one to three substituents independently selected from halogen, —CN, —OH and —O—$CH_3$; and $R^5$ is selected from hydrogen, halogen, —$CH_3$, and —OH.

17. The compound of claim 1 of Formula Ib:

(Ib)

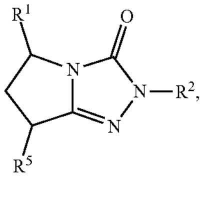

or a pharmaceutically acceptable salt thereof, wherein:

$R^1$ is selected from $C_3$-$C_6$cycloalkyl, phenyl and heteroaryl, wherein each of the $C_3$-$C_6$cycloalkyl, phenyl and heteroaryl is optionally substituted with one to three substituents independently selected from:
(1) halogen;
(2) —CN;
(3) —$C_1$-$C_6$alkyl, optionally substituted with one to three substituents independently selected from halogen and —CN;
(4) —$C_2$-$C_6$alkynyl;
(5) —$C_3$-$C_6$cycloalkyl; and
(6) —O—$C_1$-$C_6$alkyl;

$R^2$ is selected from $C_3$-$C_{10}$cycloalkyl and heterocycloalkyl, wherein each of the $C_3$-$C_{10}$cycloalkyl and heterocycloalkyl is optionally substituted with one to three substituents independently selected from:

(1) halogen;

(2) —CN;

(3) —$C_1$-$C_6$alkyl, optionally substituted with one to three substituents independently selected from halogen, —CN, —OH, and —O—$C_1$-$C_6$alkyl;

(4) —O—$C_1$-$C_6$alkyl, optionally substituted with one to three substituents independently selected from halogen and —CN;

(5) —C(O)—$R^a$, wherein $R^a$ is selected from —OH, —$C_1$-$C_6$alkyl, —O—$C_1$-$C_6$alkyl, and —$NR^bR^c$, wherein each of $R^b$ and $R^c$ is independently selected from hydrogen and —$C_1$-$C_6$alkyl optionally substituted with an heteroaryl; and (6) aryl, optionally substituted with one to three halogens; and $R^5$ is selected from hydrogen, halogen, —$C_1$-$C_6$alkyl and —OH.

18. The compound of claim 17, or a pharmaceutically acceptable salt thereof, wherein:

$R^1$ is phenyl, substituted with one to three substituents selected from:

(1) halogen;

(2) —CN;

(3) —$CH_3$, optionally substituted with one to three substituents independently selected from halogen and —CN;

(4) cyclopropyl; and (5) —O—$CH_3$;

$R^2$ is

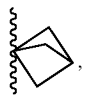, substituted with one to three substituents independently selected from:

(1) halogen;

(2) —CN;

(3) —$CH_3$, optionally substituted with one to three substituents independently selected from halogen, —CN, —OH and —O—$CH_3$;

(4) —C(O)O—$CH_3$;

(5) —C(O)—$NHCH_2$-thienyl; and (6) phenyl; and $R^5$ is hydrogen.

19. The compound of claim 1, or a pharmaceutically acceptable salt thereof, selected from:

(5S)-2-(bicyclo[2.2.1]heptan-1-yl)-5-phenyl-2,5,6,7-tetrahydro-3H-pyrrolo[2,1-c][1,2,4]triazol-3-one, (5S)-5-(3,5-difluorophenyl)-2-(3-fluorobicyclo[1.1.1]pentan-1-yl)-2,5,6,7-tetrahydro-3H-pyrrolo[2,1-c][1,2,4]triazol-3-one, (5S)-5-(3,5-difluorophenyl)-2-(4-fluorobicyclo[2.2.1]heptan-1-yl)-2,5,6,7-tetrahydro-3H-pyrrolo[2,1-c][1,2,4]triazol-3-one, (5S)-2-(bicyclo[2.1.1]hexan-1-yl)-5-(3,5-difluorophenyl)-2,5,6,7-tetrahydro-3H-pyrrolo[2,1-c][1,2,4]triazol-3-one, 3-[(5S)-5-(3,5-difluorophenyl)-3-oxo-6,7-dihydro-3H-pyrrolo[2,1-c][1,2,4]triazol-2(5H)-yl]bicyclo[1.1.1]pentane-1-carbonitrile, (5S)-2-(3-fluorobicyclo[1.1.1]pentan-1-yl)-5-phenyl-2,5,6,7-tetrahydro-3H-pyrrolo[2,1-c][1,2,4]triazol-3-one, (5S)-2-(bicyclo[1.1.1]pentan-1-yl)-5-(3,5-difluorophenyl)-2,5,6,7-tetrahydro-3H-pyrrolo[2,1-c][1,2,4]triazol-3-one, (5S)-2-(3-chlorobicyclo[1.1.1]pentan-1-yl)-5-(3,5-difluorophenyl)-2,5,6,7-tetrahydro-3H-pyrrolo[2,1-c][1,2,4]triazol-3-one, (5S)-2-(3-fluorobicyclo[1.1.1]pentan-1-yl)-5-(2-fluorophenyl)-2,5,6,7-tetrahydro-3H-pyrrolo[2,1-c][1,2,4]triazol-3-one, (5S)-2-(3-fluorobicyclo[1.1.1]pentan-1-yl)-5-(5-fluoropyridin-3-yl)-2,5,6,7-tetrahydro-3H-pyrrolo[2,1-c][1,2,4]triazol-3-one, 3-[(5S)-5-(5-fluoropyridin-3-yl)-3-oxo-6,7-dihydro-3H-pyrrolo[2,1-c][1,2,4]triazol-2(5H)-yl]bicyclo[1.1.1]pentane-1-carbonitrile, (5S)-5-(3,5-difluorophenyl)-2-(3-phenylbicyclo[1.1.1]pentan-1-yl)-2,5,6,7-tetrahydro-3H-pyrrolo[2,1-c][1,2,4]triazol-3-one, (5S)-5-(5-fluoropyridin-3-yl)-2-(3-phenylbicyclo[1.1.1]pentan-1-yl)-2,5,6,7-tetrahydro-3H-pyrrolo[2,1-c][1,2,4]triazol-3-one, (5S)-5-(3,5-difluorophenyl)-2-(1-methyl-2-oxabicyclo[2.1.1]hexan-4-yl)-2,5,6,7-tetrahydro-3H-pyrrolo[2,1-c][1,2,4]triazol-3-one, (5S)-2-(3-chlorobicyclo[1.1.1]pentan-1-yl)-5-(5-fluoropyridin-3-yl)-2,5,6,7-tetrahydro-3H-pyrrolo[2,1-c][1,2,4]triazol-3-one, (S)-2-(3-fluorobicyclo[1.1.1]pentan-1-yl)-5-(3-fluorophenyl)-2,5,6,7-tetrahydro-3H-pyrrolo[2,1-c][1,2,4]triazol-3-one, 3-[(5S)-3-oxo-5-phenyl-6,7-dihydro-3H-pyrrolo[2,1-c][1,2,4]triazol-2(5H)-yl]bicyclo[1.1.1]pentane-1-carbonitrile, methyl 3-[(5S)-5-(3,5-difluorophenyl)-3-oxo-6,7-dihydro-3H-pyrrolo[2,1-c][1,2,4]triazol-2(5H)-yl]bicyclo[1.1.1]pentane-1-carboxylate, methyl 3-[(5S)-3-oxo-5-phenyl-6,7-dihydro-3H-pyrrolo[2,1-c][1,2,4]triazol-2(5H)-yl]bicyclo[1.1.1]pentane-1-carboxylate, (5S)-5-(3,5-difluorophenyl)-2-(-4-fluoropentacyclo[4.2.0.0]-octan-1-yl)-2,5,6,7-tetrahydro-3H-pyrrolo[2,1-c][1,2,4]triazol-3-one, 4-[(5S)-5-(3,5-difluorophenyl)-3-oxo-6,7-dihydro-3H-pyrrolo[2,1-c][1,2,4]triazol-2(5H)-yl]pentacyclo[4.2.0.0]octane-1-carbonitrile, (S)-3-(5-(5-chloropyridin-3-yl)-3-oxo-6,7-dihydro-3H-pyrrolo[2,1-c][1,2,4]triazol-2(5H)-yl)bicyclo[1.1.1]pentane-1-carbonitrile, 3-[(5S)-5-(2-fluorophenyl)-3-oxo-6,7-dihydro-3H-pyrrolo[2,1-c][1,2,4]triazol-2(5H)-yl]bicyclo[1.1.1]pentane-1-carbonitrile, (S)-3-(5-(3-fluorophenyl)-3-oxo-6,7-dihydro-3H-pyrrolo[2,1-c][1,2,4]triazol-2(5H)-yl)bicyclo[1.1.1]pentane-1-carbonitrile, (5S)-2-(bicyclo[2.2.2]octan-1-yl)-5-(3,5-difluorophenyl)-2,5,6,7-tetrahydro-3H-pyrrolo[2,1-c][1,2,4]triazol-3-one, (5S)-5-(3,5-difluorophenyl)-2-(4-methoxybicyclo[2.2.1]heptan-1-yl)-2,5,6,7-tetrahydro-3H-pyrrolo[2,1-c][1,2,4]triazol-3-one, (5S)-2-[4-(difluoromethyl)bicyclo[2.2.1]heptan-1-yl]-5-(3,5-difluorophenyl)-2,5,6,7-tetrahydro-3H-pyrrolo[2,1-c][1,2,4]triazol-3-one, (5S)-2-[3-(difluoromethyl)bicyclo[1.1.1]pentan-1-yl]-5-(3,5-difluorophenyl)-2,5,6,7-tetrahydro-3H-pyrrolo[2,1-c][1,2,4]triazol-3-one, 4-[(5S)-5-(3,5-difluorophenyl)-3-oxo-6,7-dihydro-3H-pyrrolo[2,1-c][1,2,4]triazol-2(5H)-yl]bicyclo[2.2.1]heptane-1-carbonitrile, 4-[(5S)-3-oxo-5-phenyl-6,7-dihydro-3H-pyrrolo[2,1-c][1,2,4]triazol-2(5H)-yl]bicyclo[2.2.1]heptane-1-carbonitrile, (5S)-2-[3-(difluoromethyl)bicyclo[1.1.1]pentan-1-yl]-5-phenyl-2,5,6,7-tetrahydro-3H-pyrrolo[2,1-c][1,2,4]triazol-3-one, (5S)-2-[3-(1,1-difluoroethyl)bicyclo[1.1.1]pentan-1-yl]-5-phenyl-2,5,6,7-tetrahydro-3H-pyrrolo[2,1-c][1,2,4]triazol-3-one, (5S)-2-[3-(difluoromethyl)bicyclo[1.1.1]pentan-1-yl]-5-(3-fluorophenyl)-2,5,6,7-tetrahydro-3H-pyrrolo[2,1-c][1,2,4]triazol-3-one, (5S)-2-[3-(1,1-difluoroethyl)bicyclo[1.1.1]pentan-1-yl]-5-(3-fluorophenyl)-2,5,6,7-tetrahydro-3H-pyrrolo[2,1-c][1,2,4]triazol-3-one, 4-[(5S)-5-(3,5-difluorophenyl)-3-oxo-6,7-dihydro-3H-pyrrolo[2,1-c][1,2,4]triazol-2(5H)-yl]bicyclo[2.1.1]hexane-1-carbonitrile, methyl 3-[(5S)-5-(3,5-difluorophenyl)-3-oxo-6,7-dihydro-3H-pyrrolo[2,1-c][1,2,4]triazol-2(5H)-yl]-2,2-difluorobicyclo[1.1.1]pentane-1-carboxylate, (5S)-2-(3-fluorobicyclo[1.1.1]pentan-1-yl)-5-(4-fluorophenyl)-2,5,6,7-tetrahydro-3H-pyrrolo[2,1-c][1,2,4]triazol-3-one, 3-[(5S)-5-(4-fluorophenyl)-3-oxo-6,7-dihydro-3H-pyrrolo[2,1-c][1,2,4]triazol-2(5H)-yl]bicyclo[1.1.1]pentane-1-carbonitrile, 4-[(5S)-3-oxo-5-phenyl-6,7-dihydro-3H-pyrrolo[2,1-c][1,2,4]triazol-2(5H)-yl]bicyclo[2.1.1]hexane-1-carbonitrile, (S)-5-(2,6-difluorophenyl)-2-(3-fluorobicyclo[1.1.1]pentan-1-yl)-2,5,6,7-tetrahydro-3H-pyrrolo[2,1-c][1,2,4]triazol-3-one, (5S)-2-(3-chlorobicyclo[1.1.1]pentan-1-yl)-5-phenyl-2,5,6,7-tetrahydro-3H-pyrrolo[2,1-c][1,2,4]triazol-3-one, (S)-2-(3-chlorobicyclo[1.1.1]pentan-1-yl)-5-(3-fluorophenyl)-2,5,6,7-tetrahydro-3H-pyrrolo[2,1-c][1,2,4]triazol-3-one, (S)-3-(5-(2,6-difluorophenyl)-3-oxo-6,7-dihydro-3H-pyrrolo[2,1-c][1,2,4]triazol-2(5H)-yl)bicyclo[1.1.1]pentane-1-carbonitrile, (S)-3-(5-(3,4-difluorophenyl)-3-oxo-6,7-dihydro-3H-pyrrolo[2,1-c][1,2,4]triazol-2(5H)-yl)bicyclo[1.1.1]pentane-1-carbonitrile, (S)-5-(4-chlorophenyl)-2-(3-fluorobicyclo[1.1.1]pentan-1-yl)-2,5,6,7-tetrahydro-3H-pyrrolo[2,1-c][1,2,4]triazol-3-one, (S)-3-(5-(4-chlorophenyl)-3-oxo-6,7-dihydro-3H-pyrrolo[2,1-c][1,2,4]triazol-2(5H)-yl)bicyclo[1.1.1]pentane-1-carbonitrile, (S)-3-(5-(2,4-difluorophenyl)-3-oxo-6,7-dihydro-3H-pyrrolo[2,1-c][1,2,4]triazol-2(5H)-yl)bicyclo[1.1.1]pentane-1-carbonitrile, (S)-5-(2,4-difluorophenyl)-2-(3-fluorobicyclo[1.1.1]pentan-1-yl)-2,5,6,7-tetrahydro-3H-pyrrolo[2,1-c][1,2,4]triazol-3-one, (S)-3-(3-oxo-5-(3-(trifluoromethyl)phenyl)-6,7-dihydro-3H-pyrrolo[2,1-c][1,2,4]triazol-2(5H)-yl)bicyclo[1.1.1]pentane-1-carbonitrile, (S)-3-(3-oxo-5-(4-(trifluoromethyl)phenyl)-6,7-dihydro-3H-pyrrolo[2,1-c][1,2,4]triazol-2(5H)-yl)bicyclo[1.1.1]pentane-1-carbonitrile, (S)-3-(5-(3,5-difluoro-4-methylphenyl)-3-oxo-6,7-dihydro-3H-pyrrolo[2,1-c][1,2,4]triazol-2(5H)-yl)bicyclo[1.1.1]pentane-1-carbonitrile, 3-[5-(S)-(3,5-difluorophenyl)-6-(S)-methyl-3-oxo-6,7-dihydro-3H-pyrrolo[2,1-c][1,2,4]triazol-2(5H)-yl]bicyclo[1.1.1]pentane-1-carbonitrile, 3-[5-(R)-(3,5-difluorophenyl)-6-(R)-methyl-3-oxo-6,7-dihydro-3H-pyrrolo[2,1-c][1,2,4]triazol-2(5H)-yl]bicyclo[1.1.1]pentane-1-carbonitrile, 3-[5-(S)-(3,5-difluorophenyl)-6-(R)-methyl-3-oxo-6,7-dihydro-3H-pyrrolo[2,1-c][1,2,4]triazol-2(5H)-yl]bicyclo[1.1.1]pentane-1-carbonitrile, 3-[5-(R)-(3,5-difluorophenyl)-6-(S)-methyl-3-oxo-6,7-dihydro-3H-pyrrolo[2,1-c][1,2,4]triazol-2(5H)-yl]bicyclo[1.1.1]pentane-1-carbonitrile, (S)-3-(5-(3,5-difluorophenyl)-3-oxo-5,6,7,8-tetrahydro-[1,2,4]triazolo[4,3-a]pyridin-2(3H)-yl)bicyclo[1.1.1]pentane-1-carbonitrile, 3-(5-(S)-cyclopentyl-3-oxo-6,7-dihydro-3H-pyrrolo[2,1-c][1,2,4]triazol-2 (5H)-yl) bicyclo[1.1.1]pentane-1-carbonitrile, 3-(5-(R)-cyclopentyl-3-oxo-6,7-dihydro-3H-pyrrolo[2,1-c][1,2,4]triazol-2(5H)-yl) bicyclo[1.1.1]pentane-1-carbonitrile, 3-(5-(S)-cyclohexyl-3-oxo-6,7-dihydro-3H-pyrrolo[2,1-c][1,2,4]triazol-2(5H)-yl) bicyclo[1.1.1]pentane-1-carbonitrile, 3-(5-(R)-cyclohexyl-3-oxo-6,7-dihydro-3H-pyrrolo[2,1-c][1,2,4]triazol-2(5H)-yl) bicyclo[1.1.1]pentane-1-carbonitrile, (5S)-5-(3,5-difluorophenyl)-2-[3-(methoxymethyl)bicyclo[1.1.1]pentan-1-yl]-2,5,6,7-tetrahydro-3H-pyrrolo[2,1-c][1,2,4]triazol-3-one, 3-[(5S)-5-(3,5-difluorophenyl)-3-oxo-6,7-dihydro-3H-pyrrolo[2,1-c][1,2,4]triazol-2(5H)-yl]-N-[(thiophen-2-yl)methyl]bicyclo[1.1.1]pentane-1-carboxamide, 3-[(5S)-5-(3,5-difluorophenyl)-3-oxo-6,7-dihydro-3H-pyrrolo[2,1-c][1,2,4]triazol-2(5H)-yl]-N-[(thiophen-3-yl)methyl]bicyclo[1.1.1]pentane-1-carboxamide, (S)-2-(3-(5-(3,5-difluorophenyl)-3-oxo-6,7-dihydro-3H-pyrrolo[2,1-c][1,2,4]triazol-2(5H)-yl)bicyclo[1.1.1]pentan-1-yl)acetonitrile, (5S)-2-(3-acetylbicyclo[1.1.1]pentan-1-yl)-5-(3,5-difluorophenyl)-2,5,6,7-tetrahydro-3H-pyrrolo[2,1-c][1,2,4]triazol-3-one, 3-[(5S)-5-(3,5-difluorophenyl)-3-oxo-6,7-dihydro-3H-pyrrolo[2,1-c][1,2,4]triazol-2(5H)-yl]-2,2-difluorobicyclo[1.1.1]pentane-1-carbonitrile, 2,2-difluoro-3-[(5S)-3-oxo-5-phenyl-6,7-dihydro-3H-pyrrolo[2,1-c][1,2,4]triazol-2(5H)-yl]bicyclo[1.1.1]pentane-1-carbonitrile, (±)-3-(3-oxo-5-(pyrazin-2-yl)-6,7-dihydro-3H-pyrrolo[2,1-c][1,2,4]triazol-2(5H)-yl)bicyclo[1.1.1]pentane-1-carbonitrile, (±)-2-(3-fluorobicyclo[1.1.1]pentan-1-yl)-5-(3-fluoro-5-methoxyphenyl)-2,5,6,7-tetrahydro-3H-pyrrolo[2,1-c][1,2,4]triazol-3-one, (±)-3-[2-(3-fluorobicyclo[1.1.1]pentan-1-yl)-3-oxo-2,5,6,7-tetrahydro-3H-pyrrolo[2,1-c][1,2,4]triazol-5-yl]benzonitrile, (±)-5-(3-ethynylphenyl)-2-(3-fluorobicyclo[1.1.1]pentan-1-yl)-2,5,6,7-tetrahydro-3H-pyrrolo[2,1-c][1,2,4]triazol-3-one, (±)-5-(2,3-difluorophenyl)-2-(3-fluorobicyclo[1.1.1]pentan-1-yl)-2,5,6,7-tetrahydro-3H-pyrrolo[2,1-c][1,2,4]triazol-3-one, (±)-2-(3-fluorobicyclo[1.1.1]pentan-1-yl)-5-(3-fluoro-5-methylphenyl)-2,5,6,7-tetrahydro-3H-pyrrolo[2,1-c][1,2,4]triazol-3-one, (S)-3-(3-oxo-5-(p-tolyl)-6,7-dihydro-3H-pyrrolo[2,1-c][1,2,4]triazol-2(5H)-yl)bicyclo[1.1.1]pentane-1-carbonitrile, (S)-3-(3-oxo-5-(pyrazin-2-yl)-6,7-dihydro-3H-pyrrolo[2,1-c][1,2,4]triazol-2(5H)-yl)bicyclo[1.1.1]pentane-1-carbonitrile, (S)-5-(3-fluoro-5-methylphenyl)-2-(3-fluorobicyclo[1.1.1]pentan-1-yl)-2,5,6,7-tetrahydro-3H-pyrrolo[2,1-c][1,2,4]triazol-3-one, (S)-5-(4-(difluoromethyl)phenyl)-2-(3-fluorobicyclo[1.1.1]pentan-1-yl)-2,5,6,7-tetrahydro-3H-pyrrolo[2,1-c][1,2,4]triazol-3-one, (S)-5-(4-cyclopropylphenyl)-2-(3-fluorobicyclo[1.1.1]pentan-1-yl)-2,5,6,7-tetrahydro-3H-pyrrolo[2,1-c][1,2,4]triazol-3-one, (S)-2-(3-fluorobicyclo[1.1.1]pentan-1-yl)-5-(pyrazin-2-yl)-2,5,6,7-tetrahydro-3H-pyrrolo[2,1-c][1,2,4]triazol-3-one, (S)-2-(3-fluorobicyclo[1.1.1]pentan-1-yl)-5-(6-methylpyrazin-2-yl)-2,5,6,7-tetrahydro-3H-pyrrolo[2,1-c][1,2,4]triazol-3-one, (S)-2-(3-fluorobicyclo[1.1.1]pentan-1-yl)-5-(5-methylpyrazin-2-yl)-2,5,6,7-tetrahydro-3H-pyrrolo[2,1-c][1,2,4]triazol-3-one, (5S,7R)-5-(3,5-difluorophenyl)-2-(3-fluorobicyclo[1.1.1]pentan-1-yl)-7-hydroxy-2,5,6,7-tetrahydro-3H-pyrrolo[2,1-c][1,2,4]triazol-3-one, (5S,7S)-5-(3,5-difluorophenyl)-2-(3-fluorobicyclo[1.1.1]pentan-1-yl)-7-hydroxy-2,5,6,7-tetrahydro-3H-pyrrolo[2,1-c][1,2,4]triazol-3-one, (5S)-5-(3,5-difluorophenyl)-7-(S)-fluoro-2-(3-fluorobicyclo[1.1.1]pentan-1-yl)-2,5,6,7-tetrahydro-3H-pyrrolo[2,1-c][1,2,4]triazol-3-one, (5S)-5-(3,5-difluorophenyl)-7-(R)-fluoro-2-(3-fluorobicyclo[1.1.1]pentan-1-yl)-2,5,6,7-tetrahydro-3H-pyrrolo[2,1-c][1,2,4]triazol-3-one, (5S)-5-(3,5-difluorophenyl)-7-(S)-fluoro-2-(3-fluorobicyclo[1.1.1]pentan-1-yl)-2,5,6,7-tetrahydro-3H-pyrrolo[2,1-c][1,2,4]triazol-3-one, (5S)-5-(3,5-difluorophenyl)-7-(R)-fluoro-2-(3-fluorobicyclo[1.1.1]pentan-1-yl)-2,5,6,7-tetrahydro-3H-pyrrolo[2,1-c][1,2,4]triazol-3-one, (5S)-7-(S)-fluoro-2-(3-fluorobicyclo[1.1.1]pentan-1-yl)-5-phenyl-2,5,6,7-tetrahydro-3H-pyrrolo[2,1-c][1,2,4]triazol-3-one, (5S)-7-(R)-fluoro-2-(3-fluorobicyclo[1.1.1]pentan-1-yl)-5-phenyl-2,5,6,7tetrahydro-3H-pyrrolo[2,1-c][1,2,4]triazol-3-one, (5S)-7-(S)-fluoro-2-(3-fluorobicyclo[1.1.1]pentan-1-yl)-5-phenyl-2,5,6,7-tetrahydro-3H-pyrrolo[2,1-c][1,2,4]triazol-3-one, (5S)-7-(R)-fluoro-2-(3-fluorobicyclo[1.1.1]pentan-1-yl)-5-phenyl-2,5,6,7-tetrahydro-3H-pyrrolo[2,1-c][1,2,24]triazol-3-one, 3-[(5S)-5-(3,5-difluorophenyl)-7-(S)-fluoro-3-oxo-6,7-dihydro-3H-pyrrolo[2,1-c][1,2,4]triazol-2(5H)-yl]bicyclo[1.1.1]pentane-1-carbonitrile, 3-[(5S)-5-(3,5-difluorophenyl)-7-(R)-fluoro-3-oxo-6,7-dihydro-3H-pyrrolo[1,2,4]triazol-5(5H)-yl]bicyclo[1.1 1]pentane-1-carbonitrile, 3-[(5S)-5-(3,5-difluorophenyl)-7-(S)-fluoro-3-oxo-6,7-dihydro-3H-pyrrolo[2,1-c][1,2,4]triazol-2(5H)-yl]bicyclo[1.1.1]pentane-1-carbonitrile, 3-[(5S)-5-(3,5-difluororphenyl)-7-(R)-fluoro-3-oxo-6,7-dihydro-3H-pyrrolo[2,1-c][1,2,4]triazol-2(5H)-yl]bicyclo[1.1.1]pentane-1-carbonitrile, 3-[(5S)-7-(S)-fluoro-3-oxo-5-phenyl-6,7-dihydro-3H-pyrrolo[2,1-c][1,2,4]triazol-2(5H)-yl]bicyclo[1.1.1]pentane-1-carbonitrile, 3-[(5S)-7-(R)-fluoro-3-oxo-5-6,7-dihydro-3H-pyrrolo[2,1-c][1,2,4]triazol-2(5H)-yl]bicyclo[1.1.1]pentane-1-carbonitrile, 3-[(5S)-7-(S)-fluoro-3-oxo-5-phenyl-6,7-dihydro-3H-pyrrolo[2,1-c][1,2,4]triazol-2(5H)-yl]bicyclo[1.1.1]pentane-1-carbonitrile, 3-[(5S)-7-(R)-fluoro-3-oxo-5-6,7-dihydro-3H-pyrrolo[2,1-c][1,2,4]triazol-2(5H)-yl]bicyclo[1.1.1]pentane-1-carbonitrile, 3-[(5S)-7-(S)-fluoro-5-(2-fluorophenyl)-3-oxo-6,7-dihydro-3H-pyrrolo[2,1-c][1,2,4]triazol-2(5H)-yl]bicyclo[1.1.1]pentane-1-carbonitrile, 3-[(5S)-7-(R)-fluoro-5-(2-fluorophenyl)-3-oxo-6,7-dihydro-3H-pyrrolo[2,1-c][1,2,4]triazol-2(5H)-yl]bicyclo[1.1.1]pentane-1-carbonitrile, 3-[(5S)-7-(S)-fluoro-5-(2-fluorophenyl)-3-oxo-6,7-dihydro-3H-pyrrolo[2,1-c][1,2,4]triazol-2(5H)-yl]bicyclo[1.1.1]pentane-1-carbonitrile, 3-[(5S)-7-(R)-fluoro-5-(2-fluorophenyl)-3-oxo-6,7-dihydro-3H-pyrrolo[2,1-c][1,2,4]triazol-2(5H)-yl]bicyclo[1.1.1]pentane-1-carbonitrile, (S)-5-(3,5-difluoro-4-methylphenyl)-2-(3-fluorobicyclo[1.1.1]pentan-1-yl)-2,5,6,7-tetrahydro-3H-pyrrolo[2,1-c][1,2,4]triazol-3-one, (S)-2-(3-(difluoromethyl)bicyclo[1.1.1]pentan-1-yl)-5-(5-fluoropyridin-3-yl)-2,5,6,7-tetrahydro-3H-pyrrolo[2,1-c][1,2,4]triazol-3-one, (S)-5-(3,5-difluorophenyl)-2-(3-fluorobicyclo[1.1.1]pentan-1-yl)-5,6,7,8-tetrahydro-[1,2,4]triazolo[4,3-a]pyridin-3(2H)-one, (S)-2-(3-chlorobicyclo[1.1.1]pentan-1-yl)-5-(pyrazin-2-yl)-2,5,6,7-tetrahydro-3H-pyrrolo[2,1-c][1,2,4]triazol-3-one, (S)-4-(3-oxo-5-(pyrazin-2-yl)-6,7-dihydro-3H-pyrrolo[2,1-c][1,2,4]triazol-2(5H)-yl)bicyclo[2.1.1]hexane-1-carbonitrile, (S)-2-(bicyclo[2.1.1]hexan-1-yl)-5-(pyrazin-2-yl)-2,5,6,7-tetrahydro-3H-pyrrolo[2,1-c][1,2,4]triazol-3-one, (S)-3-(5-(3-chlorophenyl)-3-oxo-6,7-dihydro-3H-pyrrolo[2,1-c][1,2,4]triazol-2(5H)-yl)bicyclo[1.1.1]pentane-1-carbonitrile, (S)-5-(3-chlorophenyl)-2-(3-fluorobicyclo[1.1.1]pentan-1-yl)-2,5,6,7-tetrahydro-3H-pyrrolo[2,1-c][1,2,4]triazol-3-one, (S)-3-(5-(3,5-difluorophenyl)-3-oxo-5,6-dihydrothiazolo[2,3-c][1,2,4]triazol-2(3H)-yl)bicyclo[1.1.1]pentane-1-carbonitrile, (R)-3-(5-(3,5-difluorophenyl)-3-oxo-5,6-dihydrothiazolo[2,3-c][1,2,4]triazol-2(3H)-yl)bicyclo[1.1.1]pentane-1-carbonitrile, (S)-2-(3-fluorobicyclo[1.1.1]pentan-1-yl)-5-(4-methoxyphenyl)-2,5,6,7-tetrahydro-3H-pyrrolo[2,1-c][1,2,4]triazol-3-one, (S)-4-(2-(3-fluorobicyclo[1.1.1]pentan-1-yl)-3-oxo-2,5,6,7-tetrahydro-3H-pyrrolo[2,1-c][1,2,4]triazol-5-yl)benzonitrile, (S)-2-(3-fluorobicyclo[1.1.1]pentan-1-yl)-5-(6-methylpyrazin-2-yl)-2,5,6,7-tetrahydro-3H-pyrrolo[2,1-c][1,2,4]triazol-3-one,
3-((5S,7R)-5-(3,5-difluorophenyl)-7-methyl-3-oxo-6,7-dihydro-3H-pyrrolo[2,1-c][1,2,4]triazol-2(5H)-yl)bicyclo[1.1.1]pentane-1-carbonitrile,
3-((5S,7S)-5-(3,5-difluorophenyl)-7-methyl-3-oxo-6,7-dihydro-3H-pyrrolo[2,1-c][1,2,4]triazol-2(5H)-yl)bicyclo[1.1.1]pentane-1-carbonitrile,
(S)-2-(3-chlorobicyclo[1.1.1]pentan-1-yl)-5-(5-fluoropyridin-2-yl)-2,5,6,7-tetrahydro-3H-pyrrolo[2,1-c][1,2,4]triazol-3-one,
(S)-5-(3-chloro-5-fluoro-4-methylphenyl)-2-(3-fluorobicyclo[1.1.1]pentan-1-yl)-2,5,6,7-tetrahydro-3H-pyrrolo[2,1-c][1,2,4]triazol-3-one,
(S)-5-(3,5-difluoro-4-hydroxyphenyl)-2-(3-fluorobicyclo[1.1.1]pentan-1-yl)-2,5,6,7-tetrahydro-3H-pyrrolo[2,1-c][1,2,4]triazol-3-one,
(S)-5-(2,6-difluoro-4-methylphenyl)-2-(3-fluorobicyclo[1.1.1]pentan-1-yl)-2,5,6,7-tetrahydro-3H-pyrrolo[2,1-c][1,2,4]triazol-3-one,
(S)-5-(4-chloro-3-fluorophenyl)-2-(3-fluorobicyclo[1.1.1]pentan-1-yl)-2,5,6,7-tetrahydro-3H-pyrrolo[2,1-c][1,2,4]triazol-3-one,
(S)-2-(3-fluorobicyclo[1.1.1]pentan-1-yl)-5-(3,4,5-trifluorophenyl)-2,5,6,7-tetrahydro-3H-pyrrolo[2,1-c][1,2,4]triazol-3-one,
(S)-5-(4-chloro-3,5-difluorophenyl)-2-(3-fluorobicyclo[1.1.1]pentan-1-yl)-2,5,6,7-tetrahydro-3H-pyrrolo[2,1-c][1,2,4]triazol-3-one,
(R)-2-(3-fluorobicyclo[1.1.1]pentan-1-yl)-5-phenyl-2,5,6,8-tetrahydro-3H-[1,2,4]triazolo[3,4-c][1,4]oxazin-3-one,
(R)-3-(5-(3,5-difluorophenyl)-3-oxo-5,6-dihydro-3H-[1,2,4]triazolo[3,4-c][1,4]oxazin-2(8H)-yl)bicyclo[1.1.1]pentane-1-carbonitrile,
(S)-2-(3-fluorobicyclo[1.1.1]pentan-1-yl)-5-phenyl-5,6,7,8-tetrahydro-[1,2,4]triazolo[4,3-a]pyridin-3(2H)-one,
3-[(5S)-5-(3,5-difluorophenyl)-3-oxo-6,7-dihydro-3H-pyrrolo[2,1-c][1,2,4]triazol-2(5H)-yl]-2,2-difluorobicyclo[1.1.1]pentane-1-carbonitrile,
methyl (S)-2,2-difluoro-3-(3-oxo-5-phenyl-6,7-dihydro-3H-pyrrolo[2,1-c][1,2,4]triazol-2(5H)-yl)bicyclo[1.1.1]pentane-1-carboxylate,
2,2-difluoro-3-[(5S)-3-oxo-5-phenyl-6,7-dihydro-3H-pyrrolo[2,1-c][1,2,4]triazol-2(5H)-yl]bicyclo[1.1.1]pentane-1-carbonitrile,
(S)-2-(3-fluorobicyclo[1.1.1]pentan-1-yl)-5-(o-tolyl)-2,5,6,7-tetrahydro-3H-pyrrolo[2,1-c][1,2,4]triazol-3-one,
(S)-2-(3-fluorobicyclo[1.1.1]pentan-1-yl)-5-(5-(trifluoromethyl)pyrazin-2-yl)-2,5,6,7-tetrahydro-3H-pyrrolo[2,1-c][1,2,4]triazol-3-one,
(5S,7S)-7-fluoro-2-(3-fluorobicyclo[1.1.1]pentan-1-yl)-5-(pyrazin-2-yl)-2,5,6,7-tetrahydro-3H-pyrrolo[2,1-c][1,2,4]triazol-3-one, and
(S)-3-(5-(4-(difluoromethyl)phenyl)-3-oxo-6,7-dihydro-3H-pyrrolo[2,1-c][1,2,4]triazol-2(5H)-yl)bicyclo[1.1.1]pentane-1-carbonitrile.

20. A method for treating a RIPK1-mediated disease or disorder comprising administering to a patient in need thereof the compound of claim 1, or a pharmaceutically acceptable salt thereof, wherein the RIPK1-mediated disease or disorder is selected from Alzheimer's disease, multiple sclerosis, Parkinson's disease, rheumatoid arthritis, ulcerative colitis, inflammatory bowel disease, psoriasis, and acute tissue injury caused by stroke or traumatic brain injury.

21. A method of treating Alzheimer's disease comprising administering to a patient in need thereof the compound, or pharmaceutically acceptable salt thereof, of claim 1.

22. A pharmaceutical composition comprising the compound of claim 1, or a pharmaceutically acceptable salt thereof and a pharmaceutically acceptable carrier.

23. A pharmaceutical composition comprising the compound of claim 1 and a pharmaceutically acceptable carrier.

24. A compound of formula II:

(II)

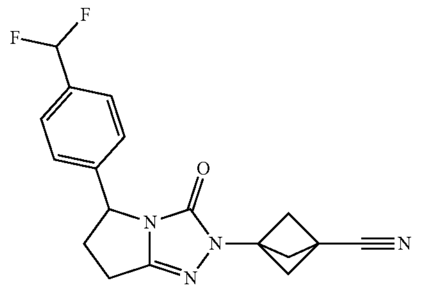

or a pharmaceutically acceptable salt thereof.

25. The compound according to claim 24 which is

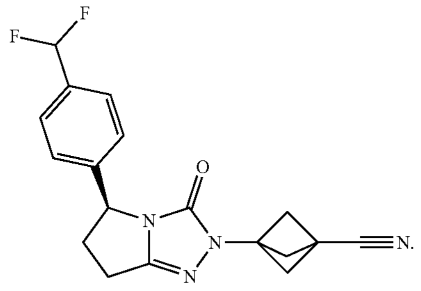 [SMILES: N#CC12CC(n3nc4n(c3=O)[C@H](c3ccc(C(F)F)cc3)CC4)(C1)C2]

26. The compound of claim 24 in the form of a pharmaceutically acceptable salt.

27. A pharmaceutical composition comprising (i) a pharmaceutically acceptable carrier and (ii) the compound of claim 25.

28. A pharmaceutical composition comprising (i) a pharmaceutically acceptable carrier and (ii) the compound of claim 26.

29. A method for treating a RIPK1-mediated disease or disorder comprising administering to a patient in need thereof the compound of claim 24, or a pharmaceutically acceptable salt thereof, wherein the RIPK1-mediated disease or disorder is selected from Alzheimer's disease, multiple sclerosis, Parkinson's disease, rheumatoid arthritis, ulcerative colitis, inflammatory bowel disease, psoriasis, and acute tissue injury caused by stroke or traumatic brain injury.

30. A method of treating Alzheimer's disease comprising administering to a patient in need thereof a compound, or pharmaceutically acceptable salt thereof, of claim 24.

31. A compound of formula III:

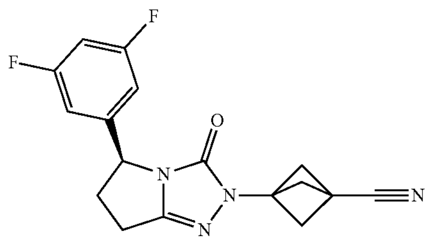

(III)

or a pharmaceutically acceptable salt thereof.

32. A compound according to claim 31 which is

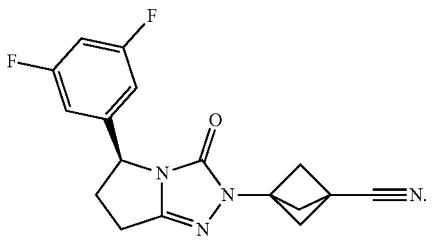 [SMILES: N#CC12CC(n3nc4n(c3=O)[C@H](c3cc(F)cc(F)c3)CC4)(C1)C2]

33. The compound of claim 31 in the form of a pharmaceutically acceptable salt.

34. A pharmaceutical composition comprising (i) a pharmaceutically acceptable carrier and (ii) the compound of claim 32.

35. A pharmaceutical composition comprising (i) a pharmaceutically acceptable carrier and (ii) the compound of claim 33.

36. A method for treating a RIPK1-mediated disease or disorder comprising administering to a patient in need thereof the compound of claim 31, or a pharmaceutically acceptable salt thereof, wherein the RIPK1-mediated disease or disorder is selected from Alzheimer's disease, multiple sclerosis, Parkinson's disease, rheumatoid arthritis, ulcerative colitis, inflammatory bowel disease, psoriasis, and acute tissue injury caused by stroke or traumatic brain injury.

37. A method of treating Alzheimer's disease comprising administering to a patient in need thereof a compound, or pharmaceutically acceptable salt thereof, of claim 31.

38. A compound of formula IV:

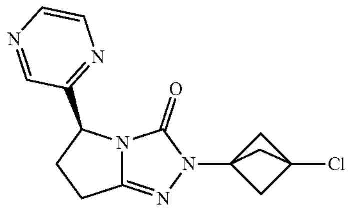

(IV)

or a pharmaceutically acceptable salt thereof.

39. A compound according to claim 38 which is

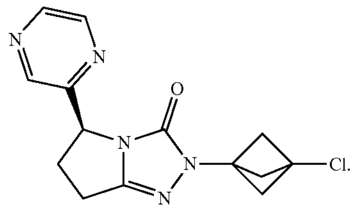 [SMILES: O=c1n(C23CC(Cl)(C2)C3)nc2n1[C@H](c1cnccn1)CC2]

40. The compound of claim 38 in the form of a pharmaceutically acceptable salt.

41. A pharmaceutical composition comprising (i) a pharmaceutically acceptable carrier and (ii) the compound of claim 39.

42. A pharmaceutical composition comprising (i) a pharmaceutically acceptable carrier and (ii) the compound of claim 40.

43. A method for treating a RIPK1-mediated disease or disorder comprising administering to a patient in need thereof the compound of claim 38, or a pharmaceutically acceptable salt thereof, wherein the RIPK1-mediated disease or disorder is selected from Alzheimer's disease, multiple sclerosis, Parkinson's disease, rheumatoid arthritis, ulcerative colitis, inflammatory bowel disease, psoriasis, and acute tissue injury caused by stroke or traumatic brain injury.

44. A method of treating Alzheimer's disease comprising administering to a patient in need thereof a compound, or pharmaceutically acceptable salt thereof, of claim 38.

45. A compound of formula V:

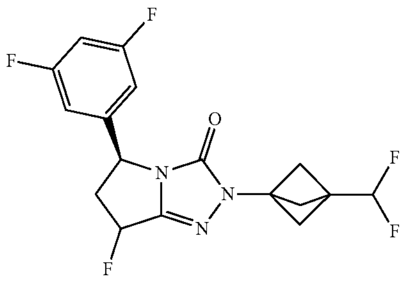

(V)

or a pharmaceutically acceptable salt thereof.

46. A compound according to claim 45 which is

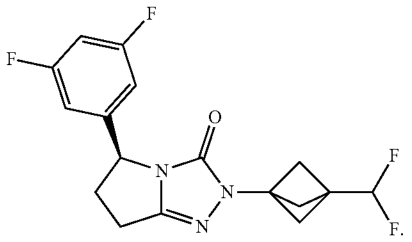 [SMILES: O=c1n(C23CC(C(F)F)(C2)C3)nc2n1[C@H](c1cc(F)cc(F)c1)CC2]

47. The compound of claim 45 in the form of a pharmaceutically acceptable salt.

48. A pharmaceutical composition comprising (i) a pharmaceutically acceptable carrier and (ii) the compound of claim 45.

49. A pharmaceutical composition comprising (i) a pharmaceutically acceptable carrier and (ii) the compound of claim 46.

50. A method for treating a RIPK1-mediated disease or disorder comprising administering to a patient in need thereof the compound of claim 45, or a pharmaceutically acceptable salt thereof, wherein the RIPK1-mediated disease or disorder is selected from Alzheimer's disease, multiple sclerosis, Parkinson's disease, rheumatoid arthritis, ulcerative colitis, inflammatory bowel disease, psoriasis, and acute tissue injury caused by stroke or traumatic brain injury.

51. A method of treating Alzheimer's disease comprising administering to a patient in need thereof a compound, or pharmaceutically acceptable salt thereof, of claim 45.

52. A compound of formula VI:

(VI)

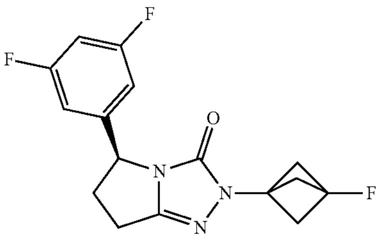

or a pharmaceutically acceptable salt thereof.

53. A compound according to claim 52 which is

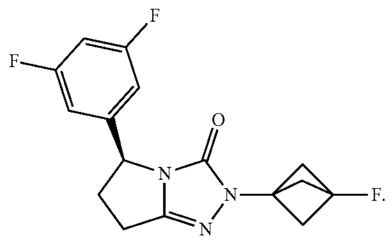 [SMILES: O=c1n(C23CC(F)(C2)C3)nc2n1[C@H](c1cc(F)cc(F)c1)CC2]

54. The compound of claim 52 in the form of a pharmaceutically acceptable salt.

55. A pharmaceutical composition comprising (i) a pharmaceutically acceptable carrier and (ii) the compound of claim 53.

56. A pharmaceutical composition comprising (i) a pharmaceutically acceptable carrier and (ii) the compound of claim 54.

57. A method for treating a RIPK1-mediated disease or disorder comprising administering to a patient in need thereof the compound of claim 52, or a pharmaceutically acceptable salt thereof, wherein the RIPK1-mediated disease or disorder is selected from Alzheimer's disease, multiple sclerosis, Parkinson's disease, rheumatoid arthritis, ulcerative colitis, inflammatory bowel disease, psoriasis, and acute tissue injury caused by stroke or traumatic brain injury.

58. A method of treating Alzheimer's disease comprising administering to a patient in need thereof a compound, or pharmaceutically acceptable salt thereof, of claim 52.

* * * * *